US009439980B2

(12) United States Patent
Medin et al.

(10) Patent No.: US 9,439,980 B2
(45) Date of Patent: Sep. 13, 2016

(54) THYMIDYLATE KINASE FUSIONS AND USES THEREOF

(71) Applicant: University Health Network, Toronto (CA)

(72) Inventors: Jeffrey A. Medin, North York (CA); Sean Devine, Toronto (CA)

(73) Assignee: Univeristy Health Network, Toronto (CA)

( * ) Notice: Subject to any disclaimer, the term of this patent is extended or adjusted under 35 U.S.C. 154(b) by 0 days.

(21) Appl. No.: 14/037,931

(22) Filed: Sep. 26, 2013

(65) Prior Publication Data

US 2014/0093485 A1 Apr. 3, 2014

Related U.S. Application Data

(63) Continuation of application No. 12/933,460, filed as application No. PCT/CA2009/000342 on Mar. 20, 2009, now Pat. No. 8,568,709.

(60) Provisional application No. 61/038,398, filed on Mar. 20, 2008.

(51) Int. Cl.

| | |
|---|---|
| ***A61K 48/00*** | (2006.01) |
| ***C12N 15/00*** | (2006.01) |
| ***C12N 15/63*** | (2006.01) |
| ***C12P 21/04*** | (2006.01) |
| ***C07H 21/04*** | (2006.01) |
| ***C07K 14/705*** | (2006.01) |
| ***C12N 9/12*** | (2006.01) |
| ***C12N 15/86*** | (2006.01) |
| *C12N 15/85* | (2006.01) |
| *C12N 5/16* | (2006.01) |
| *A61K 38/00* | (2006.01) |

(52) U.S. Cl.

CPC ..... *A61K 48/0058* (2013.01); *C07K 14/70503* (2013.01); *C12N 9/1229* (2013.01); *C12N 15/86* (2013.01); *A61K 38/00* (2013.01); *C07H 21/04* (2013.01); *C07K 2319/00* (2013.01); *C12N 5/16* (2013.01); *C12N 15/63* (2013.01); *C12N 15/85* (2013.01); *C12N 2740/16043* (2013.01); *C12N 2840/203* (2013.01)

(58) Field of Classification Search

CPC ...... C12N 15/63; C12N 15/85; C12N 15/86; C12N 5/16; C12N 2740/16043; C12N 2840/203; C07H 21/04; C07K 2319/00

USPC .................. 435/69.7, 320.1, 455; 424/93.21; 536/23.5, 24.1

See application file for complete search history.

(56) References Cited

U.S. PATENT DOCUMENTS

| | | | |
|---|---|---|---|
| 5,240,846 | A | 8/1993 | Collins et al. |
| 5,399,346 | A | 3/1995 | Anderson et al. |
| 5,436,146 | A | 7/1995 | Shenk et al. |
| 5,529,774 | A | 6/1996 | Barba et al. |
| 5,547,932 | A | 8/1996 | Curiel et al. |
| 5,639,642 | A | 6/1997 | Kjeldsen et al. |
| 5,645,829 | A | 7/1997 | Shockley et al. |
| 5,656,465 | A | 8/1997 | Panicali et al. |
| 5,670,488 | A | 9/1997 | Gregory et al. |
| 5,672,344 | A | 9/1997 | Kelley et al. |
| 5,741,486 | A | 4/1998 | Pathak et al. |
| 5,817,492 | A | 10/1998 | Saito et al. |
| 5,830,880 | A | 11/1998 | Sedlacek et al. |
| 5,854,019 | A | 12/1998 | Sedlacek et al. |
| 5,869,040 | A | 2/1999 | Oin |
| 5,910,488 | A | 6/1999 | Nabel et al. |
| 5,911,983 | A | 6/1999 | Barranger et al. |
| 5,928,214 | A | 7/1999 | Rubinstein et al. |
| 5,928,914 | A | 7/1999 | Leboulch et al. |
| 6,423,692 | B2 | 7/2002 | Fine et al. |
| 2004/0258661 | A1 | 12/2004 | Fowler |
| 2005/0008648 | A1 | 1/2005 | Lavie et al. |
| 2009/0068158 | A1 | 3/2009 | Medin |
| 2009/0074733 | A1 | 3/2009 | Medin et al. |
| 2010/0233200 | A1 | 9/2010 | Medin |
| 2010/0291043 | A1 | 11/2010 | Medin |
| 2011/0014165 | A1 | 1/2011 | Medin |
| 2011/0027310 | A1 | 2/2011 | Medin |
| 2011/0104130 | A1 | 5/2011 | Medin |
| 2014/0193449 | A1 | 7/2014 | Medin |

FOREIGN PATENT DOCUMENTS

| | | |
|---|---|---|
| CA | 2246005 | 10/1998 |
| CA | 2253790 | 4/2000 |
| CA | 2566267 | 6/2007 |
| CA | 2719711 | 10/2008 |
| CA | 2723320 | 11/2008 |

(Continued)

OTHER PUBLICATIONS

Whitehurst et al., 2006, Virology, vol. 347, p. 199-207.*
Pandey, Prativa, 2007, Abstracts, 59th Southeast regional Meeting of the American Chemical Society, Greenville, SC, United States, GEN-671, Publisher: American Chemical Society, Washington D.C.*
Gorecki, D., 2001, Expert Opin. Emerging Drugs, 6(2): 187-198.*
Thomas et al., 2003, Nature Reviews/ Genetics, vol. 4, p. 346-358.*
Kodama et al., 2006, Current Medicinal Chemistry, vol. 13, p. 2155-2161.*
Takahashi et al., 2012, Frontiers in Bioscience, vol. S4, p. 133-141.*
Kaur et al., 2009, Current Gene Therapy, vol. 9. p. 434-458.*
Medin et al., 2009, US 20090074733 A1, effective filed Dec. 9, 2005.*
Bennett, J., 2003, Gene Therapy, vol. 10, p. 977-982.*
Gruh et al., Shuttle system allowing simplified cloning of expression cassettes into advanced generation lentiviral vectors. Biotechniques. Apr. 2005, 3(4):530, 532, 534.

(Continued)

*Primary Examiner* — Shin Lin Chen
(74) *Attorney, Agent, or Firm* — Bereskin & Parr LLP; Carmela De Luca

(57) ABSTRACT

The application relates to a composition comprising: a stably integrating delivery vector; a modified mammalian thymidylate kinase (tmpk) wherein the modified mammalian tmpk increases phosphorylation of a prodrug relative to phosophorylation of the prodrug by wild-type human tmpk; and a detection cassette fused to tmpk. The application also relates to use of these compositions in methods of treatment of diseases such as graft versus host disease and cancer.

16 Claims, 49 Drawing Sheets

(56) References Cited

FOREIGN PATENT DOCUMENTS

| | | |
|---|---|---|
| WO | WO9941404 | 8/1999 |
| WO | 0076542 | 12/2000 |
| WO | 02080851 | 10/2002 |
| WO | 03055439 | 7/2003 |
| WO | 2008116316 | 10/2008 |
| WO | 2008134879 | 11/2008 |
| WO | WO2008134878 | 11/2008 |

OTHER PUBLICATIONS

Kanazawa et al., Suicide gene therapy using AAV-HSVtk/ganciclovir in combination with irradiation results in regression of human head and neck cancer xenografts in nude mice. Gene Ther. Jan. 2003; 10(1): 51-58.

Fukui et al., Suicide gene therapy for human oral squamous cell carcinoma cell liens with adeno-associated virus vector. Oral Oncol., Apr. 2001; 37(3): 211-215.

Lu et al., Safe two-plasmid production for the first clinical lentivirus vector that achieves >99% transduction in primary cells using a one-step protocol. Journal of Gene Medicine, 2004, 6:963-973.

Klump et al., Retroviral vector-mediated expression of HoxB4 in hematopoietic cells using a novel coexpression strategy. Gene Ther. 2001; 8(10):811-817.

Osborn et al., A picornaviral 2A-like sequence-based tricistronic vector allowing for high-level therapeutic gene expression coupled to a dual-receptor system. Molecular Therapy 2005; 12(3), 569-574.

Szymczak et al., Development of 2A peptide-based strategies in the design of multistronic vectors. Expert Opinion Bio Ther. , 2005; 5(5):627-638.

Szymczak et al., Correction of multi-gene deficiency in vivo using a single 'self-cleaving' 2A peptide-based retroviral vector. Nature Biotechnolody, 2004;22(5):589-594.

Chen et al., Synthesis and evaluation of novel thymidine analogs as antitumor and antiviral agents. J. Med Chem. 1996, 39(17):3412-3417.

Yee. Adoptive T cell therapy: addressing challenges in cancer immunotherapy. J Translational Medicine, 2005 3(17): dio;0.1186/479-5786-3-17.

Chevez-Barrios et al., Response of retinoblastoma with vitreous tumor seeding to adenovirus-mediated delivery of thymidine kinase followed by ganciclovir. J Clin Oncol. Nov. 1, 2005; 23(31):7927-7935.

Sterman et al., Adenovirus-mediated herpes simplex virus thymidine kinase/ganciclovir gene therapy in patients with localized malignancy: results of a phase I clinical trial in malignant mesothelioma (Adenoviral Gene Therapy for Mesothelioma). Hum Gen Ther. May 1, 1998; 9(7) 1083-1092.

Socie. Chronic graft-versus-host disease: clinical features and grading systems. Int J Hematol. Apr. 2004; 79(3):216-20.

Bondanza et al., Suicide gene therapy of graft-versus-host disease induced by central memory human T lymphocytes. Blood. 107(5):1828-1836, 2006.

Muller et al., Novel nucleotides analogues as potential substrates for TMPK, a key enzyme in the metabolism of AZT. Nucleosides Nucleotides Nucleic Acids. 2003; 22)5-8):821-823.

Thompson et al., Improving the sensitivity of progressive multiple sequence alignment through sequence weighting position-specific gap penalities and weight matrix choice. Nucleic Acid Res. 22:4673-4680, 1994.

Wang et al. Cancer Stem Cells: Lessons from Leukemia. Trends in Cell Biology. 15(9):494-501,2005.

Kang et al., Enhancement of dendritic cell-based vaccine potency by targeting antigen to endosomal/lysosomal compartments, Immunology Letters, vol. 106, No. 2, 2006, pp. 126-134, XP024999077.

Nair et al., Induction of primary carcinoembryonic antigen (CEA)-specific cytotoxic T lymphocytes in vitro using human dendritic cells transfected with RNA, Nature Biotechnology, vol. 16, Apr. 1998, pp. 364-369, XP001026122.

Song et al., II-12 plasmid-enhanced Dna vaccination against carcinoembryonic antigen (CEA) studied in immune-gene knockout mice, Gene Therapy, vol. 7, No. 18, Sep. 2000, pp. 1527-1535.

Lin et al., Treatment of established tumors with a novel vaccine that enhances major histocompatibility class II presentation of tumor antigen, Cancer Research, vol. 56, No. 1, Jan. 1, 1996, pp. 21-26, XP001097270.

Wu et al., Engineering an intracellular pathway for major histocompatibility complex class Ii presentation of antigens, Proc. Natl. Acad. Sci., USA vol. 92, No. 25, Dec. 1995, pp. 11671-11675, XP002180963.

Ji et al., Targeting human papillomavirus type 16 E7 to the endosomal/lysomal compartment enhances the antitumor immunity of DNA vaccines against murine human papillomavirus type 16 E7-expressing tumors, Human Gene Therapy, vol. 10, N. 17, Nov. 20, 1999, pp. 2727-2740, XP002956558.

Su et al., Enhanced induction of telomerase-specific CD4+ T Cells using dendritic cells transfected with RNA encoding a chimeric gene product, Cancer Research, vol. 62, No. 17, Sep. 1, 2002, pp. 5041-5048, XP002484304.

Humrich et al., Viral vectors for dendritic cell-based immunotherapy, Current Topics in Microbiology and Immunology, vol. 276, 2003, pp. 241-259, XP001247551.

Kaplan et al., New cancer vaccine approaches, Drugs of Today, vol. 40, No. 11, 2004, pp. 913-929.

Kirk et al., Gene-modified dendritic cells for use in tumor vaccines, Human Gene Therapy, vol. 11, No. 6, Apr. 10, 2000, pp. 797-806, XP001010046.

Strausberg et al., Generation and initial analysis of more than 15,000 full-length human and mouse cDNA sequences Proc. Natl Acad Sci., USA, Dec. 24, 2002; 99(26)16899-903. Epub Dec. 11, 2002.

Park et al., Therapeutic levels of human factor VIII and IX using HIV-1 based lentiviral vectors in mouse liver. Blood. vol. 96, No. 3, Aug. 1, 2000, pp. 1173-1176.

Sato et al., Engineered human tmpk/AZT as a novel enzyme/prodrug axis for suicide gene therapy. Molecular Therapy, Apr. 19, 2007, published online Mar. 20, 2007, vol. 15, No. 5, pp. 962-970.

Ramsubir et al., Enhancement of gene therapy approaches for the correction of Farber disease. Molecular Therapy, May 2004, vol. 9 Suppl. 1, S330, No. 868.

Kramm. Alternative concepts for suicide gene therapy for graft-versus-host disease after adotive immunotherapy. Acta Haematologica, 2003, vol. 110, No. 2-3, pp. 132-138.

Denny. Prodrugs for gene-directed enzyme-prodrug therapy (suicide gene therapy). Journal of Biomedicine and Biotechnology, 2003, vol. 2003, No. 1, pp. 4870.

Kreitman., Immunotoxins for targeted cancer therapy. American Association of Pharmaceutical Scientists Journal, 2006, vol. 8, No. 3, pp. E532-E551.

King et al., Gene therapy and targeted toxins for glioma. Current Gene Therapy, 2005, vol. 5, No. 6, pp. 535-557.

Ramsubir et al., Anti-CD25 targeted killing of bicistronically transduced cells: a novel safety mechanism against retroviral genotoxicity. Molecular Therapy, Jun. 2007, published online Mar. 27, 2007, vol. 15, No. 6, pp. 1174-1181.

Chen et al., Alterationl of T cell immunity by lentiviral transduction of human monocyte-derived dendritic cells. Retrovirology, Nov. 1, 2004, vol. 1, No. 1., pp. 37-49.

Kuwata et al., Construction of chimeric simian and human immunodeficiency viruses that produce interleukin 12, AIDS Research and Human Retroviruses, Mar. 1, 2000, vol, 16, No. 5, pp. 465-470.

Tahara et al., Effective eradication of established murine tumors with IL-12 gene therapy using a polycistronic retroviral vector, Journal of Immunology, 1995, vol. 154, No. 12, pp. 6466-6474.

Miller et al., Overexpression of interleukin-12 enables dendritic cells to active NK cells and confer system antitumor immunity, The FASEB Journal., Apr. 2003, vol. 17, No. 6, pp. 728-730.

Meko et al., High cytokine production and effective antitumor activity of a recombinant vaccinia virus encoding murine interleukin 12, Cancer Research, Nov. 1, 1995, vol. 55, pp. 4765-4770.

Suzuki et al., Vaccination of dendritic cells loaded wtih interleukin-12-secreting cancer cells augments in vivo antitumor immunity:

(56) References Cited

OTHER PUBLICATIONS characteristics of syngeneic and allogeneic antigen-presenting cell cancer hybrid cells, Clinical Cancer Research, Jan. 1, 2005, vol. 11, No. 1, pp. 58-66.
Zitvogel et al., Construction and characterization of retroviral vectors expressing biologically active human interleukin-12, Human Gene Therapy, Dec. 1994, vol. 5, pp. 1493-1506.
Robertson et al., Interleukin 12: basic biology and potential applications in cancer treatment, The Oncologist, Feb. 1, 1996, vol. 1, No. 1 & 2, pp. 88-97.
Pizzoferrato et al., Enhanced immunogenicity of B cell lymphoma genetically engineered to express both B7-1 and interleukin-12, Human Gene Therapy, vol. 8, Dec. 10, 1997, pp. 2217-2228.
Pizzoferrato, B7-2 Expression above a threshold elicits anti-tumor immunity as effective as interleukin-12 and prolongs survival in murine B-cell lymphoma, Int. J. Cancer, vol. 110, 2004, pp. 61-69.
Pizzoferrato, PhD Thesis entitled a Murine Model of B-cell lymphoma: manipulation of costimulatory and cytokine expression to generate effective immunotherapeutic cancer vaccines, National Library of Canada, 1999.
Pajtasz-Piaseck et al., Loss of tumorigenicity of murine colon carcinoma MC38/0 cell line after transduction with a retroviral vector carrying murine IL-12 genes, Folia Biologica (Prague), vol. 50, No. 1, 2004, pp. 7-14.
Gautam Subhash et al., Interleukin-12 (IL-12) gene therapy of leukemia: immune and anti-leukemic effects of IL-12-transduced hematopoietic progenitor cells, Cance Gene Therapy, vol. 7, No. 7, Jul. 2000, pp. 1060-1068.
Qian et al., Gene therapy of cancer: induction of anti-tumor immunity, Cellular & Molecular Immunology, Apr. 2004, vol. 1, No. 2, pp. 105-111.
Breckpot et al., Lentiviral vectors for cancer immunotherapy: transforming infectious particles into therapeutics, Gene Therapy, vol. 14, No. 11, Mar. 22, 2007, pp. 847-862.
Chang et al., The genetic engineering of hematopoietic stem cells: the rise of lentiviral vectors, the conundrum of the ltr, and the promise of lineage-restricted vectors, Molecular Therapy: The Journal of the American Society of Gene Therapy, Mar. 2007, vol. 15, No. 3, pp. 445-456.
Obana et al., Induction of anti-tumor immunity by mouse tumor cells transfected with mouse interleukin-12 gene, Japanese Journal of medical Science and Biology, Tokyo Japan, vol. 48, Jan. 1, 1995, pp. 221-236.
Columbo et al., Amount of interleukin 12 available at the tumor site is critical for tumor regression, Cancer Research, vol. 56, No. 11, 1996, pp. 2531-2534.
Mazzolini et al., Gene therapy of cancer with interleukin-12, Current Pharmaceutical Design, vol. 9, No. 24, Sep. 1, 2003, pp. 1981-1991.
Labbe et al., Murine model of immune-mediated rejection of the acute lymphoblastic leukemia 7OZ/3, Journal of Immunology, May 1, 2006, vol. 176, No. 9, pp. 5354-5361.
Labbe et al., IL-12 immunotherapy of murine leukaemia: comparison of systemic versus gene modified cell therapy. Journal of Cellular and Molecular Medicine, Aug. 2009, vol. 13, No. 8B, pp. 1962-1976.
Miltenyi Biotec product brochure dated 2006, downloaded Dec. 17, 2012.
Devine et al., Development of novel suicide systems in therapeutic lentiviral vectors, Poster Presentation, May 7, 2006.
Neschadim et al., Cell fate control gene therapy based on engineered variants of human deoxycytidine kinasae. Molecular Therapy, Received Mar. 29, 2011; accepted Dec. 16, 2011; advance online publication 2012. doi: 10.1038/mt.2011.298.
Bonini et al., Safety of retroviral gene marking with a truncated NGF receptor. Nature Medicine, vol. 9, No. 4, Apr. 2003, pp. 367-369.
Ohtake et al., Retrograde degeneration and colchicine protection of basal forebrain cholinergic neurons following hippocampal injections of an immunotoxin against the P75 nerve growth factor receptor. Neuroscience, vol. 78, No. 1, pp. 123-133, 1997.
PhD Dissertation of Shobha Ramsubir, Retrovirus-mediated gene therapy for Farber Disease, published 2008; Graduate Dept. of Medical Biophysics, University of Toronto.
Scaife, et al., Engineered human Tmpk fused with truncated cell-surface markers: versatile cell-fate control safety cassettes, Gene Therapy, 20, 24-34, 2013.
Amarnath et al., The PDL1-PD1 axis converts human Th1 cells into regulatory T cells, Sci Transl. Med., Nov. 30, 2011, (111):111ra120. doi:10.1126/scitranslmed.3003130.
Ostermann et al., Structures of Human Thymidylate Kinase in Complex with Prodrugs: Implications for the Structure-Based Design of Novel Compounds. 2003, Biochemistry, vol. 42, p. 2568-2577.
Skolnick et al., From genes to protein structure and function: novel applications of computational approaches in the genomic era.2000, Trends in Biotech., vol. 18, p. 34-39.
Tomasinsig et al., The Cathelicidins—Structure, Function and Evolution. 2005, Current Protein and Peptide Science, vol. 6, p. 23-34.
Smallwood et al., Different Substitutions at Conserved Amino Acids in Domains II and III in the Sendai L RNA Polymerase Protein Inactibate Viral RNA Synthesis. 2002, Virology, vol. 304, p. 135-145.
Chattopadhyay et al., Effect of single amino acid mutations in the conserved GDNQ motif of L protein of Rinderpest virus on RNA synthesis in vitro and in vivo. 2004, Virus Research, vol. 99, p. 139-145.
Strausberg et al., 2006, GenEmbl Accession No. BC001827, computer printout pp. 7-11, SEQ ID No. 21.
Gruh et al., Shuttle system allowing simplified cloning of expression cassettes into advanced generation lentiviral vectors. 2005, BiotTechniques, vol. 38, No. 4, p. 530, 532 and 534.
Park et al., Therapeutic levels of human factor VIII and IX using HIV-1-based lentiviral vectors in mouse liver. 2000, Blood, vol. 96, No. 3, p. 1173-1176.
Sato et al., A Novel Suicide Gene Therapy Approach for Reduction of GvHD using Lentiviral Delivery of a Modified Human Thymidylate Monophosphate Kinase. Blood, 2006, 106: Abstract, 5252.
Vroemen, Maurice et al. Loss of gene expression in lentivirus- and retrovirus-transduced neural progenitor cells is correlated to migration and differentiation in the adult spinal cord. Experimental Neurology 195 (2005) 127-139.
Vroemen, Maurice and Weidner, Norbert. Purification of Schwann cells by selection of p75 low affinity nerve growth factor receptor expressing cells from adult peripheral nerve. Journal of Neuroscience Methods 124 (2003) 135-143.
Ostermann, et al. Insights into the phosphoryltransfer mechanism of human thymidylate kinase gained from crystal structures of enzyme complexes along the reaction coordinate. Structure with Folding & Design, 2000, vol. 8, No. 6, 629-642.
Hacein-Bey-Abina S, et al. LMO2-associated clonal T cell proliferation in two patients after gene therapy for SCID-X1. Science. 2003; 302: 415-419.
Roy NS, et al. Functional engraftment of human ES cell-derived dopaminergic neurons enriched by coculture with telomerase-immortalized midbrain astrocytes. Nat. Med. 12(11):1259-36, 2006.
Nishiyama Y, Rapp F. Anticellular effects of 9-(2-hydroxyethoxymethyl) guanine against herpes simplex virus-transformed cells. J Gen Virol. 1979; 45: 227-230.
Moolten FL. Tumor chemosensitivity conferred by inserted herpes thymidine kinase genes: paradigm for a prospective cancer control strategy. Cancer Res. 1986; 46: 5276-5281.
Wildner O, et al. Therapy of colon cancer with oncolytic adenovirus is enhanced by the addition of herpes simplex virus-thymidine kinase. Cancer Res. 1999; 59: 410-413.
Moolten FL, Wells JM. Curability of tumors bearing herpes thymidine kinase genes transferred by retroviral vectors. J Natl Cancer Inst. 1990; 82: 297-300.
Hamel W, et al. Herpes simplex virus thymidine kinase/ganciclovir-mediated apoptotic death of bystander cells. Cancer Res. 1996; 56: 2697-2702.

(56) References Cited

OTHER PUBLICATIONS

Kokoris MS, Black ME. Characterization of herpes simplex virus type 1 thymidine kinase mutants engineered for improved ganciclovir or acyclovir activity. Protein Sci. 2002; 11: 2267-2272.
Qasim W, et al. T cell transduction and suicide with an enhanced mutant thymidine kinase. Gene Ther. 2002; 9: 824-827.
Riddell SR, et al. T-cell mediated rejection of gene-modified HIV-specific cytotoxic T lymphocytes in HIV-infected patients. Nat Med. 1996; 2: 216-223.
Berger C, et al. Analysis of transgene-specific immune responses that limit the in vivo persistence of adoptively transferred HSV-TK-modified donor T cells after allogeneic hematopoietic cell transplantation. Blood. 2006; 107: 2294-2302.
Van Rompay AR, et al. Phosphorylation of nucleosides and nucleoside analogs by mammalian nucleoside monophosphate kinases. Pharmacol Ther. 2000; 87: 189-198.
Furman PA, et al. Phosphorylation of 3'-azido-3'-deoxythymidine and selective interaction of the 5'-triphosphate with human immunodeficiency virus reverse transcriptase. Proc Natl Acad Sci U S A. 1986; 83: 8333-8337.
St Clair MH, et al. 3'-Azido-3'-deoxythymidine triphosphate as an inhibitor and substrate of purified human immunodeficiency virus reverse transcriptase. Antimicrob Agents Chemother. 1987; 31: 1972-1977.
Frick LW, et al. Effects of 3'-azido-3'-deoxythymidine on the deoxynucleotide triphosphate pools of cultured human cells. Biochem Biophys Res Commun. 1988; 154: 124-129.
Johnson AA, et al. Toxicity of antiviral nucleoside analogs and the human mitochondrial DNA polymerase. J Biol Chem. 2001; 276: 40847-40857.
Lavie A, et al. The bottleneck in AZT activation. Nat Med. 1997; 3: 922-924.
Coplan NL, Bruno MS. Acquired immunodeficiency syndrome and heart disease: the present and the future. Am Heart J. 1989; 117: 1175-1177.
Cazzalini O, et al. Early effects of Azt on mitochondrial functions in the absence of mitochondrial DNA depletion in rat myotubes. Biochem Pharmacol. 2001; 62: 893-902.
Sales SD, et al, Back DJ. Zidovudine phosphorylation and mitochondrial toxicity in vitro. Toxicol Appl Pharmacol. 2001; 177: 54-58.
Masini A, et al. Zidovudine-induced experimental myopathy: dual mechanism of mitochondrial damage. J Neurol Sci. 1999; 166: 131-140.
McKee EE, et al. Phosphorylation of thymidine and AZT in heart mitochondria: elucidation of a novel mechanism of AZT cardiotoxicity. Cardiovasc Toxicol. 2004; 4: 155-167.
Brundiers R, et al. Modifying human thymidylate kinase to potentiate azidothymidine activation. J Biol Chem. 1999; 274: 35289-35292.
Ostermann N, et al. Potentiating AZT activation: structures of wild-type and mutant human thymidylate kinase suggest reasons for the mutants' improved kinetics with the HIV prodrug metabolite AZTMP. J Mol Biol. 2000; 304: 43-53.
Naldini L, Blomer U, Gallay P, Ory D, Mulligan R, Gage FH, et al. In vivo gene delivery and stable transduction of nondividing cells by a lentiviral vector. Science. 1996; 272: 263-267.
Blomer U, et al. Highly efficient and sustained gene transfer in adult neurons with a lentivirus vector. J Virol. 1997; 71: 6641-6649.
Yoshimitsu M, et al. Bioluminescent imaging of a marking transgene and correction of Fabry mice by neonatal injection of recombinant lentiviral vectors. Proc Natl Acad Sci U S A. 2004; 101: 16909-16914.
Sadelain M, Riviere I. Sturm and drang over suicidal lymphocytes. Mol Ther. 2002; 5: 655-657.
Migita M, et al. Selection of transduced CD34+ progenitors and enzymatic correction of cells from Gaucher patients, with bicistronic vectors. Proc Natl Acad Sci U S A. 1995; 92: 12075-12079.
Medin JA, et al. A bicistronic therapeutic retroviral vector enables sorting of transduced CD34+ cells and corrects the enzyme deficiency in cells from Gaucher patients. Blood. 1996; 87: 1754-1762.
Qin G, et al. Preselective gene therapy for Fabry disease. Proc Natl Acad Sci U S A. 2001; 98: 3428-3433.
Siatskas C, et al. Specific pharmacological dimerization of KDR in lentivirally transduced human hematopoietic cells activates anti-apoptotic and proliferative effects. FASEB J. 2005; 19: 1752-1754.
Medin JA, et al. Efficient transfer of PSA and PSMA cDNAs into DCs generates antibody and T cell antitumor responses in vivo. Cancer Gene Ther. 2005; 12: 540-551.
Bonini C, et al. HSV-TK gene transfer into donor lymphocytes for control of allogeneic graft-versus-leukemia. Science. 1997; 276: 1719-1724.
Li Z, et al. Murine leukemia induced by retroviral gene marking. Science. 2002; 296: 497.
Doody GM, et al. Activation of B lymphocytes: integrating signals from CD19, CD22 and Fc gamma RIIb1. Curr Opin Immunol. 1996; 8: 378-382.
Fujimoto M, et al. CD19 regulates intrinsic B lymphocyte signal transduction and activation through a novel mechanism of processive amplification. Immunol Res. 2000; 22: 281-298.
Tedder TF, et al. The CD19/CD21 signal transduction complex of B lymphocytes. Immunol Today. 1994; 15: 437-442.
Sato S, et al. Regulation of B lymphocyte development and activation by the CD19/CD21/CD81/Leu 13 complex requires the cytoplasmic domain of CD19. J Immunol. 1997; 159: 3278-3287.
Greco O, Dachs GU. Gene directed enzyme/prodrug therapy of cancer: historical appraisal and future prospectives. J Cell Physiol. 2001; 187: 22-36.
Smiley ST, et al. Intracellular heterogeneity in mitochondrial membrane potentials revealed by a J-aggregate-forming lipophilic cation JC-1. Proc Natl Acad Sci U S A. 1991; 88: 3671-3675.
Green DR, Reed JC. Mitochondria and apoptosis. Science. 1998; 281: 1309-1312.
Mahmoud MS, et al. Enforced CD19 expression leads to growth inhibition and reduced tumorigenicity. Blood. 1999; 94: 3551-3558.
Cohen JL, et al. Prevention of graft-versus-host disease in mice using a suicide gene expressed in T lymphocytes. Blood. 1997; 89: 4636-4645.
Spencer DM. Developments in suicide genes for preclinical and clinical applications. Curr Opin Mol Ther. 2000; 2: 433-440.
Lal S, et al. Suicide genes: past, present and future perspectives. Immunol Today. 2000; 21: 48-54.
Kershaw MH, et al. Supernatural T cells: genetic modification of T cells for cancer therapy. Nat Rev Immunol. 2005; 5: 928-940.
Chow HH, et al. In vivo tissue disposition of 3'-azido-3'-deoxythymidine and its anabolites in control and retrovirus-infected mice. Drug Metab Dispos. 1997; 25: 412-422.
Weichold FF, et al. Regulation of a graft-versus-leukemia effect by major histocompatibility complex class II molecules on leukemia cells: HLA-DR1 expression renders K562 cell tumors resistant to adoptively transferred lymphocytes in severe combined immunodeficiency mice/nonobese diabetic mice. Blood. 1997; 90: 4553-4558.
Fehse, B et al. A novel "sort-suicide" fusion gene vector for T cell manipulation. Gene Therapy. 2002; 9:1633-1638.

* cited by examiner

(A) Wild-type human TmpK (SEQ ID NO: 1)

ATGGCGGCCCGGCGCGGGGCTCTCATAGTGCTGGAGGGCGTGGACCGCGCCGGGAAG
AGCACGCAGAGCCGCAAGCTGGTGGAAGCGCTGTGCGCCGCGGGCCACCGCGCCGAA
CTGCTCCGGTTCCCGGAAAGATCAACTGAAATCGGCAAACTTCTGAGTTCCTACTTG
CAAAAGAAAAGTGACGTGGAGGATCACTCGGTGCACCTGCTTTTTTCTGCAAATCGC
TGGGAACAAGTGCCGTTAATTAAGGAAAAGTTGAGCCAGGGCGTGACCCTCGTCGTG
GACAGATACGCATTTTCTGGTGTGGCCTTCACCGGTGCCAAGGAGAATTTTTCCCTA
GATTGGTGTAAACAGCCAGACGTGGGCCTTCCCAAACCCGACCTGGTCCTGTTCCTC
CAGTTACAGCTGGCGGATGCTGCCAAGCGGGGAGCGTTTGGCCATGAGCGCTATGAG
AACGGGGCTTTCCAGGAGCGGGCGCTCCGGTGTTTCCACCAGCTCATGAAAGACACG
ACTTTGAACTGGAAGATGGTGGATGCTTCCAAAAGCATCGAAGCTGTCCATGAGGAC
ATCCGCGTGCTCTCTGAGGACGCCATCCGCACTGCCACAGAGAAGCCGCTGGGGGAG
CTATGGAAGTGA (B) Nucleic acid and the corresponding amino acid sequence of human tmpk (Wild-type, ours, 212 amino acids) (SEQ ID NO: 2)

```
1/1                                     31/11                                   61/21                                   91/31
ATG GCG GCC CGG CGC GGG GCT CTC ATA GTG CTG GAG GGC GTG GAC CGC GCC GGG AAG AGC ACG CAG AGC CGC AAG CTG GTG GAA GCG CTG TGC GCC GCG GGC CAC CGC GCC GAA CTG CTC
Met ala ala arg arg gly ala leu ile val leu glu gly val asp arg ala gly lys ser thr gln ser arg lys leu val glu ala leu cys ala ala gly his arg ala glu leu leu
121/41                                  151/51                                  181/61                                  211/71
CGG TTC CCG GAA AGA TCA ACT GAA ATC GGC AAA CTT CTG AGT TCC TAC TTG CAA AAG AAA AGT GAC GTG GAG GAT CAC TCG GTG CAC CTG CTT TTT TCT GCA AAT CGC TGG GAA CAA GTG
arg phe pro glu arg ser thr glu ile gly lys leu leu ser ser tyr leu gln lys lys ser asp val glu asp his ser val his leu leu phe ser ala asn arg trp glu gln val
241/81                                  271/91                                  301/101                                 331/111
CCG TTA ATT AAG GAA AAG TTG AGC CAG GGC GTG ACC CTC GTC GTG GAC AGA TAC GCA TTT TCT GGT GTG GCC TTC ACC GGT GCC AAG GAG AAT TTT TCC CTA GAT TGG TGT AAA CAG CCA
pro leu ile lys glu lys leu ser gln gly val thr leu val val asp arg tyr ala phe ser gly val ala phe thr gly ala lys glu asn phe ser leu asp trp cys lys gln pro
361/121                                 391/131                                 421/141                                 451/151
GAC GTG GGC CTT CCC AAA CCC GAC CTG GTC CTG TTC CTC CAG TTA CAG CTG GCG GAT GCT GCC AAG CGG GGA GCG TTT GGC CAT GAG CGC TAT GAG AAC GGG GCT TTC CAG GAG CGG GCG
asp val gly leu pro lys pro asp leu val leu phe leu gln leu gln leu ala asp ala ala lys arg gly ala phe gly his glu arg tyr glu asn gly ala phe gln glu arg ala
481/161                                 511/171                                 541/181                                 571/191
CTC CGG TGT TTC CAC CAG CTC ATG AAA GAC ACG ACT TTG AAC TGG AAG ATG GTG GAT GCT TCC AAA AGC ATC GAA GCT GTC CAT GAG GAC ATC CGC GTG CTC TCT GAG GAC GCC ATC CGC
leu arg cys phe his gln leu met lys asp thr thr leu asn trp lys met val asp ala ser lys ser ile glu ala val his glu asp ile arg val leu ser glu asp ala ile arg
601/201                                 631/211
ACT GCC ACA GAG AAG CCG CTG GGG GAG CTA TGG AAG TGA
thr ala thr glu lys pro leu gly glu leu trp lys OPA
```

(C) Wild-type Homo sapiens deoxythymidylate kinase (thymidylate kinase) (DTYMK), mRNA. Genbank ACCESSION NM_012145 (SEQ ID NO: 3)

atggcggcccggcgcggggctctcatagtgctggagggcgtggaccgcgccgggaag
agcacgcagagccgcaagctggtggaagcgctgtgcgccgcgggccaccgcgccgaa
ctgctccggttcccggaaagatcaactgaaatcggcaaacttctgagttcctacttg
caaaagaaaagtgacgtggaggatcactcggtgcacctgcttttttctgcaaatcgc
tgggaacaagtgccgttaattaaggaaaagttgagccagggcgtgaccctcgtcgtg
gacagatacgcattttctggtgtggccttcaccggtgccaaggagaatttttcccta
gattggtgtaaacagccagacgtgggccttcccaaacccgacctggtcctgttcctc
cagttacagctggcggatgctgccaagcggggagcgtttggccatgagcgctatgag
aacggggctttccaggagcgggcgctccggtgtttccaccagctcatgaaagacacg
actttgaactggaagatggtggatgcttccaaaagcatcgaagctgtccatgaggac
atccgcgtgctctctgaggacgccatccgcactgccacagagaagccgctgggggag
ctatggaagtga

FIG. 13 (Cont.)

(D) Nucleic acid and the corresponding amino acid sequence of human tmpk (Wild-type, ACCESSION NM 012145, 212 amino acids) (SEQ ID NO: 4)

```
1/1                                     31/11                                   61/21                                   91/31
atg gcg gcc cgg cgc ggg gct ctc ata gtg ctg gag ggc gtg gac cgc gcc ggg aag agc acg cag agc cgc aag ctg gtg gaa gcg ctg tgc gcc gcg ggc cac cgc gcc gaa ctg ctc
Met ala ala arg arg gly ala leu ile val leu glu gly val asp arg ala gly lys ser thr gln ser arg lys leu val glu ala leu cys ala ala gly his arg ala glu leu leu
121/41                                  151/51                                  181/61                                  211/71
cgg ttc ccg gaa aga tca act gaa atc ggc aaa ctt ctg agt tcc tac ttg caa aag aaa agt gac gtg gag gat cac tcg gtg cac ctg ctt ttt tct gca aat cgc tgg gaa caa gtg
arg phe pro glu arg ser thr glu ile gly lys leu leu ser ser tyr leu gln lys lys ser asp val glu asp his ser val his leu leu phe ser ala asn arg trp glu gln val
241/81                                  271/91                                  301/101                                 331/111
ccg tta att aag gaa aag ttg agc cag ggc gtg acc ctc gtc gtg gac aga tac gca ttt tct ggt gtg gcc ttc acc ggt gcc aag gag aat ttt tcc cta gac tgg tgt aaa cag cca
pro leu ile lys glu lys leu ser gln gly val thr leu val val asp arg tyr ala phe ser gly val ala phe thr gly ala lys glu asn phe ser leu asp trp cys lys gln pro
361/121                                 391/131                                 421/141                                 451/151
gac gtg ggc ctt ccc aaa ccc gac ctg gtc ctg ttc ctc cag tta cag ctg gcg gat gct gcc aag cgg gga gcg ttt ggc cat gag cgc tat gag aac ggg gct ttc cag gag cgg gcg
asp val gly leu pro lys pro asp leu val leu phe leu gln leu gln leu ala asp ala ala lys arg gly ala phe gly his glu arg tyr glu asn gly ala phe gln glu arg ala
481/161                                 511/171                                 541/181                                 571/191
ctc cgg tgt ttc cac cag ctc atg aaa gac acg act ttg aac tgg aag atg gtg gat gct tcc aaa agc atc gaa gct gtc cat gag gac atc cgc gtg ctc tct gag gac gcc atc cgc
leu arg cys phe his gln leu met lys asp thr thr leu asn trp lys met val asp ala ser lys ser ile glu ala val his glu asp ile arg val leu ser glu asp ala ile arg
601/201                                 631/211
act gcc aca gag aag ccg ctg ggg gag cta tgg aag tga
thr ala thr glu lys pro leu gly glu leu trp lys OPA
```

(E) DEFINITION Human mRNA for thymidylate kinase EC 2.7.4.9 - ACCESSION X54729 (SEQ ID NO: 5)

atggcggcccggcgcggggctctcatagtgctggagggcgtggaccgcgccgggaag
agcacgcagagccgcaagctggtggaagcgctgtcgcgcgggccaccgcccgaactg
ctccggttcccggaaagatcaactgaaatcggcaaacttctgagttcctacttgcaa
aagaaaagtgacgtggaggatcactcggtgcacctgctttttctgcaaatcgctgg
gaacaagtgccgttaattaaggaaaagttgagccagggcgtgaccctcgtcgtggac
agatacgcattttctggtgtggccttcaccggtgccaaggagaatttttccctagac
tggtgtaaacagccagacgtgggccttcccaaacccgacctggtcctgttcctccag
ttacagctggcggatgctgccaagcggggagcgtttggccatgagcgctatgagaac
ggggctttccaggagcgggcgctccggtgtttccaccagctcatgaaagacacgact
ttgaactggaagatggtggatgcttccaaaagactcgaagctgtccatgaggaactc
cgcgtgctctctgaggacgccatccgcactgccacagagaagccgctgggggagcta
tggaagtga (F) Nucleic acid and the corresponding amino acid sequence of human tmpk (Wild-type, ACCESSION X54729, 211 amino acids) (SEQ ID NO: 6)

```
1/1                                     31/11                                   61/21                                   91/31
atg gcg gcc cgg cgc ggg gct ctc ata gtg ctg gag ggc gtg gac cgc gcc ggg aag agc acg cag agc cgc aag ctg gtg gaa gcg ctg tcg cgc ggg cca ccg ccc gaa ctg ctc cgg
Met ala ala arg arg gly ala leu ile val leu glu gly val asp arg ala gly lys ser thr gln ser arg lys leu val glu ala leu ser arg gly pro pro pro glu leu leu arg
121/41                                  151/51                                  181/61                                  211/71
ttc ccg gaa aga tca act gaa atc ggc aaa ctt ctg agt tcc tac ttg caa aag aaa agt gac gtg gag gat cac tcg gtg cac ctg ctt ttt tct gca aat cgc tgg gaa caa gtg ccg
phe pro glu arg ser thr glu ile gly lys leu leu ser ser tyr leu gln lys lys ser asp val glu asp his ser val his leu leu phe ser ala asn arg trp glu gln val pro
241/81                                  271/91                                  301/101                                 331/111
tta att aag gaa aag ttg agc cag ggc gtg acc ctc gtc gtg gac aga tac gca ttt tct ggt gtg gcc ttc acc ggt gcc aag gag aat ttt tcc cta gac tgg tgt aaa cag cca gac
leu ile lys glu lys leu ser gln gly val thr leu val val asp arg tyr ala phe ser gly val ala phe thr gly ala lys glu asn phe ser leu asp trp cys lys gln pro asp
361/121                                 391/131                                 421/141                                 451/151
gtg ggc ctt ccc aaa ccc gac ctg gtc ctg ttc ctc cag tta cag ctg gcg gat gct gcc aag cgg gga gcg ttt ggc cat gag cgc tat gag aac ggg gct ttc cag gag cgg gcg ctc
val gly leu pro lys pro asp leu val leu phe leu gln leu gln leu ala asp ala ala lys arg gly ala phe gly his glu arg tyr glu asn gly ala phe gln glu arg ala leu
481/161                                 511/171                                 541/181                                 571/191
cgg tgt ttc cac cag ctc atg aaa gac acg act ttg aac tgg aag atg gtg gat gct tcc aaa aga ctc gaa gct gtc cat gag gaa ctc cgc gtg ctc tct gag gac gcc atc cgc act
arg cys phe his gln leu met lys asp thr thr leu asn trp lys met val asp ala ser lys arg leu glu ala val his glu glu leu arg val leu ser glu asp ala ile arg thr
601/201                                 631/211
gcc aca gag aag ccg ctg ggg gag cta tgg aag tga
ala thr glu lys pro leu gly glu leu trp lys OPA
```

(G) Synthetic construct Homo sapiens clone FLH131255.01L deoxythymidylate kinase (DTYMK) mRNA, partial cds. ACCESSION AY893951 (SEQ ID NO: 7)

atggcggcccggcgcggggctctcatagtgctggagggcgtggaccgcgccgggaag
agcacgcagagccgcaagctggtggaagcgctgtgcgccgcgggccaccgcgccgaa
ctgctccggttcccggaaagatcaactgaaatcggcaaacttctgagttcctacttg
caaaagaaaagtgacgtggaggatcactcggtgcacctgctttttctgcaaatcgc
tgggaacaagtgccgttaattaaggaaaagttgagccagggcgtgaccctcgtcgtg

FIG. 13 (Cont.)

gacagatacgcattttctggtgtggccttcaccggtgccaaggagaatttttcccta
gattggtgtaaacagccagacgtgggccttcccaaacccgacctggtcctgttcctc
cagttacagctggcggatgctgccaagcggggagcgtttggccatgagcgctatgag
aacggggctttccaggagcgggcgctccggtgtttccaccagctcatgaaagacacg
actttgaactggaagatggtggatgcttccaaaagcatcgaagctgtccatgaggac
atccgcgtgctctctgaggacgccatccgcactgccacagagaagccgctgggggag
ctatggaaggac (H) Nucleic acid and the corresponding amino acid sequence of human tmpk (Wild-type, ACCESSION AY893951, 213 amino acids, but stop codon less sequence) (SEQ ID NO: 8)

```
1/1                                     31/11                                   61/21                                   91/31
atg gcg gcc cgg cgc ggg gct ctc atc gtg ctg gag ggc gtg gac cgc gcc ggg aag agc acg cag agc cgc aag ctg gtg gaa gcg ctg tgc gcc gcg ggc cac cgc gcc gaa ctg ctc
Met ala ala arg arg gly ala leu ile val leu glu gly val asp arg ala gly lys ser thr gln ser arg lys leu val glu ala leu cys ala ala gly his arg ala glu leu leu
121/41                                  151/51                                  181/61                                  211/71
cgg ttc ccg gaa aga tcg act gaa atc ggc aaa ctt ctg agt tcc tac ttg caa aag aaa agt gac gtg gag gat cac tcg gtg cac ctg ctt ttt tct gca aat cgc tgg gaa caa gtg
arg phe pro glu arg ser thr glu ile gly lys leu leu ser ser tyr leu gln lys lys ser asp val glu asp his ser val his leu leu phe ser ala asn arg trp glu gln val
241/81                                  271/91                                  301/101                                 331/111
ccg tta att aag gaa aag ttg agc cag ggc gtg acc ctc gtc gtg gac aga tac gca ttt tct ggt gtg gcc ttc acc ggt gcc aag gag aat ttt tcc cta gat tgg tgt aaa cag cca
pro leu ile lys glu lys leu ser gln gly val thr leu val val asp arg tyr ala phe ser gly val ala phe thr gly ala lys glu asn phe ser leu asp trp cys lys gln pro
361/121                                 391/131                                 421/141                                 451/151
gac gtg ggc ctt ccc aaa ccc gac ctg gtc ctg ttc ctc cag tta cag ctg gcg gat gct gcc aag cgg gga gcg ttt ggc cat gag cgc tat gag aac ggg gct ttc cag gag cgg gcg
asp val gly leu pro lys pro asp leu val leu phe leu gln leu gln leu ala asp ala ala lys arg gly ala phe gly his glu arg tyr glu asn gly ala phe gln glu arg ala
481/161                                 511/171                                 541/181                                 571/191
ctc cgg tgt ttc cac cag ctc atg aaa gac acg act ttg aac tgg aag atg gtg gat gct tcc aaa agc atc gaa gct gtc cat gag gac atc cgc gtg ctc tct gag gac gcc atc cgc
leu arg cys phe his gln leu met lys asp thr thr leu asn trp lys met val asp ala ser lys ser ile glu ala val his glu asp ile arg val leu ser glu asp ala ile arg
601/201                                 631/211
act gcc aca gag aag ccg ctg ggg gag cta tgg aag gac
thr ala thr glu lys pro leu gly glu leu trp lys asp
```

(I) Mus musculus deoxythymidylate kinase, mRNA (cDNA clone MGC:29227 IMAGE:5039765), complete cds. ACCESSION BC030178 (SEQ ID NO: 9)

atggcgtcgcgtcggggagcgctcatcgtgctggagggtgtggaccgtgctggcaag
accacgcagggcctcaagctggtgaccgcgctgtgcgcctcgggccacagagcggag
ctgctgcgtttccccgaaagatcaacggaaatcggcaagcttctgaattcctacttg
gaaaagaaaacggaactagaggatcactccgtgcacctgctcttctctgcaaaccgc
tgggaacaagtaccattaattaaggcgaagttgaaccagggtgtgacccttgttttg
gacagatacgccttttctggggttgccttcactggtgccaaagagaattttccctg
gattggtgtaaacaaccggacgtgggccttcccaaacctgacctgatcctgttcctt
cagttacaattgctggacgctgctgcacggggagagtttggccttgagcgatatgag
accgggactttccaaaagcaggttctgttgtgtttccagcagctcatggaagagaaa
aacctcaactggaaggtggttgatgcttccaaaagcattgaggaagtccataaagaa
atccgtgcacactctgaggacgccatccgaaacgctgcacagaggccactgggggag
ctatggaaataa (J) Nucleic acid and the corresponding amino acid sequence of mouse tmpk (Wild-type, ACCESSION BC030178, 212 amino acids) (SEQ ID NO: 10)

```
1/1                                     31/11                                   61/21                                   91/31
atg gcg tcg cgt cgg gga gcg ctc atc gtg ctg gag ggt gtg gac cgt gct ggc aag acc acg cag ggc ctc aag ctg gtg acc gcg ctg tgc gcc tcg ggc cac aga gcg gag ctg ctg
Met ala ser arg arg gly ala leu ile val leu glu gly val asp arg ala gly lys thr thr gln gly leu lys leu val thr ala leu cys ala ser gly his arg ala glu leu leu
121/41                                  151/51                                  181/61                                  211/71
cgt ttc ccc gaa aga tca acg gaa atc ggc aag ctt ctg aat tcc tac ttg gaa aag aaa acg gaa cta gag gat cac tcc gtg cac ctg ctc ttc tct gca aac cgc tgg gaa caa gta
arg phe pro glu arg ser thr glu ile gly lys leu leu asn ser tyr leu glu lys lys thr glu leu glu asp his ser val his leu leu phe ser ala asn arg trp glu gln val
241/81                                  271/91                                  301/101                                 331/111
cca tta att aag gcg aag ttg aac cag ggt gtg acc ctt gtt ttg gac aga tac gcc ttt tct ggg gtt gcc ttc act ggt gcc aaa gag aat ttt tcc ctg gat tgg tgt aaa caa ccg
pro leu ile lys ala lys leu asn gln gly val thr leu val leu asp arg tyr ala phe ser gly val ala phe thr gly ala lys glu asn phe ser leu asp trp cys lys gln pro
361/121                                 391/131                                 421/141                                 451/151
gac gtg ggc ctt ccc aaa cct gac ctg atc ctg ttc ctt cag tta caa ttg ctg gac gct gct gca cgg gga gag ttt ggc ctt gag cga tat gag acc ggg act ttc caa aag cag gtt
asp val gly leu pro lys pro asp leu ile leu phe leu gln leu gln leu leu asp ala ala ala arg gly glu phe gly leu glu arg tyr glu thr gly thr phe gln lys gln val
481/161                                 511/171                                 541/181                                 571/191
ctg ttg tgt ttc cag cag ctc atg gaa gag aaa aac ctc aac tgg aag gtg gtt gat gct tcc aaa agc att gag gaa gtc cat aaa gaa atc cgt gca cac tct gag gac gcc atc cga
leu leu cys phe gln gln leu met glu glu lys asn leu asn trp lys val val asp ala ser lys ser ile glu glu val his lys glu ile arg ala his ser glu asp ala ile arg
601/201                                 631/211
aac gct gca cag agg cca ctg ggg gag cta tgg aaa taa
asn ala ala gln arg pro leu gly glu leu trp lys OCH
```

FIG. 13 (Cont.)

(K) Nucleic acid and the corresponding amino acid sequence of human tmpk (F105Y) (SEQ ID NO: 11)

```
1/1                                     31/11                                   61/21                                   91/31
ATG GCG GCC CGG CGC GGG GCT CTC ATA GTG CTG GAG GGC GTG GAC CGC GCC GGG AAG AGC ACG CAG AGC CGC AAG CTG GTG GAA GCG CTG TGC GCC GCG GGC CAC CGC GCC GAA CTG CTC
Met ala ala arg arg gly ala leu ile val leu glu gly val asp arg ala gly lys ser thr gln ser arg lys leu val glu ala leu cys ala ala gly his arg ala glu leu leu
121/41                                  151/51                                  181/61                                  211/71
CGG TTC CCG GAA AGA TCA ACT GAA ATC GGC AAA CTT CTG AGT TCC TAC TTG CAA AAG AAA AGT GAC GTG GAG GAT CAC TCG GTG CAC CTG CTT TTT TCT GCA AAT CGC TGG GAA CAA GTG
arg phe pro glu arg ser thr glu ile gly lys leu leu ser ser tyr leu gln lys lys ser asp val glu asp his ser val his leu leu phe ser ala asn arg trp glu gln val
241/81                                  271/91                                  301/101                                 331/111
CCG TTA ATT AAG GAA AAG TTG AGC CAG GGC GtG ACC CTC GTC GTG GAC AGA TAC GCA TTT TCT GGT GTG GCC TAC ACa GGT GCC AAG GAG AAT TTT TCC CTA GAC TGG TGT AAA CAG CCA
pro leu ile lys glu lys leu ser gln gly val thr leu val val asp arg tyr ala phe ser gly val ala tyr thr gly ala lys glu asn phe ser leu asp trp cys lys gln pro
361/121                                 391/131                                 421/141                                 451/151
GAC GTG GGC CTT CCC AAA CCC GAC CTG GTC CTG TTC CTC CAG TTA CAG CTG GCG GAT GCT GCC AAG CGG GGA GCG TTT GGC CAT GAG CGC TAT GAG AAC GGG GCT TTC CAG GAG CGG GCG
asp val gly leu pro lys pro asp leu val leu phe leu gln leu gln leu ala asp ala ala lys arg gly ala phe gly his glu arg tyr glu asn gly ala phe gln glu arg ala
481/161                                 511/171                                 541/181                                 571/191
CTC CGG TGT TTC CAC CAG CTC ATG AAA GAC ACG ACT TTG AAC TGG AAG ATG GTG GAT GCT TCC AAA AGC ATC GAA GCT GTC CAT GAG GAC ATC CGC GTG CTC TCT GAG GAC GCC ATC GCC
leu arg cys phe his gln leu met lys asp thr thr leu asn trp lys met val asp ala ser lys ser ile glu ala val his glu asp ile arg val leu ser glu asp ala ile ala
601/201                                 631/211
ACT GCC ACA GAG AAG CCG CTG GgG GAG CTA TGG AAG TGA
thr ala thr glu lys pro leu gly glu leu trp lys OPA
```

(L) Nucleic acid and the corresponding amino acid sequence of human tmpk (R16GLL) (SEQ ID NO: 12)

```
1/1                                     31/11                                   61/21                                   91/31
ATG GCG GCC CGG CGC GGG GCT CTC ATA GTG CTG GAG GGC gTG GAC GGc GCC GGG AAG AGC ACG CAG AGC CGC AAG CTG GTG GAA GCG CTG TGC GCC GCG GGC CAC CGC GCC GAA CTG CTC
Met ala ala arg arg gly ala leu ile val leu glu gly val asp gly ala gly lys ser thr gln ser arg lys leu val glu ala leu cys ala ala gly his arg ala glu leu leu
121/41                                  151/51                                  181/61                                  211/71
CGG TTC CCG GAA AGA TCA ACT GAA ATC GGC AAA CTT CTG AGT TCC TAC TTG CAA AAG AAA AGT GAC GTG GAG GAT CAC TCG GTG CAC CTG CTT TTT TCT GCA AAT CGC TGG GAA CAA GTG
arg phe pro glu arg ser thr glu ile gly lys leu leu ser ser tyr leu gln lys lys ser asp val glu asp his ser val his leu leu phe ser ala asn arg trp glu gln val
241/81                                  271/91                                  301/101                                 331/111
CCG TTA ATT AAG GAA AAG TTG AGC CAG GGC GTG ACC CTC GTC GTG GAC AGA TAC GCA TTT TCT GGT GTG GCC TTC ACC GGT GCC AAG GAG AAT TTT TCC CTA GAC TGG TGT AAA CAG CCA
pro leu ile lys glu lys leu ser gln gly val thr leu val val asp arg tyr ala phe ser gly val ala phe thr gly ala lys glu asn phe ser leu asp trp cys lys gln pro
361/121                                 391/131                                 421/141                                 451/151
GAC GTG GGC CTT CCC AAA CCC GAC CTG GTC CTG TTC CTG CAG TTA ACT CCG GAA GTT GGC TTA AAA CGC GCA CGT GCT CGC GGC GAG CTt GAc CGC TAT GAG AAC GGG GCT TTC CAG GAG
asp val gly leu pro lys pro asp leu val leu phe leu gln leu thr pro glu val gly leu lys arg ala arg ala arg gly glu leu asp arg tyr glu asn gly ala phe gln glu
481/161                                 511/171                                 541/181                                 571/191
CGG GCG CTC CGG TGT TTC CAC CAG CTC ATG AAA GAC ACG ACT TTG AAC TGG AAG ATG GTG GAT GCT TCC AAA AGC ATC GAA GCT GTC CAT GAG GAC ATC CGC GTG CTC TCT GAG GAc GCC
arg ala leu arg cys phe his gln leu met lys asp thr thr leu asn trp lys met val asp ala ser lys ser ile glu ala val his glu asp ile arg val leu ser glu asp ala
601/201                                 631/211
ATC GCC ACT GCC ACA GAG AAG CCG CTG gGG GAG CTA TGG AAG TGA
ile ala thr ala thr glu lys pro leu gly glu leu trp lys OPA
```

(M) The DNA elements and nucleotide sequence of plasmid pHR'-cppt-EF-tmpk(R16GLL)-IRES-hCD19-W-SIN.
(SEQ ID NO: 13)

DNA elements on the plasmid
(position)
1-634; 5'-Long tereminal repeat (LTR)
635-684; HIV signal sequence
685-823; HIV Psi signal
743-745; 5'-splice site (SD)
790-1151; delta-GAG
1152-2022; Rev Responsive Element (RRE)
1906-1908; 3'-splice site (SA)
2023-2140; cPPT sequence
2147-2232; SV40 sequence
2233-3415; Elongation factor (EF) 1-alpha promoter
3537-4181; Human thymidylate monophosphate kinase (tmpk) R16GLL mutant cDNA.
4182-4818; Internal ribosome entry site (IRES) elements derived from encephalomyocarditis virus (EMCV).
4819-5760; Truncated form of human CD19 cDNA that have both extracellular and transmembrane domain.
5802-6393; Woodchuck Posttranscriptional Regulatory Element (WPRE).

FIG. 13 (Cont.)

6394-6612; HIV-nef sequence
6612-6811; 3'-Self inactivating LTR (SIN-LTR)

(Nucleotide sequence)

tggaagggctaattcactcccaacgaagacaagatatccttgatctgtggatctacc
acacacaaggctacttccctgattggcagaactacacaccaggaccagggatcagat
atccactgacctttggatggtgctacaagctagtaccagttgagccagataaggtag
aagaggccaacaaaggagagaacaccagcttgttacaccctgtgagcctgcatggaa
tggatgacccggagagagaagtgttagagtggaggtttgacagccgcctagcatttc
atcacgtggcccgagagctgcatccggagtacttcaagaactgctgatatcgagctt
gctacaagggactttccgctggggactttccagggaggcgtggcctgggcgggactg
gggagtggcgagccctcagatgctgcatataagcagctgctttttgcctgtactggg
tctctctggttagaccagatctgagcctgggagctctctggctaactagggaaccca
ctgcttaagcctcaataaagcttgccttgagtgcttcaagtagtgtgtgcccgtctg
ttgtgtgactctggtaactagagatccctcagacccttttagtcagtgtggaaaatc
tctagcagtggcgcccgaacagggacttgaaagcgaaagggaaaccagaggagctct
ctcgacgcaggactcggcttgctgaagcgcgcacggcaagaggcgaggggcggcgac
tggtgagtacgccaaaaattttgactagcggaggctagaaggagagagatgggtgcg
agagcgtcagtattaagcgggggagaattagatcgcgatgggaaaaaattcggttaa
ggccagggggaaagaaaaaatataaattaaaacatatagtatgggcaagcagggagc
tagaacgattcgcagttaatcctggcctgttagaaacatcagaaggctgtagacaaa
tactgggacagctacaaccatcccttcagacaggatcagaagaacttagatcattat
ataatacagtagcaaccctctattgtgtgcatcaaaggatagagataaaagacacca
aggaagctttagacaagatagaggaagagcaaaacaaaagtaagaccaccgcacagc
aagcggccgctgatcttcagacctggaggaggagatatgagggacaattggagaagt
gaattatataaatataaagtagtaaaaattgaaccattaggagtagcacccaccaag
gcaaagagaagagtggtgcagagagaaaaaagagcagtgggaataggagctttgttc
cttgggttcttgggagcagcaggaagcactatgggcgcagcgtcaatgacgctgacg
gtacaggccagacaattattgtctggtatagtgcagcagcagaacaatttgctgagg
gctattgaggcgcaacagcatctgttgcaactcacagtctggggcatcaagcagctc
caggcaagaatcctggctgtggaaagatacctaaaggatcaacagctcctggggatt
tggggttgctctggaaaactcatttgcaccactgctgtgccttggaatgctagttgg
agtaataaatctctggaacagatttggaatcacacgacctggatggagtgggacaga
gaaattaacaattacacaagcttaatacactccttaattgaagaatcgcaaaaccag
caagaaaagaatgaacaagaattattggaattagataaatgggcaagtttgtggaat
tggtttaacataacaaattggctgtggtatataaaattattcataatgatagtagga
ggcttggtaggtttaagaatagtttttgctgtactttctatagtgaatagagttagg
cagggatattcaccattatcgtttcagacccacctcccaaccccgaggggacccgac
aggcccgaaggaatagaagaagaaggtggagagagagacagagacagatccattcga
ttagtgaacggatctcgacggtatCGCTtttaaaagaaaaggggggattggggggta
cagtgcaggggaaagaatagtagacataatagcaacagacatacaaactaaagaatt
acaaaaacaaattacaaaaattcaaaattttATcgataagctttgcaaagatggata
aagttttaaacagagaggaatctttgcagctaatggaccttctaggtcttgaaagga
gtgggaattggctccggtgcccgtcagtgggcagagcgcacatcgcccacagtcccc
gagaagttggggggaggggtcggcaattgaaccggtgcctagagaaggtggcgcggg
gtaaactgggaaagtgatgtcgtgtactggctccgcctttttcccgagggtggggga
gaaccgtatataagtgcagtagtcgccgtgaacgttctttttcgcaacgggtttgcc
gccagaacacaggtaagtgccgtgtgtggttcccgcgggcctggcctctttacgggt
tatggcccttgcgtgccttgaattacttccacgcccctggctgcagtacgtgattct
tgatcccgagcttcgggttggaagtgggtgggagagttcgaggccttgcgcttaagg

FIG. 13 (Cont.)

agccccttcgcctcgtgcttgagttgaggcctggcctgggcgctggggccgccgcgt
gcgaatctggtggcaccttcgcgcctgtctcgctgctttcgataagtctctagccat
ttaaaatttttgatgacctgctgcgacgctttttttctggcaagatagtcttgtaaa
tgcgggccaagatctgcacactggtatttcggtttttggggccgcgggcggcgacgg
ggcccgtgcgtcccagcgcacatgttcggcgaggcggggcctgcgagcgcggccacc
gagaatcggacgggggtagtctcaagctggccggcctgctctggtgcctggcctcgc
gccgccgtgtatcgccccgccctgggcggcaaggctggcccggtcggcaccagttgc
gtgagcggaaagatggccgcttcccggccctgctgcagggagctcaaaatggaggac
gcggcgctcgggagagcgggcgggtgagtcacccacacaaaggaaaagggcctttcc
gtcctcagccgtcgcttcatgtgactccacggagtaccgggcgccgtccaggcacct
cgattagttctcgagcttttggagtacgtcgtctttaggttgggggggaggggtttta
tgcgatggagtttccccacactgagtgggtggagactgaagttaggccagcttggca
cttgatgtaattctccttggaatttgcccttttttgagtttggatcttggttcattct
caagcctcagacagtggttcaaagtttttttcttccatttcaggtgtcgtgagagga
attctgcagTCGAGCGGagcgcgcgtaatacgactcactatagggcgCCAtgggtac
cgggccccccctcgaTCGaaCAACAACAACAATAACACATGGTTCCGCGTGGCTCTC
ATATGGCGGCCCGGCGCGGGGCTCTCATAGTGCTGGAGGGCgTGGACGGcGCCGGGA
AGAGCACGCAGAGCCGCAAGCTGGTGGAAGCGCTGTGCGCCGCGGGCCACCGCGCCG
AACTGCTCCGGTTCCCGGAAAGATCAACTGAAATCGGCAAACTTCTGAGTTCCTACT
TGCAAAAGAAAAGTGACGTGGAGGATCACTCGGTGCACCTGCTTTTTTCTGCAAATC
GCTGGGAACAAGTGCCGTTAATTAAGGAAAAGTTGAGCCAGGGCGTGACCCTCGTCG
TGGACAGATACGCATTTTCTGGTGTGGCCTTCACCGGTGCCAAGGAGAATTTTTCCC
TAGACTGGTGTAAACAGCCAGACGTGGGCCTTCCCAAACCCGACCTGGTCCTGTTCC
TGCAGTTAACTCCGGAAGTTGGCTTAAAACGCGCACGTGCTCGCGGCGAGCTtGAcC
GCTATGAGAACGGGGCTTTCCAGGAGCGGGCGCTCCGGTGTTTCCACCAGCTCATGA
AAGACACGACTTTGAACTGGAAGATGGTGGATGCTTCCAAAAGCATCGAAGCTGTCC
ATGAGGACATCCGCGTGCTCTCTGAGGAcGCCATCGCCACTGCCACAGAGAAGCCGC
TGgGGAGCTATGGAAGTGAGGATCAGTCGAcggtatCGATTCCCCCTCTCCCTCCC
CCCCCCCTAACGTTACTGGCCGAAGCCGCTTGGAATAAGGCCGGTGTGCGTTTGTCT
ATATGTTATTTTCCACCATATTGCCGTCTTTTGGCAATGTGAGGGCCCGGAAACCTG
GCCCTGTCTTCTTGACGAGCATTCCTAGGGGTCTTTCCCCTCTCGCCAAAGGAATGC
AAGGTCTGTTGAATGTCGTGAAGGAAGCAGTTCCTCTGGAAGCTTCTTGAAGACAAA
CAACGTCTGTAGCGACCCTTTGCAGGCAGCGGAACCCCCCACCTGGCGACAGGTGCC
TCTGCGGCCAAAAGCCACGTGTATAAGATACACCTGCAAAGGCGGCACAACCCCAGT
GCCACGTTGTGAGTTGGATAGTTGTGGAAAGAGTCAAATGGCTCTCCTCAAGCGTAT
TCAACAAGGGGCTGAAGGATGCCCAGAAGGTACCCCATTGTATGGGATCTGATCTGG
GGCCTCGGTGCACATGCTTTACGTGTGTTTAGTCGAGGTTAAAAAACGTCTAGGCCC
CCCGAACCACGGGGACGTGGTTTTCCTTTGAAAAACACGATgatatcgaattcctgc
agcccgggggatccgcccctctgaccaccatgccacctcctcgcctcctcttcttc
ctcctcttcctcacccccatggaagtcaggcccgaggaacctctagtggtgaaggtg
gaagagggagataacgctgtgctgcagtgcctcaaggggacctcagatggccccact
cagcagctgacctggtctcgggagtccccgcttaaacccttcttaaaactcagcctg
gggctgccaggcctgggaatccacatgaggcccctggcatcctggcttttcatcttc
aacgtctctcaacagatgggggcttctacctgtgccagccggggcccccctctgag
aaggcctggcagcctggctggacagtcaatgtggagggcagcggggagctgttccgg
tggaatgtttcggacctaggtggcctgggctgtggcctgaagaacaggtcctcagag
ggccccagctccccttccgggaagctcatgagccccaagctgtatgtgtgggccaaa
gaccgccctgagatctgggagggagagcctccgtgtgtcccaccgagggacagcctg
aaccagagcctcagccaggacctcaccatggcccctggctccacactctggctgtcc
tgtggggtacccctgactctgtgtccaggggcccctctcctggacccatgtgcac
cccaaggggcctaagtcattgctgagcctagagctgaaggacgatcgcccggccaga

FIG. 13 (Cont.)

```
gatatgtgggtaatggagacgggtctgttgttgccccgggccacagctcaagacgct
ggaaagtattattgtcaccgtggcaacctgaccatgtcattccacctggagatcact
gctcggccagtactatggcactggctgctgaggactggtggctggaaggtctcagct
gtgactttggcttatctgatcttctgcctgtgttcccttgtgggcattcttcatctt
TAAGGCGCGCcccgggatccaagcttcaattgtggtcactcgacaatcaacctctgg
attacaaaatttgtgaaagattgactggtattcttaactatgttgctccttttacgc
tatgtggatacgctgctttaatgcctttgtatcatgctattgcttcccgtatggctt
tcattttctcctccttgtataaatcctggttgctgtctctttatgaggagttgtggc
ccgttgtcaggcaacgtggcgtggtgtgcactgtgtttgctgacgcaacccccactg
gttggggcattgccaccacctgtcagctcctttccgggactttcgctttccccctcc
ctattgccacggcggaactcatcgccgcctgccttgcccgctgctggacaggggctc
ggctgttgggcactgacaattccgtggtgttgtcggggaagctgacgtcctttccat
ggctgctcgcctgtgttgccacctggattctgcgcgggacgtccttctgctacgtcc
cttcggccctcaatccagcggaccttccttcccgcggcctgctgccggctctgcggc
ctcttccgcgtcttcgccttcgccctcagacgagtcggatctccctttgggccgcct
ccccgcctgtctcgagacctagaaaaacatggagcaatcacaagtagcaatacagca
gctaccaatgctgattgtgcctggctagaagcacaagaggaggaggaggtgggtttt
ccagtcacacctcaggtacctttaagaccaatgacttacaaggcagatcttagccac
tttttaaaagaaaaggggggactggaagggctaattcactcccaacgaagacaagat
ctgctttttgcttgtactgggtctctctggttagaccagatctgagcctgggagctc
tctggctaactagggaacccactgcttaagcctcaataaagcttgccttgagtgctt
caagtagtgtgtgcccgtctgttgtgtgactctggtaactagagatccctcagaccc
ttttagtcagtgtggaaaatctctagca
```

(N) The DNA elements and nucleotide sequence of plasmid pHR'-cppt-EF-tmpk(F105Y)-IRES-hCD19-W-SIN
(SEQ ID NO: 14)

DNA elements on the plasmid
(position)
1-634; 5'-Long tereminal repeat (LTR)
635-684; HIV signal sequence
685-823; HIV Psi signal
743-745; 5'-splice site (SD)
790-1151; delta-GAG
1152-2022; Rev Responsive Element (RRE)
1906-1908; 3'-splice site (SA)
2023-2140; cPPT sequence
2147-2232; SV40 sequence
2233-3415; Elongation factor (EF) 1-alpha promoter
3537-4175; Human thymidylate monophosphate kinase (tmpk) F105Y mutant cDNA.
4176-4812; Internal ribosome entry site (IRES) elements derived from encephalomyocarditis virus (EMCV).
4813-5754; Truncated form of human CD19 cDNA that have both extracellular and transmembrane domain.

FIG. 13 (Cont.)

5796-6387; Woodchuck Posttranscriptional Regulatory Element (WPRE)
6388-6606; HIV-nef sequence
6606-6805; 3'-Self inactivating LTR (SIN-LTR)

(Nucleotide sequence)

tggaagggctaattcactcccaacgaagacaagatatccttgatctgtggatctacc
acacacaaggctacttccctgattggcagaactacacaccaggaccagggatcagat
atccactgacctttggatggtgctacaagctagtaccagttgagccagataaggtag
aagaggccaacaaaggagagaacaccagcttgttacaccctgtgagcctgcatggaa
tggatgacccggagagagaagtgttagagtggaggtttgacagccgcctagcatttc
atcacgtggcccgagagctgcatccggagtacttcaagaactgctgatatcgagctt
gctacaagggactttccgctggggactttccagggaggcgtggcctgggcgggactg
gggagtggcgagccctcagatgctgcatataagcagctgctttttgcctgtactggg
tctctctggttagaccagatctgagcctgggagctctctggctaactagggaaccca
ctgcttaagcctcaataaagcttgccttgagtgcttcaagtagtgtgtgcccgtctg
ttgtgtgactctggtaactagagatccctcagacccttttagtcagtgtggaaaatc
tctagcagtggcgcccgaacagggacttgaaagcgaaagggaaaccagaggagctct
ctcgacgcaggactcggcttgctgaagcgcgcacggcaagaggcgaggggcggcgac
tggtgagtacgccaaaaattttgactagcggaggctagaaggagagagatgggtgcg
agagcgtcagtattaagcgggggagaattagatcgcgatgggaaaaaattcggttaa
ggccagggggaaagaaaaaatataaattaaaacatatagtatgggcaagcagggagc
tagaacgattcgcagttaatcctggcctgttagaaacatcagaaggctgtagacaaa
tactgggacagctacaaccatcccttcagacaggatcagaagaacttagatcattat
ataatacagtagcaaccctctattgtgtgcatcaaaggatagagataaaagacacca
aggaagctttagacaagatagaggaagagcaaaacaaaagtaagaccaccgcacagc
aagcggccgctgatcttcagacctggaggaggagatatgagggacaattggagaagt
gaattatataaatataaagtagtaaaaattgaaccattaggagtagcacccaccaag
gcaaagagaagagtggtgcagagagaaaaaagagcagtgggaataggagctttgttc
cttgggttcttgggagcagcaggaagcactatgggcgcagcgtcaatgacgctgacg
gtacaggccagacaattattgtctggtatagtgcagcagcagaacaatttgctgagg
gctattgaggcgcaacagcatctgttgcaactcacagtctggggcatcaagcagctc
caggcaagaatcctggctgtggaaagatacctaaaggatcaacagctcctggggatt
tggggttgctctggaaaactcatttgcaccactgctgtgccttggaatgctagttgg
agtaataaatctctggaacagatttggaatcacacgacctggatggagtgggacaga
gaaattaacaattacacaagcttaatacactccttaattgaagaatcgcaaaaccag
caagaaaagaatgaacaagaattattggaattagataaatgggcaagtttgtggaat
tggtttaacataacaaattggctgtggtatataaaattattcataatgatagtagga
ggcttggtaggtttaagaatagtttttgctgtactttctatagtgaatagagttagg
cagggatattcaccattatcgtttcagacccacctcccaaccccgaggggacccgac
aggcccgaaggaatagaagaagaaggtggagagagagacagagacagatccattcga
ttagtgaacggatctcgacggtatCGCTttaaaagaaaaggggggattggggggta
cagtgcaggggaaagaatagtagacataatagcaacagacatacaaactaaagaatt
acaaaaacaaattacaaaaattcaaaattttATcgataagctttgcaaagatggata
aagttttaaacagagaggaatctttgcagctaatggaccttctaggtcttgaaagga
gtgggaattggctccggtgcccgtcagtgggcagagcgcacatcgcccacagtcccc
gagaagttggggggaggggtcggcaattgaaccggtgcctagagaaggtggcgcggg
gtaaactgggaaagtgatgtcgtgtactggctccgcctttttcccgagggtggggga
gaaccgtatataagtgcagtagtcgccgtgaacgttctttttcgcaacgggtttgcc

FIG. 13 (Cont.)

gccagaacacaggtaagtgccgtgtgtggttcccgcgggcctggcctctttacgggt
tatggcccttgcgtgccttgaattacttccacgcccctggctgcagtacgtgattct
tgatcccgagcttcgggttggaagtgggtgggagagttcgaggccttgcgcttaagg
agccccttcgcctcgtgcttgagttgaggcctggcctgggcgctggggccgccgcgt
gcgaatctggtggcaccttcgcgcctgtctcgctgctttcgataagtctctagccat
ttaaaatttttgatgacctgctgcgacgctttttttctggcaagatagtcttgtaaa
tgcgggccaagatctgcacactggtatttcggtttttggggccgcgggcggcgacgg
ggcccgtgcgtcccagcgcacatgttcggcgaggcggggcctgcgagcgcggccacc
gagaatcggacgggggtagtctcaagctggccggcctgctctggtgcctggcctcgc
gccgccgtgtatcgccccgccctgggcggcaaggctggcccggtcggcaccagttgc
gtgagcggaaagatggccgcttcccggccctgctgcagggagctcaaaatggaggac
gcggcgctcgggagagcgggcgggtgagtcacccacacaaaggaaaagggcctttcc
gtcctcagccgtcgcttcatgtgactccacggagtaccgggcgccgtccaggcacct
cgattagttctcgagcttttggagtacgtcgtctttaggttgggggggaggggtttta
tgcgatggagtttccccacactgagtgggtggagactgaagttaggccagcttggca
cttgatgtaattctccttggaatttgccctttttgagtttggatcttggttcattct
caagcctcagacagtggttcaaagtttttttcttccatttcaggtgtcgtgagagga
attctgcagTCGAGCGGagcgcgcgtaatacgactcactatagggcgCCAtgggtac
cgggccccccctcgaTCGaaCAACAACAACAATAACACATGGTTCCGCGTGGCTCTC
ATATGGCGGCCCGGCGCGGGGCTCTCATAGTGCTGGAGGGCGTGGACCGCGCCGGGA
AGAGCACGCAGAGCCGCAAGCTGGTGGAAGCGCTGTGCGCCGCGGGCCACCGCGCCG
AACTGCTCCGGTTCCCGGAAAGATCAACTGAAATCGGCAAACTTCTGAGTTCCTACT
TGCAAAAGAAAAGTGACGTGGAGGATCACTCGGTGCACCTGCTTTTTTCTGCAAATC
GCTGGGAACAAGTGCCGTTAATTAAGGAAAAGTTGAGCCAGGGCGtGACCCTCGTCG
TGGACAGATACGCATTTTCTGGTGTGGCCTACACaGGTGCCAAGGAGAATTTTTCCC
TAGACTGGTGTAAACAGCCAGACGTGGGCCTTCCCAAACCCGACCTGGTCCTGTTCC
TCCAGTTACAGCTGGCGGATGCTGCCAAGCGGGGAGCGTTTGGCCATGAGCGCTATG
AGAACGGGGCTTTCCAGGAGCGGGCGCTCCGGTGTTTCCACCAGCTCATGAAAGACA
CGACTTTGAACTGGAAGATGGTGGATGCTTCCAAAAGCATCGAAGCTGTCCATGAGG
ACATCCGCGTGCTCTCTGAGGACGCCATCGCCACTGCCACAGAGAAGCCGCTGGgGG
AGCTATGGAAGTGAGGATCAGTCGAcggtatCGATTCCCCCTCTCCCTCCCCCCCCC
CTAACGTTACTGGCCGAAGCCGCTTGGAATAAGGCCGGTGTGCGTTTGTCTATATGT
TATTTTCCACCATATTGCCGTCTTTTGGCAATGTGAGGGCCCGGAAACCTGGCCCTG
TCTTCTTGACGAGCATTCCTAGGGGTCTTTCCCCTCTCGCCAAAGGAATGCAAGGTC
TGTTGAATGTCGTGAAGGAAGCAGTTCCTCTGGAAGCTTCTTGAAGACAAACAACGT
CTGTAGCGACCCTTTGCAGGCAGCGGAACCCCCCACCTGGCGACAGGTGCCTCTGCG
GCCAAAAGCCACGTGTATAAGATACACCTGCAAAGGCGGCACAACCCCAGTGCCACG
TTGTGAGTTGGATAGTTGTGGAAAGAGTCAAATGGCTCTCCTCAAGCGTATTCAACA
AGGGGCTGAAGGATGCCCAGAAGGTACCCCATTGTATGGGATCTGATCTGGGGCCTC
GGTGCACATGCTTTACGTGTGTTTAGTCGAGGTTAAAAAACGTCTAGGCCCCCCGAA
CCACGGGGACGTGGTTTTCCTTTGAAAAACACGATgatatcgaattcctgcagcccg
ggggatccgcccccctctgaccaccatgccacctcctcgcctcctcttcttcctcctc
ttcctcacccccatggaagtcaggcccgaggaacctctagtggtgaaggtggaagag
ggagataacgctgtgctgcagtgcctcaaggggacctcagatggccccactcagcag
ctgacctggtctcgggagtccccgcttaaacccttcttaaaactcagcctggggctg
ccaggcctgggaatccacatgaggcccctggcatcctggcttttcatcttcaacgtc
tctcaacagatgggggcttctacctgtgccagccggggcccccctctgagaaggcc
tggcagcctggctggacagtcaatgtggagggcagcggggagctgttccggtggaat
gtttcggacctaggtggcctgggctgtggcctgaagaacaggtcctcagagggcccc
agctccccttccgggaagctcatgagccccaagctgtatgtgtgggccaaagaccgc
cctgagatctgggagggagagcctccgtgtgtcccaccgagggacagcctgaaccag

FIG. 13 (Cont.)

agcctcagccaggacctcaccatggcccctggctccacactctggctgtcctgtggg
gtacccccctgactctgtgtccaggggcccctctcctggacccatgtgcaccccaag
gggcctaagtcattgctgagcctagagctgaaggacgatcgcccggccagagatatg
tgggtaatggagacgggtctgttgttgccccgggccacagctcaagacgctggaaag
tattattgtcaccgtggcaacctgaccatgtcattccacctggagatcactgctcgg
ccagtactatggcactggctgctgaggactggtggctggaaggtctcagctgtgact
ttggcttatctgatcttctgcctgtgttcccttgtgggcattcttcatcttTAAGGC
GCGCcccgggatccaagcttcaattgtggtcactcgacaatcaacctctggattaca
aaatttgtgaaagattgactggtattcttaactatgttgctccttttacgctatgtg
gatacgctgctttaatgcctttgtatcatgctattgcttcccgtatggctttcattt
tctcctccttgtataaatcctggttgctgtctctttatgaggagttgtggcccgttg
tcaggcaacgtggcgtggtgtgcactgtgtttgctgacgcaacccccactggttggg
gcattgccaccacctgtcagctcctttccgggactttcgctttccccctccctattg
ccacggcggaactcatcgccgcctgccttgcccgctgctggacaggggctcggctgt
tgggcactgacaattccgtggtgttgtcggggaagctgacgtcctttccatggctgc
tcgcctgtgttgccacctggattctgcgcgggacgtccttctgctacgtcccttcgg
ccctcaatccagcggaccttccttcccgcggcctgctgccggctctgcggcctcttc
cgcgtcttcgccttcgccctcagacgagtcggatctccctttgggccgcctccccgc
ctgtctcgagacctagaaaaacatggagcaatcacaagtagcaatacagcagctacc
aatgctgattgtgcctggctagaagcacaagaggaggaggaggtgggttttccagtc
acacctcaggtacctttaagaccaatgacttacaaggcagatcttagccactttta
aaagaaaaggggggactggaagggctaattcactcccaacgaagacaagatctgctt
tttgcttgtactgggtctctctggttagaccagatctgagcctgggagctctctggc
taactagggaacccactgcttaagcctcaataaagcttgccttgagtgcttcaagta
gtgtgtgcccgtctgttgtgtgactctggtaactagagatccctcagacccttttag
tcagtgtggaaaatctctagca (O) tmpk (R200A) nucleotide sequence (SEQ ID NO: 15)

5'-
ATGGCGGCCCGGCGCGGGGCTCTCATAGTGCTGGAGGGCGTGGACCGCGCCGGGAAGA
GCACGCAGAGCCGCAAGCTGGTGGAAGCGCTGTGCGCCGCGGGCCACCGCGCCGAAC
TGCTCCGGTTCCCGGAAAGATCAACTGAAATCGGCAAACTTCTGAGTTCCTACTTGC
AAAAGAAAAGTGACGTGGAGGATCACTCGGTGCACCTGCTTTTTTCTGCAAATCGCT
GGGAACAAGTGCCGTTAATTAAGGAAAAGTTGAGCCAGGGCGtGACCCTCGTCGTGG
ACAGATACGCATTTTCTGGTGTGGCCTTCACaGGTGCCAAGGAGAATTTTTCCCTAG
ACTGGTGTAAACAGCCAGACGTGGGCCTTCCCAAACCCGACCTGGTCCTGTTCCTCC
AGTTACAGCTGGCGGATGCTGCCAAGCGGGGAGCGTTTGGCCATGAGCGCTATGAGA
ACGGGGCTTTCCAGGAGCGGGCGCTCCGGTGTTTCCACCAGCTCATGAAAGACACGA
CTTTGAACTGGAAGATGGTGGATGCTTCCAAAAGCATCGAAGCTGTCCATGAGGACA
TCCGCGTGCTCTCTGAGGACGCCATCCGCACTGCCACAGAGAAGCCGCTGGgGGAGC
TATGGAAGTGA-3'

(P) Amino acid sequence of tmpk (R200A). (SEQ ID NO: 16)

MAARRGALIVLEGVDRAGKSTQSRKLVEALCAAGHRAELLRFPERSTEIGKLLSSYLQ
KKSDVEDHSVHLLFSANRWEQVPLIKEKLSQGVTLVVDRYAFSGVAFTGAKENFSLD
WCKQPDVGLPKPDLVLFLQLQLADAAKRGAFGHERYENGAFQERALRCFHQLMKDTT

FIG. 13 (Cont.)

LNWKMVDASKSIEAVHEDIRVLSEDAIATATEKPLGELWK (Q) E. coli Large lid sequence. (SEQ ID NO: 17)
142TPEVGLKRARARGEL156
E. coli Large lid sequence. (Ref. Ralf Brundiers, Arnon Lavie, et al., Modifying human thymidylate kinase to potentiate azidothymidine activation. J. Bioi. Chem. 274 (50) 35289-35292, 1999.

(R) cPPT sequence (SEQ ID NO: 18)

5'-
ttttaaaagaaaaggggggattggggggtacagtgcaggggaaagaatagtagacat
aatagcaacagacatacaaactaaagaattacaaaaacaaattacaaaaattcaaaa
tttt-3'

(S) WPRE sequence (SEQ ID NO: 19)

5'-
aatcaacctctggattacaaaatttgtgaaagattgactggtattcttaactatgtt
gctccttttacgctatgtggatacgctgctttaatgcctttgtatcatgctattgct
tcccgtatggctttcattttctcctccttgtataaatcctggttgctgtctcttat
gaggagttgtggcccgttgtcaggcaacgtggcgtggtgtgcactgtgtttgctgac
gcaacccccactggttggggcattgccaccacctgtcagctcctttccgggactttc
gctttccccctccctattgccacggcggaactcatcgccgcctgccttgcccgctgc
tggacaggggctcggctgttgggcactgacaattccgtggtgttgtcggggaagctg
acgtcctttccatggctgctcgcctgtgttgccacctggattctgcgcgggacgtcc
ttctgctacgtcccttcggccctcaatccagcggaccttccttcccgcggcctgctg
ccggctctgcggcctcttccgcgtcttcgccttcgccctcagacgagtcggatctcc
ctttgggccgcctccccgcctg-3'

(T) 136 QLADAAKRGAFGH148 of human tmpk (SEQ ID NO: 20)

(Ref. Ralf Brundiers, Arnon Lavie, et al., Modifying human thymidylate kinase to potentiate azidothymidine activation. J. Bioi. Chem. 274 (50) 35289-35292, 1999.

A)

A)

B)

C)

A)

B)

B)

Untransduced (MOI 0)

THYMIDYLATE KINASE FUSIONS AND USES THEREOF

RELATED APPLICATIONS

This application is a continuation of U.S. application Ser. No. 12/933,460, filed on Jan. 10, 2011. U.S. application Ser. No. 12/933,460 is a national stage application of International Application No. PCT/CA2009/000342, filed on Mar. 20, 2009, which claims priority to U.S. Provisional Patent Application 61/038,398, filed Mar. 3, 2008. U.S. application Ser. No. 12/933,460, International Application No. PCT/CA2009/000342 and U.S. Provisional Patent Application 61/038,398 are each incorporated herein in their entirety by reference.

INCORPORATION OF SEQUENCE LISTING

A computer readable form of the Sequence Listing "10723-P31963US03_SequenceListing.txt" (147,456 bytes), submitted via EFS-WEB and created on Sep. 26, 2013, is herein incorporated by reference.

FIELD OF THE APPLICATION

The application relates to compositions, vector constructs and isolated virus and systems comprising a vector and modified thymidylate kinase polynucleotides. The compositions are useful in treatment of diseases such as, inherited genetic disorders cancer and graft versus host disease (GVHD).

BACKGROUND OF THE APPLICATION

Integrating viral vectors are a good choice for gene therapy because they offer fairly efficient transduction and consistent long-term gene expression. Much research has been directed towards improving vector design to increase safety and reliability. A promising approach is to establish control over the fate of transduced cells in vivo. Incorporating an effective suicide gene into a therapeutic vector can ensure that any malignant clones arising from deleterious insertion of the vector can be specifically killed. Likewise, such a control schema could be used as an inserted safety component for a variety of stem cell transplantations, reducing teratomas, for example, should these outgrowth events develop as occurred in one very recent study[2]. A suicide gene schema can also be used to control post-transplant complications.

The infusion of donor lymphocytes in allogenic bone marrow transplant (BMT) recipients provides potent antitumor activity to treat recurrent malignancies. One complication, however, is severe GVHD (Graft Versus Host Disease), which is mediated by T cells in the graft. One approach to control GVHD is to employ suicide gene therapy.

Donor T cells mediate both GVHD and a GVL (Graft Versus Leukemia)-effect after allogenic haematopoietic stem cell transplantation (HCT), and the separation of GVL from GVHD has proven to be a formidable problem. The expression of an inducible suicide gene in donor T cells was conceived as a potential way to provide for the abrogation of GVHD after leukemic cells were eradicated. The most extensively studied suicide genes are derived from pathogens and include the HSV-tk and bacterial cytosine-deaminase genes, which encode enzymes that metabolize ganciclovir and 5-FU, respectively, and generate toxic active compounds (Carolina Berger, Mary E. Flowers, Edus H. Warren, Stanley R. Riddel. Analysis of transgene-specific immune responses that limit the in vivo persistence of adoptively transferred HSV-TK-modified donor T cells after allogenic hematopoietic cell transplantation. Blood 2006, 107:2294-302.)

In the customary adaptation of this approach, the herpes simplex virus type 1 thymidine kinase (HSV1-tk) gene, combined with the antiviral prodrug ganciclovir (GCV), is used to control GvHD after introduction of this suicide gene into donor T lymphocytes. However, the efficiency of HSV1-tk is suboptimal and the issue of host immunogenicity against this heterologous effector gene product can hamper outcomes. In addition, prophylactic GCV is often used to control cytomegalovirus infection after BMT. This confounds the broad clinical implementation of this approach.

HSV1-tk mediated cell killing requires cellular proliferation for its cytotoxic effect. This limits the effectiveness of gene therapies employing tk to only dividing cells. Quiescent disease cells will escape destruction and may persist. Tumor cells have been shown to remain quiescent for long periods of time (Trends Cell Biol. 15(9):494-501, 2005).

SUMMARY OF THE APPLICATION

The inventors' novel cell fate control or suicide gene therapy strategy combines the use of human thymidylate monophosphate kinase (tmpk) fused to a detection cassette such as a CD19 or fluorescent molecule, in a delivery vector such as a lentiviral vector (LV) format and the prodrug Zidovudine (AZT). Since tmpk is endogenously expressed in human cells, immunogenic responses will be limited. This is also true when the detection cassette is human, for example human CD19 or human CD19Δ.

The application provides in one aspect a fusion polypeptide comprising:

(i) a modified mammalian thymidylate kinase (tmpk) wherein the modified mammalian tmpk increases phosphorylation of a prodrug relative to phosophorylation of the prodrug by wild-type mammalian (eg. human) tmpk; and (i) a detection cassette fused to tmpk wherein the detection cassette polynucleotidpeptide fused to the tmpk polynucleotidepeptide is a tmpk/detection cassette fusion polypeptide.

In an embodiment, the fusion polypeptide is an isolated polypeptide.

In another aspect, the application provides a fusion polynucleotide comprising:

(i) a modified mammalian thymidylate kinase (tmpk) polynucleotide wherein the modified mammalian tmpk polynucleotide encodes a modified mammalian tmpk polypeptide that increases phosphorylation of a prodrug relative to phosophorylation of the prodrug by wild type mammalian tmpk polypeptide; and (ii) a detection cassette polynucleotide fused to the tmpk polynucleotide;

wherein the detection cassette polynucleotide fused to the tmpk polynucleotide is a tmpk/detection cassette fusion polynucleotide.

In an embodiment, the fusion polynucleotide is an isolated fusion polynucleotide.

In another aspect, the application provides a vector construct comprising:

(i) a promoter functional in a mammalian cell;

(ii) a modified mammalian thymidylate kinase (tmpk) polynucleotide wherein the modified mammalian tmpk polynucleotide encodes a modified mammalian tmpk polypeptide that increases phosphorylation of a prodrug relative to phosophorylation of the prodrug by wild type mammalian tmpk polypeptide;

(iii) a detection cassette polynucleotide fused to the tmpk polynucleotide;

wherein the detection cassette polynucleotide fused to the tmpk polynucleotide is a tmpk/detection cassette fusion and wherein the coding sequence of the tmpk/detection cassette fusion is operably connected to the promoter.

The application provides in another aspect a vector construct comprising:

(i) a stably integrating delivery vector;

(ii) a modified mammalian thymidylate kinase (tmpk) wherein the modified mammalian tmpk increases phosphorylation of a prodrug relative to phosophorylation of the prodrug by wild-type mammalian (eg. human) tmpk; and (iii) a detection cassette fused to tmpk wherein the detection cassette fused to the tmpk is a tmpk/detection cassette fusion.

A further aspect provides an isolated cell that expresses a modified tmpk/detection cassette fusion.

A further aspect provides an actuable cell destruction component of an expression vector comprising:

(i) a modified mammalian tmpk polynucleotide wherein the modified mammalian tmpk polynucleotide increases phosphorlyation of a prodrug relative to phosphorylation of the prodrug by wild type mammalian tmpk;

(ii) a detection cassette fused to tmpk;

(iii) optionally comprising a therapeutic polynucleotide for expression

Yet a further aspect provides an isolated virus comprising a viral genome that encodes:

a modified mammalian thymidylate kinase (tmpk) polynucleotide wherein the modified mammalian tmpk polynucleotide encodes a modified mammalian tmpk polypeptide that increases phosphorylation of a prodrug relative to phosophorylation of the prodrug by wild type mammalian tmpk polypeptide;

a detection cassette polynucleotide fused to the tmpk polynucleotide;

wherein the isolated virus is infective for a mammalian cell.

Also provided is a cell fate control system comprising:

a composition, vector construct, or isolated virus for expressing a tmpk/detection cassette fusion;

wherein a cell expressing the tmpk/detection cassette fusion is susceptible to being killed by a prodrug toxic to the cell expressing the tmpk/detection cassette fusion. In this system, the prodrug is administered only if it is desired that the tmpk/detection cassette expressing cells are to be destroyed e.g. killed.

Optionally, the cell fate control system further comprises a prodrug toxic to cells expressing the modified tmpk fused to a detection cassette.

As the detection cassette is fused to tmpk, permissible cells transfected or transduced with the construct will express tmpk and the detection cassette. This is useful for a number of applications including ensuring that all cells isolated using the detection cassette express the tmpk safety component. A detection cassette fused to tmpk (e.g components (ii) and (iii)) are alternatively referred to as tmpk/detection cassette fusion.

In another aspect the application provides a composition comprising:

(i) a stably integrating delivery vector;

(ii) a modified mammalian thymidylate kinase (tmpk) wherein the modified mammalian tmpk increases phosphorylation of a prodrug relative to phosophorylation of the prodrug by wild-type mammalian (eg. human) tmpk;

(iii) a detection cassette fused to tmpk wherein the detection cassette fused to the tmpk polynucleotide is a tmpk/detection cassette fusion.

In an embodiment, the tmpk/detection cassette fusion is a tmpk/detection cassette fusion polynucleotide. The tmpk/detection cassette fusion polypeptide encodes a tmpk/detection cassette fusion polypeptide. Optionally the modified mammalian tmpk/detection cassette fusion polypeptide increases phosphorylation of a prodrug relative to phosophorylation of the prodrug by the wild type mammalian tmpk and/or tmpk/detection cassette fusion polypeptides. Optionally, increased phosphorylation can be determined in a side by side phosphorlyation assay comparing modified mammalian tmpk to wild-type mammalian (eg. human) tmpk.

In one embodiment, the application relates to a composition comprising:

(i) a stably integrating delivery vector;

(ii) a modified mammalian thymidylate kinase (tmpk) polynucleotide wherein the modified mammalian tmpk polynucleotide encodes a modified mammalian tmpk polypeptide that increases phosphorylation of a prodrug relative to phosophorylation of the prodrug by wild type mammalian tmpk polypeptide;

(iii) a detection cassette polynucleotide fused to tmpk polynucleotide.

A detection cassette polynucleotide fused to tmpk (e.g components (ii) and (iii) are alternatively referred to as tmpk/detection cassette fusion polynucleotide. The tmpk polynucleotide optionally comprises a polynucleotide with at least 80% sequence identity to a modified tmpk polynucleotide of any one of SEQ ID NOS: 15, 21, and 22. The modified mammalian tmpk polynucleotide optionally comprises a modified human tmpk polynucleotide. The polynucleotide optionally comprises a human polynucleotide and the polypeptides optionally comprise human polypeptides. The modified mammalian tmpk optionally comprises a truncated mammalian tmpk. The modified mammalian tmpk polynucleotide optionally comprises a mammalian tmpk polynucleotide with a point mutation. The point mutation optionally comprises a mutation in a codon of the polynucleotide selected from the group consisting of a mutation that encodes a F to Y mutation at amino acid position 105 (SEQ ID NO: 21), a mutation that encodes a R to G point mutation at amino acid position 16 (SEQ ID NO: 22), and a mutation that encodes a R to A mutation at amino acid position 200 (SEQ ID NO: 16). The polynucleotide optionally further comprises all or part of the large lid or small lid domain of *E. coli* (SEQ ID NO: 17). It will be readily apparent that one could make 2 or 3 or more amino acid changes and/or combine various mutations. For example F105Y (SEQ ID NO:21) can be combined with R200A (SEQ ID NO: 22). For example, other mutations are readily modeled and derived from the crystal structure of tmpk. Mutations are optionally designed that are inert relative to the active site of the enzyme. The tmpk polynucleotide optionally further comprises all or part of the large lid or small lid domain of *E. coli* (SEQ ID NO: 17). It will be readily apparent that all or part of large lid or small lid domains from other species of bacteria as well as other organisms such as yeast are useful. Utility is readily established by determining if the large lid or small lid from other sources increases phosphorylation of a prodrug relative to phosophorylation of the prodrug by wild type mammalian tmpk polypeptide. In an embodiment, the tmpk comprises tmpkF105YR200A.

The modified mammalian tmpk optionally comprises one or more deletions. The modified mammalian tmpk polynucleotide optionally has been modified by substituting a portion of wild type tmpk polynucleotide sequence with an exogenous polynucleotide sequence. The substituted portion comprises all or part of a large lid or small lid domain, for example, from *E. coli*. The exogenous sequence optionally comprises all or part of a bacterial sequence, optionally all or part of a bacterial small lid or large lid domain sequence, optionally an *E. coli* sequence, optionally TPEVGLKRARARGEL (SEQ ID NO: 17). The small lid domain optionally comprises all or part of amino acids AFGH corresponding to positions 145-148 of human tmpk of SEQ ID NO: 1. The exogenous sequence optionally comprises all or part of a bacterial sequence, optionally all or part of a bacterial small lid sequence, optionally an *E. coli* sequence, optionally all or part of the amino acid sequence RARGEL corresponding to positions 151-156 of SEQ ID NO: 17. The various mutations, substitutions, deletions can be combined. For example, F105Y and R200A can be combined with a substitution and/or deletion described herein. Other combinations are also contemplated. In addition, other mutations not herein disclosed may be combined with the aforementioned mutations.

The detection cassette which is fused to tmpk is optionally selected from the group consisting of CD19, truncated CD19, EGFP, CD25, LNGFR, truncated LNGFR, CD24 truncated CD34, EpoR, HSA and CD20. The detection cassette polynucleotide optionally comprises a truncated CD19 polynucleotide (for example Genbank Accession No. M84371 for full length CD19). For example in one embodiment the truncated CD19 polynucleotide comprises a CD19 polynucleotide truncated at base 939 of CD19 resulting in deletion of the cytoplasmic region of the protein. The polynucleotide optionally comprises a human polynucleotide and the polypeptides optionally comprise human polypeptides. Truncated CD19 is alternatively referred to as CD19Δ or ΔCD19. In an embodiment the truncated CD19 polynucleotide encodes all or part of the amino acid sequence of SEQ ID NO: 28, 29, 31 or 37, optionally encoding SEQ ID NO:37 and/or is optionally the polynucleotide of SEQ ID NO:35.

The tmpk/detection cassette fusion optionally comprises a linker. Optionally, the detection cassette is fused to the tmpk polynucleotide by a linker. The linker in an embodiment encodes all or part of an amino acid sequence of SEQ ID NO:32. The linker, in an embodiment, comprises all or part of the nucleotide sequence of SEQ ID NO:33.

Another aspect provides a composition, vector construct or isolated virus wherein the detection cassette is fused to the tmpk polynucleotide by a linker, where in the linker optionally codes for the amino acid sequence of SEQ ID NO:32. In an embodiment, the composition, vector construct or isolated virus comprises the sequence of the tmpk/detection cassette fusion is the sequence of SEQ ID NO:38, wherein T is optionally substituted with U.

The integrating viral vector optionally comprises a promoter operably linked to the detection cassette polynucleotide and/or the tmpk/detection cassette fusion.

The composition, vector construct, isolated virus, isolated cell, actuable cell destruction component, or cell fate control system, optionally further comprises a therapeutic polynucleotide cassette.

In an embodiment, the therapeutic polynucleotide cassette is selected from the group consisting of adenosine deaminase, γc interleukin receptor subunit, α-galactosidase A, codon optimized α-galactosidase A, acid ceramidase, galactocerebrosidase, and CFTR molecules.

The integrating delivery vector is optionally selected from the group comprising a retroviral vector, an adenoviral vector, an adeno-associated viral vector, spumaviral, a lentiviral vector and a plasmid or other vector, such as transposons, described in the application. The retroviral vector optionally comprises an oncoretroviral vector. The retroviral vector optionally comprises a lentiviral vector. The vector is optionally a lentiviral vector that has a pHR' backbone and comprises 5'-Long terminal repeat (LTR), HIV signal sequence, HIV Psi signal 5'-splice site (SD), delta-GAG element, Rev Responsive Element (RRE), 3'-splice site (SA), Elongation factor (EF) 1-alpha promoter and 3'-Self inactivating LTR (SIN-LTR). Optionally, one makes vectors with the CMV promoter. The lentiviral vector optionally comprises a central polypurine tract (cPPT; SEQ ID NO: 18) and a woodchuck hepatitis virus post-transcriptional regulatory element (WPRE; SEQ ID NO: 19), optionally the polypurine tract comprises nucleotide nos. 2023 to 2140 and the woodchuck hepatitis virus post-transcriptional regulatory element comprises nucleotide nos. 5802 to 6393 of (SEQ ID NO: 13 or the corresponding nucleotide numbers in SEQ ID NO:14); in a variation, optionally the vector comprises sequences comprising at least 70% sequence identity to one of the foregoing sequences. The lentiviral vector optionally comprises the nucleotides corresponding to the vector backbone portions of SEQ ID NO:13 or SEQ ID NO:14 or the vector backbones pHR', pDY or pCCL. The composition, vector construct, isolated virus, isolated cell, actuable cell destruction component, or cell fate control system optionally further comprises an additional kinase wherein the additional kinase contributes to activation of the prodrug. The compositions, polypeptides, polynucleotides, vector construct, isolated virus, isolated cell, actuable cell destruction component, or cell fate control system of the application are optionally combined with a carrier and form a pharmaceutical composition.

The application also optionally relates to use of these compositions vector construct, isolated virus, isolated cell, actuable cell destruction component, or cell fate control system in methods of treatment of diseases such as inherited genetic diseases, graft versus host disease and cancer.

Another aspect optionally provides a method of killing mammalian cells expressing a modified mammalian thymidylate kinase/detection cassette fusion.

In an embodiment, the method comprises:

i) contacting the mammalian cells with a composition, vector construct or isolated virus of the application;
ii) optionally isolating and/or purifying the cells; and
iii) contacting the cells with a prodrug, such as AZT.

Another embodiment of the application relates to a method of killing mammalian cells expressing a modified mammalian thymidylate kinase/detection cassette fusion, comprising:

i) contacting the mammalian cells with a composition, vector construct or isolated virus of the application;
ii) optionally isolating and/or purifying the cells;
iii) transplanting the cells into a transplant recipient; and iv) administering a prodrug to the transplant recipient wherein the prodrug kills the cells.

It is another object of the application to optionally provide a method of killing mammalian cells expressing a modified mammalian thymidylate kinase/detection cassette fusion comprising:

i) contacting mammalian cells with a composition of the application to produce modified cells expressing a modified mammalian thymidylate kinase/detection cassette fusion polypeptide;

ii) optionally isolating and/or purifying said modified cells; and iii) contacting said modified cells with a prodrug, such as AZT.

Another embodiment of the application relates to a method of killing mammalian cells expressing a modified mammalian thymidylate kinase/detection cassette fusion polynucleotide, comprising:

i) contacting the mammalian cells with a composition of the application to produce modified cells expressing a modified mammalian thymidylate kinase/detection cassette fusion polypeptide;

ii) isolating and/or purifying said modified cells;

iii) transplanting said modified cells into a transplant recipient; and iv) administering a prodrug to the transplant recipient wherein the prodrug kills the modified cells.

In another embodiment, the application relates to a method of transplanting cells into a subject comprising administering mammalian cells of the application expressing modified mammalian tmpk/detection cassette fusion (preferably human cells expressing modified tmpk) or other suitable polynucleotide described herein, to the subject.

The application also relates to a method of treating a transplant recipient exhibiting symptoms of a transplant mediated disease comprising administering a prodrug to the transplant recipient. The modified tmpk/detection cassette fusion activates a prodrug by phosphorylation and the activated drug kills the modified tmpk/detection cassette fusion-transduced cells. The method optionally further comprises detecting the presence of the mammalian cells in said transplant recipient one or more times during treatment. Graft versus host disease is an example of a transplant-mediated disease.

The application also optionally relates to a suicide gene safety system for killing a genetically modified cell, the system comprising a construct comprising a suicide gene, such as modified mammalian tmpk/detection cassette fusion polynucleotide or other suitable polynucleotide described herein, capable of activating a prodrug and a polynucleotide of interest to be expressed in said genetically modified cell. A polynucleotide of interest optionally includes a therapeutic molecule. Therapeutic molecules optionally include a normal gene, toxic molecules, cell growth enhancing molecules, or anti-sense molecules. Examples of therapeutic molecules of interest are described in this application, for example therapeutic molecules for treating Fabry disease.

The application also includes a method of expressing a modified mammalian tmpk/detection cassette fusion polynucleotide in a mammalian cell comprising contacting the mammalian cell with a composition, vector construct, isolated virus or cell fate control system of the application.

The contacting is optionally in vitro or ex vivo.

The mammalian cells are optionally selected from the group consisting of stem cells, such as an embryonic stem cell, a mesenchymal stem cell, an induced pluripotent stem (IPS) cell, hematopoietic cells, T cells and human cells. In an embodiment, the cell is a cell from a transplant patient, optionally a bone marrow transplant patient. In an embodiment, the cell is a bone marrow cell.

The mammalian cell is optionally a tumor cell. The tumor cell is optionally contacted with the composition in vivo, for example, using a method selected from the group consisting of microinjection, in vivo electroporation and liposome based methods. The method optionally further comprises administering an effective amount of a prodrug to eradicate the tumor cell. The prodrug optionally comprises AZT. The cells are optionally contacted using a method selected from the group consisting of transfection, transduction, infection and electroporation. The method optionally further comprises isolating the cells. The mammalian cells are optionally isolated by contacting the cells with an antibody that binds to the detection cassette polypeptide wherein the detection cassette polypeptide is selected from the group consisting of CD19, truncated CD19, EGFP, CD25, LNGFR, truncated LNGFR, CD24, truncated CD34, EpoR, HSA and CD20. In a preferred embodiment the detection cassette comprise CD19 or truncated CD19, for example truncated at amino acid 313. The method optionally further comprises a step wherein the isolated mammalian cells are transplanted into a mammal. The mammalian cells are optionally transplanted to a subject, for example to mediate tumor regression.

Another aspect provides a method of expressing a modified mammalian tmpk/detection cassette fusion polypeptide in a subject comprising:

administering a composition, vector construct, or isolated virus to the subject;

wherein administration of the composition, vector construct, or isolated virus results in expression of the modified tmpk polynucleotide.

Another aspect of the application relates to a method of killing mammalian cells expressing a modified mammalian tmpk/detection cassette fusion polynucleotide comprising:

contacting the mammalian cells with a composition, vector construct or isolated virus of the application;

optionally isolating the cells; and contacting the cells with an effective amount of a prodrug to kill the cells.

Another embodiment of the application relates to a method of killing mammalian cells expressing a thymidylate kinase/detection cassette fusion polynucleotide comprising:

(i) contacting the mammalian cells with a composition vector construct or isolated virus of the application;

(ii) isolating the cells;

(iii) transplanting the isolated cells into a transplant recipient; and (iv) administering an effective amount of a prodrug to the transplant recipient to kill the transplanted, isolated cells.

The prodrug optionally comprises a substrate that is phosphorylated by a thymidylate kinase polypeptide. The prodrug is optionally selected from the group consisting of thymidine analog, uracil analog, AZT, dT4 and 5-FU.

The mammalian cells expressing said thymidylate kinase polynucleotide are optionally isolated by contacting the cells with an antibody that binds to a detection cassette protein wherein the detection cassette protein is optionally selected from the group consisting of CD19, truncated CD19, EGFP, CD25, LNGFR, truncated LNGFR, CD24, truncated CD34, EpoR, HSA and CD20. The transplant recipient is typically a human and, in certain embodiments, the transplant recipient has, or exhibits, symptoms of graft versus host disease.

Yet a further aspect provides a method of killing a mammalian cell in a subject expressing a modified mammalian tmpk/detection cassette fusion polypeptide comprising:

administering a composition, vector construct or isolated virus described herein and/or a cell contacted with the composition, vector construct or isolated virus; and administering an effective amount of a prodrug to kill the cell.

Another aspect of the application relates to a cell fate control or suicide gene system comprising:

(i) a stably integrating delivery vector;

(ii) a modified mammalian tmpk wherein the modified mammalian tmpk increases phosphorylation of a prodrug relative to phosophorylation of the prodrug by wild type human tmpk;

(iii) a detection cassette fused to tmpk; and (iv) a prodrug that is phosphorylated and activated by the modified mammalian tmpk.

Another aspect of the application relates to a suicide gene vector construct comprising a modified mammalian tmpk a detection cassette. The vector construct optionally further comprises a therapeutic cassette. The therapeutic cassette is optionally under the control of a tissue specific promoter and/or an inducible promoter.

Another aspect of the invention relates to an actuable cell destruction component of an expression vector construct comprising:

(i) a modified mammalian tmpk polynucleotide wherein the modified mammalian tmpk polynucleotide increases phosphorlyation of a prodrug relative to phosphorylation of the prodrug by wild type mammalian tmpk;

(ii) a detection cassette polynucleotide fused to tmpk; and (iii) optionally comprising a therapeutic polynucleotide for expression.

In the actuable cell fate control component comprising a therapeutic polynucleotide, the therapeutic polynucleotide is optionally selected from the group comprising: adenosine deaminase, γc interleukin receptor subunit, α-galactosidase A, codon optimized α-galactosidase A, acid ceramidase, galactocerebrosidase, and CFTR molecules.

Another aspect of the application relates to a method of killing a cell expressing a modified tmpk/detection cassette fusion polynucleotide comprising contacting the cell with a prodrug that is activated by a composition of the application. The prodrug is optionally a thymidine analog, such as AZT. The modified tmpk polynucleotide is optionally selected from the group comprising SEQ ID NO: 11, SEQ ID NO: 12, SEQ ID NO: 15; SEQ ID NO: 16, SEQ ID NO: 21 and SEQ ID NO: 22. A detection cassette is polynucleotide is optionally fused to a modified tmpk polynucleotide wherein the tmpk polynucleotide is optionally selected from the group comprising SEQ ID NO: 11, SEQ ID NO: 12, SEQ ID NO: 15; SEQ ID NO: 16, SEQ ID NO: 21 and SEQ ID NO: 22.

Another aspect of the application relates to a method of killing a cell expressing a modified tmpk/detection cassette fusion polynucleotide in a transplant recipient comprising administering an effective amount of a prodrug that is activated by the modified tmpk polynucleotide. The prodrug is optionally a thymidine analog, such as AZT. In one embodiment, the transplant recipient developed a transplant related adverse event, such as graft versus host disease.

Another aspect of the application relates to a method of reducing cell proliferation, such as treating cancer, in a mammal in need thereof comprising:

contacting a mammalian cell with a composition of the application to produce modified cells expressing the modified mammalian tmpk/detection cassette fusion;

isolating the modified cells; and transplanting said modified cells in the mammal wherein the modified cells induce a graft versus cancer effect.

The method optionally further comprises determining if the transplanted cells induce symptoms of graft versus host disease in the transplant recipient. The method optionally further comprises administering an effective amount of a prodrug to a transplant recipient who exhibits symptoms of graft versus host disease. In a variation, the cancer is leukemia.

Another aspect provides use of a composition, vector construct or isolated virus for expressing a modified mammalian tmpk/detection cassette fusion polypeptide in a mammalian cell or subject.

A further aspect provides use of a composition vector construct or isolated virus for gene therapy.

Yet a further aspect provides use of a composition, vector construct or isolated virus for treating a disease selected from the group consisting of cancer, GVHD or inherited genetic diseases eg diseases resulting from a deficiency of a gene product, optionally Fabry disease.

Also provided is use of an effective amount of a prodrug for killing a cell expressing a modified mammalian tmpk/detection cassette fusion polynucleotide wherein the expression of the modified mammalian tmpk results from contact with a composition vector construct or isolated virus described herein.

Furthermore the application provides compositions, vector constructs, actuable cell destruction components the isolated virus for use as a pharmaceutical, for treating cancer, for treating GVHD, or for treating an inherited genetic disease or disorder.

A further embodiment provides a polynucleotide comprising COalphaGalA (SEQ ID NO:46) wherein T is optionally substituted with U and/or a sequence with at least 95% identity to SEQ ID NO:46, wherein the sequence is not identical to the polynucleotide having accession number NM_000169.

Another embodiment of the application relates to a method of identifying novel thymidine and uracil analog compounds that are useful as prodrugs in combination with a modified tmpk/detection cassette fusion molecule comprising determining if a thymidine or uracil analog is phosphorylated by the modified tmpk/detection cassette fusion molecule. Optionally the determining step comprises, a cell based assay comprising the steps of:

i) introducing a modified tmpk/detection cassette fusion molecule into a cell;

ii) providing a thymidine analog; and iii) determining whether said thymidine analog is a substrate for said modified tmpk.

The determining step optionally comprises a cell free assay comprising the steps of:

i) providing an enzymatically active modified tmpk/detection cassette fusion, ii) providing a thymidine analog;

iii) determining whether said thymidine analog is a substrate for said modified tmpk/detection cassette fusion.

Other features and advantages of the present application will become apparent from the following detailed description. It should be understood, however, that the detailed description and the specific examples while indicating preferred embodiments of the application are given by way of illustration only, since various changes and modifications within the scope of the application will become apparent to those skilled in the art from this detailed description.

BRIEF DESCRIPTION OF THE DRAWINGS

Preferred embodiments of the application will be described in relation to the drawings in which:

FIG. 13 is a listing of sequences.

DETAILED DESCRIPTION OF THE APPLICATION

Figure 1:
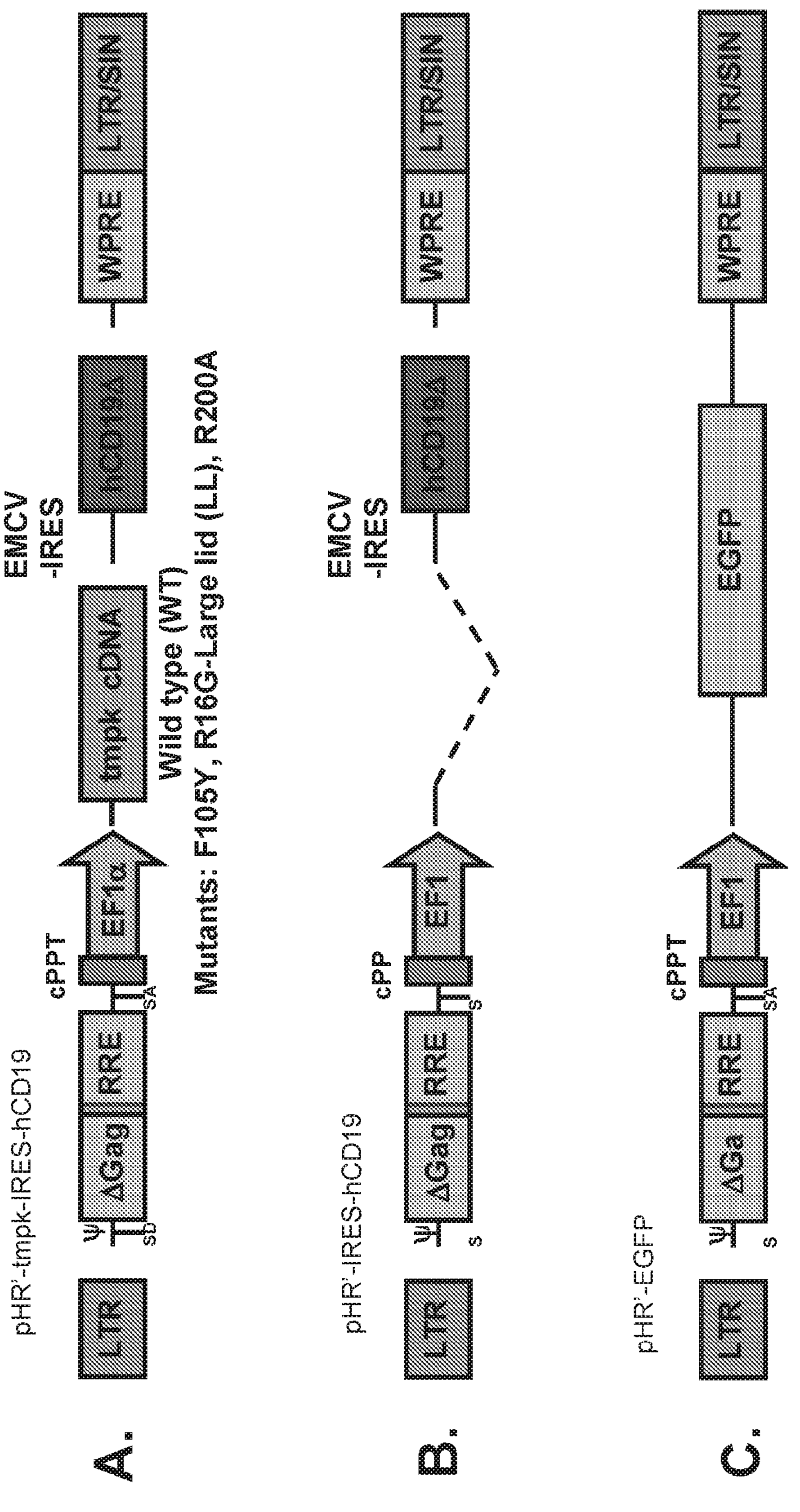
FIG. 1 is a schematic diagram of recombinant lentiviral transfer vector constructs. A. pHR'-tmpk-IRES-hCD19 is a schematic diagram of a lentiviral vector used to express wild-type tmpk, and mutants F105Y, R-16G-large lid and R200A in combination with a truncated CD19 detection molecule. B. pHR'-IRES-hCD19 is a schematic diagram of a lentiviral vector used to express a truncated CD19 detection molecule. C. pHR'-EGFP is a schematic diagram of a lentiviral vector used to express an EGFP detection molecule. The vector elements illustrated are: LTR—long terminal repeat; ψ—HIV packaging signal, SD—5' splice signal, RRE—Rev responsive element; SA—3' splice site, cPPT—central polypurine tract, EF1α—elongation factor 1α promoter; WPRE woodchuck hepatitis virus post-transcriptional regulatory element; SIN—self-inactivating LTR.

The inventors herein present a novel prodrug/enzyme combination for suicide gene therapy also known as cell fate controlled gene therapy, for treating GVHD and therapeutic gene therapy. Catalytically improved variants of human tmpk/detection cassette fusions were delivered into target cells by novel lentiviruses (LVs), and the ability to selectively clear these cells in vitro in response to increasing AZT concentrations was evaluated. The inventors demonstrate the highly efficient transfer of these suicide genes fused to a truncated huCD19 marker into cell lines. AZT sensitivity in transduced cells was further analysed. The inventors additionally demonstrate that increased accumulation of intracellular AZT-TP in tmpk-mutant-transduced cells decreases cell viability. Without wishing to be bound by theory, this is in part due to the activation of a mitochondria-mediated apoptosis pathway. These results show that the rationally designed minimal mutants of tmpk/detection cassette fusions employed are a practical choice for suicide gene therapy and establish the next generation of safer integrating viral vectors. In addition, this system is useful to endow stem cells (both embryonic and of later ontogeny) destined for utility in clinical transplantation, for example, with a reliable safety system. Further the system provides a novel safety feature for therapeutic gene therapy, such as for treating Fabry disease.

Accordingly, the application relates to tmpk/detection cassette fusion polypeptides and nucleic acids, vector constructs, compositions and cells comprising these, and systems employing as well as methods of using said tmpk/detection cassette fusions. For example said tmpk/detection cassette fusion gene mutants can be inserted in transplant cells for treatment of cancer and controlling transplant-associated graft versus host disease. A lentivirus is optionally used to deliver tmpk/detection cassette fusions. Other methods of delivery are also useful.

The application prodrug/enzyme combination works by increasing phosphorylation of prodrugs such as AZT. For example, the prodrug AZT is converted through a series of phosphorylation steps into AZT-triphosphate (AZT-TP)[12]. This is the active metabolite that inhibits replication of the human immunodeficiency virus (HIV)[13-15], and to a lesser extent, DNA replication in eukaryotic cells[16]. Safety profiles for this compound are well known and concentrations of AZT in the bloodstream of AIDS patients being treated with this agent can reach high levels. The rate-limiting step in the conversion of AZT to the toxic AZT-TP form is the intermediate step of phosphorylation of AZT-monophosphate (AZT-MP) to AZT-diphosphate (AZT-DP) catalyzed by the cellular thymidylate kinase (tmpk), which has a low enzymatic efficiency for AZT-MP[17]. Accumulation of AZT-metabolites in the cells of AZT-treated AIDS patients reportedly induces toxic mitochondrial myopathy[18-22]. To harness this dual toxicity of AZT-TP, the inventors developed a novel suicide gene therapy approach based on the engineered overexpression of human tmpk. In order to improve the processing of AZT-MP to AZT-DP, thereby increasing intracellular AZT-TP concentrations, the inventors have engineered minimally modified tmpk mutants (F105Y and R16G-Large lid (RG16GLL)) with approximately 200-fold enhanced activity for AZT-MP[23,24].

Phosphorylation of the prodrug leads to its activation and increases its effectiveness in killing tmpk transduced cells (also called "suicide gene therapy")."). As used herein "suicide gene therapy" and "cell fate controlled gene therapy" are used interchangeably.

The application is useful in the event of a transplant related adverse event. A transplant related adverse event typically comprises graft versus host disease where following T-cell (or other cell) transplant to a recipient the transplanted cells attack the host. A transplant adverse event also comprises any situation where it would be beneficial to eliminate the transplanted cells, including where transplanted cells comprise integrations that can cause disease. For example, the transplanted cells express mutant tmpk so that upon detection of graft versus host disease, a prodrug such as AZT is optionally administered to the patient to kill the transplanted cells.

For cancer treatment, the above method is useful to treat leukemia where donor transplant cells are used to kill leukemic cells. The transplanted cells expressing tmpk are likely to also attack the host, so the application allows the transplanted cells to be killed after detection of the onset of graft versus host disease.

In a variation of the application, tmpk/detection cassette fusion vector constructs are inserted directly into the solid tumor and expression of tmpk/detection cassette fusion sensitizes the cells to the prodrug.

Additionally, the tmpk/detection cassette fusion gene mutants are useful as a general 'safety component' in gene therapy. For example, use of the tmpk/detection cassette fusion in combination with alpha-galactosidase is useful for treating patients with Fabry disease. Also, in patients with Severe Combined Immunodeficiency Disease (SCID), gene therapy has been used successfully to introduce deficient genes however at least one clinical trial was halted due to safety concerns arising from inappropriate DNA integrations. The prior art also includes much discussion about the dangers of gene therapy due to vector integrations that can cause cancer. The safety component overcomes this problem by allowing the transplanted cells to be destroyed upon administration of a prodrug.

Tmpk/Detection Cassette Fusion Molecules

One aspect of the application relates to isolated polypeptides and isolated nucleic acids that encode a tmpk/detection cassette fusion.

As used herein "tmpk/detection cassette fusion" refers to a molecule comprising a tmpk component such as a modified tmpk or tmpk variant described herein and a detection cassette component fused in frame with tmpk. Tmpk/detection cassette fusion molecules include, polypeptides, polynucleotides, as well as variants and fragments thereof that maintain detection capacity and tmpk catalytic activity.

The tmpk/detection cassette fusion is optionally constructed such that the tmpk component can be N-terminal (or 5') or C-terminal (or 3') in continuous or discontinuous relationship to the detection cassette component. For example, in a continuous relationship the fusion polypeptide can comprise a tmpk component fused to a detection cassette (e.g. NH2-tmpk-GFP-COOH) or alternatively can comprise a detection cassette component fused to a tmpk molecule (e.g NH2-GFP-tmpk-COOH). Similarly, a fusion polynucleotide can comprise a tmpk component fused to a detection cassette (e.g. 5'-tmpkGFP) or alternatively can comprise a detection cassette component fused to a tmpk molecule (e.g 5'-GFP-tmpk-3')).

In addition the tmpk and detection cassette components are optionally discontinuous. For example a linker sequence is optionally present between the tmpk and detection cassette components.

The term "linker sequence" as used in reference to a tmpk/detection cassette fusion refers to residues that link the tmpk and detection cassette components. In a polypeptide, the residues are generally amino acids. In a polynucleotide, the residues are generally nucleotides. The term "linker sequence" as used in reference to a tmpk/detection cassette fusion polypeptide accordingly generally refers to a sequence of amino acids that link the tmpk and detection cassette components. The term "linker sequence" as used in reference to a tmpk/detection cassette fusion polynucleotide accordingly generally refers to a sequence of nucleotides that link the tmpk and detection cassette components. The linker when referring to a polypeptide sequence optionally comprises 3, 4, 5, 6, 6-10, 10-15 or 15-25 amino acids or longer and when referring to a polynucleotide sequence comprises 3-6, 6-12, 18, 12-24, or 24-72 nucleic acid residues or longer. A linker sequence is useful for several reasons. A linker sequence can be used to facilitate cloning. Further a linker sequence can provide a gap between the components that facilitates proper folding and/or activity (e.g. antigenic activity for the detection cassette and/or catalytic activity for the tmpk component). A person skilled in the art will recognize that a number of linker sequences can be used and a number of linker sequences are known in the art. The linker sequence can comprise any sequence of amino acids or nucleotides that is suitable. For example, suitable refers to the amino acid composition of the linker. For example uncharged amino acids are preferable. Amino acids such as proline which could limit the flexibility of the linker are generally not preferred. In one embodiment of a discontinuous relationship, the fusion polypeptide optionally comprises a tmpk component fused to a linker fused to a detection cassette (e.g. NH2-tmpk-linker-GFP-COOH or alternatively comprises a detection cassette component fused to a linker fused to a tmpk molecule (e.g NH2-truncated CD19-linker-tmpk-COOH). Similarly, a fusion polynucleotide can comprise a tmpk component fused to a linker fused to a detection cassette (e.g. 5'-tmpk-linker-GFP-3') or alternatively can comprise a detection cassette component fused to a linker fused to a tmpk molecule (e.g 5'-truncated CD19-linker-tmpk-3'; such as SEQ ID NO: 28, 29, 31 or 37 fused to a linker sequence described herein fused to SEQ ID NO:36)). The tmpk and detection cassette components are fused in frame such that both components are expressed together as one continuous polypeptide sequence in each cell. The various tmpk and detection cassette components are further described below.

Fusion Polypeptides

As mentioned, the application provides isolated tmpk/detection cassette fusion polypeptides. A tmpk/detection cassette fusion polypeptide comprises a tmpk polypeptide component and a detection cassette polypeptide component.

The term "isolated polypeptide" refers to a polypeptide substantially free of cellular material or culture medium when produced by recombinant DNA techniques, or chemical precursors or other chemicals when chemically synthesized.

As mentioned, tmpk polypeptide components that can be comprised by the tmpk/detection cassette fusion polypeptide are described in detail below. In one embodiment the tmpk polypeptide component comprises TmpkF105YR200A. In a more specific embodiment the tmpk polypeptide component comprises the amino acid sequence in SEQ ID NO:36.

In another preferred embodiment, the detection cassette polypeptide component comprises truncated CD19 polypeptide. In a more specific preferred embodiment, the truncated CD19 polypeptide component comprises the sequence in SEQ ID NO:37.

In another embodiment the tmpk/detection cassette fusion polypeptide comprises a linker sequence, for example amino acids A G G A A G (SEQ ID NO: 32).

In another embodiment, the tmpk/detection cassette fusion polypeptide comprises a truncated CD19, a linker sequence and tmpkF105YR200A. In one embodiment the amino acid sequence comprises the amino acid sequence in SEQ ID NO:38.

A person skilled in the art will recognize that conservative amino acid substitutions as well as additions/deletions or a number of divergent amino acid sequences can be used are readily made to the disclosed sequences and are within the scope of the present disclosure.

A "conservative amino acid substitution" as used herein, is one in which one amino acid residue is replaced with another amino acid residue without abolishing the protein's desired properties. Conservative amino acid substitutions are known in the art. For example, conservative substitutions include substituting an amino acid in one of the following groups for another amino acid in the same group: alanine (A), serine (S), and threonine (T); aspartic acid (D) and glutamic acid (E); asparagine (N) and glutamine (Q); arginine (R) and lysine (L); isoleucine (I), leucine (L), methionine (M), valine (V); and phenylalanine (F), tyrosine (Y), and tryptophan (W).

Fusion Nucleic Acids

The application also provides isolated tmpk/detection cassette polynucleotides. A tmpk/detection cassette fusion polynucleotide comprises a tmpk polynucleotide component and a detection cassette polynucleotide component.

The term "polynucleotide" and/or "nucleic acid sequence" as used herein refers to a sequence of nucleoside or nucleotide monomers consisting of naturally occurring bases, sugars and intersugar (backbone) linkages. The term also includes modified or substituted sequences comprising non-naturally occurring monomers or portions thereof. The nucleic acid sequences of the present application may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine.

The term "isolated polynucleotide" or "isolated nucleic acid sequences" as used herein refers to a nucleic acid substantially free of cellular material or culture medium when produced by recombinant DNA techniques, or chemical precursors, or other chemicals when chemically synthesized. An isolated nucleic acid is also substantially free of sequences which naturally flank the nucleic acid (i.e. sequences located at the 5' and 3' ends of the nucleic acid) from which the nucleic acid is derived. The term "nucleic acid" is intended to include DNA and RNA and can be either double stranded or single stranded, and represents the sense or antisense strand. Further, the term "nucleic acid" includes the complementary nucleic acid sequences.

As mentioned, tmpk polynucleotide components that can be comprised by the tmpk/detection cassette fusion polynucleotide are described in detail below. In a preferred embodiment, the tmpk polynucleotide component comprises tmpkF105YR200A. In a more specific embodiment the tmpk polynucleotide component comprises the nucleic acid sequence in SEQ ID NO:34.

In another preferred embodiment, the detection cassette polypeptide component comprises truncated CD19 polynucleotide. In a more specific preferred embodiment, the truncated CD19 polynucleotide component comprises the sequence in SEQ ID NO:35.

In another embodiment the tmpk/detection cassette fusion polynucleotide comprises a linker sequence, for example GCCGGCGGGGCTGCAGGG (SEQ ID NO: 33).

In another embodiment, the tmpk/detection cassette fusion polynucleotide comprises a truncated CD19, a linker sequence and tmpkF105YR200A. In one embodiment the polynucleotide sequence comprises the sequence in SEQ ID NO:39.

The tmpk polynucleotide sequence provided above comprises silent mutations compared to the wildtype sequence of tmpk (in addition to the F105YR200A encoding mutations). Base 318 is converted from "C" to "A" and base 345 is converted from "T" to "C". These mutations do not alter the amino acid sequence of the protein. Accordingly a person skilled in the art will recognize that sequence variants that do not result in an amino acid change are useful and within the scope of the present disclosure. In addition, nucleotide changes that result in conservative changes and/or changes wherein the activity of the components is maintained (e.g. antigenic activity of detection cassette and catalytic activity of the tmpk component).

The application also provides for polynucleotides that bind tmpk/detection cassette polynucleotides and/or their complements under at least moderately stringent hybridization conditions. The polynucleotides that hybridize can comprise polynucleotides with sequence identity with the tmpk, linker, and/or detection cassette and which retain activity. In one embodiment, the polynucleotide that hybridize comprises 60%, 60-70%, 70-80%, 80-90%, 90-95%, 95-99%, 99-99.9% or more sequence identity.

The term "hybridize" refers to the sequence specific non-covalent binding interaction with a complementary nucleic acid.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.−16.6 (Log 10 [Na+])+0.41(% (G+C)−600/l), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm−5° C. based on the above equation, followed by a wash of 0.2×SSC/0.1% SDS at 60° C. Moderately stringent hybridization conditions include a washing step in 3×SSC at 42° C. It is understood, however, that equivalent stringencies may be achieved using alternative buffers, salts and temperatures. Additional guidance regarding hybridization conditions may be found in: Current Protocols in Molecular Biology, John Wiley & Sons, N.Y., 2002, and in: Sambrook et al., Molecular Cloning: a Laboratory Manual, Cold Spring Harbor Laboratory Press, 2001.

The term "sequence identity" as used herein refers to the percentage of sequence identity between two polypeptide sequences or two nucleic acid sequences. To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions.times.100%). In one embodiment, the two sequences are the same length. The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present application. BLAST protein searches can be performed with the XBLAST program parameters set, e.g., to score-50, wordlength=3 to obtain amino acid sequences homologous to a protein molecule of the present application. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). The percent identity between two sequences can be determined using techniques similar to those described above, with or without allowing gaps. In calculating percent identity, typically only exact matches are counted.

Vector Constructs

The aforementioned isolated polynucleotides are optionally comprised in a vector to provide a vector construct, optionally herein referred to as a vector. The vector construct optionally comprises:

(i) a stably integrating delivery vector;

(ii) a modified mammalian thymidylate kinase (tmpk) wherein the modified mammalian tmpk increases phosphorylation of a prodrug relative to phosophorylation of the prodrug by wild-type mammalian (eg. human) tmpk;

(iii) a detection cassette fused to tmpk.

Each of these components is further described below.

Tmpk Variants

Thymidylate kinase is a kinase that catalyzes the addition of a phosphoryl group to thymidylate as well as thymidine analogs such as AZT. Several wild-type human sequences have been reported. SEQ ID NOS: 1, 3, 5 and 7 are reported nucleotide sequences of human thymidylate kinase (SEQ ID NO: 7 does not have a stop codon). The different sequences represent natural polymorphic variations present in the population and it will be recognized in the art that future identified molecules with polymorphic variations will also be considered to be wildtype tmpk. SEQ ID NO: 9 is the reported mouse thymidylate kinase sequence. The mouse sequence shares 82% nucleotide identity 81% amino acid identity and several residues that have been identified as limiting the nucleoside analog activity of the human tmpk enzyme and which result in increased enzymatic activity when modified, are conserved in the murine sequence. The corresponding amino acid sequences are reported in SEQ ID NOS: 2, 4, 6, 8, and 10. SEQ ID NO: 2 provides the amino acid sequence for the wild-type tmpk polynucleotide described in SEQ ID NO: 1; SEQ ID NO: 4 provides the amino acid sequence for the wild-type tmpk polynucleotide reported in SEQ ID NO: 3, SEQ ID NO: 6 provides the amino acid sequence for the wild-type tmpk polynucleotide described in SEQ ID NO: 5; SEQ ID NO: 8 provides the putative sequence of the wild-type tmpk polynucleotide reported in SEQ ID NO: 7; and SEQ ID NO: 10 provides the amino acid sequence of the wild-type murine tmpk polynucleotide described in SEQ ID NO: 9. Modified tmpk molecules and mutant tmpk refer to mammalian tmpk molecules that have been modified compared to wild-type. Among the mutant tmpks, some of these showed a superior enzymatic activity to convert deoxy-thymidine-monophosphate (dTMP) to dTMP-diphosphate (dTDP) or AZT-MP to AZT-DP. Increased kinase activity relative to wild-type refers to modified tmpk molecules that exhibit improved enzymatic kinetics compared to tmpk wild-type. The improved activity comprises increases in binding and or enzymatic turnover to convert the monophosphate-form of the substrate of tmpk to the diphosphate form.

Mutations which show superior enzymatic activity included the F105Y mutant (SEQ ID NO: 11, SEQ ID NO: 21), R16GLL mutant (SEQ ID NO: 12, SEQ ID NO: 22) and the R200A mutant (SEQ ID NOS: 15 and 16).

One aspect of the application provides vector constructs comprising modified detection cassette fused tmpk enzymes with increased nucleoside analog kinase activity relative to wild-type. In one aspect, the modification that increases tmpk nucleoside analog kinase activity comprises one or more deletions. The deletions can be internal or can result in a truncated variant. In an alternate embodiment the modification that increases tmpk nucleoside analog kinase activity comprises one or more point mutations. In another embodiment an exogenous sequence replaces an endogenous sequence. For example, in one embodiment all or part of the large lid domain of human tmpk (SEQ ID NO:20) is replaced with all or part of the large lid domain of a different species. In one embodiment the different species is a bacteria species. In one embodiment, all or part of the large lid domain of human tmpk (SEQ ID NO:20) is replaced with all or part of the large lid domain of *E. coli* tmpk (SEQ ID NO:17). In another embodiment, residues 145-148 of SEQ ID NO: 1 (AFGH) are replaced with all or part of the small lid region of *E. coli* residues 151-156 in SEQ ID NO: 17 (RARGEL). In another embodiment the modified tmpk is selected from the group including the F105Y mutant (SEQ ID NO: 11, SEQ ID NO: 21), R16GLL mutant (SEQ ID NO: 12, SEQ ID NO: 22), a tmpk molecule modified by the substitution of all or part of a bacterial large lid domain such as the *E. coli* large lid domain in SEQ ID NO: 17, a tmpk molecule modified by the substitution of all or part of a bacterial small lid domain such as the *E. coli* small lid domain at 151-156 of SEQ ID NO: 17, and the R200A mutant (SEQ ID NOS: 15 and 16).

In another embodiment, the exogenous sequence is optionally synthesized or obtained from a non-mammalian thymidylate kinase such as a bacterial thymidylate kinase. As used herein a modified mammalian tmpk molecule includes a modified tmpk molecule that comprises non-mammalian sequences such as all or part of either a large lid domain or a small lid domain sequence from bacteria such as *E. coli*. A variant may comprise one or more of the aforementioned modifications. Examples of modifications are described above.

Detection/Selection Cassettes

In cell fate control or suicide gene therapy, it is typically desirable that the majority, and preferably all of transduced cells express the suicide gene. This need can be met by co-introducing a cell surface marker detection gene cassette. Vector constructs wherein the detection cassette and suicide gene are independently translated e.g separated by an IRES sequence, cells may express only one of the two genes. A fusion protein fusing the suicide gene and the detection cassette can be useful to minimize cells expressing only one of the genes. Transduced cells can be identified and enriched based on expression of the fusion protein. A good detection cassette gene should be inert in itself, devoid of signaling capacity and non-immunogenic[28]. A variety of cell surface markers can be used in this context: human CD24[29], murine HSA[30], human CD25 (huCD25)[31] and a truncated form of LNGFR[32].

While huCD25 has been an efficient and malleable marker for murine studies[27,33], it is not useful for gene transfer applications into T cells since expression of this molecule is up-regulated when this population is activated. Other groups have also used the truncated form of LNGFR[32], but over-expression of this marker has been reported to promote transformation of myeloid cells in an unusual, highly context-dependent manner[35]. A novel truncated form of CD19 (e.g. CD19Δ) is adopted in one embodiment as a detection cassette (SEQ ID NOS: 29-31). CD19 (SEQ ID NOS: 27-28) is a 95-kDa glycoprotein of the immunoglobulin superfamily. It forms a complex with CD21, CD81, and Leu-13, and collectively functions to modulate the activation threshold of the B cell receptor[36,37]. As expression of CD19 and CD21 is restricted to B cell lineages from immature progenitors to blasts[38], it is suitable for use in murine and human T cells. To further decrease any signaling capacity from the CD19 molecule, the cytoplasmic tail[39] has been deleted for the present adaptation. In one embodiment truncated CD19 comprises all or a portion of SEQ ID NO: 29. In another embodiment truncated CD19 comprises all or a portion of SEQ ID NO: 30. In another embodiment truncated CD19 comprises all or a portion of SEQ ID NO: 31.

"Detection cassette" is used to refer to a polynucleotide that directs expression of a molecule that acts as a cell marker and that optionally provides for a mode of isolating cells expressing said marker. The molecule is optionally used to select transduced or transfected cells or to determine the efficiency of cell transduction or transfection. Molecules that are useful as cell markers or detection agents comprise CD19, truncated CD19, CD25 and EGFP, HSA, CD20, GFP, ETC. EGFP is variably referred to as enGFP or GFP herein. One skilled in the art will recognize that other fluorescent molecules can similarly be used. These molecules can be fused to tmpk to provide a tmpk/detection cassette fusion molecule.

The term "fused" as used herein means that the detection cassette and tmpk molecule are in the correct reading frame eg the expression fusion comprises a functional detection cassette and functional tmpk. The tmpk detection cassette can be continuous (e.g no linker) or can be discontinous (e.g comprise a linker).

As mentioned, the detection cassette encodes a molecule that is typically used to isolate transduced or transfected cells. The detection cassette is useful in vectors comprising modified tmpk or control molecules. Control molecules include molecules that do not function as suicide gene therapy molecules which that are typically employed to assess the effect of tmpk mutants in similarly related cells. A person skilled in the art would recognize that many molecules are useful for fusing to tmpk to permit isolation of modified tmpk or control expressing cells. Choice of molecule will depend on the cell type to be transfected or transduced. Generally, the detection cassette molecule is not expressed on the cell type to be transfected or transduced in appreciable levels permitting isolation of cells expressing the detection cassette. In one embodiment the detection cassette encodes a CD19 (SEQ ID NOS: 27-28). In a preferred embodiment, the detection cassette encodes a truncated CD19 (SEQ ID NOS: 29-31). In an alternate embodiment, the detection cassette encodes CD25. In another embodiment, the detection cassette encodes a fluorescent protein such as EGFP. In another embodiment, the molecules encoded by the detection cassette comprise CD20, CD25, low affinity nerve growth factor receptor (LNGFR), truncated CD34, or erythropoietin receptor (EpoR). Additionally, the detection cassette can comprise a drug resistance gene permitting isolation of transduced or transfected cells by drug selection.

Delivery Vectors

As used herein "delivery vector" refers to a nucleic acid molecule that is used as a vehicle to deliver one or more nucleic acid molecules of interest, such as transgenes, into a cell. Delivery vector can refer optionally to the plasmid construct (e.g. vector backbone such as pHR) that is used to generate virus or to a virus genome. Optionally, the delivery vector is constructed to permit expression of one or more transgenes and can be referred to as an expression vector. A delivery vector into which has been inserted one or more nucleic acids to be transferred to a cell, is referred to as a vector construct.

It will be appreciated by one skilled in the art that a variety of delivery vectors (e.g. vector backbones) and expression vehicles are usefully employed to introduce a modified tmpk/detection cassette fusion molecule into a cell. Delivery vectors that are useful comprise lentiviruses, oncoretroviruses, expression plasmids, adenovirus, and adeno-associated virus. Other delivery vectors that are useful comprise herpes simplex viruses, transposons, vaccinia viruses, human papilloma virus, Simian immunodeficiency viruses, HTLV, human foamy virus and variants thereof. Further vectors that are useful comprise spumaviruses, mammalian type B retroviruses, mammalian type C retroviruses, avian type C retroviruses, mammalian type D retroviruses, HTLV/BLV type retroviruses, and lentiviruses.

Delivery vectors such as those listed above have been employed to introduce thymidine kinase molecules into cells for use in gene therapy. Examples of delivery vectors used to express thymidine kinase in cells include: Kanazawa T, Mizukami H, Okada T, Hanazono Y, Kume A, Nishino H, Takeuchi K, Kitamura K, Ichimura K, Ozawa K. Suicide gene therapy using AAV-HSVtk/ganciclovir in combination with irradiation results in regression of human head and neck cancer xenografts in nude mice. Gene Ther. 2003 January; 10(1):51-8. Fukui T, Hayashi Y, Kagami H, Yamamoto N, Fukuhara H, Tohnai I, Ueda M, Mizuno M, Yoshida J Suicide gene therapy for human oral squamous cell carcinoma cell lines with adeno-associated virus vector. Oral Oncol. 2001 April; 37(3):211-5.

The term "stably integrating" as used herein refers to components that permit the delivery construct and its inserts (eg modified tmpk/detection cassette fusion) to be maintained in a cell. For example, in the case of a virus, LTRs are required for genomic integration.

Lentirviral Vectors

The safety facet of suicide gene therapy relies on efficient delivery and stable, consistent expression of both the therapeutic and the cytotoxic effector genes. LVs transduce a wide range of dividing and non-dividing cell types with high efficiency, conferring stable, long-term expression of the transgene[25-27].

The use of lentivirus-based gene transfer techniques relies on the in vitro production of recombinant lentiviral particles carrying a highly deleted viral genome in which the transgene of interest is accommodated. In particular, the recombinant lentivirus are recovered through the in trans coexpression in a permissive cell line of (1) the packaging constructs, i.e., a vector expressing the Gag-Pol precursors together with Rev (alternatively expressed in trans); (2) a vector expressing an envelope receptor, generally of an heterologous nature; and (3) the transfer vector, consisting in the viral cDNA deprived of all open reading frames, but maintaining the sequences required for replication, incapsidation, and expression, in which the sequences to be expressed are inserted.

In one embodiment the Lentigen lentiviral vector described in Lu, X. et al. Journal of gene medicine (2004) 6:963-973 is used to express the modified tmpk molecules.

In an embodiment the application comprises a lentiviral vector expressing a modified tmpk molecule fused to a detection cassette. In one embodiment the lentiviral vector comprises a 5'-Long terminal repeat (LTR), HIV signal sequence, HIV Psi signal 5'-splice site (SD), delta-GAG element, Rev Responsive Element (RRE), 3'-splice site (SA), Elongation factor (EF) 1-alpha promoter and 3'-Self inactivating LTR(SIN-LTR). It will be readily apparent to one skilled in the art that optionally one or more of these regions is substituted with another region performing a similar function.

Gene therapy requires the transgene product to be expressed at sufficiently high levels. Enhancer elements can be used to increase expression of modified tmpk molecules or increase the lentiviral integration efficiency. In one embodiment the lentiviral vector further comprises a nef sequence. In a preferred embodiment the lentiviral further comprises a cPPT sequence which enhances vector integration. The cPPT acts as a second origin of the (+)-strand DNA synthesis and introduces a partial strand overlap in the middle of its native HIV genome. The introduction of the cPPT sequence in the transfer vector backbone strongly increased the nuclear transport and the total amount of genome integrated into the DNA of target cells. In an alternate preferred embodiment, the lentiviral vector further comprises a Woodchuck Posttranscriptional Regulatory Element (WPRE). The WPRE acts at the transcriptional level, by promoting nuclear export of transcripts and/or by increasing the efficiency of polyadenylation of the nascent transcript, thus increasing the total amount of mRNA in the cells. The addition of the WPRE to lentiviral vector results in a substantial improvement in the level of transgene expression from several different promoters, both in vitro and in vivo. In a further preferred embodiment, the lentiviral vector comprises both a cPPT sequence and WPRE sequence.

The vector also comprises in an alternate embodiment an internal ribosome entry site (IRES) sequence that permits the expression of multiple polypeptides from a single promoter. For example the IRES can permit the expression of a therapeutic gene. For example, the therapeutic gene is in one embodiment, alpha-galactosidase A (NM_000169). In another embodiment, the therapeutic gene is codon optimized alpha-galactaside A (COalphaGalA:all or part of SEQ ID NO:46; optionally the coding sequence of SEQ ID NO:46). In an embodiment, the COalphaGalA comprises all or part of SEQ ID NO:46, all of the coding sequence of SEQ ID NO:46, and/or a sequence with at least 95% identity to SEQ ID NO:46, wherein the sequence is not identical to the polynucleotide having accession number NM_000169 and/or encodes SEQ ID NO:47, any of which wherein T is optionally substituted with U. Codon optimized alphaGalA refers to a alphaGalA coding sequence that is optimized for human codon usage.

In another embodiment the integrating vector is pHR'-cppt-EF-IRES-W-SIN. The IRES sequence is alternatively spliced out. For example where the construct comprises a tmpk/detection fusion, and no additional polypeptide, the IRES can be spliced out and/or the tmpk/detection fusion can be cloned in upstream such that the IRES is not utilized. In one embodiment the vector construct comprises pHR'-cppt-EF-tmpk/detection cassette-W-SIN. In another embodiment, the vector construct comprises pHR'-cppt-EF tmpk/detection cassette-IRES-W-SIN. In a more specific embodiment, the vector construct comprises pHR'-cppt-EF-CD19Δ/TmpkF105YR200A-W-SIN. In an alternate embodiment the vector construct comprises pHR'-cppt-EF-CD19Δ/TmpkF105YR200A-IRES-therapeutic gene-W-SIN. Additionally it will be readily apparent to one skilled in the art that optionally one or more of these elements can be added or substituted with other regions performing similar functions.

In addition to IRES sequences, other elements which permit expression of multiple polypeptides are useful. In one embodiment the vector comprises multiple promoters that permit expression more than one polypeptide. In another embodiment the vector comprises a protein cleavage site that allows expression of more than one polypeptide. Examples of protein cleavage sites that allow expression of more than one polypeptide comprise those listed in the following articles which are incorporated by reference: Retroviral vector-mediated expression of HoxB4 in hematopoietic cells using a novel coexpression strategy. Klump H, Schiedlmeier B, Vogt B, Ryan M, Ostertag W, Baum C. Gene Ther. 200; 8(10):811-7; A picornaviral 2A-like sequence-based tricistronic vector allowing for high-level therapeutic gene expression coupled to a dual-reporter system Mark J. Osborn, Angela Panoskaltsis-Mortari, Ron T. McElmurry, Scott K. Bell, Dario A. A. Vignali, Martin D. Ryan, Andrew C. Wilber, R. Scott Mclvor, Jakub Tolar and Bruce R. Blazar. Molecular Therapy 2005; 12 (3), 569-574; Development of 2A peptide-based strategies in the design of multicistronic vectors. Szymczak A L, Vignali D A. Expert Opin Biol Ther. 2005; 5(5):627-38; Correction of multi-gene deficiency in vivo using a single ‘self-cleaving’ 2A peptide-based retroviral vector. Szymczak A L, Workman C J, Wang Y, Vignali K M, Dilioglou S, Vanin E F, Vignali D A. Nat. Biotechnol. 2004; 22(5):589-94. It will be readily apparent to one skilled in the art that other elements that permit expression of multiple polypeptides which identified in the future are useful and may be utilized in the vectors of the application.

Viral Regulatory Elements

The viral regulatory elements are components of vehicles used to introduce nucleic acid molecules into a host cell. The viral regulatory elements are optionally retroviral regulatory elements. For example, the viral regulatory elements may be the LTR and gag sequences from HSC1 or MSCV. The retroviral regulatory elements may be from lentiviruses or they may be heterologous sequences identified from other genomic regions.

One skilled in the art would also appreciate that as other viral regulatory elements are identified, these may be used with the nucleic acid molecules of the application.

Variations of Nucleic Acid Molecules

Modifications

Many modifications may be made to the nucleic acid molecule DNA sequences including vector sequences disclosed in this application and these will be apparent to one skilled in the art. The application includes nucleotide modifications of the sequences disclosed in this application (or fragments thereof) that are capable of directing expression or being expressed in mammalian cells. Modifications include substitution, insertion or deletion of nucleotides or altering the relative positions or order of nucleotides.

Sequence Identity

The nucleic acid molecules of the application also include nucleic acid molecules (or a fragment thereof) having at least about: 70% identity, at least 80% identity, at least 90% identity, at least 95% identity, at least 96% identity, at least 97% identity, at least 98% identity or, most preferred, at least 99% or 99.5% identity to a nucleic acid molecule of the application and which are capable of expression of nucleic acid molecules in mammalian cells. Identity refers to the similarity of two nucleotide sequences that are aligned so that the highest order match is obtained. Identity is calculated according to methods known in the art. For example, if a nucleotide sequence (called “Sequence A”) has 90% identity to a portion of SEQ ID NO: 11, then Sequence A will be identical to the referenced portion of SEQ ID NO: 11 except that Sequence A may include up to 10 point mutations (such as substitutions with other nucleotides) per each 100 nucleotides of the referenced portion of SEQ ID NO: 11.

Sequence identity (each construct in an embodiment without a coding nucleic acid molecule insert) is preferably set at least about: 70% identity, at least 80% identity, at least 90% identity, at least 95% identity, at least 96% identity, at least 97% identity, at least 98% identity or, most preferred, at least 99% or 99.5% identity to the sequences provided in for example SEQ ID NO:13 and/or SEQ ID NO:14 and/or its complementary sequence. Sequence identity will preferably be calculated with the GCG program from Bioinformatics (University of Wisconsin). Other programs are also available to calculate sequence identity, such as the Clustal W program (preferably using default parameters; Thompson, J D et al., Nucleic Acid Res. 22:4673-4680).

Hybridization

The application includes DNA that has a sequence with sufficient identity to a nucleic acid molecule described in this application to hybridize under stringent hybridization conditions (hybridization techniques are well known in the art). The present application also includes nucleic acid molecules that hybridize to one or more of the sequences of for example SEQ ID NO:11 and/or SEQ ID NO:12 or its complementary sequence. Such nucleic acid molecules preferably hybridize under high stringency conditions (see Sambrook et al. Molecular Cloning: A Laboratory Manual, Most Recent Edition, Cold Spring Harbor Laboratory Press, Cold Spring Harbor, N.Y.). High stringency washes have preferably have low salt (preferably about 0.2% SSC) and a temperature of about 50-65° C. and are optionally conducted for about 15 minutes.

Prodrugs

A prodrug refers to a pharmacological substance (drug) which is administered in an inactive form (or significantly less active form, eg at least 90% or at least 95% less active than the active drug form). Once administered, the prodrug is metabolised in the body (in vivo) into the active compound and these metabolites provide cytotoxicity against the cells.

A prodrug is useful in combination with suicide gene therapy strategies. Suicide genes that make transduced cells susceptible to a molecule that is not ordinarily toxic function as a safety mechanism. The most commonly used suicide gene is the thymidine kinase gene from herpes simplex type I virus (HSV1-tk).

AZT is an example of a nucleoside prodrug that is poorly phosphorylated by thymidylate kinase enzymes. Other thymidine and uracil analogs are known and would be useful as prodrugs for killing cells expressing modified tmpk. Other known thymidine and uracil analogues that are useful comprise d4T and 5-FU. Additional thymidine and uracil analogs are known in the art. (J Med. Chem. 1996 39(17):3412-7 Synthesis and evaluation of novel thymidine analogs as antitumor and antiviral agents. Chen X, Bastow K, Goz B, Kucera L S, Morris-Natschke S L, Ishaq K S).

In a preferred embodiment, the prodrug administered is AZT. In an alternate embodiment the prodrug is a thymidine analog that is a substrate for modified tmpk enzymes. In another embodiment the prodrug is a uracil analog.

Prodrugs may require more than one enzyme activation. For example ganciclovir requires phosphorylation by thymidine kinase as well as a second phosphorylation guanylate kinase. In an embodiment of the present application, a method of tandem expression of modified tmpk and additional kinases required for prodrug is provided.

Tmpk/Detection Cassette Expressing Cells

The application also relates to a cell (for example, isolated cell in vitro, a cell in vivo, or a cell treated ex vivo and returned to an in vivo site) containing a nucleic acid molecule of the application.

The term "a cell" includes a single cell as well as a plurality or population of cells. Administering a composition to a cell includes both in vitro and in vivo administrations.

The term "a" as used herein means one or more than one.

Cells transfected with a nucleic acid molecule such as a DNA molecule, or transduced with the nucleic acid molecule such as a DNA or RNA virus vector construct, encoding a tmpk/detection cassette fusion are optionally used, for example, in bone marrow or cord blood cell transplants according to techniques known in the art. Examples of the use of transduced bone marrow or cord blood cells in transplants are for ex vivo gene therapy of Adenosine deaminase (ADA) deficiency. Other cells which are optionally transfected or transduced either ex vivo or in vivo include purified stem cells (of embryonic or later ontogeny), as described above.

Cells expressing tmpk/detection cassette optionally express a therapeutic gene, for example a therapeutic gene described herein.

Host Cells

The application also relates to a host cell (isolated cell in vitro, a cell in vivo, or a cell treated ex vivo and returned to an in vivo site) containing a nucleic acid molecule of the application.

The term "a cell" includes a single cell as well as a plurality or population of cells. Administering a composition to a cell includes both in vitro and in vivo administrations Cells transfected with a nucleic acid molecule such as a DNA molecule, or transduced with the nucleic acid molecule such as a DNA or RNA virus vector construct, are optionally used, for example, in bone marrow or cord blood cell transplants according to techniques known in the art. Examples of the use of transduced bone marrow or cord blood cells in transplants are for ex vivo gene therapy of Adenosine deaminase (ADA) deficiency. Other cells which are optionally transfected or transduced either ex vivo or in vivo include purified stem cells (of embryonic or later ontogeny), as described above.

In certain embodiments, the cell is a cancer cell.

The term "cancer cell" includes cancer or tumor-forming cells, transformed cells or a cell that is susceptible to becoming a cancer or tumor-forming cell.

Cell Types for Transplant

Modified tmpk/detection cassette fusion molecules are usefully introduced into any cell type ex vivo where it is desirable to provide a mechanism for killing the modified tmpk/detection cassette fusion expressing cells. Cell types that are useful in one embodiment of the present application include, but are not limited to, stem cells (both embryonic and of later ontogeny as well as mesenchymal stem cells, induced pluripotent stem cells (IPS)), cord blood cells, and immune cells such as T cells, bone marrow cells and peripheral blood mononuclear cells. T-cells are optionally CD4 positive, CD8 positive or double positive. In addition, T cells are optionally mature T cells. In one embodiment T cells are transduced with modified tmpk/detection cassette fusion molecules, isolated and transplanted in a host. In another embodiment the T cells are mature T cells. In an alternate embodiment stem cells are transduced, isolated and transplanted in a host. In a further embodiment, IPS cells are transduced, isolated and transplanted in a host. In yet a further embodiment, mesenchymal stem cells are transduced isolated and transplanted in a host.

Cell lines are optionally transduced. For example human T cell leukemia Jurkat T cells, human erythro-leukemic K562 cells, human prostate cell lines DU145 and PC3 cells are optionally transduced or transfected with modified tmpk/detection cassette fusion molecules.

Tissue Specific Expression

In an alternate embodiment of the application, the modified tmpk/detection cassette fusion expressing cells express tmpk/detection cassette fusion under the control of a tissue or cell specific promoter providing expression in a tissue specific manner. Expression of modified tmpk/detection cassette fusion molecules is optionally targeted to tumor cells using promoters that are active in tumor cells.

Accordingly, in one aspect of the application, vector constructs comprising modified tmpk/detection cassette fusion molecules are provided that result in tissue or cell specific expression of the modified tmpk/detection cassette fusion molecules. Tissue and cell specific expression of modified tmpk/detection cassette fusion is typically accomplished using promoters operably linked with the modified tmpk/detection cassette fusion, which limit expression of modified tmpk/detection cassette fusion to cells or tissues. One skilled in the art will recognize that a variety of promoter sequences that direct tissue or cell specific expression are useful to direct tissue or cell specific expression of modified tmpk/detection cassette fusion. For example, one skilled in the art will readily recognize that liver specific expression is accomplished using a liver specific promoter. Modified tmpk/detection cassette fusion expression is readily limited to a variety of cell and tissue types. Examples include, but are not limited to, liver, pancreas and T cells. Examples of liver specific promoters include, but are not limited to, the transthyretin promoter, albumin promoter, alpha feto protein promoter. Examples of other cell specific promoters include, but are not limited to, islet cell specific promoters such as the insulin promoter, and T cell specific promoters such as CD4-promoter. In another embodiment, expression of modified tmpk/detection cassette fusion is inducible. The hypoxia-inducible promoter is optionally used to direct expression of a cytoprotective gene such as but not limited to erythropoietin. Introduction of a cytoprotective gene under the control of an inducible promoter such as the hypoxia inducible promoter is useful, to prevent the severe tissue damage by hypoxia.

If the transduced cells cause some problems or if it is otherwise desirable to clear the transduced cells, the transduced cells are optionally cleared (killed) by suicide effect by administering prodrug to the transduced cells or subject.

Tumor cell specific expression is accomplished using a tumor specific promoter. Tumor specific promoters comprise the progression elevated gene-3 (PEG-3) promoter. This promoter functions selectively in divergence cancer cells with limited activity in normal cells, for tumor cell-specific expression. The transduced tumor cells are specifically killed by the prodrug.

Methods of Isolation

In one aspect of the present application, methods for expressing a modified tmpk/detection cassette fusion molecule in cells for transplant are provided. After transduction or transfection with vector constructs comprising modified tmpk detection cassette fusion molecules or control molecules, cells expressing these molecules are optionally isolated by a variety of means known in the art. As the detection cassette is fused to tmpk, detection of cells expressing the detection cassette protein or nucleic acid identify cells expressing tmpk. Accordingly the molecule encoded by the detection cassette is used to isolate modified tmpk/detection cassette fusion positive cells. In certain embodiments, the cells are isolated by cell sorting or flow cytometry using an antibody to the detection cassette encoded molecule. Additionally cell sorting is useful to isolate modified tmpk/detection cassette fusion expressing cells where the detection cassette is a fluorescent protein such as EGFP. Cells expressing modified tmpk/detection cassette fusion or control molecules are, in an alternate embodiment, isolated using magnetic sorting. Additionally, cells may be isolated by drug selection. In one embodiment, a vector comprising a drug resistance gene and a modified tmpk/detection cassette fusion molecule is introduced into cells. Examples of drug resistance genes include, but are not limited to, neomycin resistance gene, blasticidin resistance gene (Bsr), hygromycin resistance gene (Hph), puromycin resistance gene (Pac), Zeocin resistance gene (Sh ble), FHT, bleomycin resistance gene and ampicillin resistance gene After transduction or transfection, cells expressing modified tmpk/detection cassette fusion or control molecules and the drug resistance gene are selected by adding the drug that is inactivated by the drug resistance gene. Cells expressing the drug resistance gene survive while non-transfected or non-transduced cells are killed. A person skilled in the art would be familiar with the methods and reagents required to isolate cells expressing modified tmpk/detection cassette fusion molecules.

Methods of and Uses for Treatment

Treatment of Cancer

The present application provides modified tmpk/detection cassette fusion molecules that are useful for the reduction of cell proliferation, for example for treatment of cancer. The present application also provides methods of expressing modified tmpk/detection cassette fusion molecules for the reduction of cell proliferation, for example for treatment of cancer.

Modified tmpk/detection cassette fusion is introduced into cells that are used for transplant or introduced directly in vivo in mammals, preferably a human. The modified tmpk/detection cassette fusion molecules are typically introduced into cells ex vivo (e.g. in vitro) using methods known in the art. Methods for introducing tmpk/detection cassette fusion molecules comprise transfection, infection, electroporation. These methods optionally employ liposomes or liposome like compounds.

In one embodiment, modified tmpk/detection cassette fusion molecules are used to treat cancer by adoptive therapy. Adoptive therapy or adoptive (immuno)therapy refers to the passive transfer of immunologically competent tumor-reactive cells into the tumor-bearing host to, directly or indirectly, mediate tumor regression. The feasibility of adoptive (immuno)therapy of cancer is based on two fundamental observations. The first of these observations is that tumor cells express unique antigens that can elicit an immune response within the syngeneic (genetically identical or similar especially with respect to antigens or immunological reactions) host. The other is that the immune rejection of established tumors can be mediated by the adoptive transfer of appropriately sensitized lymphoid cells. Clinical applications include transfer of peripheral blood stem cells following non-myeloablative chemotherapy with or without radiation in patients with lymphomas, leukemias, and solid tumors.

In one aspect of the present application, donor T cells or stem cells (either embryonic or of later ontogeny) are transduced with vectors comprising modified tmpk/detection cassette fusion molecules. Cells expressing said modified tmpk/detection cassette fusion are isolated and adoptively transferred to a host in need of treatment. In one embodiment the bone marrow of the recipient is T-cell depleted. Methods of adoptive T-cell transfer are known in the art (J Translational Medicine, 2005 3(17): doi; 0.1186/1479-5876-3-17, Adoptive T cell therapy: Addressing challenges in cancer immunotherapy. Cassian Yee). This method is used to treat solid tumors and does not require targeting the modified tmpk/detection cassette fusion expressing T-cells to the tumor since the modified tmpk/detection cassette fusion donor T-cells will recognize the different MHC class molecules present in the recipient host resulting in cytotoxic killing of tumor cells.

Another aspect of the application provides for the treatment of solid tumors by injecting vectors carrying modified tmpk/detection cassette fusion molecules directly into the tumor. Methods of introducing modified tmpk/detection cassette fusion directly in vivo in a mammal, preferably a human, comprise direct viral delivery, microinjection, in vivo electroporation, and liposome mediated methods.

Thymidine kinase has been introduced by injection directly into the site of a tumor to examine results of the technique as a cancer therapeutic treatment (Chevez-Barrios P, Chintagumpala M, Mieler W, Paysse E, Boniuk M, Kozinetz C, Hurwitz M Y, Hurwitz R L. Response of retinoblastoma with vitreous tumor seeding to adenovirus-mediated delivery of thymidine kinase followed by ganciclovir. J Clin Oncol. 2005 Nov. 1; 23(31):7927-35. Sterman D H, Treat J, Litzky L A, Amin K M, Coonrod L, Molnar-Kimber K, Recio A, Knox L, Wilson J M, Albelda S M, Kaiser L R. Adenovirus-mediated herpes simplex virus thymidine kinase/ganciclovir gene therapy in patients with localized malignancy: results of a phase I clinical trial in malignant mesothelioma. Hum Gene Ther. 1998 May 1; 9(7):1083-92). The tmpk/detection cassette fusion molecules of the present application are optionally introduced directly into the site of a tumor to reduce proliferation of tumor cells, for example, to treat cancer.

In one embodiment, cells are transfected or transduced ex vivo with modified tmpk/detection cassette fusion vector constructs. In an optional embodiment, the vector construct comprises a lentiviral vector.

Graft Versus Leukemia

In addition, the application provides, in one aspect, a method of treating leukemia. Donor T cells or stem cells are transduced with vectors comprising modified tmpk/detection cassette fusion molecules, cells expressing said modified tmpk/detection cassette fusion are isolated and transplanted to a host in need of treatment. The transplanted cells induce a graft versus leukemia effect. If the transplanted cells induce graft versus host disease, the transplanted cells can be killed by administering a prodrug.

Graft versus leukemia refers to using donor transplant cells to kill host leukemic cells. Introduced cells will often also attack the cancer cells that still may be present after transplant. This was first documented in acute leukemia, and this phenomenon has been called "graft-versus-leukemia" effect. Similar effects have been observed in malignant lymphoma, myeloma, and perhaps even some solid tumors. For certain diseases, such as chronic myelogenous leukemia (CML), the graft-versus-leukemia (GvL) effect may well be the most important reason that allogeneic transplants are successful in curing the disease.

Method of Treating Graft Versus Host Disease (GVHD)

Graft versus host disease is a common complication of allogeneic bone marrow transplantation (BMT). After bone marrow transplantation, T cells present in the graft, either as contaminants or intentionally introduced into the host, attack the tissues of the transplant recipient. Graft-versus-host disease can occur even when HLA-identical siblings are the donors. HLA-identical siblings or HLA-identical unrelated donors (called a minor mismatch as opposed to differences in the HLA antigens, which constitute a major mismatch) often still have genetically different proteins that can be presented on the MHC.

Graft versus host disease is a serious complication of transplant and can lead to death in patients that develop severe graft versus host disease (the clinical manifestations of graft versus host disease are reviewed in Socie G. Chronic graft-versus-host disease: clinical features and grading systems. Int J. Hematol. 2004 April; 79(3):216-20). Viral thymidine kinase has been introduced into transplant cells and used in combination with drugs such as ganciclovir to determine the results in individuals who develop graft versus host disease. (Bonini C, Ferrari G, Verzeletti S, Servida P, Zappone E, Ruggieri L, Ponzoni M, Rossini S, Mavilio F, Traversari C, Bordignon C HSV-TK gene transfer into donor lymphocytes for control of allogeneic graft-versus-leukemia. Science. 1997 June. 13; 276(5319):1719-24; Bondanza A, Valtolina V, Magnani Z, Ponzoni M, Fleischhauer K, Bonyhadi M, Traversari C, Sanvito F, Toma S, Radrizzani M, La Seta-Catamancio S, Ciceri F, Bordignon C, Bonini C Suicide gene therapy of graft-versus-host disease induced by central memory human T lymphocytes. Blood. 2005.)

While donor T-cells are undesirable as effector cells of graft-versus-host-disease, they are valuable for engraftment by preventing the recipient's residual immune system from rejecting the bone marrow graft (host-versus-graft). Additionally, as bone marrow transplantation is frequently used to cure malignant disorders (most prominently the leukemias), donor T-cells have proven to have a valuable graft-versus-tumor (GVT, graft versus leukemia described above) effect. A great deal of current research on allogeneic bone marrow transplantation involves attempts to separate the undesirable graft-vs-host-disease aspects of T-cell physiology from the desirable graft-versus-tumor effect.

The present application provides, in one embodiment, methods of treating transplant patients that develop graft versus host disease by administering compounds of the application (eg. tmpk/detection cassette fusion molecules, constructs or compositions used in combination with drugs) to a mammal in need thereof. In another embodiment, the application provides a method of promoting graft versus tumor effect by administering compounds of the application to a mammal in need thereof.

Treating Inherited Genetic Diseases and Safety Component for Gene Therapy

One problem with the use of gene therapy to stably introduce exogenous polynucleotides is the potential to develop a gene therapy related disease such as cancer. A gene therapy vector can integrate into a DNA region that could cause cancer in the gene therapy patient.

In one embodiment of the application, tmpk/detection cassette fusion molecules are useful as a safety component in gene therapy constructs. It is clear to one skilled in the art that the tmpk/detection cassette fusion mutants are useful in combination with different therapeutic polynucleotides designed to treat a variety of conditions. The tmpk/detection cassette fusions are useful in combination with a therapeutic polynucleotide that encodes a polypeptide that compensates for a deficient gene product. Examples of diseases that comprise a deficient gene product include, but not are limited to, Factor IX deficiency, Factor VIII deficiency, Gaucher disease, SCID, MPS, cystic fibrosis, Fabry disease, Farber disease, sickle cell disease, chronic granulomatous disorder (CGD). In this aspect of the application, vectors comprising a tmpk/detection cassette fusion and a deficient gene are introduced into cells ex vivo such as bone marrow cells or provided systemically to a patient deficient in the gene product. Systemically introduced vectors can integrate into host cells forming gene-modified cells. If the gene-modified cells cause a gene therapy related disease in the recipient model, a prodrug is administered to the recipient that kills the gene-modified cells.

Isolated Virus

Another aspect relates an isolated virus comprising a viral genome that encodes:

- a modified mammalian thymidylate kinase (tmpk) polynucleotide wherein the modified mammalian tmpk polynucleotide encodes a modified mammalian tmpk polypeptide that increases phosphorylation of a prodrug relative to phosophorylation of the prodrug by wild type mammalian tmpk polypeptide;
- a detection cassette polynucleotide fused to the tmpk polynucleotide;

wherein the isolated virus is infective for a mammalian cell. A person skilled in the art would readily recognize that a number of minimal elements are necessary for infection as described herein. For example flanking LTR sequences are necessary in retroviruses for genomic integration, a promoter operably linked to the insert polynucleotide eg. the tmpk/detection cassette fusion.

A person skilled in the art would readily understand that an RNA virus comprises a RNA genome such that corresponding RNA components and sequences of the components and sequences described herein would be found in an RNA virus genome. Accordingly sequences such as tmpk/detection cassette fusion sequences described herein also include sequences wherein T is optionally substituted with U.

Methods of making and isolating virus are described herein, for example in the Examples and further are known in the art.

The isolated virus can be a retrovirus, optionally a lentivirus or an adenovirus. Other viruses described herein are also contemplated. In an embodiment, the isolated virus is a clinical grade virus.

The modified tmpk and the detection cassette are optionally any modified tmpk and detection cassettes described herein.

In an embodiment, the isolated virus further comprises a therapeutic cassette, optionally any therapeutic cassette described herein, including adenosine deaminase, γc interleukin receptor subunit, α-galactosidase A, codon optimized α-galactosidase A, acid ceramidase, galactocerebrosidase, and CFTR molecules.

The isolated virus optionally infects a mammalian cell, optionally wherein the mammalian cell is selected from the group consisting of a stem cell, an embryonic stem cell, a mesenchymal stem cell, an induced pluripotent stem (IPS) cell, a hematopoietic cell, a T cell and a human cell.

The application also provides uses for treating cancer, inherited genetic diseases and cancer.

Further the application provides compositions, vector constructs the actuable destruction component, isolated viruses or cells expressing tmpk/detection cassette fusions for use as a pharmaceutical.

Also provides compositions, vector constructs the actuable destruction component, isolated viruses or cells expressing tmpk/detection cassette fusions, for treating cancer, for treating GVHD, or for treating an inherited genetic disorder (e.g gene therapy).

Furthermore, use of compositions, vector constructs the actuable destruction component, isolated viruses or cells expressing tmpk/detection cassette fusions for the manufacture of a medicament for treating cancer, for treating GVHD, or for treating an inherited genetic disorder (e.g gene therapy) is also provided.

Polynucleotides of Interest/Therapeutic Nucleic Acid Molecules

Cells transfected or transduced in vitro can be used for ex vivo gene therapy or as a research tool or for protein production. The nucleic acid molecules are also useful for gene therapy by transfecting or transducing cells in vivo to express a therapeutic polynucleotide/protein in addition to modified tmpk/detection cassette fusion. The therapeutic polynucleotide is alternatively referred to herein as the therapeutic cassette and/or therapeutic expression cassette. For example, if one were to upregulate the expression of a gene, one could insert the sense sequence into the nucleic acid molecule. If one were to downregulate the expression of the gene, one could insert the antisense sequence into the therapeutic expression cassette. Techniques for inserting sense and antisense sequences (or fragments of these sequences) would be apparent to those skilled in the art. The therapeutic nucleic acid molecule or nucleic acid molecule fragment may be either isolated from a native source (in sense or antisense orientations) or synthesized. It may also be a mutated native or synthetic sequence or a combination of these.

Examples of therapeutic coding nucleic acid molecules to be expressed include adenosine deaminase (ADA), γc interleukin receptor subunit, α-galactosidase A, codon optimized α-galactosidase A acid ceramidase, galactocerebrosidase, and transmembrane conductance regulator (CFTR) molecules.

Drug Discovery Platform

The present application also provides assays for identifying novel thymidine and uracil analog compounds that are useful as prodrugs in combination with modified tmpk/detection cassette fusion molecules. The thymidine analogs can be synthesized according to methods known in the art (J Med. Chem. 1996 39(17):3412-7 Synthesis and evaluation of novel thymidine analogs as antitumor and antiviral agents. Chen X, Bastow K, Goz B, Kucera L S, Morris-Natschke S L, Ishaq K S) and tested for the use as substrates by modified tmpk/detection cassette fusion polypeptides. Alternatively libraries of thymidine or uracil analogs can be synthesized and screened for compounds that can act as substrates for modified tmpk/detection cassette fusion polypeptides. Methods for the synthesis of molecular libraries are known in the art (Novel nucleotide analogues as potential substrates for TMPK, a key enzyme in the metabolism of AZT. Muller H C, Meier C, Balzarini J, Reinstein J. Nucleosides Nucleotides Nucleic Acids. 2003; 22(5-8):821-3).

In one aspect of the present application, compounds are identified using rational drug design and tested for their use as substrates for modified tmpk/detection cassette fusion polypeptides.

In one embodiment the assay comprises, a cell-based assay comprising the steps of:

i) introducing a modified tmpk/detection cassette fusion molecule into a cell;
ii) providing a thymidine analog to the cell; and
iii) determining whether said thymidine analog is a substrate for said modified tmpk/detection cassette fusion.

In an alternate embodiment, the assay comprises a cell free assay comprising the steps of:

i) providing an enzymatically active modified tmpk/detection cassette fusion,
ii) providing a thymidine analog to the modified tmpk/detection cassette fusion;
iii) determining whether said thymidine analog is a substrate for said modified tmpk/detection cassette fusion.

The enzymatically active modified tmpk/detection cassette fusion can comprise an additional fusion such as a GST fusion protein. In one embodiment the assay is conducted in a test tube. In an alternative embodiment the assay is conducted in a micro-titer plate. The enzymatically active modified tmpk/detection cassette fusion can be free in solution or bound to beads such as sepharose beads. The determination of whether said thymidine analog is a substrate for said modified tmpk/detection cassette fusion can comprise the use radioactive phosphorus or non-radioactive means. The methods of assessing kinase activity and substrate utilization are well known in the art.

Pharmaceutical Compositions

The pharmaceutical compositions of this application used to treat patients having diseases, disorders or abnormal physical states could include an acceptable carrier, auxiliary or excipient.

The pharmaceutical compositions are optionally administered by ex vivo and in vivo methods such as electroporation, DNA microinjection, liposome DNA delivery, and virus vectors that have RNA or DNA genomes including retrovirus vectors, lentivirus vectors, Adenovirus vectors and Adeno-associated virus (AAV) vectors, Semliki Forest Virus. Derivatives or hybrids of these vectors are also useful.

Dosages to be administered depend on patient needs, on the desired effect and on the chosen route of administration. The expression cassettes are optionally introduced into the cells or their precursors using ex vivo or in vivo delivery vehicles such as liposomes or DNA or RNA virus vectors. They are also optionally introduced into these cells using physical techniques such as microinjection or chemical methods such as coprecipitation.

The pharmaceutical compositions are typically prepared by known methods for the preparation of pharmaceutically acceptable compositions which are administered to patients, and such that an effective quantity of the nucleic acid molecule is combined in a mixture with a pharmaceutically acceptable vehicle. Suitable vehicles are described, for example in Remington's Pharmaceutical Sciences (Remington's Pharmaceutical Sciences, Mack Publishing Company, Easton, Pa., USA).

On this basis, the pharmaceutical compositions could include an active compound or substance, such as a nucleic acid molecule, in association with one or more pharmaceutically acceptable vehicles or diluents, and contained in buffered solutions with a suitable pH and isoosmotic with the physiological fluids. The methods of combining the expression cassettes with the vehicles or combining them with diluents is well known to those skilled in the art. The composition could include a targeting agent for the transport of the active compound to specified sites within cells.

Method of Medical Treatment of Disease

Vectors containing the nucleic acid molecules of the application are typically administered to mammals, preferably humans, in gene therapy using techniques described below. The polypeptides produced from the nucleic acid molecules are also optionally administered to mammals, preferably humans. The application relates to a method of medical treatment of a mammal in need thereof, preferably a human, by administering to the mammal a vector of the application or a cell containing a vector of the application. A recipient, preferably human, who develops an adverse event, such as graft versus host disease, is typically administered a drug, such as AZT, that is a substrate for the modified tmpk molecules of the application. Diseases, such as blood diseases or neural diseases (neurodegenerative), that are readily treated are described in this application and known in the art (eg. diseases, such as thalassemia or sickle cell anemia that are treated by administering a globin gene as described in Canadian patent application no. 2,246,005). Blood diseases treatable by stem cell transplant include leukemias, myelodysplastic syndromes, stem cell disorders, myeloproliferative disorders, lymphoproliferative disorders phagocyte disorders, inherited metabolic disorders, histiocytic disorders, inherited erythrocyte abnormalities, inherited immune system disorders, inherited platelet abnormalities, plasma cell disorders, malignancies (See also, Medical Professional's Guide to Unrelated Donor Stem Cell Transplants, 4th Edition). Stem cell nerve diseases to be treated by neural stem cell transplantation include diseases resulting in neural cell damage or loss, eg. paralysis, Parkinson's disease, Alzheimer's disease, ALS, multiple sclerosis). The vector of the application is useful as a stem cell marker and to express genes that cause stem cells to differentiate (e.g. growth factor).

Gene Therapy

The application includes compositions and methods for providing a coding nucleic acid molecule to a subject such that expression of the molecule in the cells provides the biological activity of the polypeptide encoded by the coding nucleic acid molecule to those cells. A coding nucleic acid as used herein means a nucleic acid that comprises nucleotides which specify the amino acid sequence, or a portion thereof, of the corresponding protein. A coding sequence may comprise a start codon and/or a termination sequence.

The application includes methods and compositions for providing a coding nucleic acid molecule to the cells of an individual such that expression of the coding nucleic acid molecule in the cells provides the biological activity or phenotype of the polypeptide encoded by the coding nucleic acid molecule. The method also relates to a method for providing an individual having a disease, disorder or abnormal physical state with a biologically active polypeptide by administering a nucleic acid molecule of the present application. The method may be performed ex vivo or in vivo. Gene therapy methods and compositions are demonstrated, for example, in U.S. Pat. Nos. 5,869,040, 5,639,642, 5,928,214, 5,911,983, 5,830,880, 5,910,488, 5,854,019, 5,672,344, 5,645,829, 5,741,486, 5,656,465, 5,547,932, 5,529,774, 5,436,146, 5,399,346 and 5,670,488, 5,240,846. The amount of polypeptide will vary with the subject's needs. The optimal dosage of vector may be readily determined using empirical techniques, for example by escalating doses (see U.S. Pat. No. 5,910,488 for an example of escalating doses).

Various approaches to gene therapy may be used. The application includes a process for providing a human with a therapeutic polypeptide including: introducing human cells into a human, said human cells having been treated in vitro or ex vivo to insert therein a vector of the application, the human cells expressing in vivo in said human a therapeutically effective amount of said therapeutic polypeptide.

The method also relates to a method for producing a stock of recombinant virus by producing virus suitable for gene therapy comprising modified DNA encoding globin. This method preferably involves transfecting cells permissive for virus replication (the virus containing modified globin) and collecting the virus produced.

Cotransfection (DNA and marker on separate molecules) may be employed (see eg U.S. Pat. No. 5,928,914 and U.S. Pat. No. 5,817,492). As well, a detection cassette or marker (such as Green Fluorescent Protein marker or a derivative, CD19 or CD25) may be used within the vector itself (preferably a viral vector).

Polypeptide Production and Research Tools

A cell line (either an immortalized cell culture or a stem cell culture) transfected or transduced with a nucleic acid molecule of the application (or variants) is useful as a research tool to measure levels of expression of the coding nucleic acid molecule and the activity of the polypeptide encoded by the coding nucleic acid molecule.

The nucleic acid molecules are useful in research to deliver marker genes or antisense RNA to cells.

The application includes a method for producing a recombinant host cell capable of expressing a nucleic acid molecule of the application comprising introducing into the host cell a vector of the application.

The application also includes a method for expressing a polypeptide in a host cell of the application including culturing the host cell under conditions suitable for coding nucleic acid molecule expression. The method typically provides the phenotype of the polypeptide to the cell.

In these methods, the host cell is optionally a stem cell or a T cell.

Another aspect of the application is an isolated polypeptide produced from a nucleic acid molecule or vector of the application according to a method of the application.

EXAMPLES

The following non-limiting examples are illustrative of the present application:

Example 1

Materials and Methods cDNA Cloning of Human CD19 and Construction of Shuttle Vector

Full-length human CD19 (hCD19) cDNA was obtained by reverse transcriptase-polymerase chain reaction (RT-PCR) from the human Burkitt's lymphoma cell line (Raji) using primers CD19 F1 and CD19 R1 described below. The cloned PCR product was directly ligated into the TA-vector, pPCR-script SK(+)(Stratagene) to give pPCR-CD19full. A truncated form of hCD19 (CD19D), which has only the extracellular and transmembrane domains, but lacks the cytoplasmic domain, was generated by inverse-PCR from pPCR-script SK(+)-CD19 using primers CD19 F2 and CD19 R2 described below, to give pPCR-CD19D. Following the sequence confirmation of cDNA inserts in pPCR-script SK(+)-CD19D, the cloned cDNA fragments were then subcloned into the EcoRI site of the shuttle vector pSV-IRES to give pSV-IRES-CD19D. The primer sequences used for cloning of human CD19 cDNA as follows: CD19 F1: 5'-atgccacctcctcgcctcctcttcttcc-3' (SEQ ID NO: 23) and CD19 R1: 5'-tcacctggtgctccaggtgccc-3' (SEQ ID NO: 24). The truncated construct was made by inverse-PCR using primers CD19 F2: 5'-ccgccaccgcggtggagctccag-3' (SEQ ID NO: 25) and CD19 R2: 5'-ttaaagatgaagaatgcccacaaggg-3' (SEQ ID NO: 26).

cDNA Cloning of Human Thymidylate Kinase, Construction of Bicistoronic Lentiviral Expression Vectors and Preparation of High-Titer Virus To clone wild-type human thymidylate monophosphate kinase (tmpk) cDNA, peripheral blood mononuclear cells (PBMNCs) were isolated from heparinized blood obtained from healthy human donors by Ficoll-Hypaque (Amersham-Pharmacia) separations. Wild-type human tmpk cDNA was amplified by PCR using first strand complementary DNA (cDNA) generated by reverse-transcription from total RNA extracted from the PBMNCs using TRIZOL reagent (Invitrogen). PCR products for wild-type tmpk and each modified version of human tmpk cDNA, such as R200A, F105Y, and R16GLL, which was constructed by Dr. A. Lavie at the University of Illinois at Chicago, were subcloned into pPCR-scriptSK(+) and sequenced. Following the sequence confirmation, each cDNA was first subcloned into shuttle vector pSV-IRES-CD19D to construct a bicistronic cassette consisting the suicide gene, internal ribosomal entry site (IRES) derived from encephalomyocardiTUS virus (EMCV), and the truncated form of human CD19. This bicistronic expression cassette with tmpk and hCD19, flanked by an EMCV IRES. Then subcloned into HIV-1 based recombinant lentiviral plasmid vector used in the production of lentivirus, pHR'-cPPT-EF-W-SIN (pHR'). The expression of gene of interests was controlled by the internal EF1a promoter. As a control for the transduction experiments, the inventors used both pHR'-cPPT-EF-IRES-hCD19-W-SIN and pHR'-cPPT-EF-EGFP-W-SIN vectors carrying either IRES-hCD19 or the enhanced GFP (EGFP) cDNAs, respectively.

VSVG-pseudotyped LVs, including an EGFP marking vector (LV-EGFP), were generated by transient transfection of 293T cells (kindly provided by Dr. Robert Pawliuk, Division of Health Sciences and Technology, MIT, Cambridge, Mass.) using the three-plasmid system (the aforementioned LV plasmid constructs, the packaging plasmid pCMVΔR8.91, and the VSVG envelope encoding plasmid pMD.G). The transfections were performed with either FuGENE6 (Roche Applied Science, Indianapolis, Ind.) or CaPO4-precipitation methods. Viral supernatants were harvested 48 h later and concentrated by ultracentrifugation at 50,000×g for 2 h at 4° C. The concentrated viral supernatants were serially diluted and titered on 293T cells (ATCC, Manassas, Va.). Table 1 lists the titers of virus used in these experiments. Flow cytometric analyses were performed 72 h later using a FACSCalibur (BD Biosciences, San Jose, Calif.) for evaluating EGFP or hCD19 expression after staining with monoclonal PE-conjugated mouse anti-human CD19. Titers are expressed as infectious particles (IP)/mL.

TABLE 1

Titer of LVs on 293T cells used in this study

| Transgene | Detection | Titer (IP/mL) |
|---|---|---|
| EGFP | EGFP | $1.4 \times 10^8$ |
| Tmpk (wild-type)-IRES-hCD19 | CD19 | $2.3 \times 10^8$ |
| Tmpk (R200A)-IRES-hCD19 | CD19 | $3.5 \times 10^8$ |
| Tmpk (F105Y + R200A)-IRES-hCD19 | CD19 | $5.9 \times 10^8$ |
| Tmpk (R16G Large Lid)-IRES-hCD19 | CD19 | $1.5 \times 10^9$ |
| IRES-hCD19 | CD19 | $1.4 \times 10^9$ |

Transduction and Analysis of Transgene Expression by Flow Cytometric Analysis.

Human T lymphoma cell line, Jurkat, and human erythroleukemic cell line, K562, were maintained in RPMI 1640 supplemented with 10% FBS, 100 U/ml of penicillin, and streptomycin to 100 μg/ml. Cells were infected with concentrated virus stocks using an MOI of 10 in the presence of 8 μg/ml protamine sulfate. Infected cells were then kept in culture for 5 days prior to evaluating gene transfer efficiency. Gene transfer efficiencies were measured by flow cytometry using a monoclonal anti-human CD19-antibody conjugated with phycoerythrin (PE). About $10^6$ non-transduced and virally transduced cells were incubated for 15 min with the antibody or the corresponding $IgG_1$ isotype control antibody at 4° C. Cells were washed with phospahate-buffered saline (PBS). Cell analysis was performed on a FACS Calibur and data were analyzed using Cell Quest software. Single-cell clones were obtained by limiting dilution and clones with the highest expression of CD19 were selected.

Western Blot Analysis of Tmpk-Overexpression by LV-Transduction in Jurkat Cells.

Tmpk overexpression in the infected cells were examined by Western blot analysis using rabbit anti-human tmpk antibody (gift from Dr. Manfred Konrad, Maxplank Institute) as well as mouse anti-human beta-actin as an internal control for the blot. Total cell lysates were resolved by 12% SDS-polyacrylamide gels (SDS-PAGE) and transferred onto polyvinylidene difluoride filters (Millipore, Billerica, Mass.). Filters were blocked with 5% fat free skim milk in Tris-buffered saline (TBS) with 0.05% Tween 20 (TBST) for 1 hr at room temperature. Human tmpk overexpression was elucidated using rabbit anti-human tmpk antiserum, diluted to 1 in 5000. Protein loading amounts in each well was confirmed with an anti-beta actin antibody diluted 1:5000. Blots were probed with a secondary anti-rabbit IgG (diluted 1:5000) or anti-mouse IgG (diluted 1:5000) horseradish peroxidase-conjugated antibodies, and protein bands were detected using an enhanced chemiluminesence kit (Perkin Elmer, Norwalk, Conn.) and Kodak BioMAX XAR film.

Comparison of Transduction Efficiencies and hCD19 Expression Levels in LV-Transduced Jurkat Cells.

Cells were infected with concentrated virus stocks using an MOI of 10 in the presence of 8 μg/ml protamine sulfate. Infected cells were then kept in culture for 5 days prior to evaluating gene transfer efficiency. Gene transfer efficiencies were measured by flow cytometry using a monoclonal anti-human CD19-antibody conjugated to phycoerythrin (PE). About $10^6$ non-transduced and virally transduced cells were incubated for 15 min with the antibody or the corresponding $IgG_1$ isotype control antibody at 4° C. Cells were washed with phospahate-buffered saline (PBS). Cell analysis was performed on a FACS Calibur and data were analyzed using Cell Quest software. Single-cell clones were obtained by limiting dilution, and clones with the highest expression of CD19 were selected. Percentages indicate EGFP or CD19 expression and mean fluorescence intensity (MFI) values indicate the levels of expression levels in the cells.

Determination of AZT-Sensitivity of Jurkat (Human T Cell Line) Transduced with LV-tmpk-IRES-hCD19 and Mutant Forms.

Transduced Jurkat cells and the single-cell clones were seeded in 96 well plates ($2\times10^5$/well) in 200 μl of medium containing increasing concentrations of AZT (0, 1, 10 and 100 μM). The medium was changed daily. After 4 days of culture, cell viability was determined by MTT assay (Promega). **, P<0.01, n=3. Data are expressed as mean±standard error of mean (SEM).

Induction of Apoptosis by Addition of 100 μM AZT in LV-tmpk-Transduced Jurkat Cells.

Cells were seeded in 24 well plates ($10^6$/well) in 1 ml of medium with or without 100 μM of AZT. The medium was changed daily. After 4 days of culture, induction of apoptosis in the cells were analyzed by annexin-V staining according to the manufacturer's protocol (Annexin V-APC: BD Pharmingen). **, P<0.01, n=3. Data are expressed as mean±SEM.

Determination of AZT-Metabolites in the Cells Treated with 100 μM AZT.

The cells were cultured in the presence of 100 μM AZT for 36 hrs. $10^7$ cells were homogenized by sonication in 100 μl of 5% (w/v) trichloroacetic acid. The supernatant is collected after homogenate had been centrifuged at 10,000×g for 15 min at 4° C. The trichloroacetic acid was removed by extraction with an equal volume of 20% tri-n-octylamine in pentane. The neutralized aqueous fraction is directly injected into HPLC. Separation of AZT and its metabolites was performed on a C18 column (Waters) with a mobile phase composed of 0.2 M phosphate buffer containing 4 mM tetrabutylammonium hydrogen sulfate (pH 7.5) and acetonitrile in the ratio of 97:3 (v/v). The mobile phase was pumped at a flow rate of 1.5 ml/min. The UV absorbance was monitored at 270 nm. Five million cell equivalents were injected and analyzed in triplicate.

AZT-Mediated Loss of Mitochondrial Function is Induced by Expression of TMPK-LargeLid.

Cells ($10^6$ cells) treated with (shown (+) in figure) or without (−) 100 μM AZT were stained with JC-1 for 15 min at 37° C., and then were analyzed by flow cytometry. ***, P<0.001, n=3.

Cellular Proliferation is not Always a Prerequisite for AZT-Induced Apoptosis.

Cells were seeded in 24-well plates ($10^6$/well) in 1 ml of medium containing 0 (shown in AZT (−) in figure) or 100 μM of AZT (shown in AZT (+)) with or without 5 μM indirubin-3'-oxime (Figure (B) and (A), respectively). The medium was refreshed daily. After 2 days of culture, induction of apoptosis by AZT was analyzed by annexin V staining according to the manufacturer's protocol described. **, P<0.01, n=3. Data are expressed as mean±SEM.

Mutant Forms of tmpk Prevent Growth of Transduced K562 Cells Xenografted into AZT-Treated NOD/SCID Mice.

Female or male 5 to 8-week-old non-obese diabetic/severe combined immunodeficient (NOD/SCID) mice were purchased from Jackson Laboratory. Lentivirally-transduced or non-transduced K562 cells ($20\times10^6$ cells) were resuspended in 0.5 mL Dulbecco's phosphate-buffered saline (D-PBS) per inoculum and injected subcutaneously (SC) into the right flanks of recipient mice. AZT treatment, which was administered intraperitoneally (IP) at the dose of 2.5 mg/kg/day, was started one day after injection and conducted for 14 days. In vivo tumor cell growth was monitored by measuring tumor size for up to 32 days post-inoculations. All experimental data were reproduced at least twice.

Transduction of Primary Cultured Human or Mouse T Cells and Analysis of Transgene Expression Human T lymphocytes are obtained from peripheral blood mononuclear cells (PBMNCs) isolated from heparinized blood obtained from healthy human donors by Ficoll-Hypaque (Amersham-Pharmacia) separations. Mouse T are prepared from the spleen following B cell depletion using goat anti-mouse IgG beads. T cells are activated by using anti-CD3 and anti-CD28 coated beads in a ratio of 1:3 (cell: beads) with 20 IU/mL of recombinant human interleukin 2 for 3 days. Cells were infected with concentrated virus stocks using an MOI of indicated in the presence of 8 μg/ml protamine sulfate. Infected cells were then kept in culture for 5 days prior to evaluating gene transfer efficiency. Gene transfer efficiencies were measured by flow cytometry using a monoclonal anti-human CD19-antibody conjugated with phycoerythrin (PE). About $10^6$ non-transduced and virally transduced cells were incubated for 15 min with the antibody or the corresponding $IgG_1$ isotype control antibody at 4° C. Cells were washed with phospahate-buffered saline (PBS). Cell analysis was performed on a FACS Calibur and data were analyzed using Cell Quest software.

Statistical Analysis

Statistical analyses was performed using Instat 2.00 (GraphPad). The unpaired Student's t test was used to determine statistical significance. In some experiments, a one-way analysis of variance (ANOVA) with a Bonferroni post-test was used to determine statistically significant results.

Example 2

Generation and Titration of tmpk cDNA Carrying Lentiviral Vectors

Two bi-cistronic lentiviral vectors with either wild-type or mutant human tmpk cDNA located at the upstream of EMCV-IRES sequence and mutant form of human CD19 which was deleted intracellular domain were constructed (FIG. 1). These vectors were derived from LV-EGFP which is a lentiviral vector expressing enhanced GFP under the control of the internal elongation factor-alpha (EF1-a) promoter. The virus titers obtained for each transfer vector were shown in Table 1.

It is known that the expression level of downstream gene by IRES-dependent manner in the bicistronic vector is in between 20 to 50% of that of upstream gene. However, the IRES-dependent expression of downstream gene also depends on the cell-type. While no CD19-expression was seen in transduced-HeLa cells, the expression was detected in the transduced 293T cells. We, however, could detect EGFP expression in the transduced HeLa cells as well as that in 293T cells. These data indicate that when the inventors used the IRES-element for expressing the gene of interests on both upstream and down stream of IRES-sequence in lentiviral system, the inventors need to use 293T cells to measure the functional titer of the virus.

Example 3

Transduction of Jurkat Cells with Recombinant Lentiviruses

Figure 3:
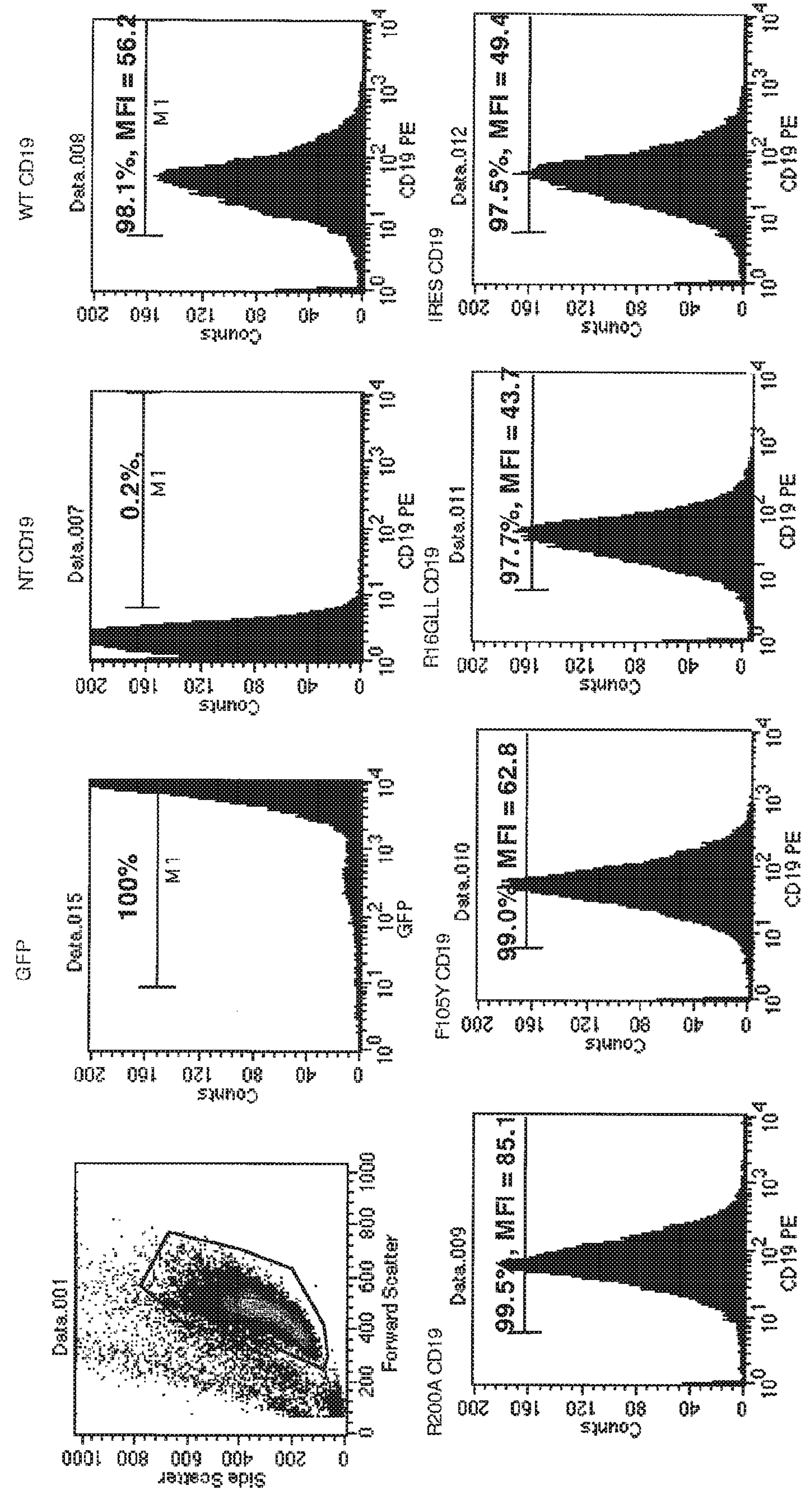
FIG. 3 is a series of graphs comparing transduction efficiencies and hCD19 expression levels in LV-transduced Jurkat cells. Percentages indicate EGFP or CD19 expression and mean fluorescence intensity (MFI) values indicate the levels of expression levels in the cells.

To compare the cell killing activity of each LV-constructs expressing tmpk cDNA, the inventors transduced human leukemia cell line Jurkat cells with using an MOI of 10 for 24 hrs. After 5 days of transduction, the inventors tested the CD19 expression in the transduced cells. While no CD19 expression was observed in non-transduced cells, strong CD19-expression was detected on each LV-transduced cells (FIG. 3). The mean fluorescent intensity of CD19 in each LV-transduced cells showed almost same levels indicates that that each LV-transduced cell expressed CD19 in a similar level.

Figure 2:
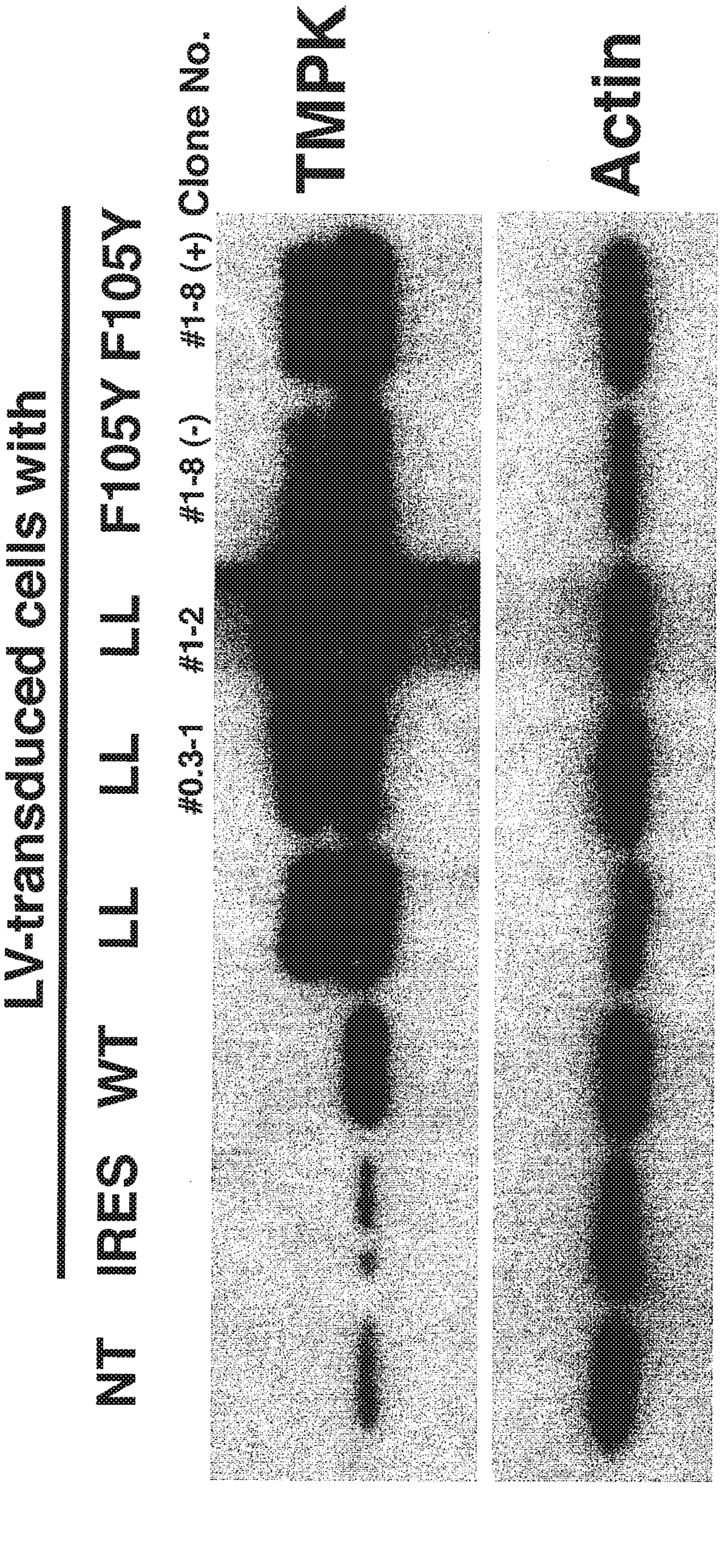
FIG. 2 shows a Western blot analysis of tmpk-overexpression by LV-transduction in Jurkat cells. NT: Non-transduced Jurkat cells, IRES: LV-IRES-hCD19-transduced Jurkat cells, WT: LV-(tmpk wild-type)-IRES-hCD19-transduced Jurkat cells, LL: LV-tmpk (R16G, Large lid)-IRES-hCD19-transduced Jurkat cells, F105Y: LV-tmpk (F105Y)-IRES-hCD19-transduced Jurkat cells.

To test the expression levels of the upstream gene in each LV-construct, the inventors examined Western blot analysis using both rabbit anti-human tmpk as well as rabbit anti-human beta actin as an internal control. Since tmpk is expressed endogenously in the non-transduced Jurkat cells, the inventors could see the tmpk-gene expression in the cells. Comparing the LV-IRES-hCD19-transduced cells and non-transduced cells, LV-tmpk (wild-type; WT)-IRES-hCD19 or LV-tmpk-mutant cDNA-IRES-hCD19-transduced cells showed an increase of tmpk expression in the cells up to 10 times (FIG. 2).

Example 4

Measure AZT-Sensitivity of the Transduced Cells

Figure 4:
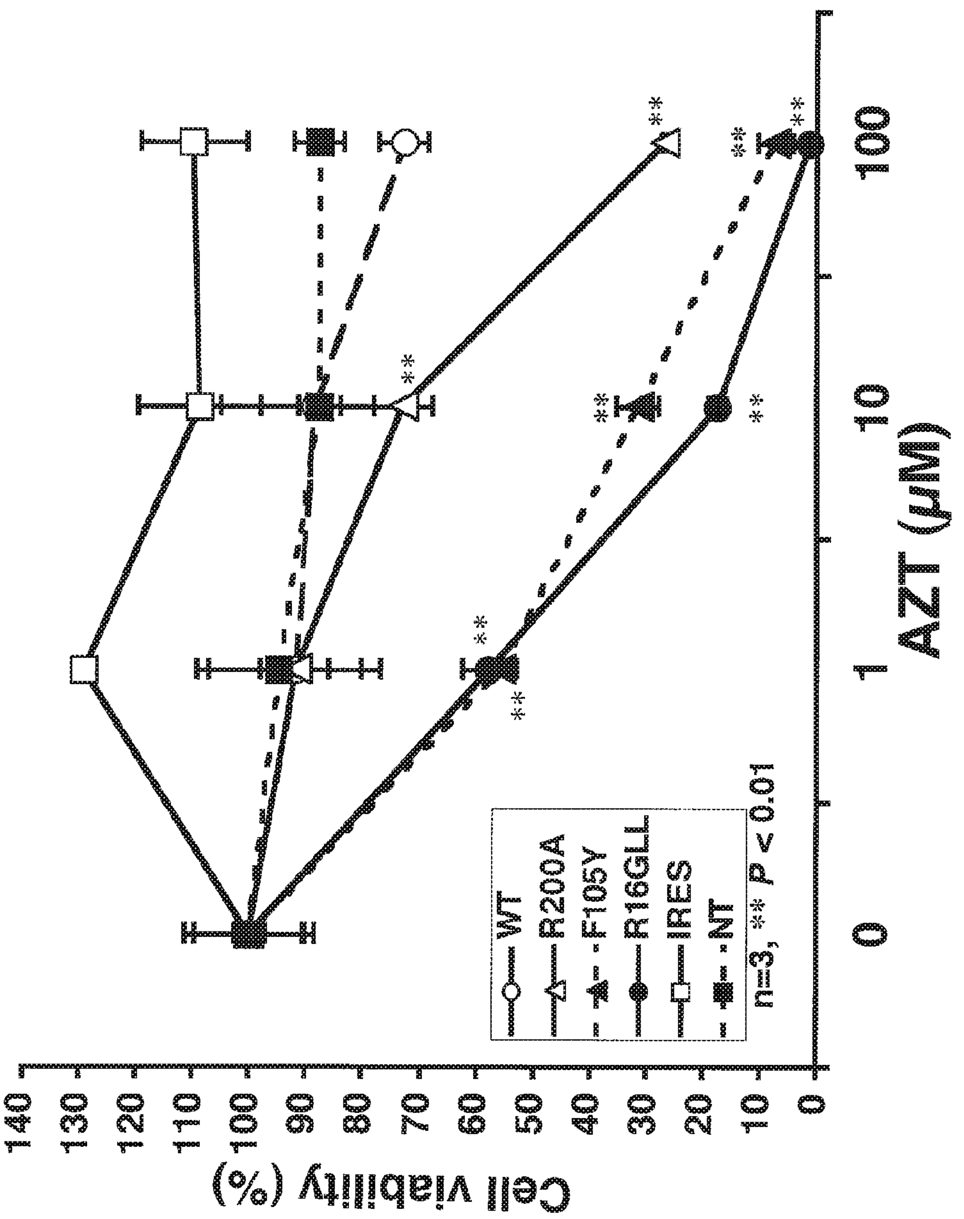
FIG. 4A is a graph illustrating the AZT-sensitivity of Jurkat cells (human T cell line) transduced with LV-tmpk-IRES-hCD19 and mutant tmpk forms. Cell viability was determined by MTT assay (Promega). **, $P<0.01$, n=3. Data are expressed as mean±standard error of mean (SEM).
FIG. 4B is a series of plots showing annexinV staining.
Figure 4:
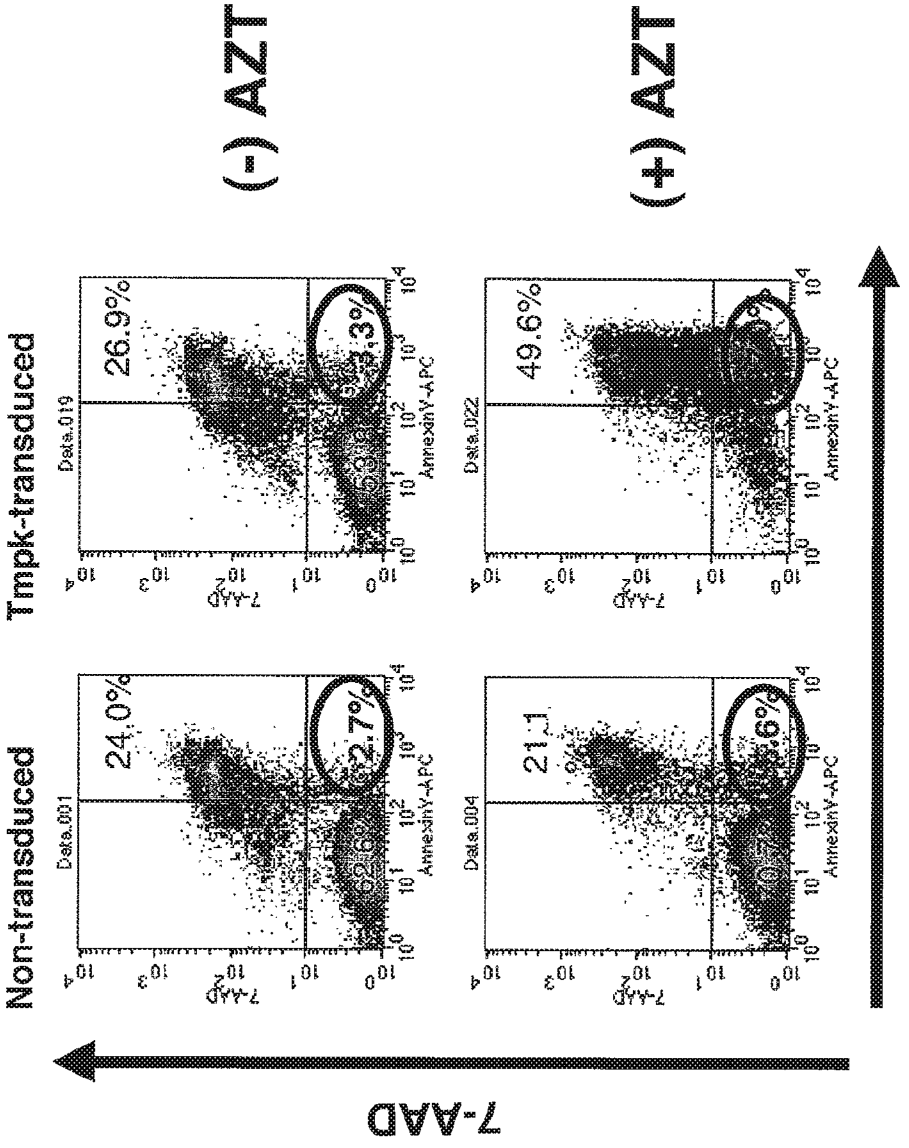
Figure 5:
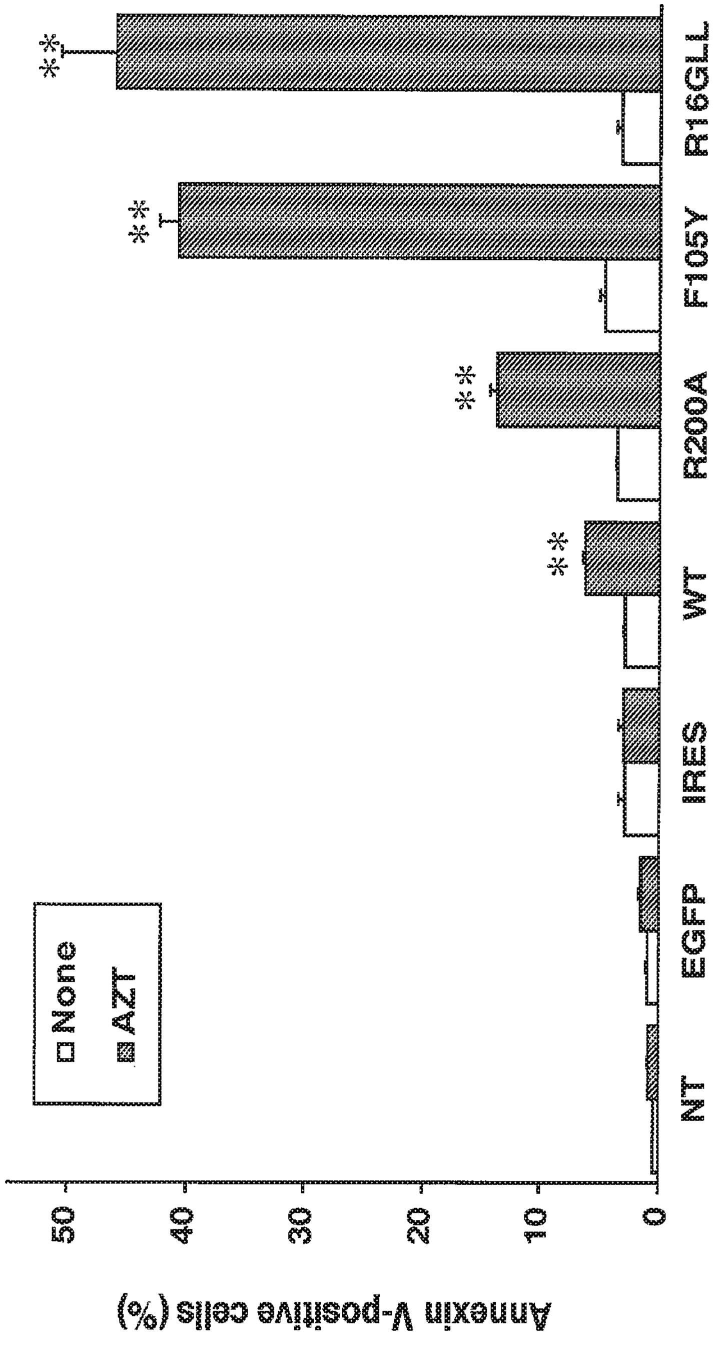
FIG. 5 is a graph illustrating the induction of apoptosis by the addition of 100 μM AZT in LV-tmpk-transduced Jurkat cells. Cells were seeded in 24 well plates ($10^6$/well) in 1 ml of medium with or without 100 μM of AZT. The medium was changed daily. After 4 days of culture, induction of apoptosis in the cells was analyzed by annexin-V staining according to the manufacturer's protocol (Annexin V-APC: BD Pharmingen). **, $P<0.01$, n=3. Data are expressed as mean±SEM.

To examine the AZT-mediated cellkilling activity of tmpk cDNA, each of transduced cells were incubated with the increasing concentration of AZT. After incubating both non-transduced and LV-transduced cells with AZT for 5 days, cell viability was determined using MTT assay (FIG. 4A). These transduced cells were efficiently and selectively killed in a dose-dependent manner by AZT ($IC_{50}$ of 2 μM), while wild-type tmpk transduced cells were non-sensitive to AZT up to 100 μM. Among of them, both LV-tmpk F105Y and LV-tmpk R16GLL transduced cells showed the dose-dependent cell killing activity. Since MTT assay reflects mitochondrial enzymatic activities in living cell to metabolize the MTT-assay substrate, AZT-metabolites supposed to inhibit mitochondrial function and induced cellular death. To confirm the induction of cellular death such as an apoptosis, the inventors next examined the induction of apoptosis following AZT-treatment in the tmpk-expressing cells by flowcytomeric analysis following the annexin V-staining of the cells. In response to AZT treatment, the early apoptotic cell indices of cells transduced with wild-type tmpk, F105Y or LL were 6.2±0.3%, 40.7±1.7%, and 46.1±4.6%, respectively (n=3). No induction of apoptosis by AZT was observed in the group of negative control group including non-transduced cells and IRES (FIG. 5). In contrast, significant increases in the apoptosis-induced cells were observed in the LV-tmpk transduced cells following AZT-treatment.

Example 5

Intracellular AZT Metabolite Concentration

Figure 6:
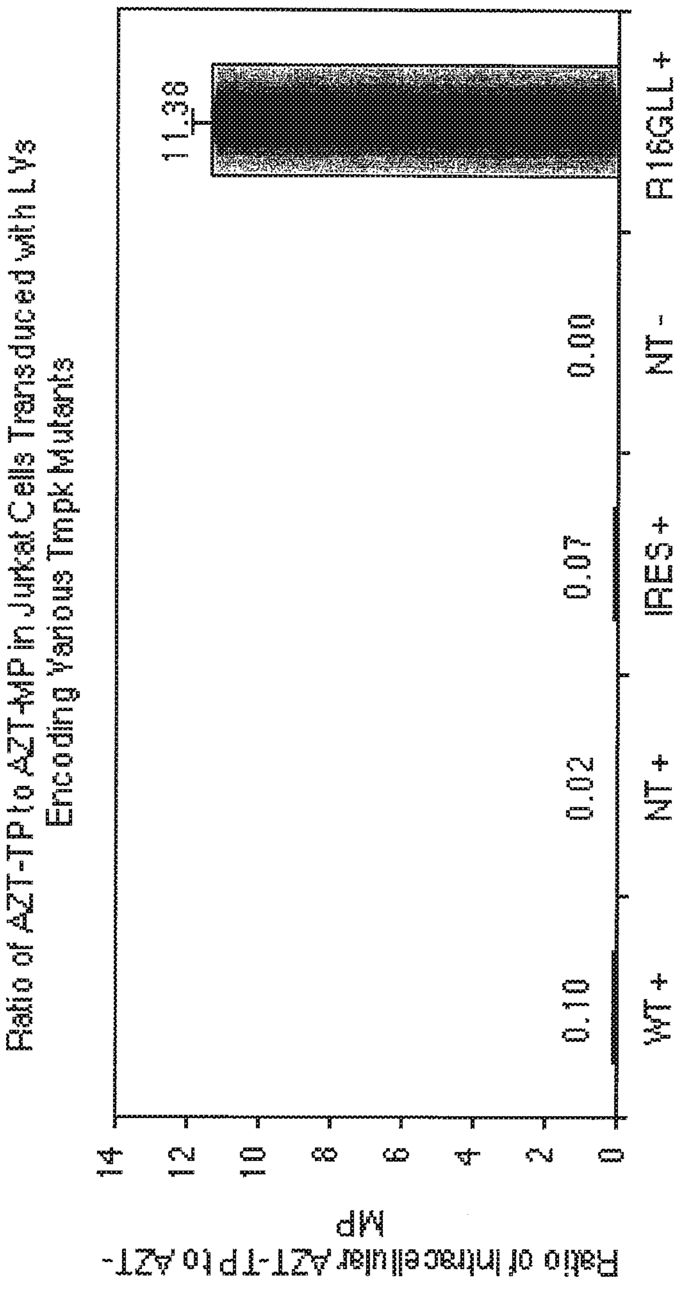
FIG. 6A is a graph showing the levels of AZT-metabolites in the cells treated with 100 μM AZT. The cells were cultured in the presence of 100 μM AZT for 36 hrs. $10^7$ cells were homogenized by sonication in 100 ml of 5% (w/v) trichloroacetic acid. The supernatant is collected after homogenate had been centrifuged at 10,000×g for 15 min at 4° C. The trichloroacetic acid was removed by extraction with an equal volume of 20% tri-n-octylamine in pentane. The neutralized aqueous fraction is directly injected into HPLC. Separation of AZT and its metabolites was performed on a C18 column (Waters, Milford Mass.) with a mobile phase composed of 0.2 M phosphate buffer containing 4 mM tetrabutylammonium hydrogen sulfate (pH 7.5) and acetonitrile in the ratio of 97:3 (v/v). The mobile phase was pumped at a flow rate of 1.5 ml/min. The UV absorbance was monitored at 270 nm. Five million cell equivalents were injected and analyzed in triplicate.
FIG. 6B Determination of AZT metabolites in transduced clonal Jurkat cell lines and controls treated with 100 μM AZT. (a) Representative chromatograms for the NT cells and the tmpk R16G-mutant expressing cells. Each arrow indicates the position of a peak of the standard for AZT-MP, AZT-DP, and AZT-TP, respectively. (b) Comparison of the ratio of the intracellular AZT-TP to AZT-MP in the AZT-treated cells. Data are mean±SEM, n=3. The statistical differences were evaluated by the one-way analysis of variance (ANOVA) followed by a Bonferroni post-hoc test with the level of significance set at $P<0.05$.
Figure 6:
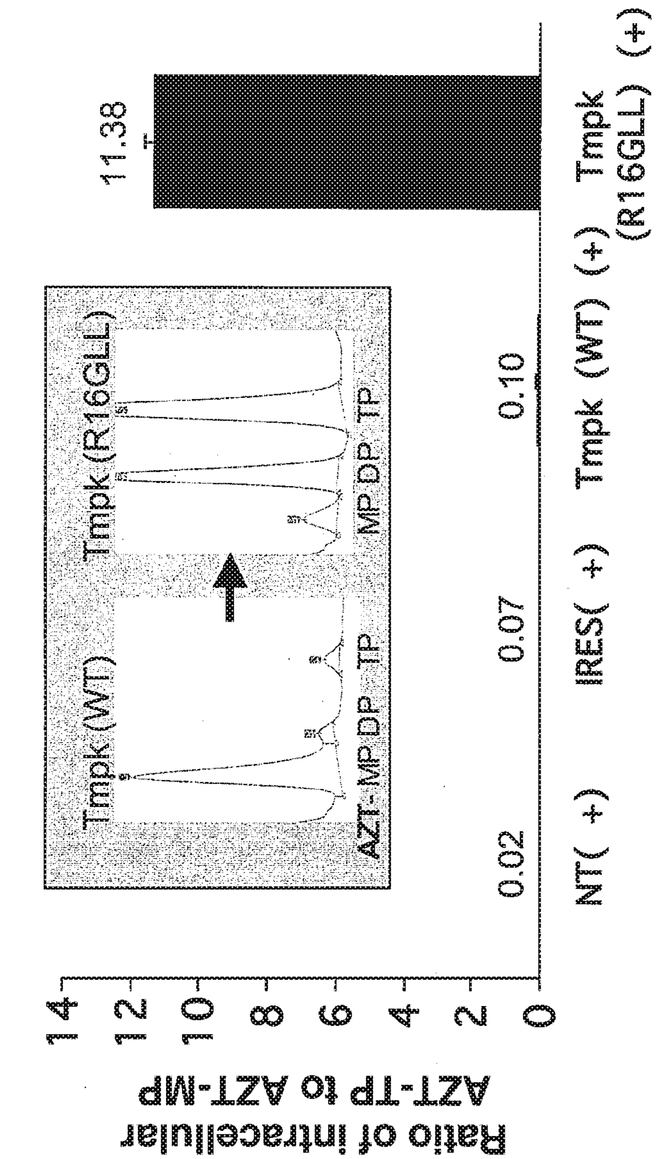

To evaluate the intracellular concentration of AZT-antimetabolites in the cells, the inventors have established by HPLC. After treatment of the cells transduced with the tmpk LL with AZT, they efficiently convert AZT into the active antimetabolite form, AZT-triphosphate (AZT-TP) (conversion ratio of AZT-TP to AZT MP 11.3 compared to 0.02 in non-transduced cells) (FIG. 6). Conversion of AZT-TP by cells transduced with wild-type tmpk (conversion ratio of 0.10) is only marginally better than the conversion in non-transduced cells (FIG. 6).

Example 6

Figure 7:
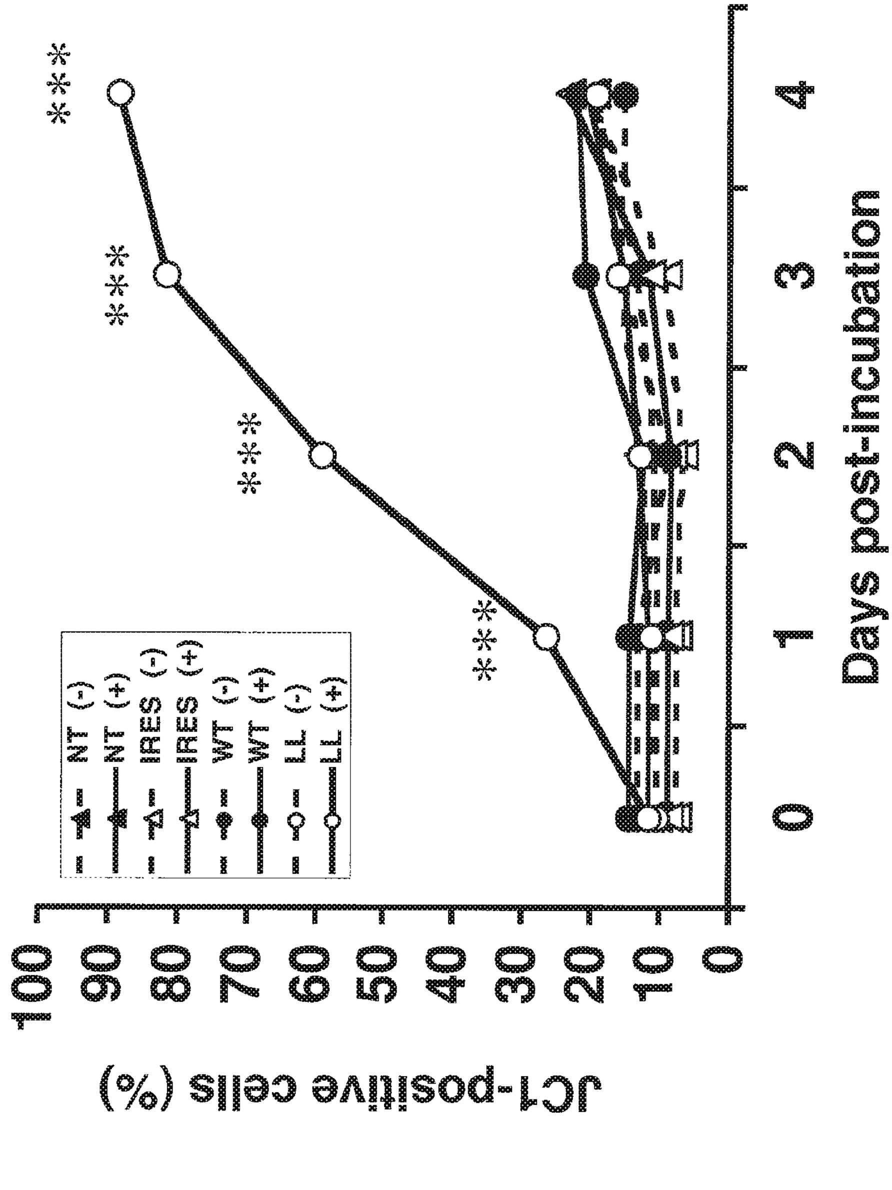
FIG. 7 is a graph showing that LV-tmpk-transduced Jurkat cells exhibit an increase in the loss of mitochondrial membrane potential following incubation of the cells with AZT. Cells ($10^6$ cells) treated with (shown (+) in figure) or without (−) 100 μM AZT were stained with JC-1 for 15 min at 37° C., and then were analyzed by flow cytometry. ***, $P<0.001$, n=3.

AZT-Mediated Loss of Mitochondrial Function is Induced by Expression of TMPK-LargeLid AZT is a potent inhibitor of HIV replication. However, many patients treated with AZT develop toxic mitochondrial myopathy. Long-term AZT treatment has been shown to induce mitochondrial biochemical dysfunction in AIDS patients. In order to prove the mechanism of the induction of cellular apoptosis after AZT-treatment in the tmpk-transduced cells, the inventors measured the membrane potential of mitochondria by analyzing the decrease of the percentage of red-fluorescence in the flow diagram followed by staining the cells with JC-1 reagent. A significant increase in the loss of mitochondrial membrane potential (Δψ) was found to occur in the LV-tmpk R16GLL transduced cells after AZT-treatment in a time dependent manner, however, negative control cell group cells did not increase the percentage of the mitochondrial membrane potential lose cells (FIG. 7).

Example 7

AZT/Tmpk Mediated Cell Killing does not Need Cellular Proliferation

Figure 8:
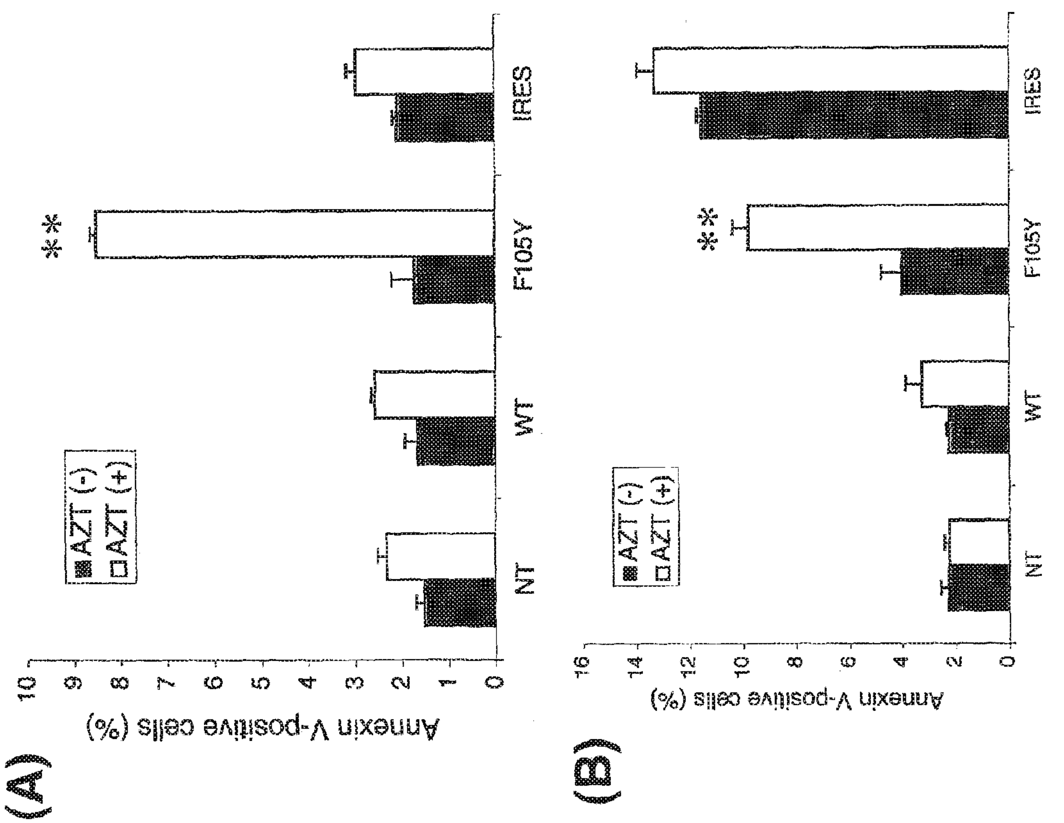
FIG. 8 is a series of graphs showing that AZT can induce apoptosis in the absence of cellular proliferation. Cellular proliferation is not always a prerequisite for AZT-induced apoptosis. Cells were seeded in 24-well plates ($10^6$/well) in 1 ml of medium containing 0 (shown in AZT (−) in figure) or 100 μM of AZT (shown in AZT (+)) with or without 5 μM indirubin-3'-oxime (Figure (B) and (A), respectively). The medium was refreshed daily. After 2 days of culture, induction of apoptosis by AZT was analyzed by annexin V staining according to the manufacturer's protocol described. **, $P<0.01$, n=3. Data are expressed as mean±SEM.

HSV1-tk mediated cell killing requires cellular proliferation for the cytotoxic effect. Here, the inventors have shown proliferation-independent cell killing using mutant tmpk and AZT. Indirubin-metabolites work as cyclin-dependent kinase inhibitors, which function by competing with ATP for binding to the catalytic subunit. They lead to G2/M arrest in many cell lines and G1/S arrest in Jurkat cells. Indirubin-3'-oxime was used to arrest cell cycling, and then transduced cells were treated with AZT. Only 2% of cells transduced with wild-type tmpk were killed, whereas the inventors attained 20% killing of cells transduced with LV-tmpkF105Y-IRES-hCD19 (FIG. 8).

Example 8

Figure 9:
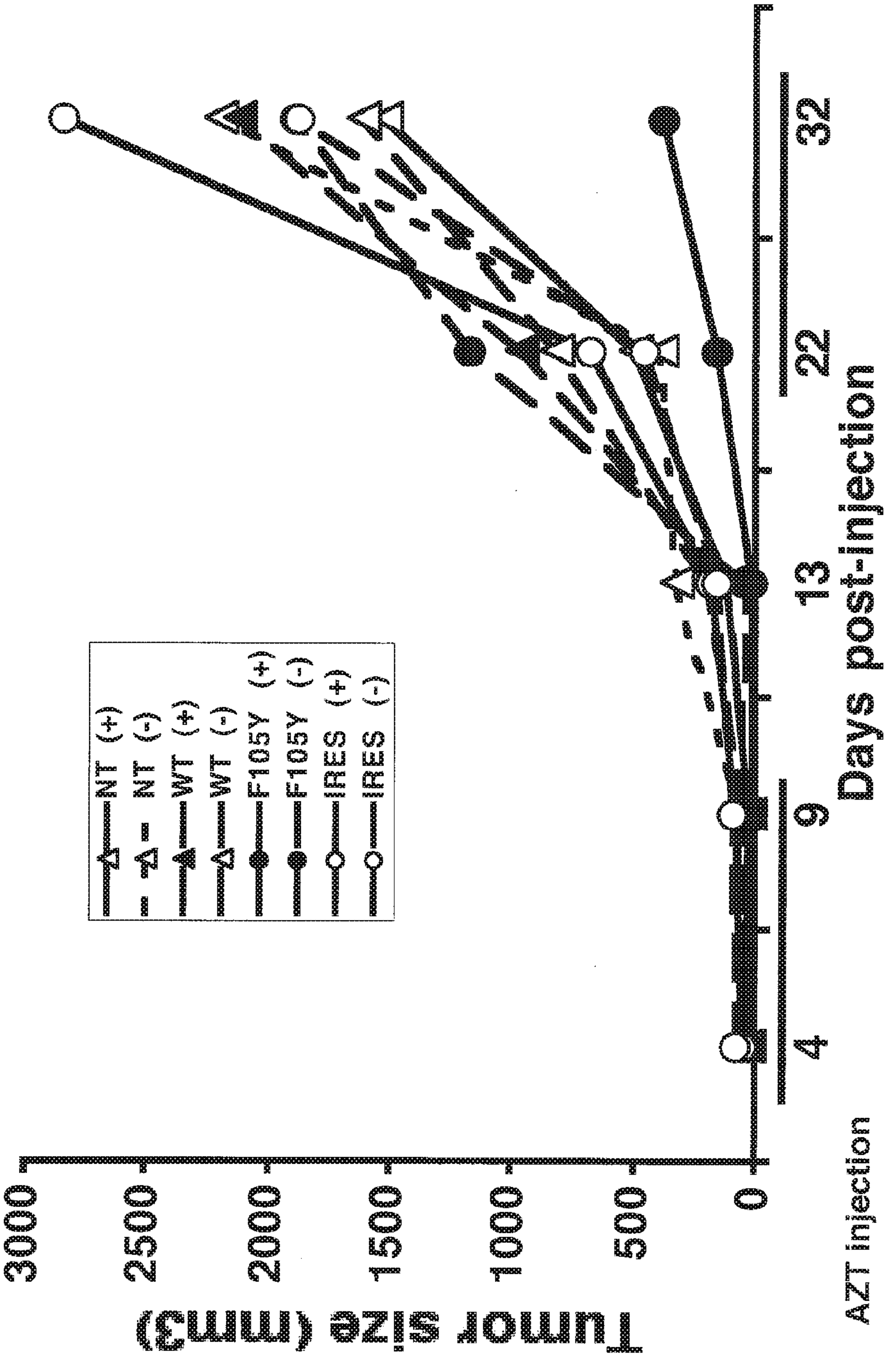
FIG. 9 is a graph showing that mutant forms of tmpk prevent growth of transduced K562 cells xenografted into AZT-treated NOD/SCID mice. Female or male 5 to 8-week-old non-obese diabetic/sever combined immunodeficient (NOD/SCID) mice were purchased from Jackson Laboratory. Lentivirally-transduced or non-transduced K562 cells ($20\times10^6$ cells) were resuspended in 0.5 mL Dulbecco's phosphate-buffered saline (D-PBS) per inoculum and injected subcutaneously (SC) into the right flanks of recipient mice. AZT treatment, which was administered intraperitoneally (IP) at the dose of 2.5 mg/kg/day, was started one day after injection and conducted for 14 days. In vivo tumor cell growth was monitored by measuring tumor size for up to 32 days post-inoculations. All experimental data were reproduced at least twice.

In Vivo Tumor Killing Effect Using the Tmpk-Transduced K562-Xenografted NOD/SCID Mouse Model The inventors next addressed the cell killing ability of the various tmpk mutants in an in vivo tumor model. K562 erythro-leukemia cells were transduced with either wild-type tmpk or the F105Y mutant and injected subcutaneously into NOD/SCID mice. Mice were then treated with 2.5 mg/kg of AZT for the following two-weeks. Non-transduced K562 cells gave rise to tumors of an average 2000 $mm^2$ in size at four and a half weeks past injection. Strikingly, while no significant reduction in tumor volume was apparent in AZT-treated mice injected with K562 cells transduced with wild-type tmpk (2000 $mm^2$ on average), the inventors have observed a 6 to 20 fold reduction in tumor volume in mice that were injected with K562 cells transduced with the F105Y tmpk mutant following AZT treatment (100-300 $mm^2$ final tumor volume consisting primarily of non-transduced K562 cells) (FIG. 9).

Example 9

Transduction of Primary Cultured Human or Mouse T Cells

Figure 10:
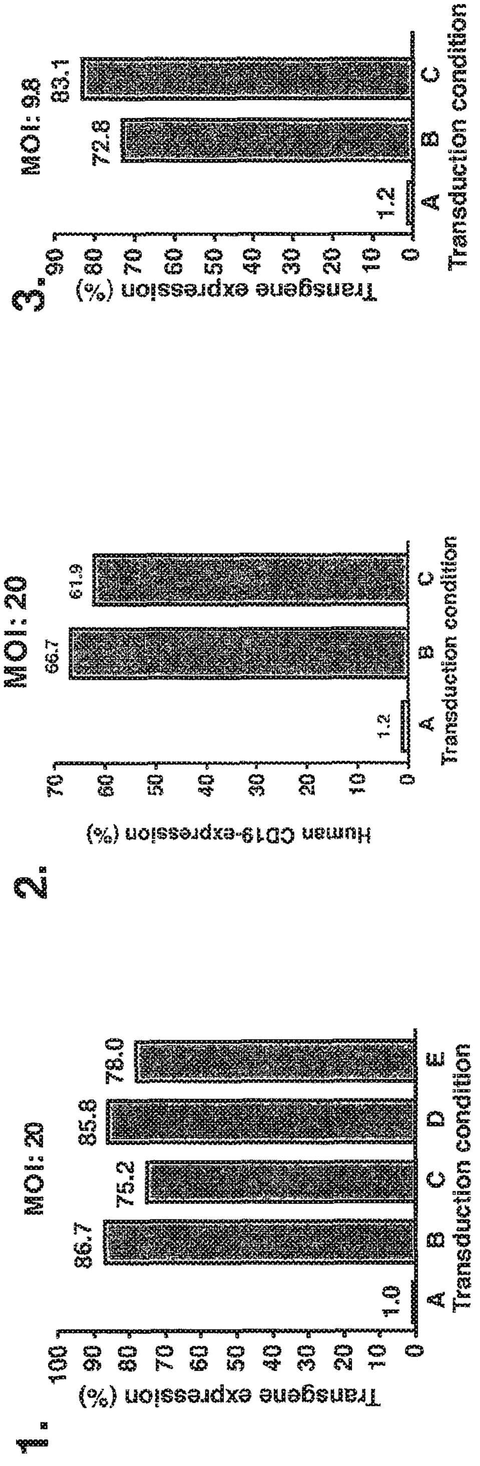
FIG. 10 is a series of graphs evaluating the transduction efficiencies in the infected primary human T cells by detecting the transgene expression 6 days after transduction. 1-3: Transgene expression in primary human T cells transduced with 1:LV-EGFP, 2: LV-(tmpk R-16GLL)-IRES-hCD19, 3: LV-IRES-hCD19 Condition A-No transduction, Condition B-Single transduction using fibronectin (FN), Condition C-Three repeated transductions using FN, Condition D-Single transduction without FN, Condition E-Three transductions without FN. The cells are transduced repeatedly every 24 h at the MOI indicated.
Figure 11:
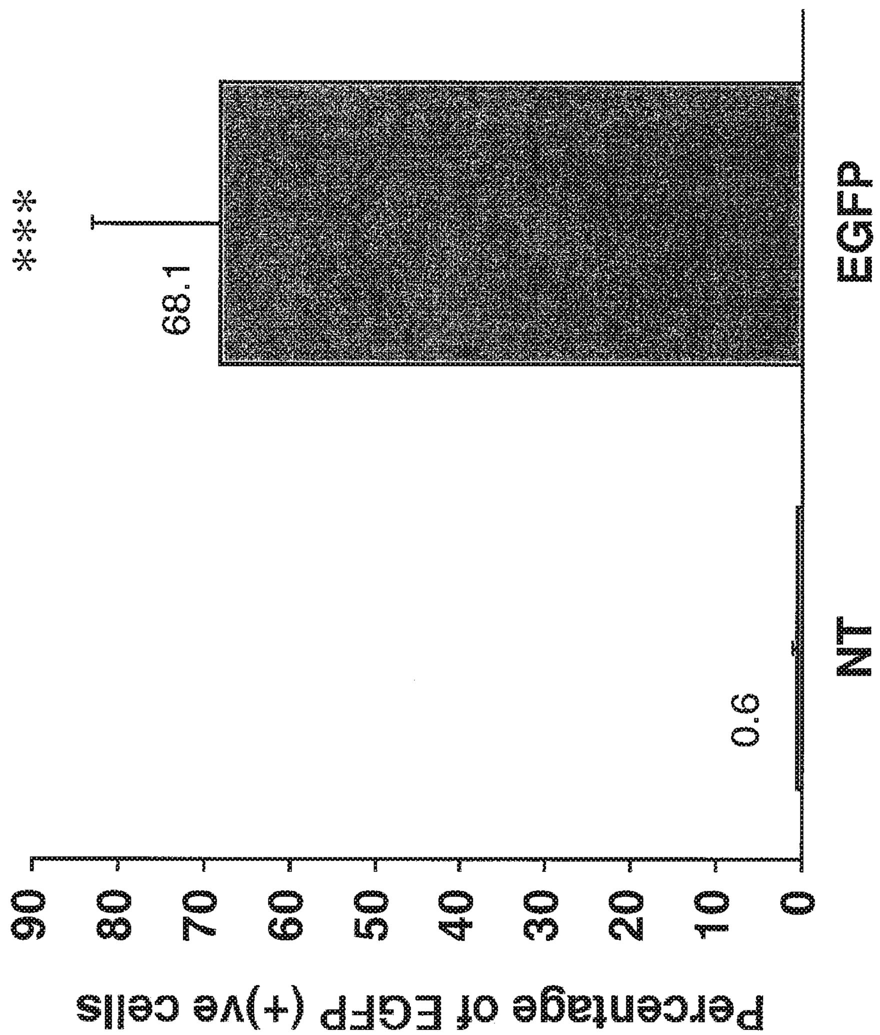
FIG. 11 is a graph confirming transgene expression in the primary cultured mouse T cells isolated from spleen. Primary murine splenic T cells were isolated from the spleen of a Balb/c mouse. The cells were cultured for 3 days using anti-CD3/28 beads and 20 IU/ml recombinant human interleukin-2 (rhIL2). Cells were transduced using fibronectin (FN)-coated plates using an MOI of 20. EGFP-expression in the infected cells was confirmed 6 days post-transduction. Data are expressed as mean±SEM. $P<0.001$, n=3.
Figure 12:
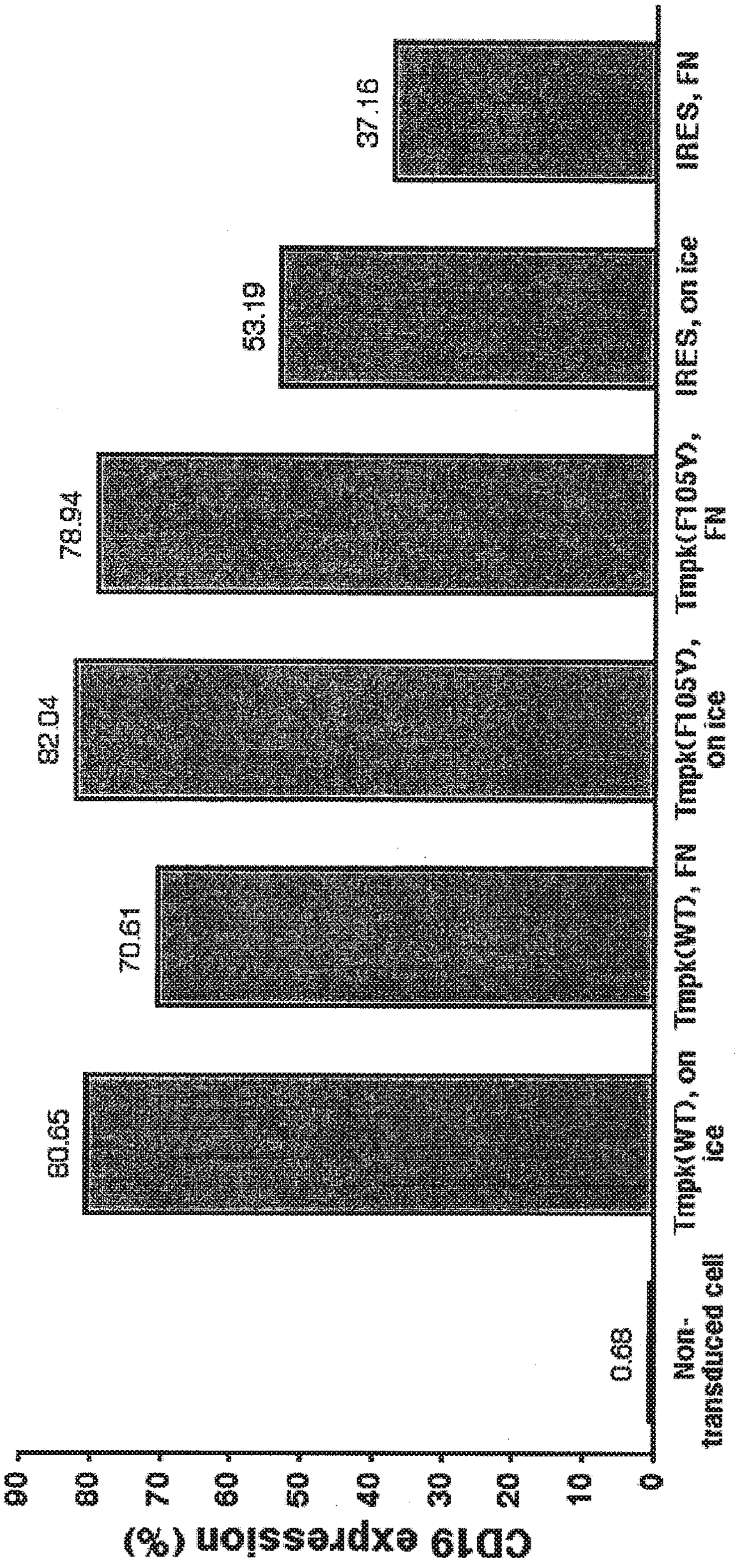
FIG. 12 is a graph comparing transgene expression in the cultured primary mouse T cells isolated from the spleen. The activated murine T cells were transduced with LVs indicated in the figure using either an FN-coated plate or transduction-on-ice methods. Transgene expression in the infected cells was confirmed 6 days post-transduction, n=2.

Primary cultures of human and mouse T cells were transduced with LV constructs containing tmpk cDNAs using an MOI as indicated in FIGS. 10-12. After 6 days of culture, T cells were assessed for their level of EGFP or CD19 expression. While no EGFP or CD19 expression was observed in non-transduced cells, strong EGFP or CD19-expression was detected in each of the LV-transduced cell cultures (FIGS. 10, 11 and 12).

Example 10

The inventors constructed a LV expression system was constructed carrying wild-type or one of two modified forms of tmpk. These engineered tmpk mutants (F105Y and LL) show substantially increased catalytic conversion of AZT compared to wild-type tmpk. Our vector also includes a truncated form of human CD19 (hCD19D), not normally expressed on the T cell lineage, that can be used to enrich and track transduced cells. Highly efficient (95%) transduction of Jurkat cells (human T cell leukemia line) was attained by a single infection with our LVs (MOI of 10). Both LV-tmpk (F105Y)-IRES-hCD19 and LV-tmpk (LL)-IRES-hC19 transduced cells were efficiently and selectively killed in a dose-dependent manner by AZT ($IC_{50}$ of 2 μM), while wild-type tmpk transduced cells were unaffected by AZT up to 100 μM. In response to AZT treatment, the apoptotic cell indices of cells transduced with wild-type tmpk, F105Y, or LL were 6.2±0.3%, 40.7±1.7%, and 46.1±4.6%, respectively (n=3). The inventors next established by HPLC that cells transduced with a LV encoding a mutant form of tmpk effectively convert AZT into its active antimetabolite form, AZT-triphosphate (AZT-TP). Intracellular ratio of AZT-TP to AZT-monophosphate (MP) is 11.3 in cells transduced with a LV encoding the LL mutant of tmpk, compared to 0.02 in non-transduced cells and 0.10 in wild-type tmpk transduced cells. Our findings also revealed that following incubation with indirubin-3-oxime, which inhibits cellular proliferation, and AZT treatment, transduced cells were successfully killed. Thus the cytotoxic mechanism differs from HSV1-tk mediated cell killing and is independent of cell proliferation. The inventors also succeeded in the infection of primary mouse and human T cells to over 40% and 70% transduction efficiency, respectively. Lastly, the inventors have shown that in vivo growth of tumor cells transduced with these mutant tmpk LVs was totally inhibited by treatment with AZT. These results demonstrate that our novel suicide gene therapy system has significant potential for many clinical applications.

Example 11

Safety Component of Vectors Used in Gene Therapy

A lentiviral-alpha galactosidase-A GLA)-IRES-tmpk (F105Y) mutant construct is used to transduce the murine myeloid leukemia cell line, C1498. After transduction of the cells with this virus, the congenic recipient GLA-deficient mice will receive the cells by iv-injection. Without prodrug treatment, the host mouse leads to reproducible death from leukemia in a dose-dependence fashion. The host mouse is administered a prodrug. such as AZT. Prodrug treatment results in killing of the responder cells. The enzymatic activity of GLA in the peripheral blood is monitored. The expansion of C1498 cells in the peripheral blood, bone marrow, liver, and spleen of host animals is determined by flow cytometric analysis. Cells are stained for a marker that identifies C1498 cells and not host cells, such as Ly5.1 and for a marker that identifies recipient cells and C1498 cells such as Ly5.2. The survival of mice with or without prodrug-treatment is determined.

Example 12

In Vivo GvHD in Mouse Models

Differentially labeled activated T cells are transplanted into permissive murine hosts. Upon determination of GvHD AZT or other nucleoside analogy is administered. The mouse receiving modified tmpk expressing cells exhibits a reduction of GvHD compared to controls. GvHD is eradicated in the mouse.

Ly5.1-mouse derived T cells and/or Ly5.2-mouse derived T cells will be transduced with LV-tmpk (F105Y)-IRES-hCD19 or LV-IRES-hCD19 as well as LV-EGFP as a control using an MOI of 20.

Host mice, CB6F1 will receive total body irradiation with a single dose of lethal irradiation (11 Gy), and transduced cells with T cell depleted bone-marrow cells prepared from CB6F1 recipient mice will be infused into host recipients (20M cells/mouse, n=10 of each group). Mice will be monitored for clinical GvHD everyday.

The following signs are included into clinical index: weight loss, hunching, activity, fur texture, and skin integrity.

T cell chimerism are determined by flow cytometry after bleeding from the tail vein. Plasma is isolated from the remaining blood and stored at −80° C. for later determination of cytokines.

When chimerism of Ly5.1-derived T cells will go up to over 10%, mice will receive daily ip AZT-injections using a dose of 2.5 mg/kg.

Organs will be isolated and prepared for histology and immunohistochemistry to evaluate the T cell) infiltration in the tissues.

Example 13

Adoptive Transfer of Human T Cells

Activated human T cells are transduced with either a modified tmpk molecule or a control gene. Isolated cells expressing the modified tmpk or control gene are adoptively transferred into permissive murine strains that can accept human xenografts. AZT or other thymidine analog is administered systemically. The number of T cells are determined at various time points to look for evidence of specific killing.

Human Th1 T cell will be transduced with LV-tmpk (F105Y)-IRES-hCD19 or LV-IRES-hCD19 as well as LV-EGFP as a control using an MOI of 20.

Host mice will receive total body irradiation with a single dose of lethal, and transduced cells will be infused into host recipients (20M cells/mouse, n=10 of each group). Mice will be monitored for clinical GvHD everyday. The following signs are included into clinical index: weight loss, hunching, activity, fur texture, and skin integrity.

Human chimerism are determined by flow cytometry after bleeding from the tail vein. Human chimerism is calculated as follows: human chimerism (%)=[huCD3+/(huCD3++ mCD45+)]×100. Plasma is isolated from the remaining blood and stored at −80° C. for later determination of human IgGs and cytokines.

When human chimerism will go up to over 10%, mice will receive daily ip AZT-injections using a dose of 2.5 mg/kg.

Organs will be isolated and prepared for histology and immunohistochemistry to evaluate the T cell infiltration in the tissues.

Example 14

Bystander Killing Effects

PC3 cells are transduced using LV-tmpk (wild-type)-IRES-hCD19 or LV-tmpk (F105Y)-IRES-hCD19 and tmpk-overexpressing cells are screened by Western blotting using rabbiit anti-human tmpk antibody. The resultant cells are used for checking the AZT-sensitivity. The cells are split into 96-well plates (2500 cells/well), and expose to AZT for 4 days. Cell viability is determined using MTS-reagent. For bystander studies, the tmpk-transduced cells are cocultured with LV-EGFP transduced PC3 cells in 24 well plate (50000 cells/well). After incubation with 100 μM AZT for 4 days cells, the percentage of EGFP-positive cell in each wells are determined by flow cytometry. If the bystander cell killing occur, EGFP-positive cell population treated with AZT show the decrease in their number compared to that without AZT-treatment.

Example 15

Materials and Methods cDNA Cloning of Human CD19 and Construction of LV Shuttle Vector

Total RNA was extracted from the human Burkitt's lymphoma cell line (Raji) using the TRIZOL reagent (Invitrogen, Carlsbad, Calif.). cDNA templates were generated from total RNA by reverse transcription using oligo-dT primer and Superscript II reverse transcriptase (Invitrogen). The cDNA of full-length huCD19 was obtained by PCR using Platinum Hifi Taq DNA polymerase (Invitrogen) and primers CD19 F1 and CD19 R1 described below. The amplified PCR product was directly ligated into the TA-vector, pPCR-script SK (+) (Stratagene, La Jolla, Calif.) to give pPCR-huCD19full. A truncated form of huCD19 (huCD19Δ), which has the extracellular and transmembrane domains but lacks the cytoplasmic domain, was generated by inverse PCR from pPCR-huCD19full using primers CD19 F2 and CD19 R2 (described below), to give pPCR-huCD19Δ. The F2 primer has a complementary sequence to the stop codon just after the end of the transmembrane domain. Following sequence confirmation of the cDNA inserts in pPCR-huCD19Δ, the cDNA fragments were then isolated and subcloned into the EcoRI site of the shuttle vector pSV-IRES that has a sequence for an IRES element from the EMCV, to give pSV-IRES-huCD19Δ. The primer sequences used for subcloning of the human CD19 cDNA were as follows: CD19 F1: 5'-atgccacctcctcgcctcctcttcttcc-3' (SEQ ID NO:23) and CD19 R1: 5'-tcacctggtgctccaggtgccc-3' (SEQ ID NO:24). The truncated CD19 construct was made by inverse-PCR using primers CD19 F2: 5'-ccgccaccgcggtggagctccag-3' (SEQ ID NO:25) and CD19 R2: 5'-ttaaagatgaagaatgcccacaaggg-3' (SEQ ID NO:26).

Subcloning of Human Tmpk cDNA and Construction of Bicistronic LVs

To subclone the cDNA for wild-type (WT) human tmpk, PBMNCs were isolated from heparinized blood obtained from healthy donors by Ficoll-Hypaque density gradient separations (GE Healthcare Biosciences, Inc. Freiburg, Germany). The WT human tmpk cDNA was amplified by PCR using first strand cDNA generated from PBMNC RNA by the method above. PCR products containing the WT tmpk cDNA were subcloned into pPCR-scriptSK (+) and sequenced. Mutant forms of tmpk, denoted F105Y and R16GLL, were previously generated[23,24]. The cDNAs for the WT and each mutant form of tmpk were first subcloned into a shuttle vector (pSV-IRES-huCD19Δ) to construct bicistronic expression cassettes that allow simultaneous expression a single mRNA strand, encoding the suicide gene and huCD19Δ. The constructs were then each subcloned downstream of the internal EF1α promoter into an HIV-1-based recombinant LV plasmid, pHR'-cPPT-EF-W-SIN[27]. As a control for the transduction experiments, the inventors constructed a pHR'-cPPT-EF-IRES-huCD19Δ-W-SIN LV by subcloning the IRES-huCD19Δ cassette from the pSV-IRES-huCD19Δ plasmid into pHR'-cPPT-EF-W-SIN. In addition, the inventors used the pHR'-cPPT-EF-enGFP-W-SIN LV[32] containing the enhanced GFP (enGFP AKA EGFP) cDNA.

Preparation of High-Titer LV.

Vesicular stomatitis virus glycoprotein (VSV-g)-pseudotyped lentivectors (LVs), including an enGFP marking vector, were generated by transient transfection of 293T cells with a three plasmid system (the aforementioned pHR' plasmid constructs, the packaging plasmid pCMVΔR8.91, and the VSV-g envelope encoding plasmid pMD.G[32] using $CaPO_4$ precipitation. Viral supernatants were harvested 48 h later, passed through a 0.45 μm filter, and suspended in PBS containing 0.1% (w/v) BSA after ultracentrifugation at 50,000×g for 2 h at 4° C. The concentrated viral supernatants were serially diluted and titered on 293T cells. Transgene expression in transduced cells was assessed 72 h later using a FACS Calibur (BD Biosciences, San Jose, Calif.) following staining of the transduced and control cells with monoclonal mouse anti-human CD19 conjugated with PE (BD Biosciences) or for enGFP expression. Analysis of the data was performed using Cell Quest software (BD Biosciences).

Transduction and Analysis of Transgene Expression by Flow Cytometric Analysis.

Cells of the human T lymphoma cell line, Jurkat, and of the human erythro-leukemic cell line, K562, were maintained in RPMI 1640 supplemented with 10% FBS (CPAA Laboratories, Etobicoke, ON), 100 U/ml of penicillin, and streptomycin to 100 μg/ml (both Sigma, Oakville, ON). Cells were infected with concentrated virus stocks using an MOI of 10 in the presence of 8 μg/ml protamine sulfate.

Infected cells were then kept in culture for 5 days prior to evaluating gene transfer efficiency. Gene transfer efficiencies were measured by flow cytometry as described above. Individual clone cell lines were used for all subsequent experiments. They were derived by limiting dilution and selected based on comparable huCD19Δ expression as determined by flow cytometry (above).

To compare the relative expression levels of tmpk, the transduced cells were first fixed with 4% buffered formalin for 15 min then permeabilized by treatment with PBS containing 0.1% Triton X-100 for 10 min. Cells were incubated with 20% normal goat serum for 30 min and then incubated with rabbit anti-human tmpk (diluted 1:500) for 1 h. The cells were further incubated with goat anti-rabbit IgG conjugated to Alexa488 (diluted 1:500, Molecular Probes Inc., Eugene, Oreg.) for 1 h. All incubations were performed at room temperature. Levels of tmpk expressed in the transduced cells were determined by flow cytometry.

HPLC for AZT-Metabolites.

Cells were cultured in the presence of 100 μM AZT for 36 h. $10^7$ cells were homogenized by sonication in 100 μl of 5% (w/v) trichloroacetic acid (TCA). The supernatant was collected after centrifugation at 10,000×g for 15 min at 4° C. TCA was removed by extraction with an equal volume of 20% tri-n-octylamine in pentane. The neutralized aqueous fraction was directly injected into the HPLC machine (Waters, Milford. Mass.). Separation of AZT and its metabolites were performed on a C18 column (Waters), with a mobile phase composed of 0.2 M phosphate buffer containing 4 mM tetrabutylammonium hydrogen sulfate (pH 7.5) and acetonitrile in the ratio of 97:3 (v/v)[48] at a flow rate of 1.5 ml/min. The UV absorbance was monitored at 270 nm. Standards for each AZT-metabolite (AZT-MP, AZT-DP, and AZT-TP) were purchased from Moravek Biochemicals (Brea, Calif.). Five million cell equivalents were injected and analyzed in triplicate.

Determination of AZT-Sensitivity of tmpk-Transduced Jurkat Cells.

Transduced Jurkat cells and single-cell clones were seeded in 96 well plates ($2\times10^5$ cells/well) in 200 μl of the RPMI medium described above with increasing concentrations of AZT (0, 0.1, 1, 10, 100 μM, and 1 mM). The medium was changed daily. After 4 days of culture, cell viability was determined by using Cell Titer 96 Aqueous One Solution Cell Proliferation Assay kit (Promega, Madison, Wis.).

For evaluation of the induction of apoptosis, treated Jurkat clonal cells were stained with Annexin V. Briefly, cells were seeded in 24 well plates ($10^6$ cells/well) in 1 ml of medium with or without 100 μM AZT. After 4 days of culture, Annexin V staining was performed according to the manufacturer's protocol (Annexin V-APC: BD Pharmingen). For testing whether AZT-mediated cell killing depends on the cellular proliferation, indirubin-3'-monoxime (final concentration 5 μM, Sigma-Aldrich, St. Louis, Mo.) was added simultaneously with 100 μM AZT to the culture.

To simplify comparative studies a relative apoptotic index was calculated. Here data obtained was normalized by dividing results from AZT treated cells in each condition by the results obtained without added AZT. Values were reported as fold increases. Statistical significance between groups was calculated by ANOVA.

Transduction of Primary T Cells with LVs and Evaluation of Induction of Apoptosis Following AZT Exposure Human T lymphocytes were isolated from PBMNCs contained within heparinized blood obtained from healthy human donors by Ficoll-Hypaque (GE Healthcare) separations. Mouse T cells were prepared from B cell-depleted splenocyte preparations using goat anti-mouse IgG beads (BioMag, Qiagen, Mississauga, ON). T cells were activated by using anti-CD3 and anti-CD28 coated beads (PMID: 12855580) in a ratio of 1:3 (cell: beads) with 20 IU/mL of recombinant human interleukin 2 (R&D Systems, Minneapolis, Minn.) for 3 days. Cells were infected with concentrated virus stocks for 3 h on ice using an indicated MOI in the presence of 8 μg/ml protamine sulfate. Infected cells were then kept in culture for 5 days prior to evaluating gene transfer efficiency. Gene transfer efficiencies were measured by flow cytometry using a monoclonal anti-human CD19-antibody conjugated with phycoerythrin (PE) as described above. Induction of apoptosis following AZT-exposure was evaluated by Annexin V-staining as above.

Measurement of Mitochondrial Inner Membrane Potential and Activation of Caspase-3.

Transduced cells ($10^6$) were treated with 100 μM AZT for 4 days or left untreated. To detect changes in the mitochondrial inner membrane potential, the cells were incubated with 5,5',6,6'-tetrachloro-1,1',3,3'-tetraethylbenzimidazolylcarbocyanine iodide (JC-1, Molecular Probes Inc.) for 30 min at 37° C., and were then analyzed using a FACS Calibur. The activation of caspase-3 in cells was examined using the FACS Calibur following incubation with an FITC-labeled caspase 3 inhibitor peptide (FITC-DEVD-FMK, Calbiochem, San Diego, Calif.) for 1 hr at 37° C.

Transduced K562 Cells in a NOD/SCID Xenograft Model

Transduced K562 cells were affinity-purified by MACS using magnetic beads conjugated with an anti-human CD19 monoclonal antibody (Miltenyi Biotec Inc., Auburn, Calif.). The purity of the cells following isolation was evaluated by FACS Calibur. Non-obese diabetic/severe combined immunodeficiency (NOD/SCID) mice (5 to 8-weeks old, purchased from Jackson Laboratories, Bar Harbor, Me.) were maintained at the Animal Resource Centre at the Princess Margaret Hospital (Toronto, ON, Canada). The entire animal experimental procedure followed a protocol approved by the Animal Care Committee of the UHN. Experimental groups consisted of male and female NOD/SCID mice injected with $2\times10^7$ K562 cells (resuspended in 0.5 mL D-PBS; Oxoid, Basingstoke, England) that were either lentivirally-transduced (n=10 for each LV) or non-transduced (NT) (n=10). Injections were performed subcutaneously (sc) into the dorsal right flanks of recipient mice as previously described[49]. One day after injection of the cells, half of the mice in each group (n=5) began receiving daily AZT injections, administered intraperitoneally (ip) at a dose of 2.5 mg/kg/day for 14 days. Tumor growth was measured by caliper and calculated as 0.5×length×width$^2$ (in mm$^3$) for up to 14 days post-inoculations.

Statistical Analysis

Data are presented as the mean±standard error of the mean (SEM) for in vitro experiments and the mean±standard deviation of the mean (SD) for in vivo experiments. Statistical analyses were performed using StatView version 4.5 software for Macintosh (SAS). For in vitro experiments, a one-way analysis of variance (ANOVA) with either a Bonferroni or a Dunnett post-hoc test was used to determine statistically significant results with the level of significance set at $P<0.05$. Statistical comparison of means was performed by a two-tailed unpaired Student's t test for in vivo experiments.

Results

Synthesis of Novel Suicide LVs Expressing Modified tmpks and Truncated CD19

FIG. 1 shows a schematic structure of the LVs constructed for this study. Jurkat cells were transduced a single time with our recombinant LVs using an MOI of 10. Five days after transduction, CD19 expression on transduced cells was examined. While no CD19 expression was observed on non-transduced (NT) Jurkat cells, over 95% of the cells transduced with each LV showed strong CD19-expression (data not shown). Next, individual cell clones were isolated by flow cytometry and limiting dilution. The mean fluorescent intensity (MFI) of huCD19Δ expressed on isolated clones of cells transduced with each LV showed similar values (data not shown). To compare the expression levels of the upstream tmpk gene on a gross level, transduced cells were also examined by flow cytometry following intracellular immunostaining with rabbit anti-human tmpk. Since tmpk is endogenously expressed in Jurkat cells, the inventors detected basal expression of tmpk in NT cells. Cells transduced with LV-tmpk(WT)-IRES-huCD19Δ or either LV-tmpk mutant-IRES-huCD19Δ showed an increase in tmpk expression, up to 5 times higher compared with non-transduced and LV-IRES-huCD19 transduced cells (data not shown).

Determination of the Major Intracellular AZT Metabolites in LV/Tmpk-Transduced Cells To confirm functionality of the tmpk mutants overexpressed in transduced cells for the metabolic conversion of AZT, the intracellular amounts of AZT-metabolites were measured by reverse-phase HPLC. Following a 36 h incubation with 100 μM AZT, the cells expressing the R16GLL mutant tmpk efficiently converted AZT-MP into AZT-DP and then to the cytotoxically active metabolite form, AZT-TP, whereas the main metabolite that accumulated in the NT-Jurkat cells was AZT-MP (FIG. 2A). Also no significant increases in the accumulation of AZT-TP or induction of cell death in the cells overexpressing WT tmpk itself were observed (data not shown). To compare the effectiveness of the conversion of AZT-MP to its active metabolite, AZT-TP, the ratio of AZT-TP to AZT-MP in each cell population was calculated from the values of the area under curve of each chromatogram. FIG. 6B shows that overexpression of the R16GLL mutant induced a 615-fold increase (P<0.0001) in the AZT-TP/AZT-MP ratio compared to that of the NT cells, the tmpk WT-overexpressing cells, or the LV-IRES-huCD19Δ-transduced cells. SIMILAR DATA WAS ALSO OBTAINED FOR THE F105Y MUTANT. These data indicate that the cells overexpressing this mutant form of tmpk more efficiently converted AZT-MP to AZT-DP, which was subsequently transformed into its active antimetabolite, AZT-TP, likely by cellular nucleotide diphosphate kinase[12].

AZT Sensitivity of tmpk-Transduced Cells

Figure 14:
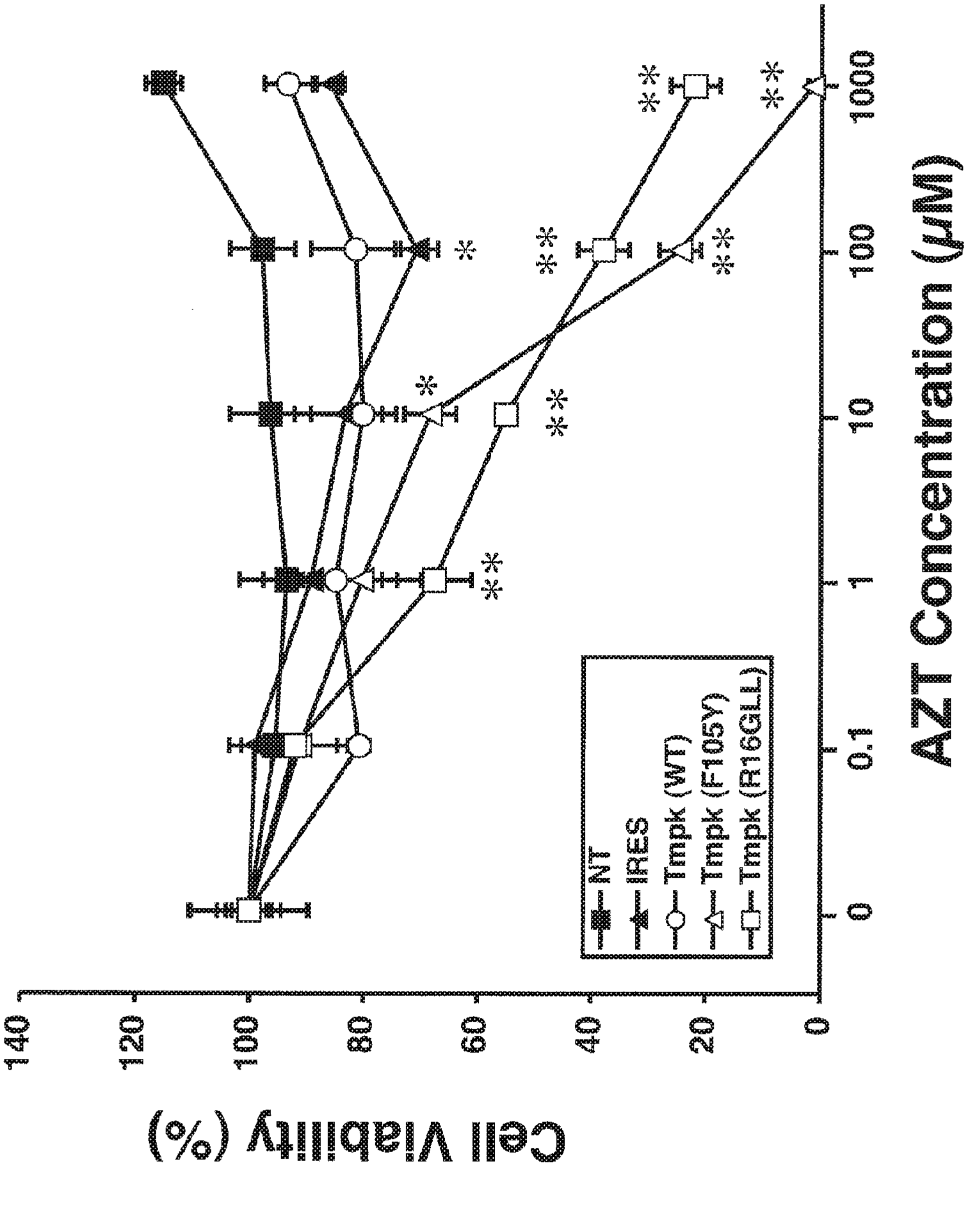
FIG. 14 is a graph showing the measurement of AZT sensitivity of clonally-derived Jurkat cells transduced with LV-tmpk-IRES-huCD19Δ and control vectors. Cell viability was measured by MTT assay following 4 days incubation with or without AZT. The results were shown as percentage of the A595 nm value from the assay. The negative control values (without AZT) and the values without cells were deemed as 100% and 0%, respectively. Data are presented as the mean±SEM, n=3. The statistical significance of experimental observation was determined by the one-way ANOVA followed by a Dunnett post-hoc test with the level of significance set at $P<0.05$ compared with the values of the control group of cells that were not treated with AZT. *, $P<0.05$, and **, $P<0.01$ vs. the cells without AZT-treatment in each group.

As transduced cells expressing the mutant forms of tmpk revealed differences in intracellular accumulation of AZT-metabolites, the effect of exposure to AZT on cell viability was next measured. Note that by itself, transduction of Jurkat cells with LVs engineering expression of controls or our modified suicide genes and huCD19Δ did not affect their proliferation (data not shown). For the sensitivity experiments the tmpk-expressing cells were incubated with increasing concentrations of AZT, and after four days determined the percentage of living cells using an MTT assay (FIG. 14). Transduced cells expressing the tmpk mutants F105Y or R16GLL were minimally viable upon addition of AZT in a dose-dependent manner (P<0.0001). In contrast, limited cell killing, even at high doses of AZT up to 1 mM, was observed in the negative control cells including: the tmpk WT- and LV-IRES-huCD19Δ-transduced cells as well as the NT Jurkat cells (P values for the tmpk WT, LV-IRES-huCD19Δ-transduced, and NT cells were 0.0677, 0.0426, and 0.1375, respectively).

Since the formation of nuclear apoptotic bodies were observed by DAPI-staining in the tmpk-mutant-expressing cells treated with AZT (data not shown), active metabolites of AZT may have induced cellular death by apoptosis. The induction of apoptosis in the tmpk-expressing cells was examined following AZT treatment, by staining the cells with Annexin V and performing flow cytometric analyses. In response to AZT exposure, early apoptotic indices of cells expressing the F105Y and the R16GLL tmpk mutants were significantly increased (FIG. 15A) compared to those in the absence of AZT treatment (9.5±0.8, and 8.3±0.4-fold increases of apoptotic index by AZT-treatment for F105Y- and R16GLL-expressing cells, respectively).

HSV-tk-mediated cell killing has been reported to require cellular proliferation to demonstrate the cytotoxic effect of the produced anti-metabolites through DNA chain termination[40]. Thus, for these experiments, the cytotoxic events of AZT on tmpk-expressing cells were assessed to see if they were also dependent on cellular proliferation. Transduced cells were cultured with or without 100 μM AZT in the presence of indirubin-3'-monoxime to arrest cell cycle progression. After 4 days incubation with 5 μM indirubin-3'-monoxime in the absence of AZT, the cells showed cell cycle arrest at G2/M-phase (data not shown). By treating the cells with 100 μM AZT in the presence of 5 μM indirubin-3'-monoxime, the apoptotic indices of the F105Y- and R16GLL-expressing cells were still significantly increased (FIG. 15B) compared to those without AZT-treatment (2.3±0.4, and 2.2±0.2-fold increases, respectively). No significant increases were seen in the apoptotic indices of NT cells, WT tmpk-overexpressing cells, or control LV-IRES-huCD19Δ-transduced cells (FIG. 15B). This suggests that the induction of apoptosis by AZT in the tmpk mutant-expressing cells is, in part, independent of their proliferation status.

Transduction and AZT Sensitivity of Primary Human and Mouse T Cells

Figure 16:
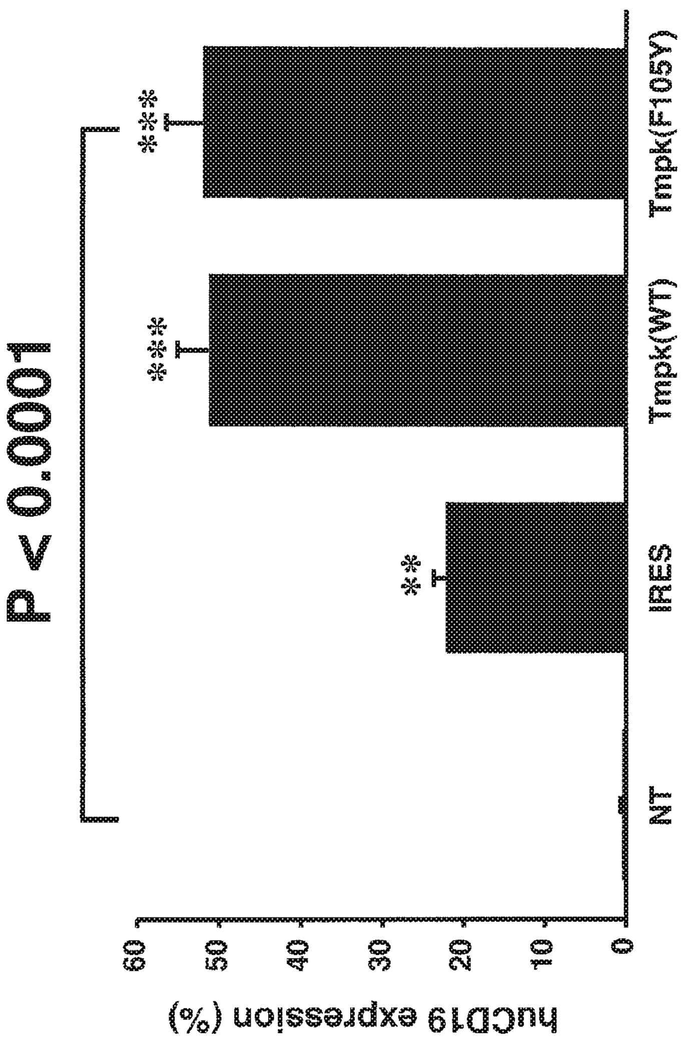
FIG. 16 shows the transduction of primary murine and human T cells. (A) Observed levels of huCD19Δ expression on primary murine T cells 5 days after cells were transduced a single time with concentrated LV at an MOI of 20. (B) Observed levels of huCD19Δ expression on transduced primary human T cells. (C) Fold increases in the apoptotic index in the presence of 100 μM AZT.
Figure 16:
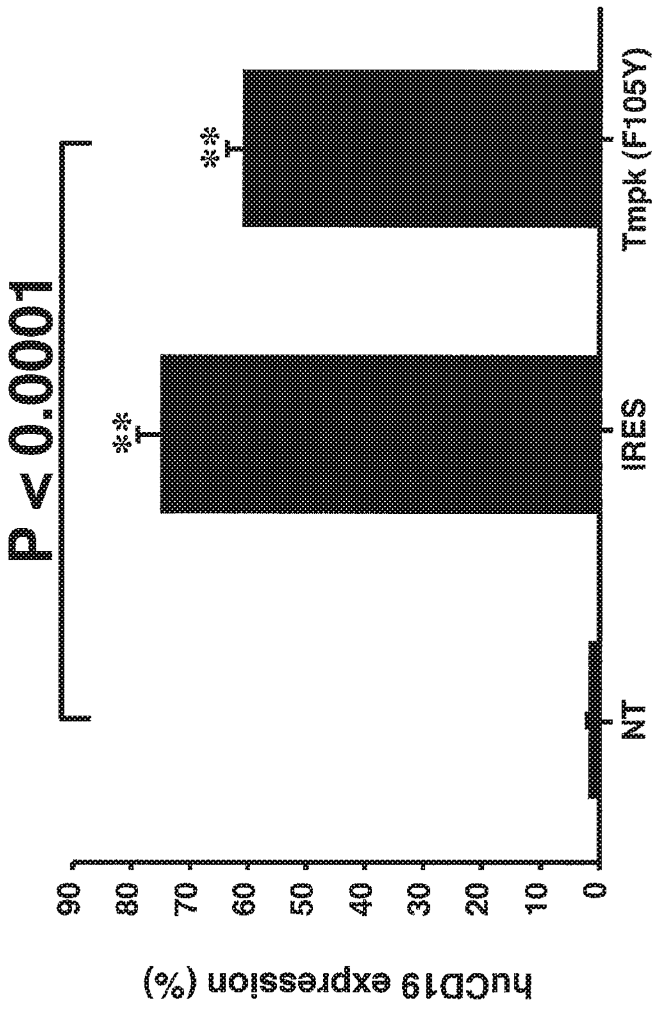
Figure 16:
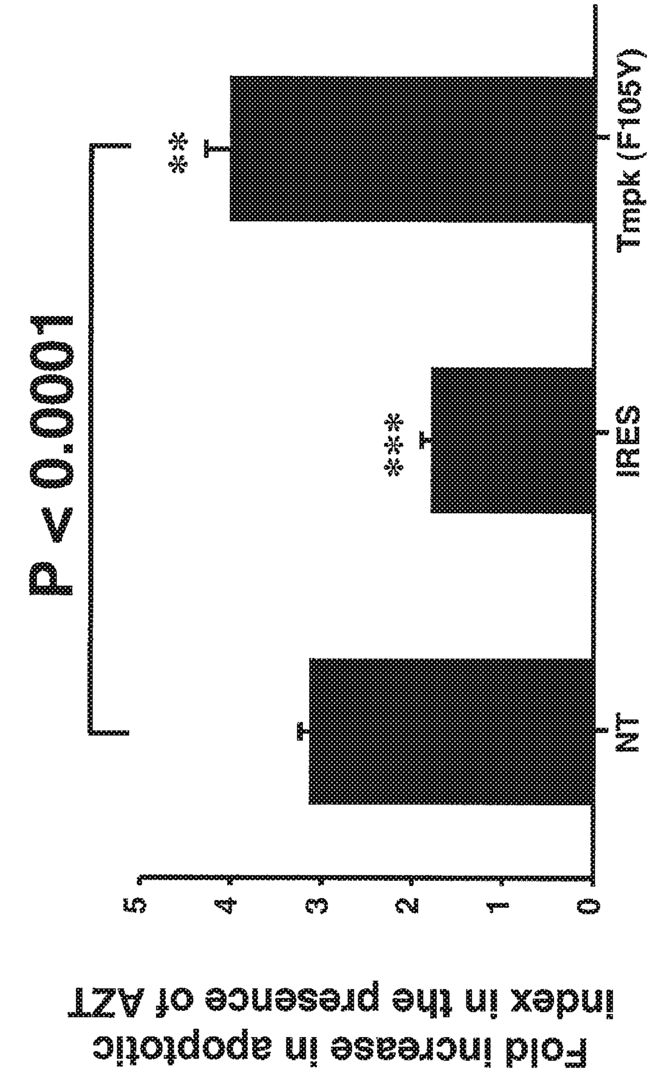

Primary cultures of human and mouse T cells were transduced with LV tmpk constructs using an MOI of 20. The LV-tmpk (R16GLL) mutant was not used for the transduction of primary T cells since this version contains bacterial tmpk-sequence that could cause an eventual immunogenic response when used in vivo. After 6 days of culture, transduced and control T cells were assessed for their level of huCD19 expression. While very low huCD19 expression was observed in NT cells, huCD19 expression on primary mouse T cells was significantly increased in each of the LV-transduced cultures reaching levels of >50% (FIG. 16A). Likewise, even higher levels of huCD19 expression were observed on productively transduced human T cells reaching levels of >60% (FIG. 16B). These levels are considerable given that expression of downstream genes in bicistronic cassettes may be only 10% or less of upstream gene expression PMID: 10933956. To test the AZT sensitivity of the productively transduced human T cells, the cells were exposed to 100 μM AZT for 4 days and induction of apoptosis was measured by Annexin V staining. Although the early apoptotic indices of primary NT human T cells were increased by AZT exposure at this dose, the apoptotic index of cells expressing the F105Y tmpk mutant was significantly increased (FIG. 16C) compared to those without AZT treatment (4.0±0.3-fold increases; P<0.0001).

Novel Suicide Mechanism Utilized by the tmpk/AZT Axis

Figure 17:
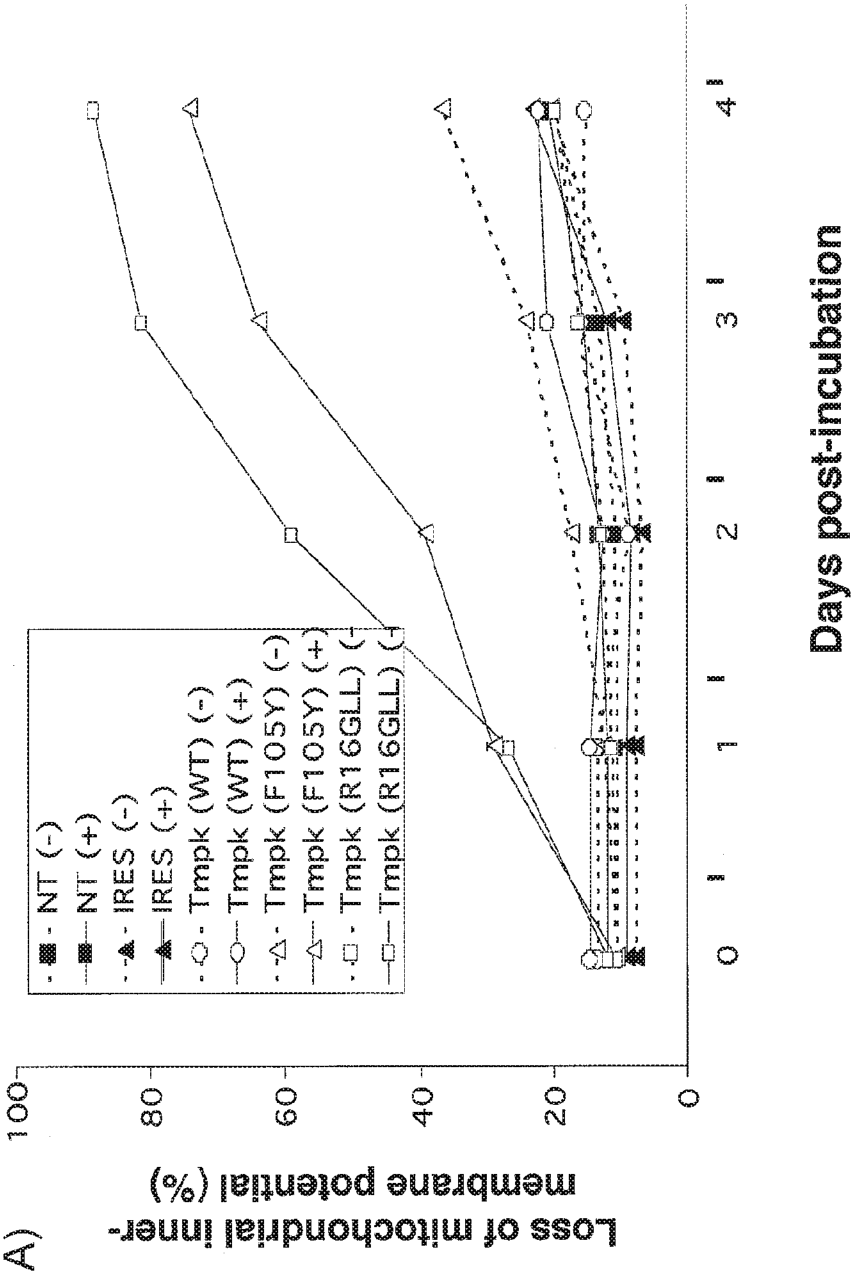
FIG. 17 presents an analysis of the mechanism of induction of apoptosis by AZT in the tmpk-mutant expressing cells. (A) The tmpk mutant expressing cells treated with AZT showed an increase in the loss of mitochondrial membrane potential. Following 4 days incubation with or without 100 μM AZT, cells were stained with JC-1 for 15 min at 37° C., and then were analyzed by flow cytometry. To compare the effect of AZT on the increase in the loss of mitochondrial membrane potential at the day 4, the statistical differences were evaluated by the one-way ANOVA followed by a Bonferroni post-test with the level of significance set at $P<0.05$. *, $P<0.001$, n=3. (B) Activation of caspase 3 in transduced cells by AZT treatment. Cells were cultured for 4 days with or without 100 μM AZT. To compare the effect of AZT on activation of caspase 3 in each group, measurement of flow cytometric analysis obtained from the cells treated with AZT were normalized by dividing those without AZT. Data are mean±SEM, n=3. The statistical differences were evaluated by the one-way ANOVA followed by a Bonferroni post-test with the level of significance set at $P<0.05$. , $P<0.01$ and ***, $P<0.001$ vs. NT.
Figure 17:
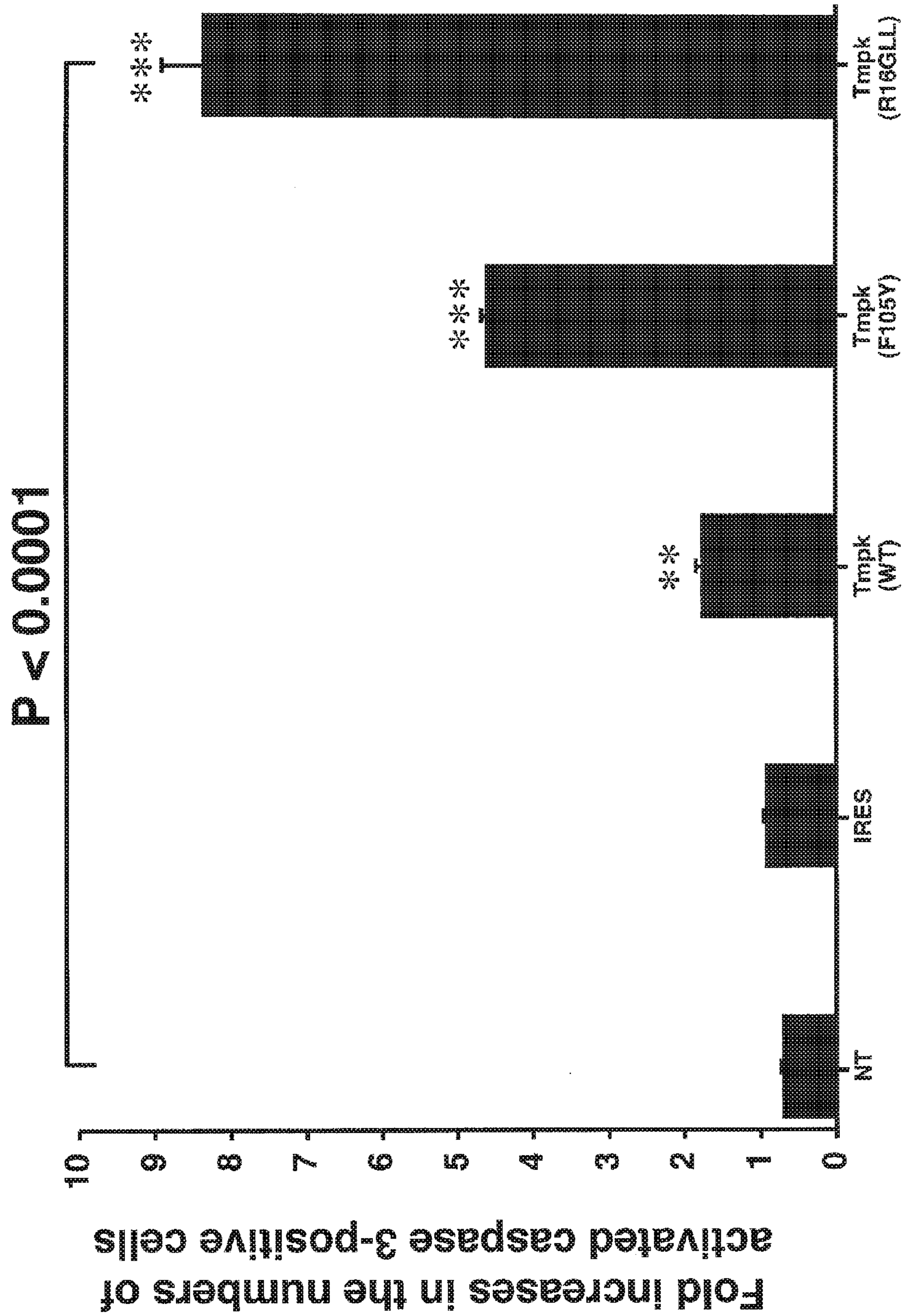

AZT is a potent inhibitor of HIV replication. That said, HIV patients treated with AZT sometimes develop toxic mitochondrial myopathy through induction of mitochondrial biochemical dysfunction[18,20,21]. In order to decipher the mechanism of cellular apoptosis induction in the tmpk-mutant-expressing cells following AZT treatment, the mitochondrial inner membrane potential was measured in intact cells. This gives a direct indication of the activity of mitochondrial energy metabolism. For these experiments, a fluorescent probe, JC-1, was used to examine living cells by flow cytometry. JC-1 is a dye that emits a green fluorescence at low mitochondrial membrane potential[41]. At higher membrane potentials, JC-1 forms red fluorescence-emitting “J-aggregates”. A significant increase (P<0.0001) in the loss of mitochondrial inner membrane potential occurred in both the F105Y- and the R16GLL-expressing Jurkat cells (FIG. 17A) following 4 days of AZT treatment compared to controls. Negative control cell groups including the NT-, the WT-overexpressing, or the LV-IRES-huCD19Δ-transduced cells treated with AZT did not demonstrate a similar loss of mitochondrial inner membrane potential (FIG. 17A).

Caspase 3 is a key molecule in the cellular apoptosis pathway; loss of mitochondrial inner membrane potential induces caspase 3 activation in cells[42]. Therefore, caspase 3 activation in tmpk mutant-expressing cells treated with AZT was next evaluated. Populations of F105Y- or R16GLL-expressing cells that were treated with AZT showed a significant increase (FIG. 17B) in the percentage of activated caspase 3-positive cells compared to populations of untreated cells (4.6±0.1 and 7.8±0.5-fold increases, respectively). No significant increases in the percentage of cells with activated caspase 3 were seen in the negative controls (NT and LV-IRES-huCD19Δ-transduced cells) following AZT incubation (FIG. 17B). Interestingly, tmpk WT-overexpressing cells that were treated with AZT showed a slight, but significant, increase of the percentage of active caspase 3-positive cells compared to untreated cells. Taken together, our data collectively demonstrates that the mechanism of the induction of apoptosis by AZT in the tmpk-mutant-expressing cells is the activation of caspase 3 resulting from the increase in the loss of the mitochondrial membrane potential, caused by the accumulation of AZT-TP in the cells.

In Vivo Killing of LV Transduced Cells Mediated by AZT

Next killing of the tmpk-mutant-expressing cells in an in vivo tumor model was examined. K562 erythroid leukemia cells were transduced with the LVs that engineered expression of IRES-huCD19Δ, WT tmpk, or a mutant form of the kinase (F105Y or R16GLL). Since the transduction efficiency of the F105Y LV into the K562 cells was fairly modest (68% of cells positive based on observed huCD19 expression; data not shown), these cells were enriched by FACS using anti-human CD19 conjugated to phycoerythrin (PE). After enrichment, the percentage of CD19-positive K562 cells was over 95% (data not shown). This also confirms the auxiliary utility of huCD19Δ as a cell surface marker enabling immuno-affinity enrichment of transduced cells. Growth characteristics of productively transduced K562 cells were then assessed. Minimal differences in growth of the LV-transduced cells were observed (data not shown). Next, $2\times10^7$ transduced K562 cells were injected s.c. into the right flank of NOD/SCID mice. Starting one day after the cell injection, the mice received daily i.p. injections of AZT (2.5 mg/kg/day) or vehicle for two weeks. According to the UHN ACC SOP for humane endpoints, mice were sacrificed when the tumor burden reached ~1.5 $cm^3$. In animals injected with non-transduced K562 cells, this endpoint occurred within two weeks post-injection. Mice not receiving AZT treatment quickly developed large tumors in a time dependent manner (FIG. 18A). In contrast, the growth of K562 cells transduced with either of the tmpk mutant LVs (F105Y or R16GLL) was strongly inhibited (P=0.0209 and 0.0174, respectively) by daily AZT injection, and the effects were sustained over time (FIG. 18B). No significant tumor growth inhibition by AZT was observed in the LV-tmpk (WT)-IRES-huCD19Δ-transduced, LV-IRES-huCD19Δ-transduced, or the NT-cell injected mice (FIG. 7B18B).

Discussion

Here the inventors have shown that overexpression of rationally-designed mutant forms of human tmpk with improved kinetics significantly reduce cellular viability following AZT treatment both in vitro and in vivo and is useful for treating disease. In addition, these results show that the mechanism of AZT-induced apoptosis is associated with loss of mitochondrial inner membrane potential and activation of caspase 3 in the tmpk-mutant expressing cells. This mechanism provides significant advantages over previous suicide schemas and also allows for killing of non-dividing cells as shown in FIG. 4.

Tmpk is crucial for the activation of a series of prodrugs, including AZT, by catalyzing the second phosphorylation step. It has been shown that this is a rate-limiting step in the activation of AZT[17], resulting in an accumulation of the intermediate metabolite, AZT-MP. AZT was the first effective treatment for AIDS patients[13-15], however, long-term treatment with AZT has been reported to induce a severe myopathy characterized by structural and functional alterations in mitochondria as a result of accumulation of AZT-MP[19,20,22]. Inhibition of the mitochondrial inner membrane potential has also been found in the muscle mitochondria of long-term AZT-treated rats[21]. The inventors have shown that accumulation of AZT-TP in the tmpk-mutant expressing cells abolished the inner membrane potential of mitochondria (FIG. 17A) and increased the apoptotic-index as a result of the activation of caspase 3 (FIG. 17B). Interestingly, these results revealed that while accumulation of AZT-MP in the tmpk (WT)-overexpressing cells did not affect the mitochondrial function (FIG. 17A), there was a slight induction of apoptosis in these cells mediated by AZT (FIG. 17B).

Another advantage of the application is that it ensures that a high percentage of transduced cells, for example, cells to be transplanted, express the suicide gene. The use of huCD19Δ as a cell-surface marker increases the ratio of gene-modified cells by immuno-affinity enrichment. The contribution of the CD19 cytoplasmic domain in signal transduction has been assessed by others; in vitro by transfecting the cells with a truncated form of the human cDNA[43], and in vivo by using CD19-deficient mouse that expresses a transgene encoding the truncated human CD19[39]. These studies demonstrated that the cytoplasmic domain of CD19 is a crucial for the signaling and for the in vivo function of the CD19/CD21/CD81/Leu-13 complex. This indicates that the truncated form of human CD19 that employed is unlikely to transmit a signal.

Adoptive immunotherapy using T cells is an efficient approach to treat hematological malignancies[11,34,44-46]. GVHD, however, still remains a major problem following non-T cell-depleted allogeneic BMT[47]. In addition to its utility in deleting gene-modified cells if they undergo transformative events, the inventors have shown that it would be advantageous to incorporate an efficient in vivo safety switch that would enable the elimination of gene-modified T cells in the event of GvHD. The drug GCV has been used to deplete HSV-tk-expressing allogeneic lymphocytes following BMT[34,44]. Depletion is not always complete, however, and unwanted host immune responses against cells expressing this foreign enzyme can impair their function and persistence[10,11]. In addition, T cell responses to multiple epitopes of HSV-tk suggests that modification of immunogenic sequences in HSV-tk would likely be ineffective in ablating this reaction[11]. The use of human gene products as an alternative suicide gene in such situations is less likely to induce an immune response. Furthermore, most BMT patients are on prophylactic GCV to minimize CMV infections, which decreases the broad clinical utility of HSV-tk-based suicide gene therapy.

Figure 15:
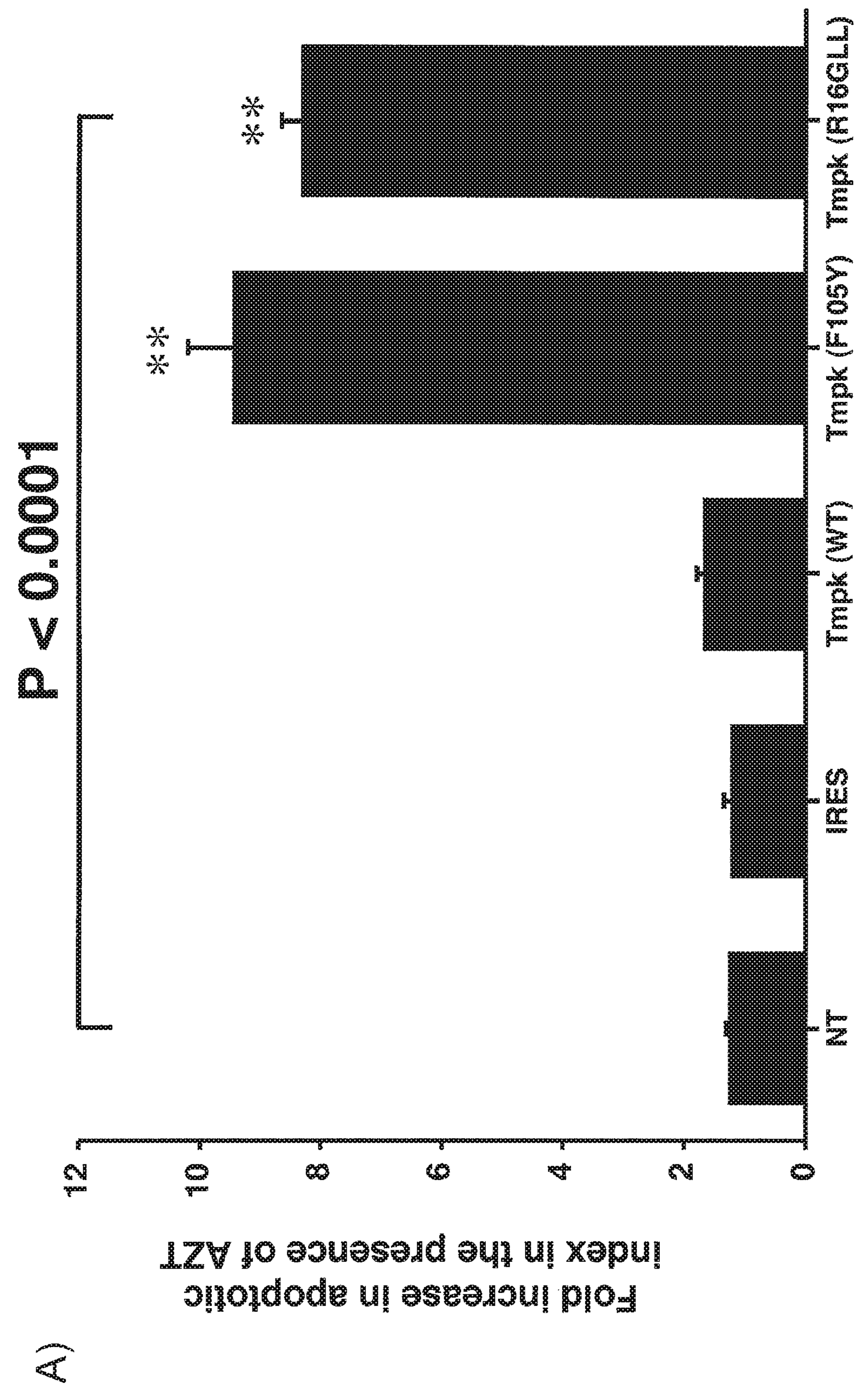
FIG. 15 shows the induction of apoptosis by addition of 100 μM AZT in clonal Jurkat cells transduced with LV-tmpk-IRES-huCD19Δ and control vectors. Cells were cultured in the absence (A) or presence (B) of 5 μM indirubin-3'-monoxime for 4 days with or without 100 μM AZT. To compare the effect of AZT on induction of apoptosis in each group, measurement of flow cytometric analyses obtained from the cells treated with AZT were normalized by dividing values by those obtained without AZT. Data are mean±SEM, n=3. The statistical differences were evaluated by the one-way ANOVA followed by a Bonferroni post-hoc test with the level of significance set at $P<0.05$. **, $P<0.01$ vs. the NT cells.
Figure 15:
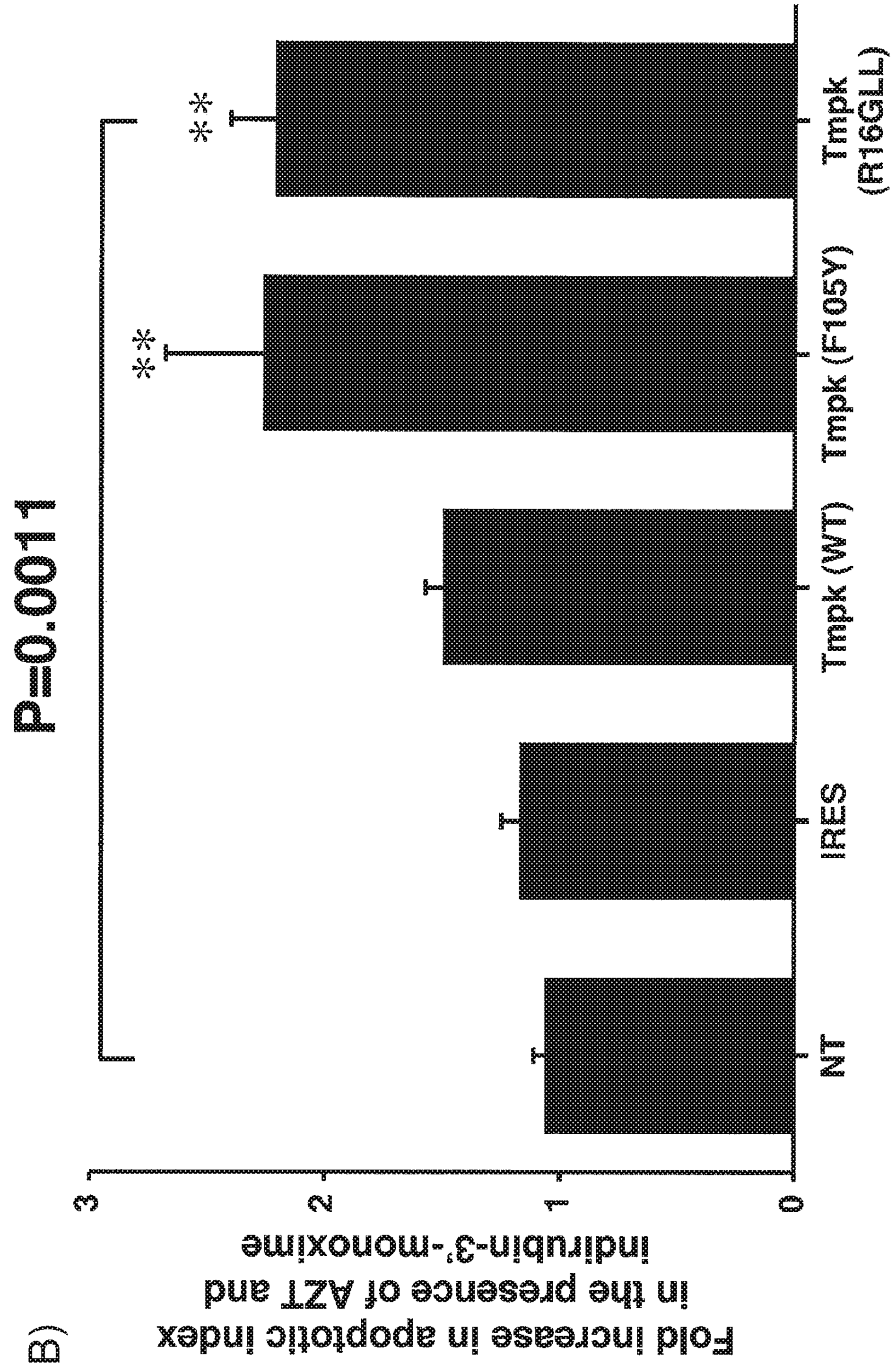
Figure 18:
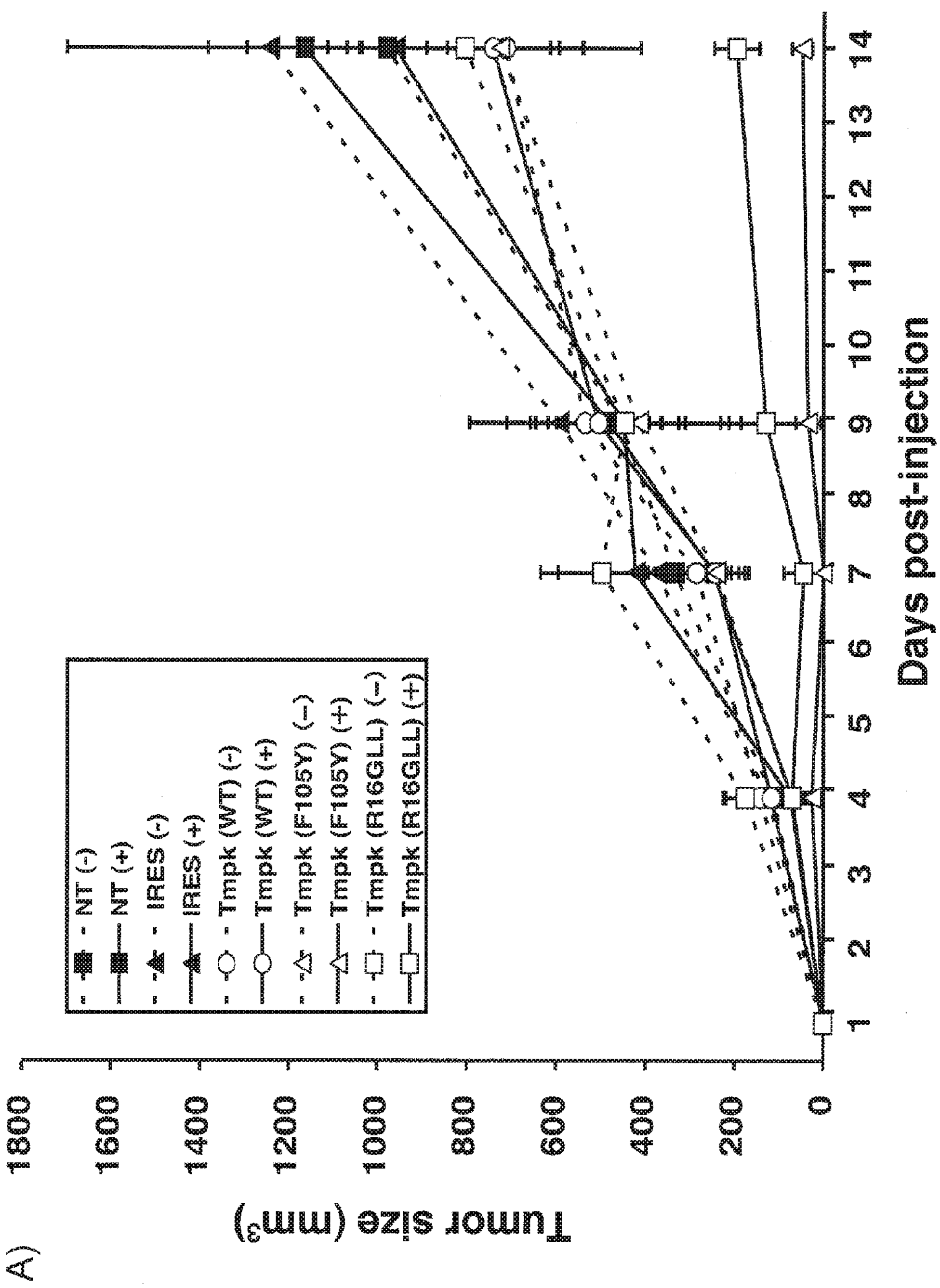
FIG. 18 shows that a daily injection of AZT prevents growth of K562 cells transduced with LV-tmpk-mutant in NOD/SCID mice. (A) NOD/SCID mice were subcutaneously injected with $2\times10^7$ cells of either the NT or the LV-transduced K562 cells into the dorsal right flank. Starting one day after the cell injection, the mice received daily intraperitoneal injections of AZT (2.5 mg/kg/day) for two weeks. Tumor volume was monitored at the day indicated in the figure. (B) The tumor volume on day 14 (at the end point of the experiment) is shown. Data are mean±SD, n=5. The statistical comparison of means was performed by a two-tailed unpaired Student's t test.
Figure 18:
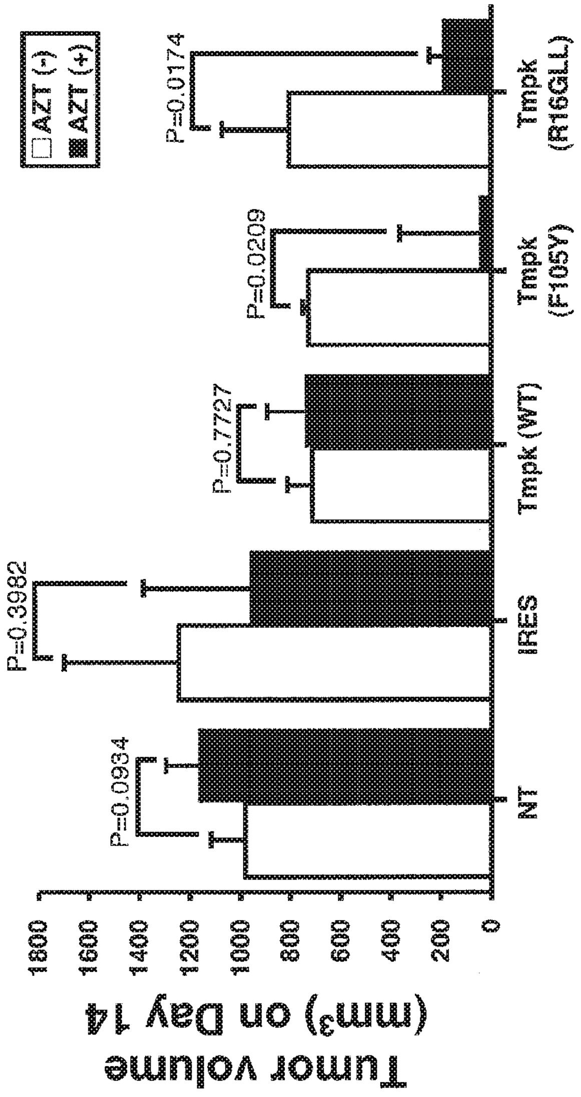

The inventors showed that the tmpk-mutant expressing Jurkat cells showed an increase in apoptotic index following AZT-treatment in vitro (FIGS. 14 and 15). NOD/SCID mice xenografted with LV-tmpk-mutant-transduced K562 cells (either F105Y or RG16LL) treated with AZT showed the suppression of tumor growth in vivo (FIG. 18). This data shows that the suicide gene methods of the application eliminate unwanted cells in vivo, including cancer cells and allografted T cells.

Example 16

Mammalian Cell CD19Δ/TMPK Fusion Expression

Methods

Synthesis of Mammalian Expression Vector Engineering Expression of CD19ΔTmpkF105YR200A Fusion Protein cDNA for CD19Δ and TmpkF105YR200A was amplified from a previously constructed shuttle vector: pSV-TmpkF105YR200A-IRES-CD19Δ.

CD19Δ cDNA was amplified using the following primers: hCD19Δ Forward: 5'-GCTA GAATTCATGCCACCTCCTCGCCTC-3' (SEQ ID NO:48) and hCD19Δ Reverse: 5'-GCTA GCCGGCAAGATGAAGAATGCCCACAAGG-3' (SEQ ID NO:49). TmpkF105YR200A-IRES cDNA was amplified using the following primers: Tmpk-IRES Forward: 5'-AAA CTGCAGGGATGGCGGCCCGGCGCGG-3' (SEQ ID NO:50) and Tmpk-IRES Reverse: 5'-GC TCTAGAATCGTGTTTTTCAAAGGAAAACCACGTCC-3' (SEQ ID NO:51). PCR products were directly ligated into the TA vector pGEM-T Easy (Promega) and sequenced (ACGT Corp.). The following sequence 5'-GCTTAC GAATTCTGACGCTAGCCGGCGGGG CTGCAGCATTACATCTAGATACC GTGAGGATC-CGTCGCATGCCATCG-3' (SEQ ID NO:52) was cloned into pGEM-4Z (Promega) using EcoRI and SphI sites to give pGEM-4Z2. TmpkF105YR200A-IRES cDNA was excised from pGEM-T Easy and subcloned into pGEM-4Z2 using PstI and XbaI sites to give pGEM-4Z2-Tmpk-IRES. CD19Δ cDNA was excised from pGEM-T Easy and subcloned into pGEM-4Z2-Tmpk-IRES using EcoRI and NgoMIV sites to give pGEM-4Z2-CD19ΔTmpk-IRES.

CD19ΔTmpkF105YR200A/IRES cDNA was excised from pGEM-4Z2-CD19ΔTmpk-IRES and subcloned into p-CI neo Mammalian Expression Vector (Promega) using EcoRI and XbaI sites to give pCIneo/CD19ΔTmpkF105YR200A/IRES.

Transfection of 293T Cells with p-CIneo/CD19ΔTmpkF105YR200A/IRES 293T cells were transiently transfected with pCIneo/CD19ΔTmpkF105YR200A/IRES using polyethylenimine. 48 hours later, transfection efficiency was determined by staining transfected cells with mouse anti-human CD19 antibody conjugated to phycoerythrin and measuring CD19 expression by FACS analysis.

HPLC for AZT Metabolites

Non-transfected 293T cells and 293T cells transfected with pCIneo/CD19ΔTmpkF105YR200A/IRES were cultured in 100 μM AZT in DMEM media for 6 hours. $1.5\times10^7$ cells were harvested and lysed by sonication in 5% (w/v) trichloroacetic acid. The lysate was centrifuged at 10,000 g for 15 minutes at 4° C. Supernatant was collected and trichloroacetic acid was extracted using an equal volume of 20% tri-n-octylamine in pentane. The aqueous fraction was injected into the HPLC machine. A C18 column (Waters) was used to separate AZT metabolites in a mobile phase of 0.2 M phosphate buffer containing 4 mM tetrabutylammonium hydrogen sulfate (pH 7.5) and acetonitrile in a ratio of 97:3 (v/v) at a flow rate of 1.5 ml/min. UV absorbance was measured at 270 nm.

Results

Figure 19:
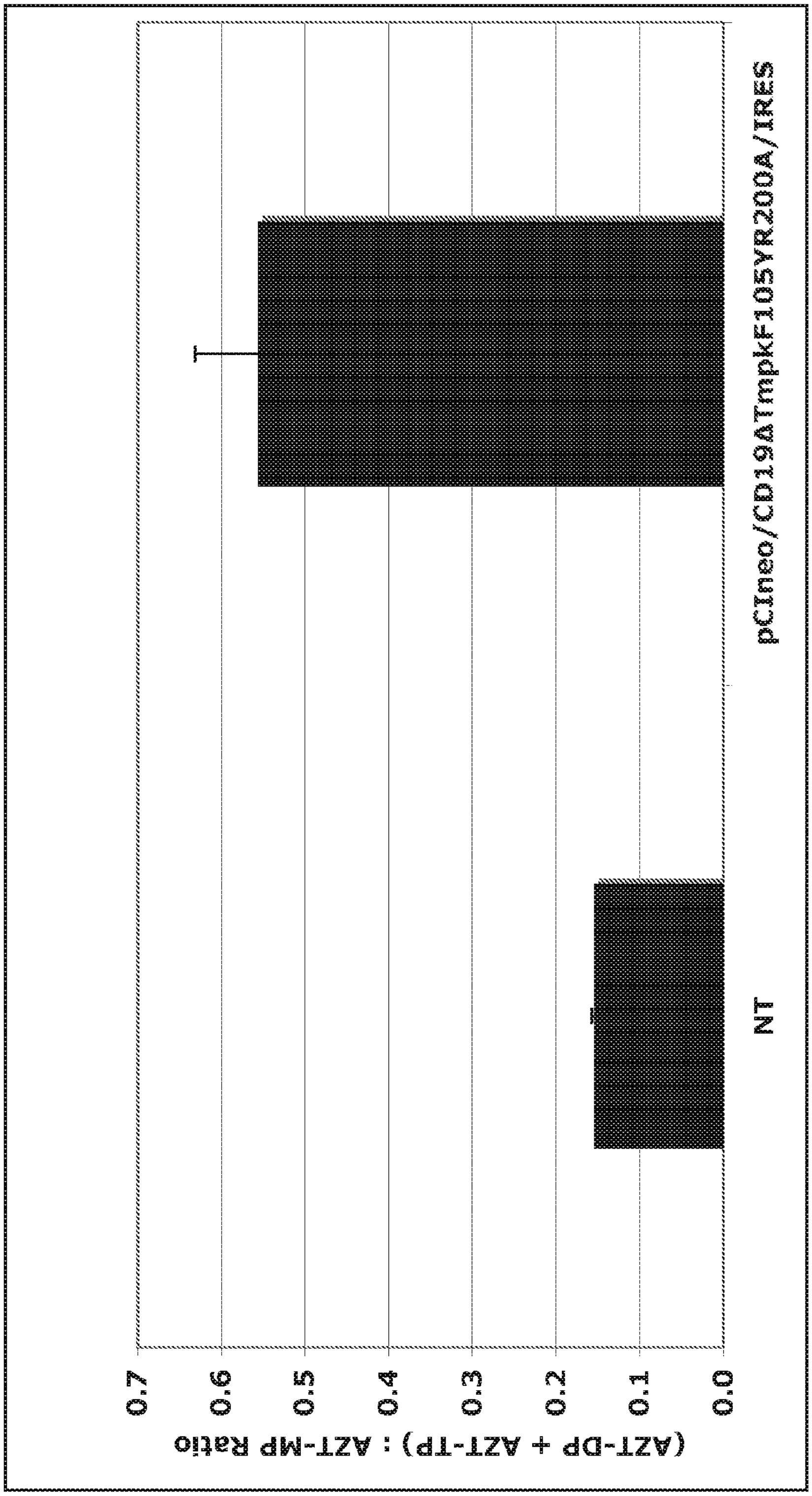
FIG. 19. Ratio of AZT-DP and AZT-TP compared to AZT-MP in 293T cells transfected with pCIneo/CD19ΔTmpkF105YR200A/IRES and a non-transfected control group (NT) determined by HPLC analysis.

HPLC for AZT Metabolites in Transfected 293T Cells 293T cells transfected with pCIneo/CD19ΔTmpkF105YR200A/IRES and cultured in 100 μM AZT for 6 hours showed an increase in the ratio of AZT-DP and AZT-TP to AZT-MP compared to the non-transfected control group (FIG. 19). This data suggests that the CD19ΔTmpkF105YR200A fusion protein is functional and has increased activity towards AZT-MP compared to wild type Tmpk.

Example 17

CD19/Tmpk Fusion Lentivirus

Methods

Synthesis of Lentiviral Vector Engineering Expression of CD19ΔTmpkF105YR200A Fusion Protein The CD19ΔTmpkF105YR200A fusion polypeptide was made as described previously. As mentioned, cDNA for CD19Δ and TmpkF105YR200A was amplified from a previously constructed shuttle vector: pSV-TmpkF105YR200A-IRES-CD19Δ. CD19Δ cDNA was amplified using the following primers: hCD19Δ Forward: 5'-GCTAGAATTCATGCCACCTCCTCGCCTC-3' (SEQ ID NO:48) and hCD19Δ Reverse: 5'-GCTA GCCGGCAAGATGAAGAATGCCCACAAGG-3' (SEQ ID NO:49). TmpkF105YR200A-IRES cDNA was amplified using the following primers: Tmpk-IRES Forward: 5'-AAA CTGCAGGGATGGCGGCCCGGCGCGG-3' (SEQ ID NO:50) and Tmpk-IRES Reverse: 5'-GC TCTAGAATCGTGTTTTTCAAAGGAAAACCACGT CC-3' (SEQ ID NO:51). PCR products were directly ligated into the TA vector pGEM-T Easy (Promega) and sequenced (ACGT Corp.). The following sequence 5'-GCTTAC GAATTCTGACGCTAGCCGGCGGGG CTGCAGCATTACATCTAGATACC GTGAGGATC-CGTCGCATGCCATCG-3' (SEQ ID NO:52) was cloned into pGEM-4Z (Promega) using EcoRI and SphI to give pGEM-4Z2. TmpkF105YR200A-IRES cDNA was excised from pGEM-T Easy and subcloned into pGEM-4Z2 using PstI and XbaI to give pGEM-4Z2-Tmpk-IRES. CD19Δ cDNA was excised from pGEM-T Easy and subcloned into pGEM-4Z2-Tmpk-IRES using EcoRI and NgoMIV to give pGEM-4Z2-CD19ΔTmpk-IRES. The CD19ΔTmpkF105YR200A fusion cDNA was then amplified from pGEM-4Z2-CD19ΔTmpk-IRES using the following primers: hCD19Δ AscI-Forward: 5'-A GGCGCGCCCGCCACCATGCCACCTCCTCGCCT CCTC-3' (SEQ ID NO:53) and Tmpk BamHI-Reverse 5'-GCAT- TACGGGATCCTCACTTCCATAGCTCCCCCAG-3' (SEQ ID NO:54). PCR product was directly ligated into the TA vector pGEM-T Easy. The CD19ΔTmpkF105YR200A fusion cDNA is then excised from pGEM-T Easy and subcloned into a lentivector backbone that is self inactivating and comprises a cPPT cassette, Elongation Factor 1 alpha promoter [and WPRE sequence such as a pHR' backbone, to give a lentiviral vector comprising CD19ΔTmpkF105YR200A. The sequence of the final construct is then confirmed.

CD19/Tmpk Fusion Polypeptide

Below is the DNA sequence for the CD19ΔTmpkF105YR200A fusion protein. Letters in green and underlined (N-terminal end) correspond to CD19Δ, letters in blue and not underlined correspond to the linker region (middle), and letters in brown and underlined correspond to TmpkF105YR200A (C-terminus end).

CD19Δ is a truncated form of the full CD19 sequence. The cDNA sequence was truncated at base 939 (amino acid 313), resulting in the deletion of the cytoplasmic region of the protein. Other truncations are also useful.

TmpkF105YR200A sequence also contains two silent mutations:

Base 318 is converted from C to A

Base 345 in converted from T to C

These mutations do not alter the sequence of the protein. Accordingly, sequences comprising "C" at base 318 and/or "T" at 345 as well as other nucleotide changes that do not result in amino acid changes, result in only conserved changes, and/or result in changes that are outside a region detected by a CD19 antibody, are also useful.

SEQ ID NO:40 provides a sequence for CD19deltaTmpkF105YR200A polynucleotide. CD19Δ to increase translation of this sequence (not shown above).

Polypeptide Sequence

The amino acid sequence of the CD19ΔTmpkF105YR200A fusion protein is provided in SEQ ID NO:41. AGGAAGrepresent the linker sequence between CD19Δ and TmpkF105YR200A.

Preparation of High-Titer Lentivirus

Vesicular stomatitis virus glycoprotein pseudotyped lentiviral vectors (LV/CD19ΔTmpkF105YR200A) are produced by transiently co-transfecting 293T cells with pCMVΔ8.91 (packaging plasmid), pMD.G (pseudotyping plasmid) and a lentiviral construct comprising CD19ΔTmpkF105YR200A using polyethylenimine. Viral supernatants are collected 48 hours after transfection, passed through a 0.45 μm filter and concentrated by ultracentrifugation at 28 000 rpm for 90 minutes. To determine functional titer, 293T cells are transduced with serial dilutions of concentrated LV/CD19ΔTmpkF105YR200. Transduced 293T cells are then stained with mouse anti-human CD19 antibody conjugated to phycoerythrin and CD19 expression is measured by FACS analysis.

Determining AZT Sensitivity of Transduced Jurkat Cells

Jurkat cells are transduced with either a LV/IRES/CD19Δ, LV/TmpkF105YR200A/IRES/CD19Δ or LV/CD19ΔTmpkF105YR200A construct. Transduced Jurkat cells and a non-transduced control group are seeded at $2\times10^5$ cells in 6-well tissue culture plates. Cells are incubated in the following concentrations of 3'-azido-3'-deoxythymidine (AZT) for 4 days: 0, 0.1, 1.0, 10, 100, 1000 μM AZT. After 4 days cell viability is determined using the Cell Titer 96 Aqueous One Solution Cell Proliferation Assay Kit (Promega). Data for each group is normalized to the 0 μM AZT value. Samples are assayed in quadruplicate.

Expected Results

Jurkat cells transduced with LV/CD19ΔTmpkF105YR200A are expected to have reduced cell viability compared to the non-transduced control group after incubation for 4 days in 100 μM and 1000 μM AZT. The reduction in cell viability is expected to be comparable to that observed with Jurkat cells transduced with LV/TMPKF105YR200A/IRES/CD19Δ.

Example 18

CD19/Tmpk Fusion Lentivirus

Methods

Synthesis of Lentiviral Vector Engineering Expression of CD19ΔTmpkF105YR200A Fusion Protein cDNA for CD19Δ and TmpkF105YR200A was amplified from a previously constructed shuttle vector: pSV-TmpkF105YR200A-IRES-CD19Δ.

Figure 21:
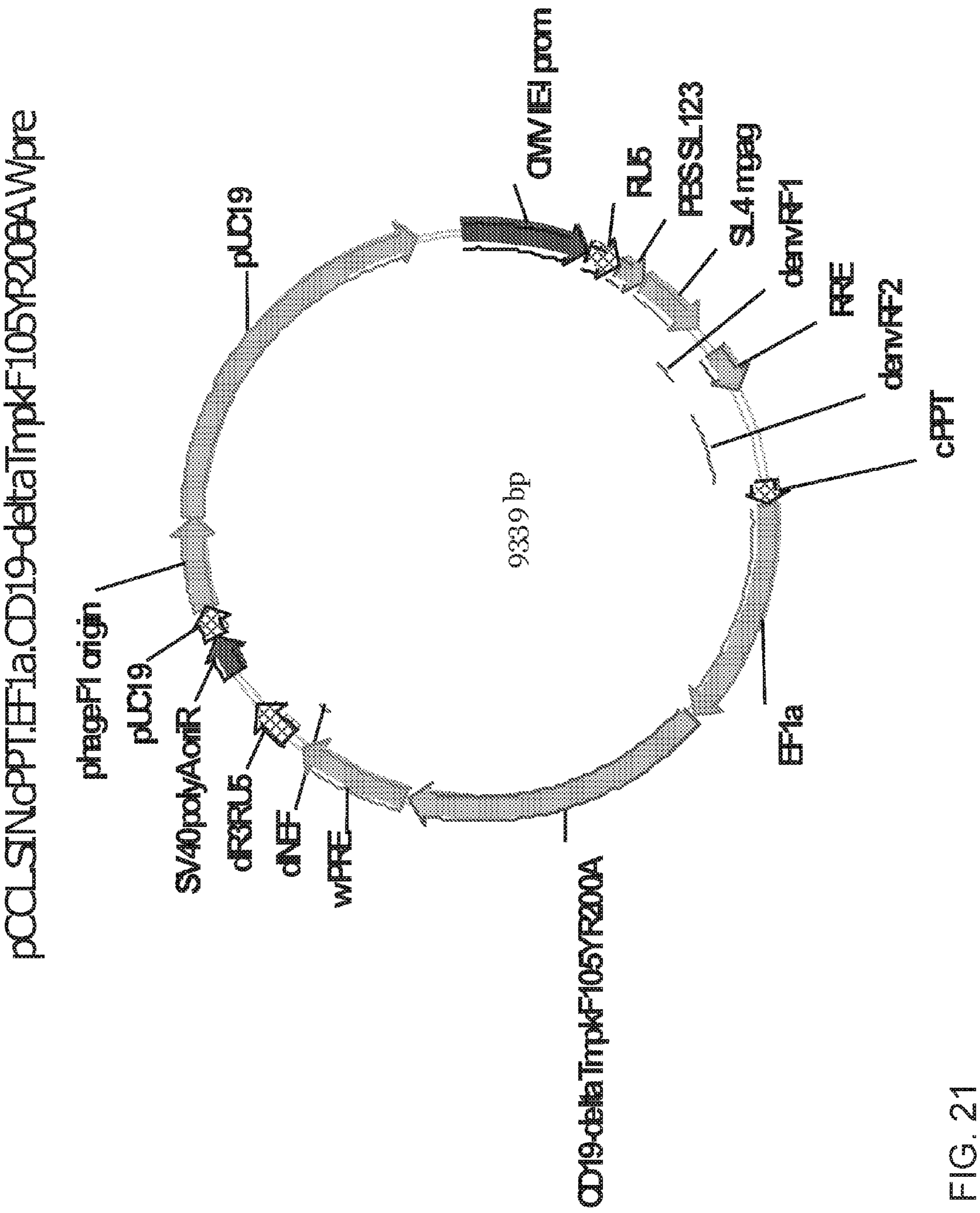
FIG. 21. A plasmid map for the lentivector pCCL.SIN-.cPPT.EF. CD19ΔTmpkF105YR200A.WPRE engineering expression of the CD19ΔTmpkF105YR200A fusion protein.

CD19Δ cDNA was amplified using the following primers: hCD19Δ Forward: 5'-GCTA GAATTCATGCCACCTCCTCGCCTC-3' (SEQ ID NO:48) and hCD19Δ Reverse: 5'-GCTA GCCGGCAAGATGAAGAATGCCCACAAGG-3' (SEQ ID NO:49). TmpkF105YR200A-IRES cDNA was amplified using the following primers: Tmpk-IRES Forward: 5'-AAA CTGCAGGGATGGCGGCCCGGCGCGG-3' (SEQ ID NO:50) and Tmpk-IRES Reverse: 5'-GC TCTAGAATCGTGTTTTTCAAAGGAAAACCAC GTCC-3' (SEQ ID NO:51). PCR products were directly ligated into the TA vector pGEM-T Easy (Promega) and sequenced (ACGT Corp.). The following sequence 5'-GCT-TACGAATTCTGACGCTAGCCGGCGGGG CTGCAGCATTACATCTAGATACC GTGAGGATC-CGTCGCATGCCATCG-3' (SEQ ID NO:52) was cloned into pGEM-4Z (Promega) using EcoRI and SphI to give pGEM-4Z2. TmpkF105YR200A-IRES cDNA was excised from pGEM-T Easy and subcloned into pGEM-4Z2 using PstI and XbaI to give pGEM-4Z2-Tmpk-IRES. CD19Δ cDNA was excised from pGEM-T Easy and subcloned into pGEM-4Z2-Tmpk-IRES using EcoRI and NgoMIV to give pGEM-4Z2-CD19ΔTmpk-IRES. The CD19ΔTmpkF105YR200A fusion cDNA was then amplified from pGEM-4Z2-CD19ΔTmpk-IRES using the following primers: hCD19Δ AscI-Forward: 5'-A GGCGCGCCCGCCACCATGCCACCTCCTCGC CTC-CTC-3' (SEQ ID NO:53) and Tmpk BamHI-Reverse 5'-GCATTACG GGATCCTCACTTCCATAGCTCCCCCAG-3' (SEQ ID NO:54). PCR product was directly ligated into the TA vector pGEM-T Easy. The CD19ΔTmpkF105YR200A fusion cDNA was then excised from pGEM-T Easy and subcloned into a lentivector backbone pCCL.SIN.cPPT.EF.WPRE using AscI and BamHI sites to give pCCL.SIN.cPPT.EF. CD19ΔTmpkF105YR200A.WPRE (FIG. 21). This construct is self inactivating and comprises a central polypurine tract (cPPT), EF and a woodchuck hepatitis virus post-transcriptional regulatory element (WPRE). The sequence of the final construct was then confirmed.

The sequence of the vector construct pCCL.SIN.cPPT.EF. CD19ΔTmpkF105YR200A.WPRE comprising CD19ΔTmpkF105YR200A fusion is provided in SEQ ID NO:42.

The Kozak consensus sequence of cgccacc has been added directly upstream of CD19D to increase translation of this sequence.

Preparation of High-Titer Lentivirus

Vesicular stomatitis virus glycoprotein pseudotyped lentiviral vectors (LV/CD19ΔTmpkF105YR200A) were produced by transiently co-transfecting 293T cells with pCMVΔ8.91 (packaging plasmid), pMD.G (pseudotyping plasmid) and pSIN.cPPT.EF.CD19ΔTmpkF105YR200A.WPRE using polyethylenimine. Viral supernatants were collected 48 hours after transfection, passed through a 0.45 μm filter and concentrated by ultracentrifugation at 28 000 rpm for 90 minutes. To determine functional titer, 293T cells were transduced with serial dilutions of concentrated LV/CD19ΔTmpkF105YR200A. Transduced 293T cells were then stained with mouse anti-human CD19 antibody conjugated to phycoerythrin and CD19 expression was measured by FACS analysis.

Determination of AZT Sensitivity of Transduced Jurkat Cells

Jurkat cells were transduced with either LV/IRES/CD19Δ, LV/TmpkF105YR200A/IRES/CD19Δ or LV/CD19ΔTmpkF105YR200A. Transduced Jurkat cells and a non-transduced control group were seeded at $2\times10^5$ cells in 6-well tissue culture plates. Cells were incubated in the following concentrations of 3'-azido-3'-deoxythymidine (AZT) for 4 days: 0, 0.1, 1.0, 10, 100, 1000 μM AZT. After 4 days cell viability was determined using the Cell Titer 96 Aqueous One Solution Cell Proliferation Assay Kit (Promega). Data for each group was normalized to the 0 μM AZT value. Samples were assayed in quadruplicate.

Results

Figure 20:
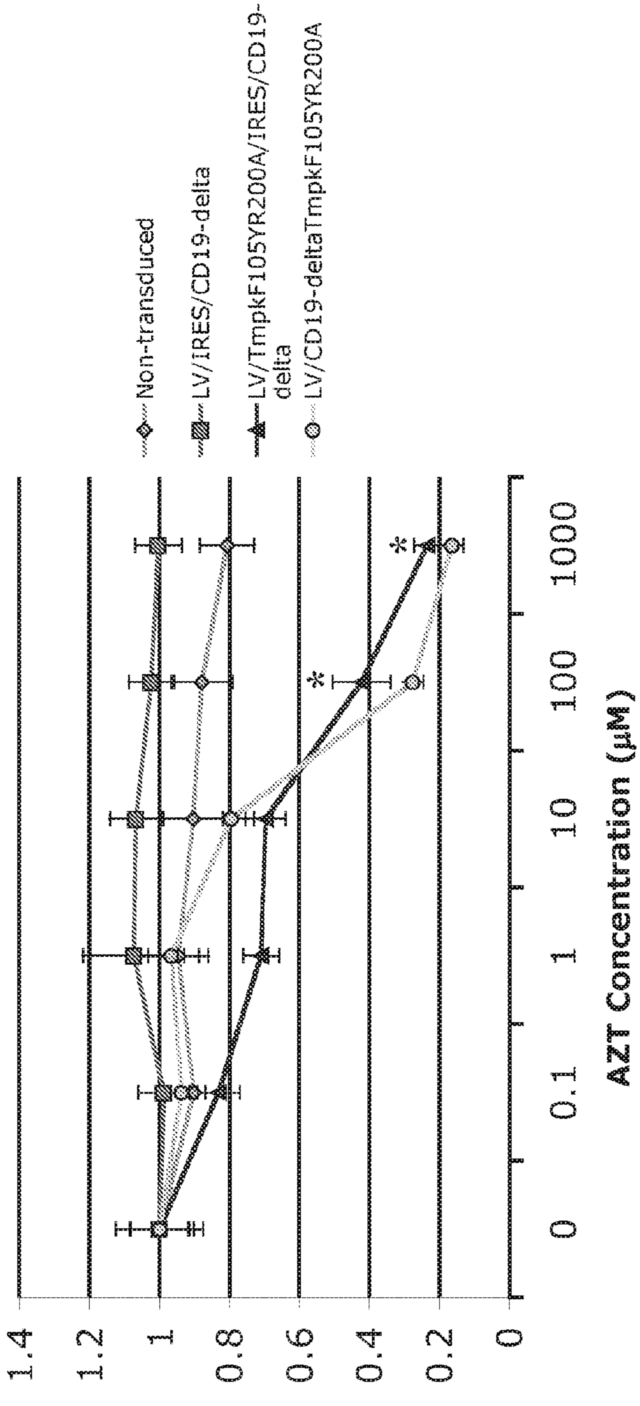
FIG. 20. Cell viability of Jurkat cells transduced with LV/CD19ΔTmpkF105YR200A is significantly reduced when incubated in 100 μM and 1000 μM compared to the non-transduced control group. Values in each group are normalized to the 0 μM AZT value, with this value being set to 1.0.

Jurkat cells transduced with LV/CD19ΔTmpkF105YR200A have significantly reduced cell viability compared to the non-transduced control group after incubation for 4 days in 100 μM and 1000 μM AZT ($p<0.001$ for both groups) (FIG. 20). The reduction in cell viability is comparable to that observed with Jurkat cells transduced with LV/TMPKF105YR200A/IRES/CD19Δ described above.

Example 19

Cloning of pHR'.cPPT.EF.CD19ΔTmpkF105YR200A.WPRE.SIN

Figure 22:
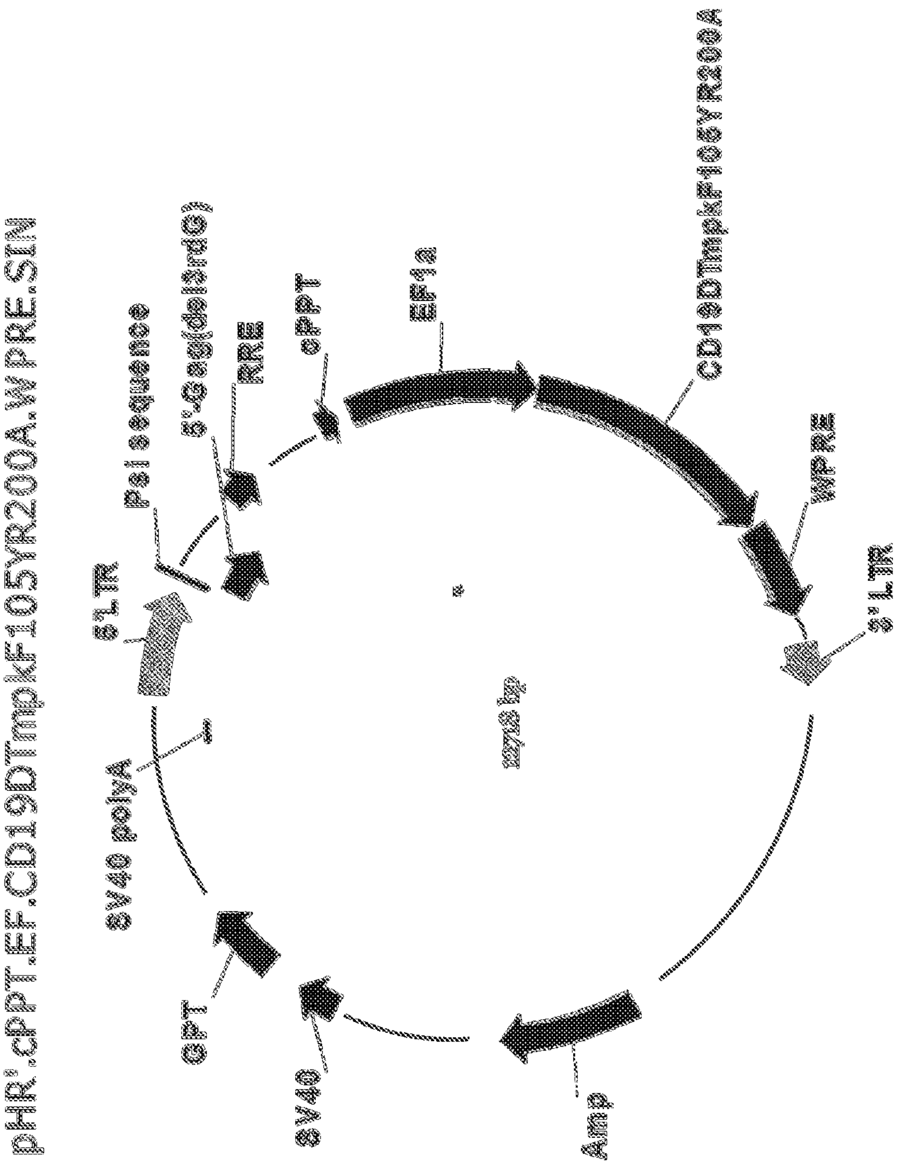
FIG. 22. A plasmid map for pHR'-CD19ΔTmpkF105YR200A.

The CD19ΔTmpkF105YR200A fusion cDNA is amplified by PCR from pGEM-4Z2-CD19ΔTmpk-IRES (described previously) using the following primers: hCD19Δ Forward: 5'-GCTA GAATTCATGCCACCTCCTCGCCTC-3' (SEQ ID NO:48) and Tmpk BamHI-Reverse 5'-GCATTACG GGATCCTCACTTCCATAGCTCCCCCAG-3' (SEQ ID NO:54). The PCR product is directly ligated into the TA vector pGEM-T Easy. The CD19ΔTmpkF105YR200A fusion cDNA is then excised from pGEM-T Easy and subcloned into pHR'.cPPT.EF.EG.WPRE.SIN using EcoRI and BamHI sites to give pHR'.cPPT.EF.CD19ΔTmpkF105YR200A.WPRE.SIN. It is also possible to use the following pairs of restriction endonucleases to subclone the CD19ΔTmpkF105YR200A fusion cDNA into pHR'.cPPT.EF.EG.WPRE.SIN: AscI and BamHI or SalI and BamHI. If using these restriction endonuclease pairs, the forward PCR primer needs to be designed accordingly to include the correct enzyme sites. A plasmid map for this construct is shown in FIG. 22.

The sequence is provided in SEQ ID NO:43.

Example 20

Jurkat Cells Transduced with LV CD19Δ are Sensitive to AZT

Figure 23:
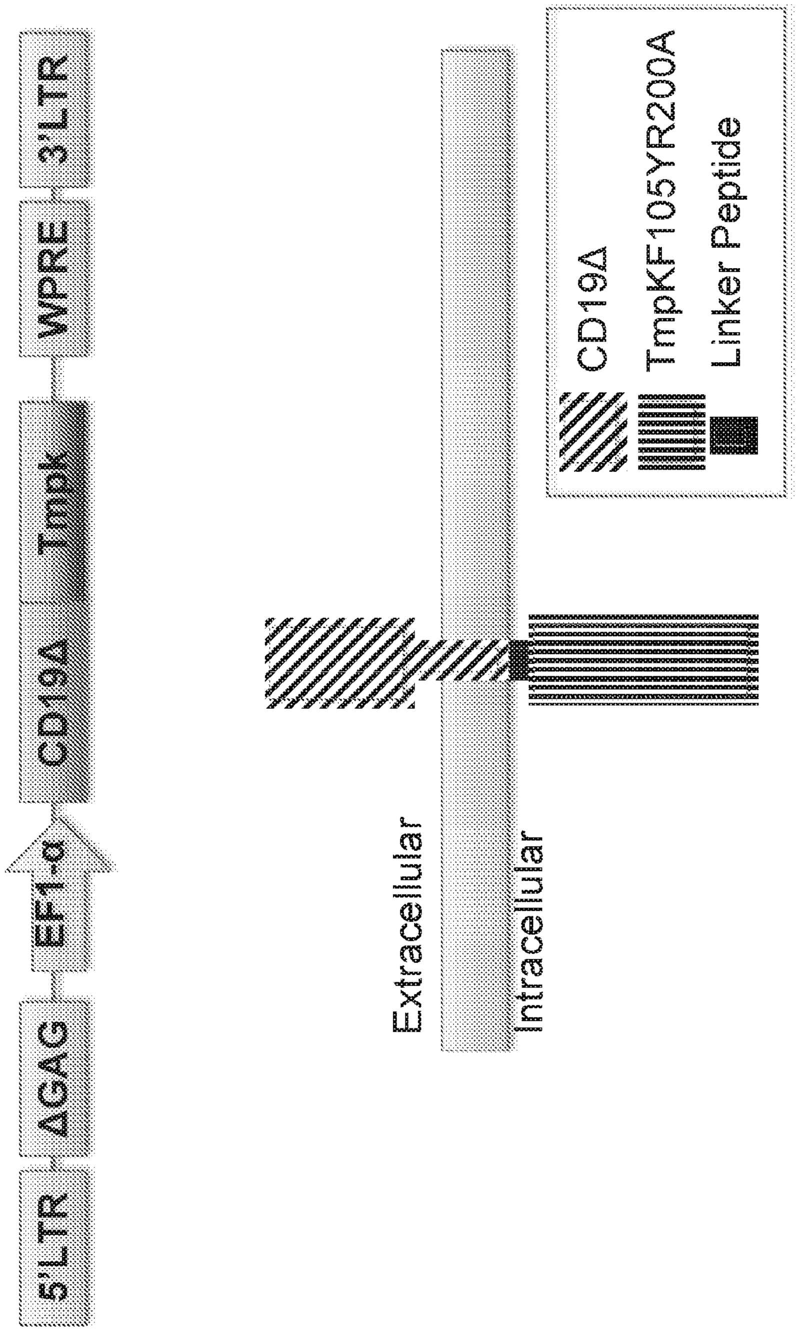
FIG. 23. Development of Novel CD19/TmpK Fusion 'Cell Fate Control' Gene Illustration.

FIG. 23 provides a schematic representation of a CD19Δ/Tmpk construct. Using the mutant Tmpk and by fusing it to a selective marker (CD19) allows for both functional proteins to be expressed by one permitting the use of a monocistronic vector. Also by fusing these two sequences genes together it allows both to be expressed at one to one ratio. Cells express the same number of ΔCD19 and mutant Tmpk functional units. Further, use of the fusion gene decreases the size of the construct.

The CD19 cassette allows selection for modified cells by FACs or beads.

Methods:

Jurkat cells were transduced with pCLL-CD19ΔTmpK and were sorted by FACs staining for CD19. Transduced cells were seeded in 6-well culture plates. Serial dilution of AZT (Sigma) in media were made from 1000 uM to 0.1 uM and added to each well. Fresh AZT was added daily for 4 days. After 4 days of culture, cells were subjected to the MTS Assay.

Cell Viability Analysis by MTS Assay

Cell viability was determined using the CellTiter 96 AQ One Solution Cell Proliferation Assay (Promega). Absorbance values were read at 490 nm using a plate reader.

Cell viability was reported by normalizing absorbance values at each concentration of AZT against the non-treated value for each group.

Figure 24:
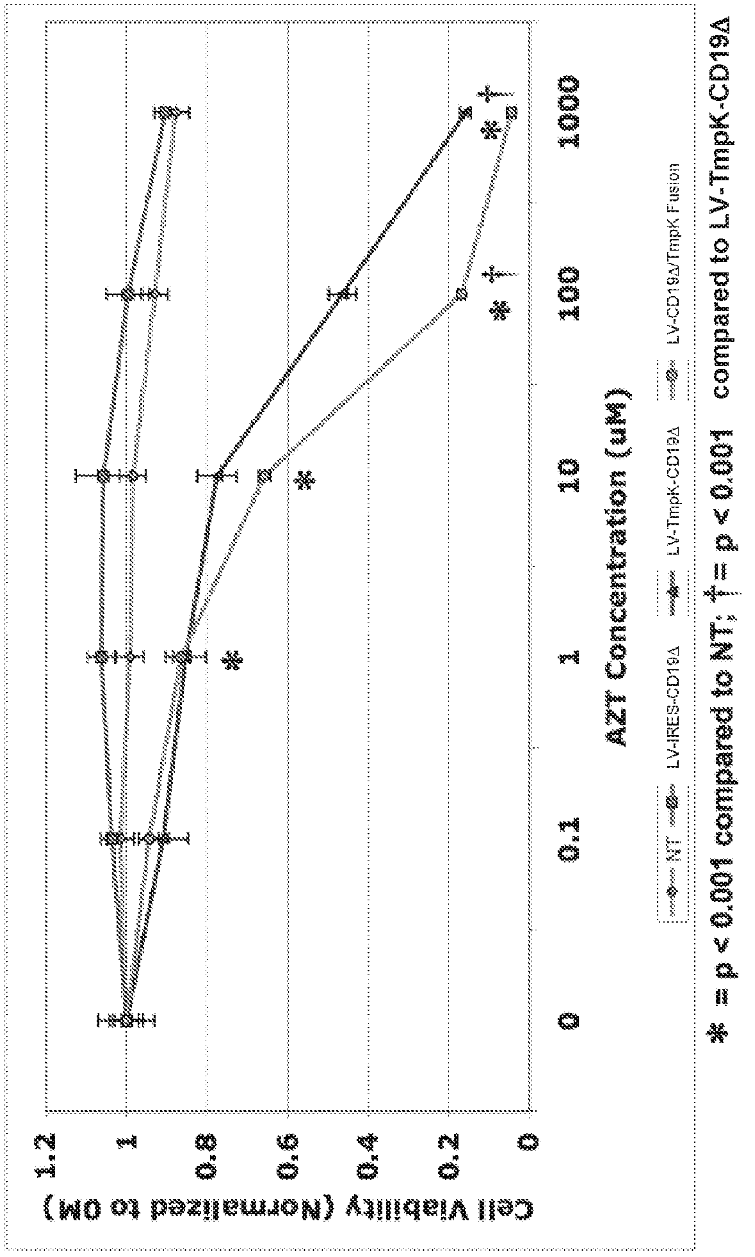
FIG. 24. A graph showing sensitivity of Jurkat Cells Transduced with LV/CD19Tmpk-Fusion Towards AZT FIG. 25. Development of Bicistronic Lentivirus: CD19/TmpK Fusion with Secondary αGalA FIG. 26. A graph showing αGalA enzyme activity of transduced Fabry Fibroblast with the LV/ΔCD19/TmpK-IRES-αGalA FIG. 27. A plasmid map of pDY.CD19deltaTmpK FIG. 28. A plasmid map of pDY.CD19deltaTmpK-IRES-CO-αGalA FIG. 29. Is a series of graphs which show K562 Cells transduced at MOI 10. Gated on live cells (7AAP).

Jurkat cells transduced with LV CD19Δ-Tmpk or LV CD19Δ/Tmpk fusion were sensitive to AZT (see FIG. 24).

Example 21

Alpha-Galactosidase A Expression and Activity

Methods:

Fabry patient Fibroblast and immortalized fabry fibroblasts were transduced with pCCL-CD19ΔTmpk-IRES-αGalA at a MOI 10. Cells were sorted using FACs for 100% CD19 expression.

α-gal A activity was measured in cell lysates of the sorted transduced fibroblast. For details on α-gal A enzyme activity assay see: Yoshimitsu, M. et al. (2007) Gene Therapy. 14, 256-265.

Results:

When considering developing a novel lentiviral vector for gene therapy it needs 3 things:

1. A selective marker.
2. Cell fate control or Suicide gene to protect against insertional mutagenesis.
3. Finally a therapeutic gene for application of to disease correction.

Figure 25:
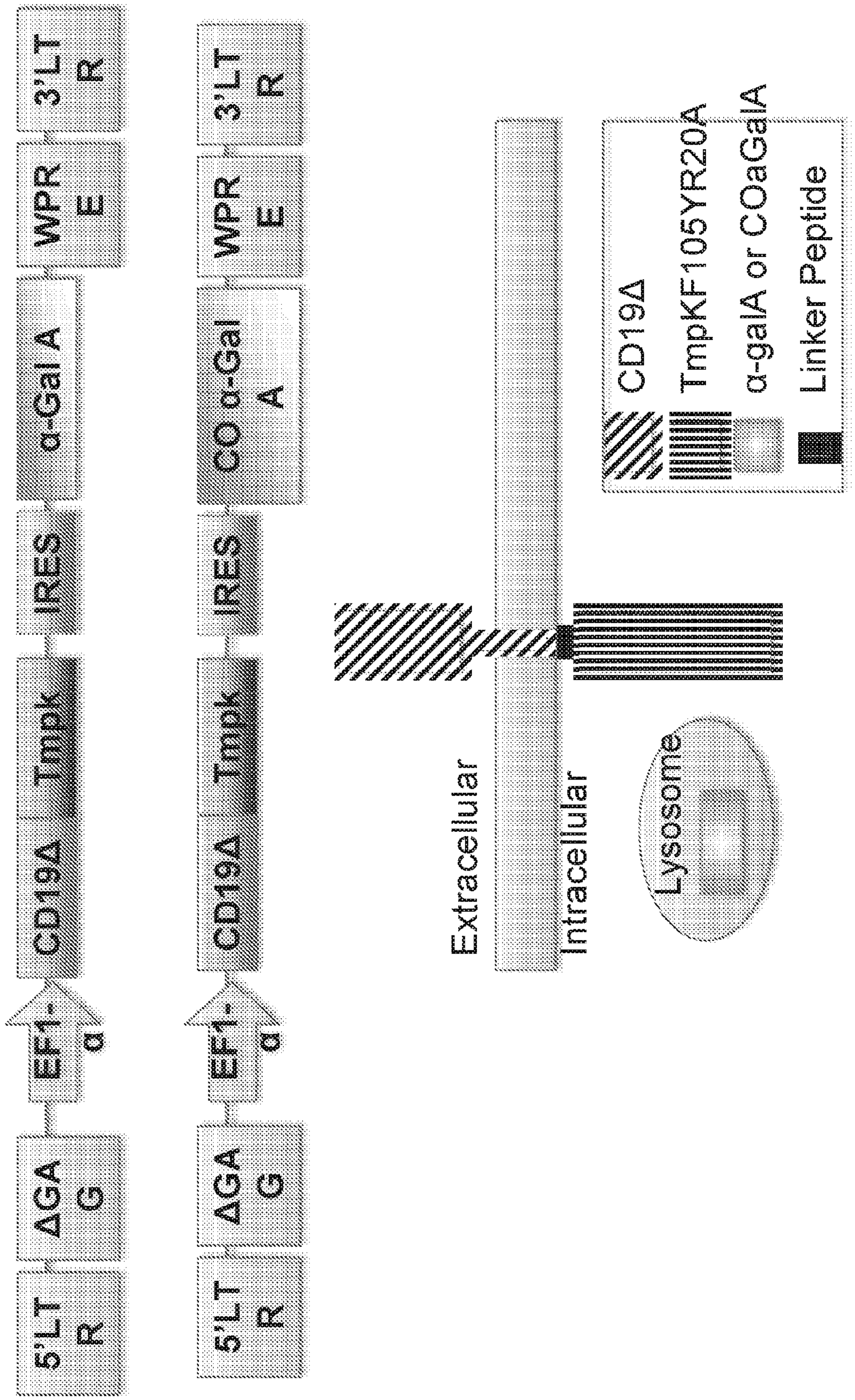

FIG. 25 shows a schematic representation of a CD19Δ/Tmpk fusion construct with secondary αGALA construct and orientation of the expressed fusion in cells.

The figure shows that the selective marker and the cell fate control or suicide gene are fused together. The fusion allows all cells that express the detection cassette to also express the modified tmpk, which is advantageous.

Figure 26:
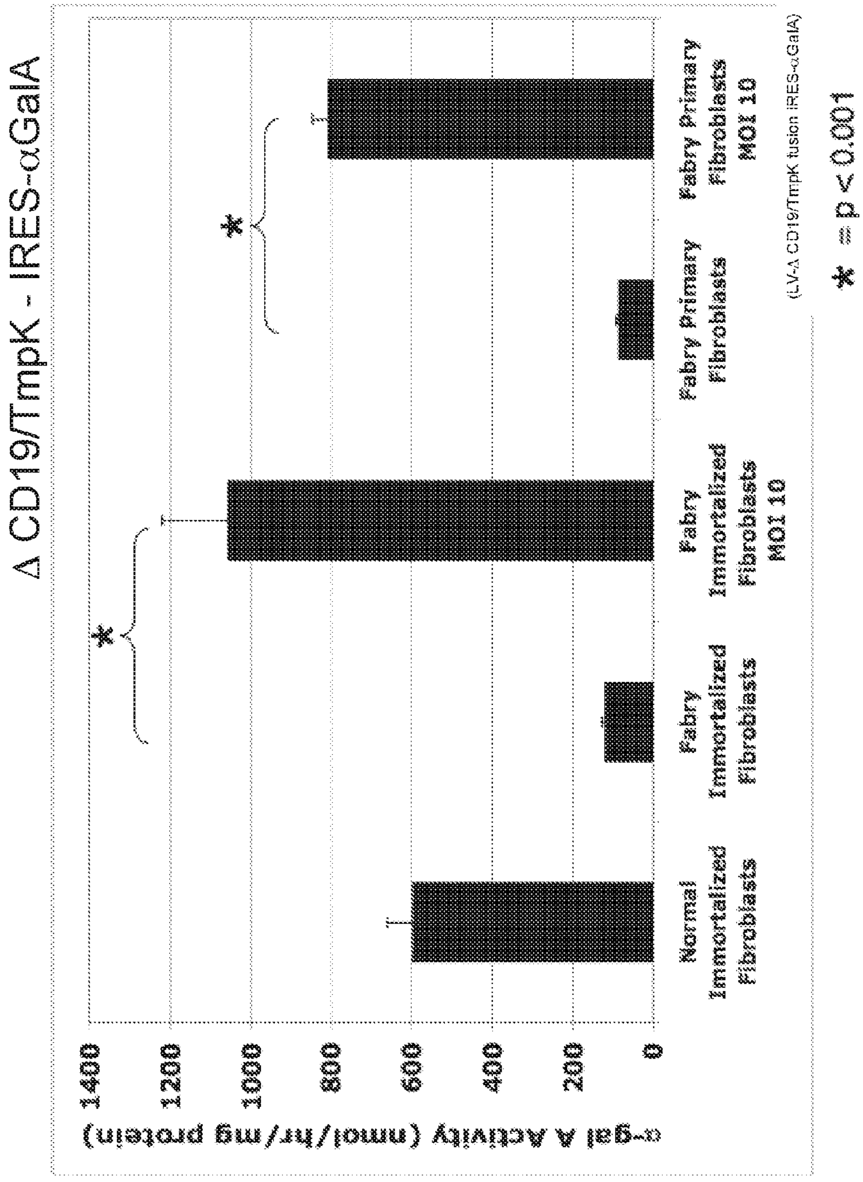

FIG. 26 shows alphaGalA enzyme activity of transduced Fabry fibroblasts. Codon optimized alphaGalA (CO alphaGalA) was used. CO alpha Gal A, is Codon optimized Alpha Gal A. It's nucleotide sequence is different from the regular Alpha-Gal A. If you align the two sequences (Codon optimized and Normal alphaGalA) you only get about 75% identity, however it you align the protein sequence you get 100% identity. This nucleic acid was synthetically constructed because codon optimization may allow us to get a higher expression for the enzyme because it uses tRNAs that are more abundant within the human cell.

Example 22

Additional Lentiviral Vectors

Two new vectors were sub-cloned from the original pCLL backbone to the pDY lentiviral backbone (note: these vectors have the same functionality as previously described, the functional genes were not altered, they were just moved to a new lentiviral backbone.

Figure 27:
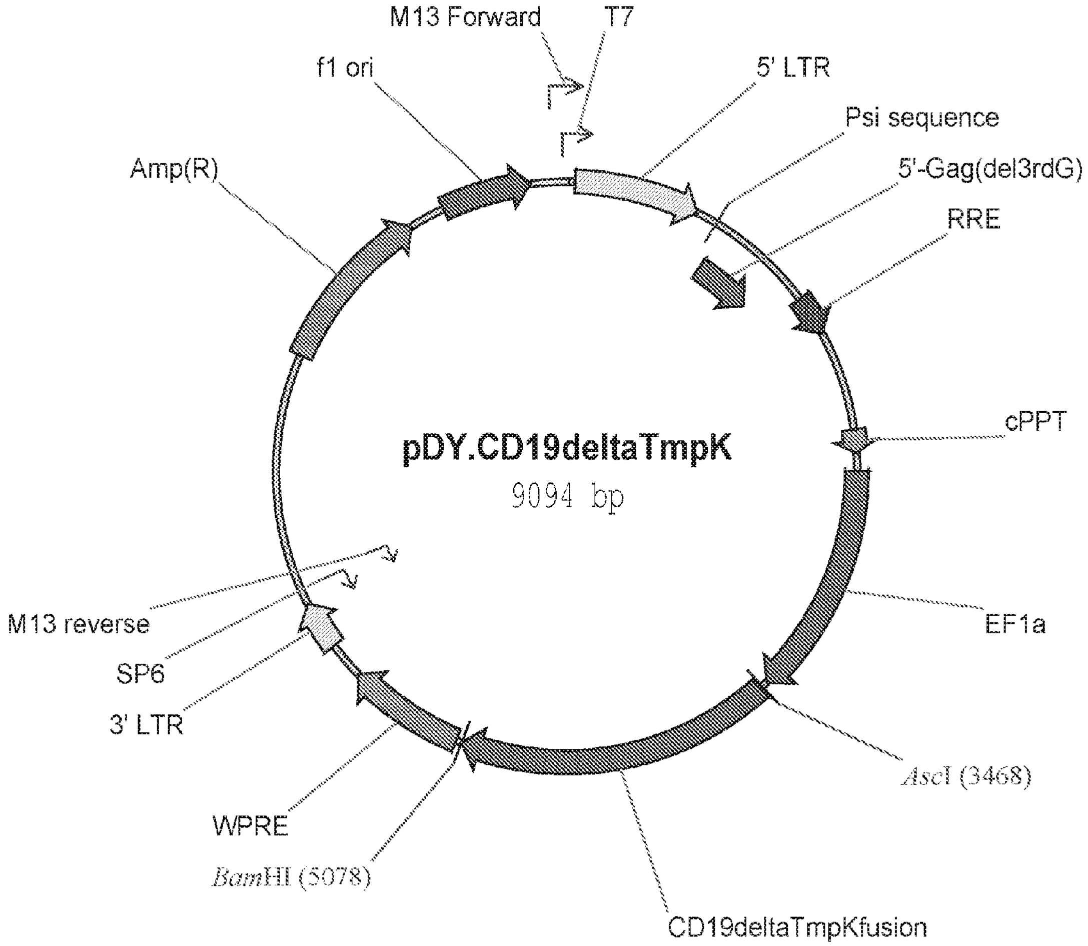
Figure 28:
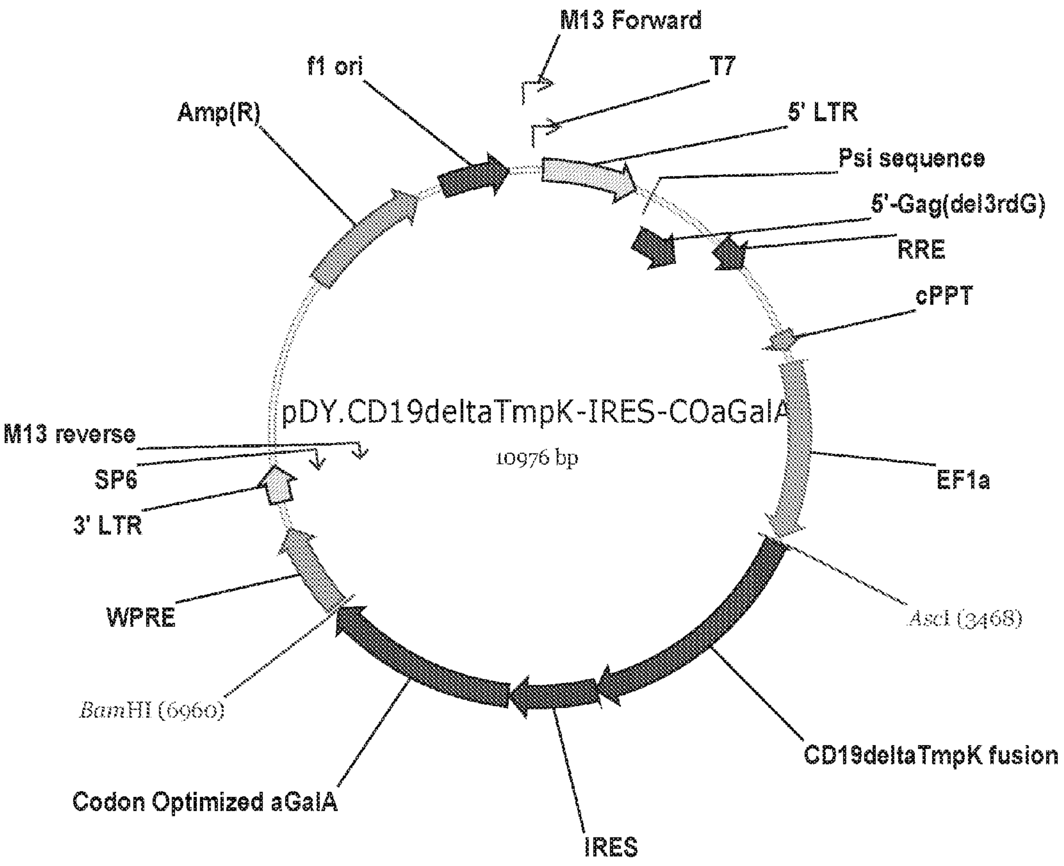

The CD19Δ/Tmpk fusion insert was subcloned into a pDY delivery vector (see SEQ ID NO: 44 for vector construct sequence) (see FIG. 27). Codon optimized αGalA (SEQ ID NO: 46; amino acid sequence provided in SEQ ID NO:47) was also cloned into the CD19Δ/Tmpk fusion containing vector (FIG. 28; SEQ ID NO:45).

Construct Names:

pDY-CD19ΔTmpK (SEQ ID NO:44)

pDY-CD19ΔTmpK-IRES-00αGalA (codon optimized alpha-Gal A gene) (SEQ ID NO:45)

K562 cells transduced with pDY-CD19ΔTmpK show sensitivity to AZT.

Experimental Design:

K562 cells were transduced with pDY-CD19ΔTmpK (suicide fusion only) at a MOI 10 to examine if this cell line shows sensitivity to AZT.

Transduced cells (only approximately 8% positive for CD19ΔTmpK) were given AZT at concentrations of 0 μM, 0.1 μM, 1.0 μM, 10.0 μM, and 100.0 μM.

Analysis was performed using Flow cytometry after 4 days of AZT treatment (fresh drug was added daily.

Figure 29:
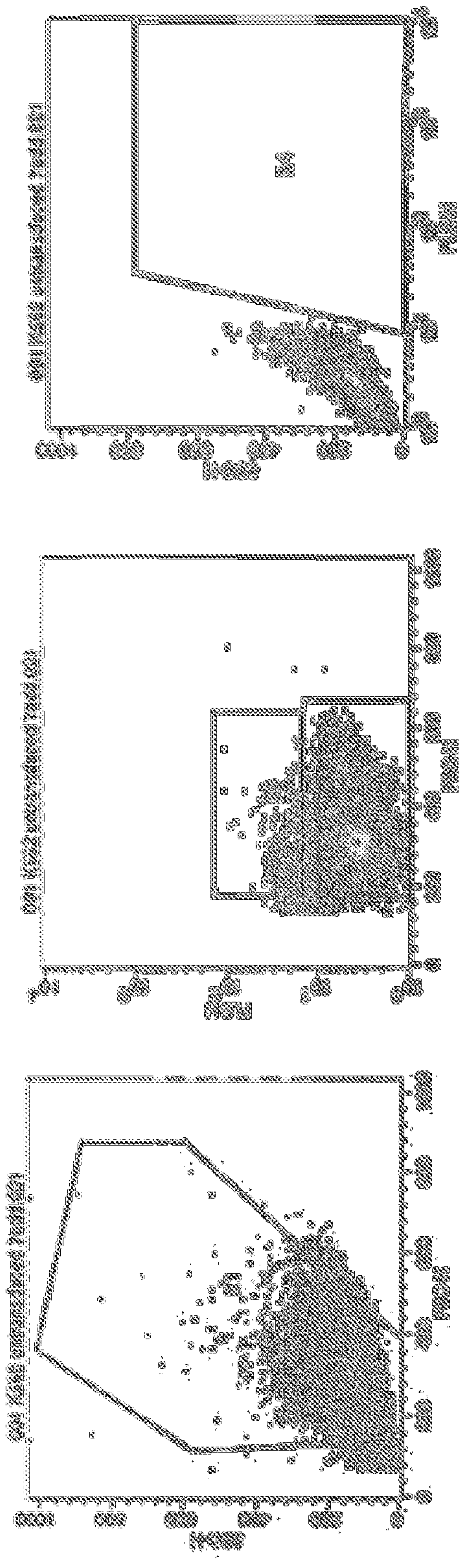
Figure 29:
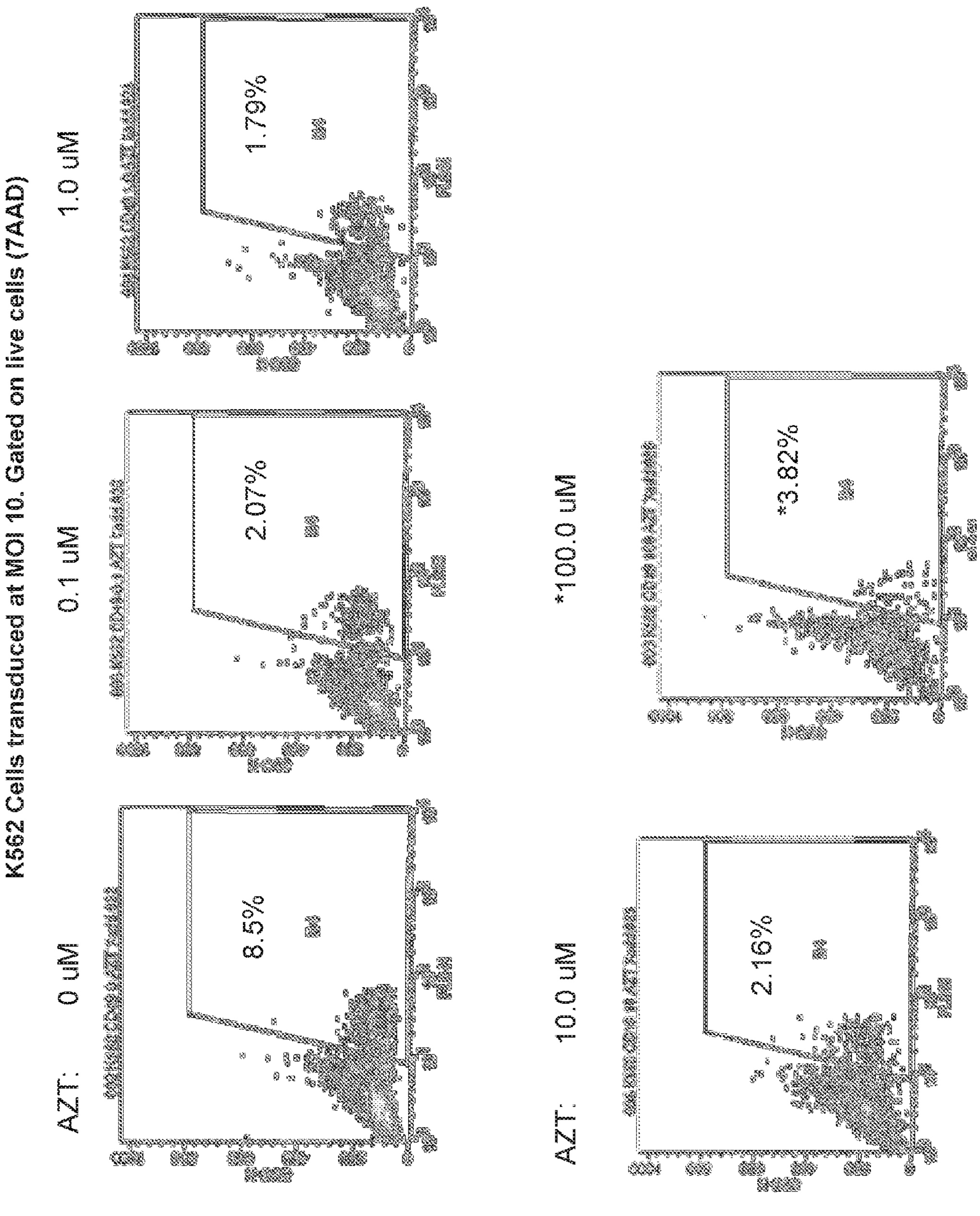

Discussion and Results:

See FIG. 29 for results. The Figure shows approximately 80% reduction in transduced cells. If cells were left in culture longer, CD19 expression may have been reduced further.

Control group: GFP positive cells showed no reduction after treatment.

Future experiments will be performed on sorted populations of cells (100% expressing CD19ΔTmpK). Once cells are sorted, a cell proliferation assay (ex. MTS assay) will be used to determine effective killing.

Example 23

Methods

Fabry patient Fibroblast were transduced with pDY-CD19ΔTmpk-IRES-αGalA at a MOI 10. Transduction efficiency was measured by CD19 expression using FAC.

α-gal A activity was measured in cell lysates. For details on α-gal A enzyme activity assay see: Yoshimitsu, M. et al. (2007) Gene Therapy. 14, 256-265.

Results

Figure 30:
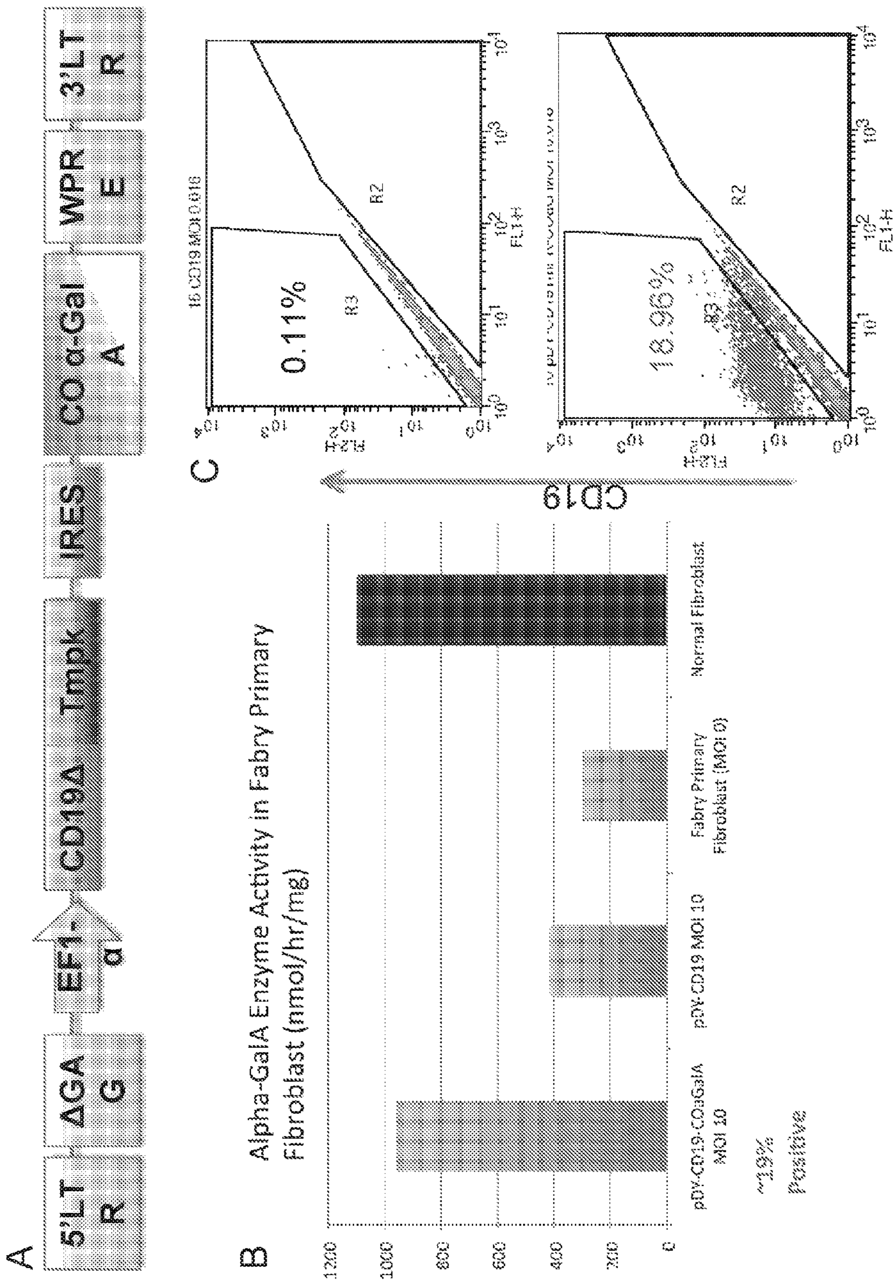
FIG. 30. Is made up of two graphs (A and B) which represent: A) Alpha-GalA Enzyme Activity in Fabry Primary Fibroblast and B) Fabry Fibroblast cells. Transduced Fabry Fibroblast with pDY-CD19ΔTmpK-IRES-COαGalA show enzyme correction.

Transduced Fabry Fibroblast with pDY-CD19ΔTmpK-IRES-COαGalA show enzyme correction (FIG. 30). Fabry primary fibroblasts were infected with the constructs. Data suggest that Fabry cells were corrected even when only approximately 19% cells were transduced with pDY-CD19ΔTmpK-IRES-COaGalA. Enzyme activity was measured in an aGalA enzyme activity assay.

Example 24

Figure 31:
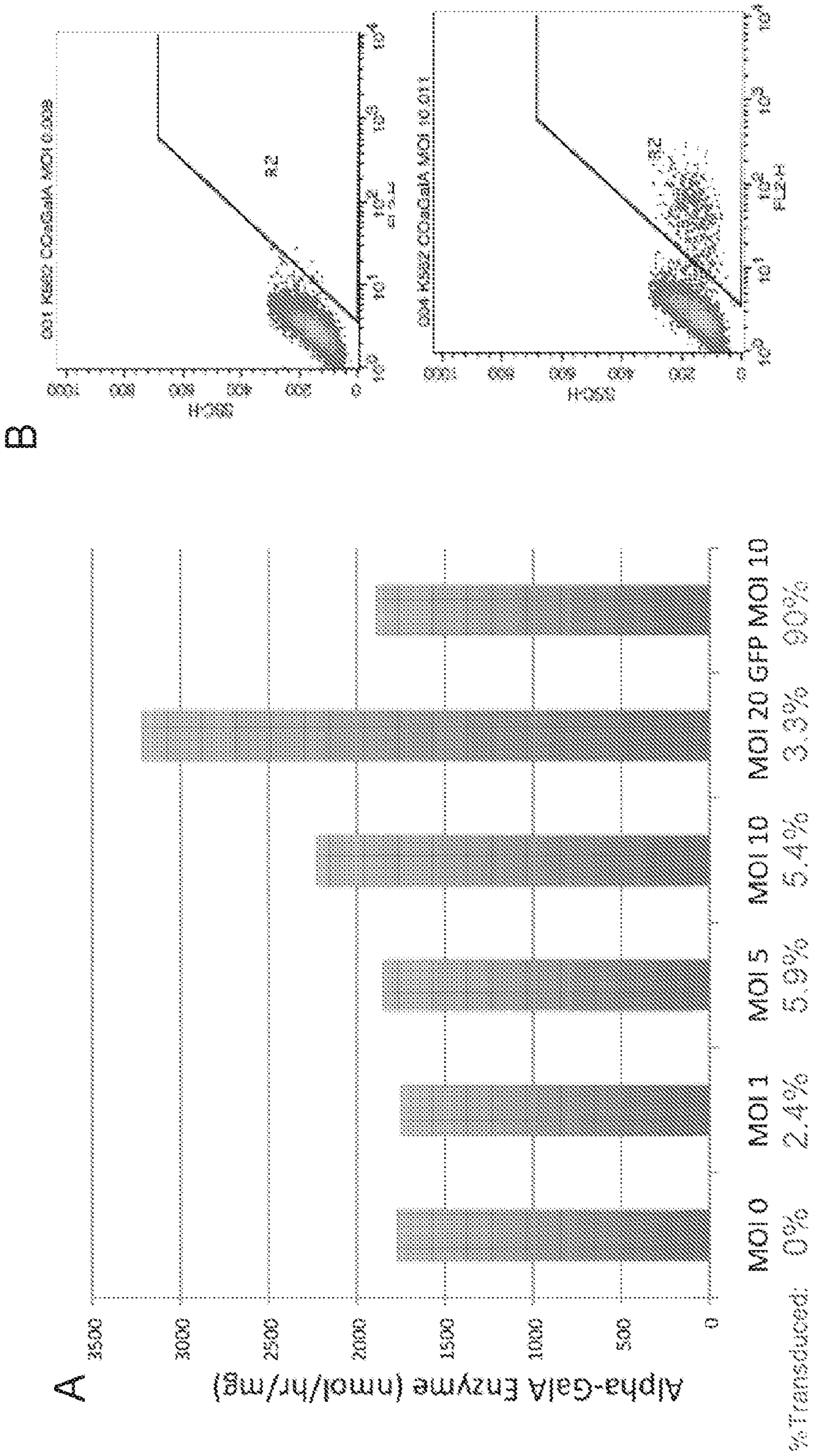
FIG. 31. Is a series of Graphs. A) shows Alpha-GalA Enzyme activity and B) shows FACS analysis of COαGalA transduced cells. Transduced K562 Cells with pDY-CD19ΔTmpK-IRES-COαGalA shows over-expression of αGalA.

Transduced K562 Cells with pDY-CD19ΔTmpK-IRES-COαGalA Show Over-Expression of αGalA Results and Discussion:

Even in K562 cells (normally express aGalA), we are able to increase aGalA levels (1.8 fold increase of MOI 20 compared to untransduced) (FIG. 31). This is an unsorted population of cells (ex. only 3.3% of cells were transduced at a MOI 20). Future experiments will be performed on sorted populations of cells which are expected to show even more striking results.

Example 25

Fabry Disease is an in-born X-linked lysosomal disorder caused by a deficiency of the α-galactosidase A (α-gal A) enzyme. As a result of this deficiency, glycosphingolipids with terminal α-galactosyl moieties accumulate in the vascular endothelium, mainly as globotriaosylceramide (GB3). Progressive GB3 accumulation results in ischemia and infarction, and eventually leads to other major clinical manifestations of the disease, such as kidney and heart failure. Emerging success in gene therapy research has led to possible treatment hopes for Fabry disease. Yoshimitsu and colleagues (2007) (Yoshimitsu, M. et al. (2007) Gene Therapy. 14, 256-265). [2] showed efficient and sustained correction of Fabry mice and patient cells mediated by lentiviral transduction of hematopoietic stem cells. The promises of gene therapy, however, are often impeded by a small number of adverse events as exemplified in past gene therapy clinical trials. In a small number of clinical trials, insertional mutagenesis resulting in oncogenesis has been observed after treatment with integrating retroviral vectors.

One of the safety strategies currently being developed is termed 'cell fate control' or suicide gene therapy. Alongside the delivery of a therapeutic gene (ex. α-Gal-A for Fabry disease) a 'suicide gene' would also be delivered to gene-knock-in/target cells. Transfer of suicide genes to modified cells endows them with the appropriate enzyme to convert prodrugs to cytotoxic metabolites. This can act as a molecular safety switch in the rare event of insertional oncogenesis. In the event of an adverse effect, the patient can be administered the prodrug for selective clearance of modified cells. Sato et al (2007) (Sato, T., et al. (2007) Molecular Therapy. 15, 962-9) describe a novel enzyme (suicide gene) and prodrug combination for selectively inducing apoptosis in lentiviral vector (LV) transduced cells. The engineered mutant human Thymidylate kinase (tmpk) can efficiently phosphorylate 3' azido-3'-deoxythymidine (AZT) to its cytotoxic form. Coupling this described suicide gene together in with the therapeutic gene (α-Gal-A) for treatment of Fabry disease in a promising avenue to pursue, it should allow for disease correction with the added benefits of protection against insertional mutagenesis.

Disclosed herein is a novel engineered lentiviral vector containing three components necessary for a gene therapeutic agent. Firstly, a selective marker to enrich for modified cells. Secondly, a 'suicide gene' as a safety mechanism. Lastly, the therapeutic gene for disease correction. By creating a fusion protein the integrity of 3 genes could be maintained within a bicistronic vector. Fusing Tmpk to the C-terminus of a truncated from of CD19 (a selective marker), has allowed for the secondary gene, α-gal A (for Fabry disease correction) to be expressed downstream of IRES element, thus creating a bicistronic vector. This novel bicistronic lentiviral vector may be capable of correcting inborn genetic disorders such as Fabry disease and furthermore contains the built-in safety 'molecular switch,' required for approving clinical protocols.

Furthermore the suicide fusion vector (CD19ΔTmpk) alone has many additional applications in regards to cell transplantation in the clinic. It may be possible to protect patients from teratomas in stem cell transplantation and Graft-versus-host disease in lymphocyte transfusions. In the event of a cell transplantation adverse event (ex. GvHD or development of a teratoma) it may be possible to eliminate the problematic cells by providing the patient with the prodrug.

Example 26

Once Fabry patients are identified as good candidates for treatment using this propose lentivirus-mediated gene therapy, the patients hematopoietic stem cells will have to be harvested, for ex vivo, genetic manipulation using the lentivirus, pDY-CD19ΔTmpK-IRES-COαGalA. Hematopoietic stem cell isolation will most likely occur from already standardized human clinical protocols such as isolating CD34+ from the blood through the process of apheresis. This procedure is similar to donating blood, the patient is administered certain drugs that stimulate the release of stem cells from the bone marrow into circulating blood. An IV is inserted into the patients arm, and the stem cells are filtered out of the blood.

Once the hematopoietic stem cells (ex. CD34+) are isolated they will be brought to the laboratory were they will be infected with lentivirus, pDY-CD19ΔTmpK-IRES-COαGalA (multiplicity of infection and number of cells unknown at this time). After cells have been successfully infected, the transduction efficiency can be evaluated by the CD19 expression. It is also possible enrich for modified cells (CD19 expressing cells) by FACs, or by using magnetic bead sorting.

The modified hematopoietic stem cells will than be re-introduced into the same patient (autogeneic transplantation). Again already human clinical protocols will be used for cell transplantation and myeloablation regimens of the patient.

After successful cell engraftment (approximately 3 months) and reconstitution of the hematopoietic system the patients α-galactisidase A enzyme activity can be measured in blood plasma to look for correction of Fabry disease (increase levels of enzyme).

In the rare case of an adverse event such as insertional oncogenesis, the patient can be administered the prodrug, 3' azido-3'-deoxythymidine (AZT), for selective clearance of the modified cells. It should also be noted that AZT is already used in the clinic for treatment of HIV and its safety profiles are well understood.

While the application has been described in connection with specific embodiments thereof, it will be understood that it is capable of further modifications and this application is intended to cover any variations, uses, or adaptations of the application following, in general, the principles of the application and including such departures from the present disclosure as come within known or customary practice within the art to which the application pertains and as may be applied to the essential features hereinbefore set forth, and as follows in the scope of the appended claims.

All publications, patents and patent applications, are herein incorporated by reference in their entirety to the same extent as if each individual publication, patent or patent application was specifically and individually indicated to be incorporated by reference in its entirety.

REFERENCES

1. Hacein-Bey-Abina S, Von Kalle C, Schmidt M, McCormack M P, Wulffraat N, Leboulch P, et al. LMO2-associated clonal T cell proliferation in two patients after gene therapy for SCID-X1. *Science.* 2003; 302: 415-419.
2. Roy N S, Cleren C, Singh S K, Yang L, Beal M F, Goldman S A. Functional engraftment of human ES cell-derived dopaminergic neurons enriched by coculture with telomerase-immortalized midbrain astrocytes. *Nat. Med.* 2006; published online: 22 Oct. 2006.
3. Nishiyama Y, Rapp F. Anticellular effects of 9-(2-hydroxyethoxymethyl) guanine against herpes simplex virus-transformed cells. *J Gen Virol.* 1979; 45: 227-230.
4. Moolten F L. Tumor chemosensitivity conferred by inserted herpes thymidine kinase genes: paradigm for a prospective cancer control strategy. *Cancer Res.* 1986; 46: 5276-5281.
5. Wildner O, Blaese R M, Morris J C. Therapy of colon cancer with oncolytic adenovirus is enhanced by the addition of herpes simplex virus-thymidine kinase. *Cancer Res.* 1999; 59: 410-413.
6. Moolten F L, Wells J M. Curability of tumors bearing herpes thymidine kinase genes transferred by retroviral vectors. *J Natl Cancer Inst.* 1990; 82: 297-300.
7. Hamel W, Magnelli L, Chiarugi V P, Israel M A. Herpes simplex virus thymidine kinase/ganciclovir-mediated apoptotic death of bystander cells. *Cancer Res.* 1996; 56: 2697-2702.
8. Kokoris M S, Black M E. Characterization of herpes simplex virus type 1 thymidine kinase mutants engineered for improved ganciclovir or acyclovir activity. *Protein Sci.* 2002; 11: 2267-2272.
9. Qasim W, Thrasher A J, Buddle J, Kinnon C, Black M E, Gaspar H B. T cell transduction and suicide with an enhanced mutant thymidine kinase. *Gene Ther.* 2002; 9: 824-827.
10. Riddell S R, Elliott M, Lewinsohn D A, Gilbert M J, Wilson L, Manley S A, et al. T-cell mediated rejection of gene-modified HIV-specific cytotoxic T lymphocytes in HIV-infected patients. *Nat. Med.* 1996; 2: 216-223.
11. Berger C, Flowers M E, Warren E H, Riddell S R. Analysis of transgene-specific immune responses that limit the in vivo persistence of adoptively transferred HSV-TK-modified donor T cells after allogeneic hematopoietic cell transplantation. *Blood.* 2006; 107: 2294-2302.
12. Van Rompay A R, Johansson M, Karlsson A. Phosphorylation of nucleosides and nucleoside analogs by mammalian nucleoside monophosphate kinases. *Pharmacol Ther.* 2000; 87: 189-198.
13. Furman P A, Fyfe J A, St Clair M H, Weinhold K, Rideout J L, Freeman G A, et al. Phosphorylation of 3'-azido-3'-deoxythymidine and selective interaction of the 5'-triphosphate with human immunodeficiency virus reverse transcriptase. *Proc Natl Acad Sci USA.* 1986; 83: 8333-8337.
14. St Clair M H, Richards C A, Spector T, Weinhold K J, Miller W H, Langlois A J, et al. 3'-Azido-3'-deoxythymidine triphosphate as an inhibitor and substrate of purified human immunodeficiency virus reverse transcriptase. *Antimicrob Agents Chemother.* 1987; 31: 1972-1977.

15. Frick L W, Nelson D J, St Clair M H, Furman P A, Krenitsky T A. Effects of 3'-azido-3'-deoxythymidine on the deoxynucleotide triphosphate pools of cultured human cells. *Biochem Biophys Res Commun.* 1988; 154: 124-129.
16. Johnson A A, Ray A S, Hanes J, Suo Z, Colacino J M, Anderson K S, et al. Toxicity of antiviral nucleoside analogs and the human mitochondrial DNA polymerase. *J Biol. Chem.* 2001; 276: 40847-40857.
17. Lavie A, Schlichting I, Vetter I R, Konrad M, Reinstein J, Goody R S. The bottleneck in AZT activation. *Nat. Med.* 1997; 3: 922-924.
18. Coplan N L, Bruno M S. Acquired immunodeficiency syndrome and heart disease: the present and the future. *Am Heart J.* 1989; 117: 1175-1177.
19. Cazzalini O, Lazze M C, Iamele L, Stivala L A, Bianchi L, Vaghi P, et al. Early effects of AZT on mitochondrial functions in the absence of mitochondrial DNA depletion in rat myotubes. *Biochem Pharmacol.* 2001; 62: 893-902.
20. Sales S D, Hoggard P G, Sunderland D, Khoo S, Hart C A, Back D J. Zidovudine phosphorylation and mitochondrial toxicity in vitro. *Toxicol Appl Pharmacol.* 2001; 177: 54-58.
21. Masini A, Scotti C, Calligaro A, Cazzalini O, Stivala L A, Bianchi L, et al. Zidovudine-induced experimental myopathy: dual mechanism of mitochondrial damage. *J Neurol Sci.* 1999; 166: 131-140.
22. McKee E E, Bentley A T, Hatch M, Gingerich J, Susan-Resiga D. Phosphorylation of thymidine and AZT in heart mitochondria: elucidation of a novel mechanism of AZT cardiotoxicity. *Cardiovasc Toxicol.* 2004; 4: 155-167.
23. Brundiers R, Lavie A, Veit T, Reinstein J, Schlichting I, Ostermann N, et al. Modifying human thymidylate kinase to potentiate azidothymidine activation. *J Biol. Chem.* 1999; 274: 35289-35292.
24. Ostermann N, Lavie A, Padiyar S, Brundiers R, Veit T, Reinstein J, et al. Potentiating AZT activation: structures of wild-type and mutant human thymidylate kinase suggest reasons for the mutants' improved kinetics with the HIV prodrug metabolite AZTMP. *J Mol. Biol.* 2000; 304: 43-53.
25. Naldini L, Blomer U, Gallay P, Ory D, Mulligan R, Gage F H, et al. In vivo gene delivery and stable transduction of nondividing cells by a lentiviral vector. *Science.* 1996; 272: 263-267.
26. Blomer U, Naldini L, Kafri T, Trono D, Verma I M, Gage F H. Highly efficient and sustained gene transfer in adult neurons with a lentivirus vector. *J. Virol.* 1997; 71: 6641-6649.
27. Yoshimitsu M, Sato T, Tao K, Walia J S, Rasaiah V I, Sleep G T, et al. Bioluminescent imaging of a marking transgene and correction of Fabry mice by neonatal injection of recombinant lentiviral vectors. *Proc Natl Acad Sci USA.* 2004; 101: 16909-16914.
28. Sadelain M, Riviere I. Sturm und drang over suicidal lymphocytes. *Mol. Ther.* 2002; 5: 655-657.
29. Migita M, Medin J A, Pawliuk R, Jacobson S, Nagle J W, Anderson S, et al. Selection of transduced CD34+ progenitors and enzymatic correction of cells from Gaucher patients, with bicistronic vectors. *Proc Natl Acad Sci USA.* 1995; 92: 12075-12079.
30. Medin J A, Migita M, Pawliuk R, Jacobson S, Amiri M, Kluepfel-Stahl S, et al. A bicistronic therapeutic retroviral vector enables sorting of transduced CD34+ cells and corrects the enzyme deficiency in cells from Gaucher patients. *Blood.* 1996; 87: 1754-1762.
31. Qin G, Takenaka T, Telsch K, Kelley L, Howard T, Levade T, et al. Preselective gene therapy for Fabry disease. *Proc Natl Acad Sci USA.* 2001; 98: 3428-3433.
32. Siatskas C, Underwood J, Ramenazi A, Hawley R G, Medin, J. A.: Specific pharmacological dimerization of KDR in lentivirally transduced human hematopoietic cells activates anti-apoptotic and proliferative effects. *FASEB J.* 2005; 19: 1752-1754.
33. Medin J A, Liang S B, Hou J W, Kelley L S, Peace D J, Fowler D H. Efficient transfer of PSA and PSMA cDNAs into DCs generates antibody and T cell antitumor responses in vivo. *Cancer Gene Ther.* 2005; 12: 540-551.
34. Bonini C, Ferrari G, Verzeletti S, Servida P, Zappone E, Ruggieri L, et al. HSV-TK gene transfer into donor lymphocytes for control of allogeneic graft-versus-leukemia. *Science.* 1997; 276: 1719-1724.
35. Li Z, Dullmann J, Schiedlmeier B, Schmidt M, von Kalle C, Meyer J, et al. Murine leukemia induced by retroviral gene marking. *Science.* 2002; 296: 497.
36. Doody G M, Dempsey P W, Fearon D T. Activation of B lymphocytes: integrating signals from CD19, CD22 and Fc gamma RIIb1. *Curr Opin Immunol.* 1996; 8: 378-382.
37. Fujimoto M, Poe J C, Hasegawa M, Tedder T F. CD19 regulates intrinsic B lymphocyte signal transduction and activation through a novel mechanism of processive amplification. *Immunol Res.* 2000; 22: 281-298.
38. Tedder T F, Zhou L J, Engel P. The CD19/CD21 signal transduction complex of B lymphocytes. *Immunol Today.* 1994; 15: 437-442.
39. Sato S, Miller A S, Howard M C, Tedder T F. Regulation of B lymphocyte development and activation by the CD19/CD21/CD81/Leu 13 complex requires the cytoplasmic domain of CD19. *J. Immunol.* 1997; 159: 3278-3287.
40. Greco O, Dachs G U. Gene directed enzyme/prodrug therapy of cancer: historical appraisal and future prospectives. *J Cell Physiol.* 2001; 187: 22-36.
41. Smiley S T, Reers M, Mottola-Hartshorn C, Lin M, Chen A, Smith T W, et al. Intracellular heterogeneity in mitochondrial membrane potentials revealed by a J-aggregate-forming lipophilic cation JC-1. *Proc Natl Acad Sci USA.* 1991; 88: 3671-3675.
42. Green D R, Reed J C. Mitochondria and apoptosis. *Science.* 1998; 281: 1309-1312.
43. Mahmoud M S, Fujii R, Ishikawa H, Kawano M M. Enforced CD19 expression leads to growth inhibition and reduced tumorigenicity. *Blood.* 1999; 94: 3551-3558.
44. Cohen J L, Boyer O, Salomon B, Onclercq R, Charlotte F, Bruel S, et al. Prevention of graft-versus-host disease in mice using a suicide gene expressed in T lymphocytes. *Blood.* 1997; 89: 4636-4645.
45. Spencer D M. Developments in suicide genes for preclinical and clinical applications. *Curr Opin Mol. Ther.* 2000; 2: 433-440.
46. Lal S, Lauer U M, Niethammer D, Beck J F, Schlegel P G. Suicide genes: past, present and future perspectives. *Immunol Today.* 2000; 21: 48-54.
47. Kershaw M H, Teng M W, Smyth M J, Darcy P K. Supernatural T cells: genetic modification of T cells for cancer therapy. *Nat Rev Immunol.* 2005; 5: 928-940.
48. Chow H H, Li P, Brookshier G, Tang Y. In vivo tissue disposition of 3'-azido-3'-deoxythymidine and its anabolites in control and retrovirus-infected mice. *Drug Metab Dispos.* 1997; 25: 412-422.

49. Weichold F F, Jiang Y Z, Dunn D E, Bloom M, Malkovska V, Hensel N F, et al. Regulation of a graft-versus-leukemia effect by major histocompatibility complex class II molecules on leukemia cells: HLA-DR1 expression renders K562 cell tumors resistant to adoptively transferred lymphocytes in severe combined immunodeficiency mice/nonobese diabetic mice. *Blood.* 1997; 90: 4553-4558.

The invention claimed is:

1. A method of enhancing the capability of a mammalian cell in phosphorylating AZT comprising introducing into the cell in vitro or ex vivo a a stably integrating delivery vector, the vector comprising;

i) a modified human thymidylate kinase (tmpk) polynucleotide that encodes a modified human tmpk polypeptide comprising a modification selected from (a) a F to Y mutation at amino acid position 105 of SEQ ID NO: 11, (b) a R to G point mutation at amino acid position 16 of SEQ ID NO: 12, or (c) a R to A mutation at amino acid position 200 of SEQ ID NO: 16 that increases phosphorylation of azidothymidine (AZT) relative to phosphorylation of AZT by wild type human tmpk polypeptide;

ii) a detection cassette polynucleotide that encodes a detection cassette polypeptide that is cell surface expressed, wherein the detection cassette polynucleotide is fused to the modified human tmpk polynucleotide and the detection cassette polypeptide is fused to the modified human tmpk polypeptide; and iii) a promoter functional in a mammalian cell operably connected to the coding sequence of the tmpk/detection cassette fusion polynucleotide;

wherein introduction of the delivery vector into the cell and expression of the modified human tmpk polypeptide enhances the capacity of the cell in phosphorylating AZT.

2. The method of claim 1, wherein the mammalian cell is selected from the group consisting of a stem cell, an embryonic stem cell, a mesenchymal stem cell, an induced pluripotent stem (IPS) cell, a hematopoietic cell, a T cell and a human cell.

3. The method of claim 1, further comprising isolating the mammalian cell.

4. The method of claim 3, wherein the mammalian cell is isolated by contacting the cell with an antibody that binds to the detection cassette polypeptide.

5. The method of claim 3, wherein the isolated mammalian cell is transplanted into a mammal.

6. The method of claim 1, wherein the modified human tmpk polynucleotide comprises a polynucleotide with at least 90% sequence identity to any one of SEQ ID NOS: 15, 21, and 22.

7. The method of claim 1, wherein the modified human tmpk polypeptide further comprises SEQ ID NO: 17 or the amino acid sequence RARGEL.

8. The method of claim 1, wherein the delivery vector further comprises a therapeutic polynucleotide cassette.

9. The method of claim 8, wherein the therapeutic polynucleotide cassette is selected from the group consisting of adenosine deaminase, γc interleukin receptor subunit, α-galactosidase A, codon optimized α-galactosidase A, acid ceramidase, galactocerebrosidase, and transmembrane conductance regulator (CFTR) molecules.

10. The method of claim 8, wherein the therapeutic polynucleotide cassette is selected from α-galactosidase A and codon optimized α-galactosidase A.

11. The method of claim 10, wherein the codon optimized α-galactosidase A comprises:

(a) SEQ ID NO: 46;

(b) SEQ ID NO: 46 wherein T is substituted with U; or (c) a sequence with at least 95% identity to SEQ ID NO:46, wherein the sequence is not identical to the polynucleotide having accession number NM_000169.

12. The method of claim 1, wherein the delivery vector is selected from the group consisting of a retroviral vector, an adenoviral vector, an adeno-associated viral vector, a spumaviral vector and a plasmid.

13. The method of claim 1, wherein the delivery vector is a lentiviral vector that has a pHR' backbone, a pDY backbone or a pCCL backbone and comprises 5'-Long terminal repeat (LTR), human immunodeficiency virus (HIV) signal sequence, HIV Psi signal 5'-splice site (SD), delta-GAG element, Rev Responsive Element (RRE), 3'-splice site (SA), Elongation factor (EF) 1-alpha promoter and 3'-Self inactivating LTR (SIN-LTR).

14. The method of claim 1, wherein the detection cassette is fused to the tmpk polynucleotide by a linker.

15. The method of claim 1, wherein the detection cassette polypeptide fused to the modified human tmpk polypeptide comprises the sequence of SEQ ID NO:38.

16. The method of claim 1, wherein the detection cassette polypeptide is epidermal growth factor receptor (EGFR), CD19, truncated CD19, low affinity nerve growth receptor (LNGFR) or truncated LNGFR.

* * * * *

SEQUENCE LISTING

```
<160> NUMBER OF SEQ ID NOS: 54

<210> SEQ ID NO 1
<211> LENGTH: 639
<212> TYPE: DNA
<213> ORGANISM: Homo sapiens

<400> SEQUENCE: 1

atggcggccc ggcgcggggc tctcatagtg ctggagggcg tggaccgcgc cgggaagagc      60

acgcagagcc gcaagctggt ggaagcgctg tgcgccgcgg gccaccgcgc cgaactgctc     120

cggttcccgg aaagatcaac tgaaatcggc aaacttctga gttcctactt gcaaaagaaa     180

agtgacgtgg aggatcactc ggtgcacctg ctttttctg caaatcgctg ggaacaagtg      240

ccgttaatta aggaaaagtt gagccagggc gtgaccctcg tcgtggacag atacgcattt     300

tctggtgtgg ccttcaccgg tgccaaggag aatttttccc tagattggtg taaacagcca     360

gacgtgggcc ttcccaaacc cgacctggtc ctgttcctcc agttacagct ggcggatgct     420

gccaagcggg gagcgtttgg ccatgagcgc tatgagaacg gggctttcca ggagcgggcg     480

ctccggtgtt tccaccagct catgaaagac acgactttga actggaagat ggtggatgct     540

tccaaaagca tcgaagctgt ccatgaggac atccgcgtgc tctctgagga cgccatccgc     600

actgccacag agaagccgct gggggagcta tggaagtga                            639


<210> SEQ ID NO 2
<211> LENGTH: 212
<212> TYPE: PRT
<213> ORGANISM: Homo sapiens

<400> SEQUENCE: 2

Met Ala Ala Arg Arg Gly Ala Leu Ile Val Leu Glu Gly Val Asp Arg
1               5                   10                  15

Ala Gly Lys Ser Thr Gln Ser Arg Lys Leu Val Glu Ala Leu Cys Ala
            20                  25                  30

Ala Gly His Arg Ala Glu Leu Leu Arg Phe Pro Glu Arg Ser Thr Glu
        35                  40                  45

Ile Gly Lys Leu Leu Ser Ser Tyr Leu Gln Lys Lys Ser Asp Val Glu
    50                  55                  60

Asp His Ser Val His Leu Leu Phe Ser Ala Asn Arg Trp Glu Gln Val
65                  70                  75                  80

Pro Leu Ile Lys Glu Lys Leu Ser Gln Gly Val Thr Leu Val Val Asp
                85                  90                  95

Arg Tyr Ala Phe Ser Gly Val Ala Phe Thr Gly Ala Lys Glu Asn Phe
            100                 105                 110

Ser Leu Asp Trp Cys Lys Gln Pro Asp Val Gly Leu Pro Lys Pro Asp
        115                 120                 125

Leu Val Leu Phe Leu Gln Leu Gln Leu Ala Asp Ala Ala Lys Arg Gly
    130                 135                 140

Ala Phe Gly His Glu Arg Tyr Glu Asn Gly Ala Phe Gln Glu Arg Ala
145                 150                 155                 160

Leu Arg Cys Phe His Gln Leu Met Lys Asp Thr Thr Leu Asn Trp Lys
                165                 170                 175
```

-continued

```
Met Val Asp Ala Ser Lys Ser Ile Glu Ala Val His Glu Asp Ile Arg
            180                 185                 190

Val Leu Ser Glu Asp Ala Ile Arg Thr Ala Thr Glu Lys Pro Leu Gly
        195                 200                 205

Glu Leu Trp Lys
    210


<210> SEQ ID NO 3
<211> LENGTH: 639
<212> TYPE: DNA
<213> ORGANISM: Homo sapiens

<400> SEQUENCE: 3

atggcggccc ggcgcggggc tctcatagtg ctggagggcg tggaccgcgc cgggaagagc      60

acgcagagcc gcaagctggt ggaagcgctg tgcgccgcgg gccaccgcgc cgaactgctc     120

cggttcccgg aaagatcaac tgaaatcggc aaacttctga gttcctactt gcaaaagaaa     180

agtgacgtgg aggatcactc ggtgcacctg cttttttctg caaatcgctg ggaacaagtg     240

ccgttaatta aggaaaagtt gagccagggc gtgaccctcg tcgtggacag atacgcattt     300

tctggtgtgg ccttcaccgg tgccaaggag aatttttccc tagattggtg taaacagcca     360

gacgtgggcc ttcccaaacc cgacctggtc ctgttcctcc agttacagct ggcggatgct     420

gccaagcggg gagcgtttgg ccatgagcgc tatgagaacg gggctttcca ggagcgggcg     480

ctccggtgtt tccaccagct catgaaagac acgactttga actggaagat ggtggatgct     540

tccaaaagca tcgaagctgt ccatgaggac atccgcgtgc tctctgagga cgccatccgc     600

actgccacag agaagccgct gggggagcta tggaagtga                            639


<210> SEQ ID NO 4
<211> LENGTH: 212
<212> TYPE: PRT
<213> ORGANISM: Homo sapiens

<400> SEQUENCE: 4

Met Ala Ala Arg Arg Gly Ala Leu Ile Val Leu Glu Gly Val Asp Arg
1               5                   10                  15

Ala Gly Lys Ser Thr Gln Ser Arg Lys Leu Val Glu Ala Leu Cys Ala
            20                  25                  30

Ala Gly His Arg Ala Glu Leu Leu Arg Phe Pro Glu Arg Ser Thr Glu
        35                  40                  45

Ile Gly Lys Leu Leu Ser Ser Tyr Leu Gln Lys Lys Ser Asp Val Glu
    50                  55                  60

Asp His Ser Val His Leu Leu Phe Ser Ala Asn Arg Trp Glu Gln Val
65                  70                  75                  80

Pro Leu Ile Lys Glu Lys Leu Ser Gln Gly Val Thr Leu Val Val Asp
                85                  90                  95

Arg Tyr Ala Phe Ser Gly Val Ala Phe Thr Gly Ala Lys Glu Asn Phe
            100                 105                 110

Ser Leu Asp Trp Cys Lys Gln Pro Asp Val Gly Leu Pro Lys Pro Asp
        115                 120                 125

Leu Val Leu Phe Leu Gln Leu Gln Leu Ala Asp Ala Ala Lys Arg Gly
    130                 135                 140

Ala Phe Gly His Glu Arg Tyr Glu Asn Gly Ala Phe Gln Glu Arg Ala
145                 150                 155                 160

Leu Arg Cys Phe His Gln Leu Met Lys Asp Thr Thr Leu Asn Trp Lys
                165                 170                 175
```

```
Met Val Asp Ala Ser Lys Ser Ile Glu Ala Val His Glu Asp Ile Arg
            180                 185                 190

Val Leu Ser Glu Asp Ala Ile Arg Thr Ala Thr Glu Lys Pro Leu Gly
            195                 200                 205

Glu Leu Trp Lys
        210

<210> SEQ ID NO 5
<211> LENGTH: 636
<212> TYPE: DNA
<213> ORGANISM: Homo sapiens

<400> SEQUENCE: 5

atggcggccc ggcgcggggc tctcatagtg ctggagggcg tggaccgcgc cgggaagagc      60

acgcagagcc gcaagctggt ggaagcgctg tcgcgcgggc caccgcccga actgctccgg     120

ttcccggaaa gatcaactga aatcggcaaa cttctgagtt cctacttgca aaagaaaagt     180

gacgtggagg atcactcggt gcacctgctt ttttctgcaa atcgctggga acaagtgccg     240

ttaattaagg aaaagttgag ccagggcgtg accctcgtcg tggacagata cgcattttct     300

ggtgtggcct tcaccggtgc caaggagaat ttttccctag actggtgtaa acagccagac     360

gtgggccttc ccaaacccga cctggtcctg ttcctccagt tacagctggc ggatgctgcc     420

aagcggggag cgtttggcca tgagcgctat gagaacgggg cttttccagga gcgggcgctc     480

cggtgtttcc accagctcat gaaagacacg actttgaact ggaagatggt ggatgcttcc     540

aaaagactcg aagctgtcca tgaggaactc cgcgtgctct ctgaggacgc catccgcact     600

gccacagaga agccgctggg ggagctatgg aagtga                              636

<210> SEQ ID NO 6
<211> LENGTH: 211
<212> TYPE: PRT
<213> ORGANISM: Homo sapiens

<400> SEQUENCE: 6

Met Ala Ala Arg Arg Gly Ala Leu Ile Val Leu Glu Gly Val Asp Arg
1               5                   10                  15

Ala Gly Lys Ser Thr Gln Ser Arg Lys Leu Val Glu Ala Leu Ser Arg
            20                  25                  30

Gly Pro Pro Pro Glu Leu Leu Arg Phe Pro Glu Arg Ser Thr Glu Ile
        35                  40                  45

Gly Lys Leu Leu Ser Ser Tyr Leu Gln Lys Lys Ser Asp Val Glu Asp
    50                  55                  60

His Ser Val His Leu Leu Phe Ser Ala Asn Arg Trp Glu Gln Val Pro
65                  70                  75                  80

Leu Ile Lys Glu Lys Leu Ser Gln Gly Val Thr Leu Val Val Asp Arg
                85                  90                  95

Tyr Ala Phe Ser Gly Val Ala Phe Thr Gly Ala Lys Glu Asn Phe Ser
            100                 105                 110

Leu Asp Trp Cys Lys Gln Pro Asp Val Gly Leu Pro Lys Pro Asp Leu
        115                 120                 125

Val Leu Phe Leu Gln Leu Gln Leu Ala Asp Ala Ala Lys Arg Gly Ala
    130                 135                 140

Phe Gly His Glu Arg Tyr Glu Asn Gly Ala Phe Gln Glu Arg Ala Leu
145                 150                 155                 160

Arg Cys Phe His Gln Leu Met Lys Asp Thr Thr Leu Asn Trp Lys Met
```

-continued

```
                165                 170                 175

Val Asp Ala Ser Lys Arg Leu Glu Ala Val His Glu Glu Leu Arg Val
            180                 185                 190

Leu Ser Glu Asp Ala Ile Arg Thr Ala Thr Glu Lys Pro Leu Gly Glu
        195                 200                 205

Leu Trp Lys
    210


<210> SEQ ID NO 7
<211> LENGTH: 639
<212> TYPE: DNA
<213> ORGANISM: Homo sapiens

<400> SEQUENCE: 7

atggcggccc ggcgcggggc tctcatagtg ctggagggcg tggaccgcgc cgggaagagc      60

acgcagagcc gcaagctggt ggaagcgctg tgcgccgcgg gccaccgcgc cgaactgctc     120

cggttcccgg aaagatcaac tgaaatcggc aaacttctga gttcctactt gcaaaagaaa     180

agtgacgtgg aggatcactc ggtgcacctg ctttttctg caaatcgctg ggaacaagtg      240

ccgttaatta aggaaaagtt gagccagggc gtgaccctcg tcgtggacag atacgcattt     300

tctggtgtgg ccttcaccgg tgccaaggag aatttttccc tagattggtg taaacagcca     360

gacgtgggcc ttcccaaacc cgacctggtc ctgttcctcc agttacagct ggcggatgct     420

gccaagcggg gagcgtttgg ccatgagcgc tatgagaacg gggctttcca ggagcgggcg     480

ctccggtgtt tccaccagct catgaaagac acgactttga actggaagat ggtggatgct     540

tccaaaagca tcgaagctgt ccatgaggac atccgcgtgc tctctgagga cgccatccgc     600

actgccacag agaagccgct gggggagcta tggaaggac                            639


<210> SEQ ID NO 8
<211> LENGTH: 213
<212> TYPE: PRT
<213> ORGANISM: Homo sapiens

<400> SEQUENCE: 8

Met Ala Ala Arg Arg Gly Ala Leu Ile Val Leu Glu Gly Val Asp Arg
1               5                   10                  15

Ala Gly Lys Ser Thr Gln Ser Arg Lys Leu Val Glu Ala Leu Cys Ala
            20                  25                  30

Ala Gly His Arg Ala Glu Leu Leu Arg Phe Pro Glu Arg Ser Thr Glu
        35                  40                  45

Ile Gly Lys Leu Leu Ser Ser Tyr Leu Gln Lys Lys Ser Asp Val Glu
    50                  55                  60

Asp His Ser Val His Leu Leu Phe Ser Ala Asn Arg Trp Glu Gln Val
65                  70                  75                  80

Pro Leu Ile Lys Glu Lys Leu Ser Gln Gly Val Thr Leu Val Val Asp
                85                  90                  95

Arg Tyr Ala Phe Ser Gly Val Ala Phe Thr Gly Ala Lys Glu Asn Phe
            100                 105                 110

Ser Leu Asp Trp Cys Lys Gln Pro Asp Val Gly Leu Pro Lys Pro Asp
        115                 120                 125

Leu Val Leu Phe Leu Gln Leu Gln Leu Ala Asp Ala Ala Lys Arg Gly
    130                 135                 140

Ala Phe Gly His Glu Arg Tyr Glu Asn Gly Ala Phe Gln Glu Arg Ala
145                 150                 155                 160
```

-continued

Leu Arg Cys Phe His Gln Leu Met Lys Asp Thr Thr Leu Asn Trp Lys
165 170 175

Met Val Asp Ala Ser Lys Ser Ile Glu Ala Val His Glu Asp Ile Arg
180 185 190

Val Leu Ser Glu Asp Ala Ile Arg Thr Ala Thr Glu Lys Pro Leu Gly
195 200 205

Glu Leu Trp Lys Asp
210

<210> SEQ ID NO 9
<211> LENGTH: 639
<212> TYPE: DNA
<213> ORGANISM: Mus musculus

<400> SEQUENCE: 9
atggcgtcgc gtcggggagc gctcatcgtg ctggagggtg tggaccgtgc tggcaagacc 60
acgcagggcc tcaagctggt gaccgcgctg tgcgcctcgg gccacagagc ggagctgctg 120
cgtttccccg aaagatcaac ggaaatcggc aagcttctga attcctactt ggaaaagaaa 180
acggaactag aggatcactc cgtgcacctg ctcttctctg caaaccgctg ggaacaagta 240
ccattaatta aggcgaagtt gaaccagggt gtgacccttg ttttggacag atacgccttt 300
tctggggttg ccttcactgg tgccaaagag aatttttccc tggattggtg taaacaaccg 360
gacgtgggcc ttcccaaacc tgacctgatc ctgttccttc agttacaatt gctggacgct 420
gctgcacggg gagagtttgg ccttgagcga tatgagaccg ggactttcca aaagcaggtt 480
ctgttgtgtt tccagcagct catggaagag aaaaacctca actggaaggt ggttgatgct 540
tccaaaagca ttgaggaagt ccataaagaa atccgtgcac actctgagga cgccatccga 600
aacgctgcac agaggccact gggggagcta tggaaataa 639

<210> SEQ ID NO 10
<211> LENGTH: 212
<212> TYPE: PRT
<213> ORGANISM: Mus musculus

<400> SEQUENCE: 10

Met Ala Ser Arg Arg Gly Ala Leu Ile Val Leu Glu Gly Val Asp Arg
1 5 10 15

Ala Gly Lys Thr Thr Gln Gly Leu Lys Leu Val Thr Ala Leu Cys Ala
20 25 30

Ser Gly His Arg Ala Glu Leu Leu Arg Phe Pro Glu Arg Ser Thr Glu
35 40 45

Ile Gly Lys Leu Leu Asn Ser Tyr Leu Glu Lys Lys Thr Glu Leu Glu
50 55 60

Asp His Ser Val His Leu Leu Phe Ser Ala Asn Arg Trp Glu Gln Val
65 70 75 80

Pro Leu Ile Lys Ala Lys Leu Asn Gln Gly Val Thr Leu Val Leu Asp
85 90 95

Arg Tyr Ala Phe Ser Gly Val Ala Phe Thr Gly Ala Lys Glu Asn Phe
100 105 110

Ser Leu Asp Trp Cys Lys Gln Pro Asp Val Gly Leu Pro Lys Pro Asp
115 120 125

Leu Ile Leu Phe Leu Gln Leu Gln Leu Leu Asp Ala Ala Ala Arg Gly
130 135 140

Glu Phe Gly Leu Glu Arg Tyr Glu Thr Gly Thr Phe Gln Lys Gln Val
145 150 155 160

Leu Leu Cys Phe Gln Gln Leu Met Glu Glu Lys Asn Leu Asn Trp Lys
165 170 175

Val Val Asp Ala Ser Lys Ser Ile Glu Glu Val His Lys Glu Ile Arg
180 185 190

Ala His Ser Glu Asp Ala Ile Arg Asn Ala Ala Gln Arg Pro Leu Gly
195 200 205

Glu Leu Trp Lys
210

<210> SEQ ID NO 11
<211> LENGTH: 212
<212> TYPE: PRT
<213> ORGANISM: Homo sapiens

<400> SEQUENCE: 11

Met Ala Ala Arg Arg Gly Ala Leu Ile Val Leu Glu Gly Val Asp Arg
1 5 10 15

Ala Gly Lys Ser Thr Gln Ser Arg Lys Leu Val Glu Ala Leu Cys Ala
20 25 30

Ala Gly His Arg Ala Glu Leu Leu Arg Phe Pro Glu Arg Ser Thr Glu
35 40 45

Ile Gly Lys Leu Leu Ser Ser Tyr Leu Gln Lys Lys Ser Asp Val Glu
50 55 60

Asp His Ser Val His Leu Leu Phe Ser Ala Asn Arg Trp Glu Gln Val
65 70 75 80

Pro Leu Ile Lys Glu Lys Leu Ser Gln Gly Val Thr Leu Val Val Asp
85 90 95

Arg Tyr Ala Phe Ser Gly Val Ala Tyr Thr Gly Ala Lys Glu Asn Phe
100 105 110

Ser Leu Asp Trp Cys Lys Gln Pro Asp Val Gly Leu Pro Lys Pro Asp
115 120 125

Leu Val Leu Phe Leu Gln Leu Gln Leu Ala Asp Ala Ala Lys Arg Gly
130 135 140

Ala Phe Gly His Glu Arg Tyr Glu Asn Gly Ala Phe Gln Glu Arg Ala
145 150 155 160

Leu Arg Cys Phe His Gln Leu Met Lys Asp Thr Thr Leu Asn Trp Lys
165 170 175

Met Val Asp Ala Ser Lys Ser Ile Glu Ala Val His Glu Asp Ile Arg
180 185 190

Val Leu Ser Glu Asp Ala Ile Arg Thr Ala Thr Glu Lys Pro Leu Gly
195 200 205

Glu Leu Trp Lys
210

<210> SEQ ID NO 12
<211> LENGTH: 214
<212> TYPE: PRT
<213> ORGANISM: Homo sapiens

<400> SEQUENCE: 12

Met Ala Ala Arg Arg Gly Ala Leu Ile Val Leu Glu Gly Val Asp Gly
1 5 10 15

Ala Gly Lys Ser Thr Gln Ser Arg Lys Leu Val Glu Ala Leu Cys Ala
20 25 30

Ala Gly His Arg Ala Glu Leu Leu Arg Phe Pro Glu Arg Ser Thr Glu
35 40 45

```
Ile Gly Lys Leu Leu Ser Ser Tyr Leu Gln Lys Lys Ser Asp Val Glu
    50                  55                  60

Asp His Ser Val His Leu Leu Phe Ser Ala Asn Arg Trp Glu Gln Val
65                  70                  75                  80

Pro Leu Ile Lys Glu Lys Leu Ser Gln Gly Val Thr Leu Val Val Asp
                85                  90                  95

Arg Tyr Ala Phe Ser Gly Val Ala Phe Thr Gly Ala Lys Glu Asn Phe
            100                 105                 110

Ser Leu Asp Trp Cys Lys Gln Pro Asp Val Gly Leu Pro Lys Pro Asp
        115                 120                 125

Leu Val Leu Phe Leu Gln Leu Thr Pro Glu Val Gly Leu Lys Arg Ala
    130                 135                 140

Arg Ala Arg Gly Glu Leu Asp Arg Tyr Glu Asn Gly Ala Phe Gln Glu
145                 150                 155                 160

Arg Ala Leu Arg Cys Phe His Gln Leu Met Lys Asp Thr Thr Leu Asn
                165                 170                 175

Trp Lys Met Val Asp Ala Ser Lys Ser Ile Glu Ala Val His Glu Asp
            180                 185                 190

Ile Arg Val Leu Ser Glu Asp Ala Ile Ala Thr Ala Thr Glu Lys Pro
        195                 200                 205

Leu Gly Glu Leu Trp Lys
    210
```

<210> SEQ ID NO 13
<211> LENGTH: 6811
<212> TYPE: DNA
<213> ORGANISM: Artificial Sequence
<220> FEATURE:
<223> OTHER INFORMATION: Vector

<400> SEQUENCE: 13

```
tggaagggct aattcactcc caacgaagac aagatatcct tgatctgtgg atctaccaca      60

cacaaggcta cttccctgat tggcagaact acacaccagg accagggatc agatatccac     120

tgacctttgg atggtgctac aagctagtac cagttgagcc agataaggta gaagaggcca     180

acaaaggaga gaacaccagc ttgttacacc ctgtgagcct gcatggaatg gatgacccgg     240

agagagaagt gttagagtgg aggtttgaca gccgcctagc atttcatcac gtggcccgag     300

agctgcatcc ggagtacttc aagaactgct gatatcgagc ttgctacaag ggactttccg     360

ctggggactt tccagggagg cgtggcctgg gcgggactgg ggagtggcga gccctcagat     420

gctgcatata agcagctgct ttttgcctgt actgggtctc tctggttaga ccagatctga     480

gcctgggagc tctctggcta actagggaac ccactgctta agcctcaata aagcttgcct     540

tgagtgcttc aagtagtgtg tgcccgtctg ttgtgtgact ctggtaacta gagatccctc     600

agaccctttt agtcagtgtg gaaaatctct agcagtggcg cccgaacagg gacttgaaag     660

cgaaagggaa accagaggag ctctctcgac gcaggactcg gcttgctgaa gcgcgcacgg     720

caagaggcga ggggcggcga ctggtgagta cgccaaaaat tttgactagc ggaggctaga     780

aggagagaga tgggtgcgag agcgtcagta ttaagcgggg gagaattaga tcgcgatggg     840

aaaaaattcg gttaaggcca gggggaaaga aaaaatataa attaaaacat atagtatggg     900

caagcaggga gctagaacga ttcgcagtta atcctggcct gttagaaaca tcagaaggct     960

gtagacaaat actgggacag ctacaaccat cccttcagac aggatcagaa gaacttagat    1020

cattatataa tacagtagca accctctatt gtgtgcatca aaggatagag ataaaagaca    1080
```

```
ccaaggaagc tttagacaag atagaggaag agcaaaacaa aagtaagacc accgcacagc   1140
aagcggccgc tgatcttcag acctggagga ggagatatga gggacaattg gagaagtgaa   1200
ttatataaat ataaagtagt aaaaattgaa ccattaggag tagcacccac caaggcaaag   1260
agaagagtgg tgcagagaga aaaaagagca gtgggaatag gagctttgtt ccttgggttc   1320
ttgggagcag caggaagcac tatgggcgca gcgtcaatga cgctgacggt acaggccaga   1380
caattattgt ctggtatagt gcagcagcag aacaatttgc tgagggctat tgaggcgcaa   1440
cagcatctgt tgcaactcac agtctggggc atcaagcagc tccaggcaag aatcctggct   1500
gtggaaagat acctaaagga tcaacagctc ctggggattt ggggttgctc tggaaaactc   1560
atttgcacca ctgctgtgcc ttggaatgct agttggagta ataaatctct ggaacagatt   1620
tggaatcaca cgacctggat ggagtgggac agagaaatta acaattacac aagcttaata   1680
cactccttaa ttgaagaatc gcaaaaccag caagaaaaga atgaacaaga attattggaa   1740
ttagataaat gggcaagttt gtggaattgg tttaacataa caaattggct gtggtatata   1800
aaattattca taatgatagt aggaggcttg gtaggtttaa gaatagtttt tgctgtactt   1860
tctatagtga atagagttag gcagggatat tcaccattat cgtttcagac ccacctccca   1920
accccgaggg gacccgacag gcccgaagga atagaagaag aaggtggaga gagagacaga   1980
gacagatcca ttcgattagt gaacggatct cgacggtatc gcttttaaaa gaaaaggggg   2040
gattgggggg tacagtgcag gggaaagaat agtagacata atagcaacag acatacaaac   2100
taaagaatta caaaaacaaa ttacaaaaat tcaaaatttt atcgataagc tttgcaaaga   2160
tggataaagt tttaaacaga gaggaatctt tgcagctaat ggaccttcta ggtcttgaaa   2220
ggagtgggaa ttggctccgg tgcccgtcag tgggcagagc gcacatcgcc cacagtcccc   2280
gagaagttgg ggggaggggt cggcaattga accggtgcct agagaaggtg gcgcggggta   2340
aactgggaaa gtgatgtcgt gtactggctc cgcctttttc ccgagggtgg gggagaaccg   2400
tatataagtg cagtagtcgc cgtgaacgtt ctttttcgca acgggtttgc cgccagaaca   2460
caggtaagtg ccgtgtgtgg ttcccgcggg cctggcctct ttacgggtta tggcccttgc   2520
gtgccttgaa ttacttccac gcccctggct gcagtacgtg attcttgatc ccgagcttcg   2580
ggttggaagt gggtgggaga gttcgaggcc ttgcgcttaa ggagcccctt cgcctcgtgc   2640
ttgagttgag gcctggcctg ggcgctgggg ccgccgcgtg cgaatctggt ggcaccttcg   2700
cgcctgtctc gctgctttcg ataagtctct agccatttaa aatttttgat gacctgctgc   2760
gacgcttttt ttctggcaag atagtcttgt aaatgcgggc caagatctgc acactggtat   2820
ttcggttttt ggggccgcgg gcggcgacgg ggcccgtgcg tcccagcgca catgttcggc   2880
gaggcggggc ctgcgagcgc ggccaccgag aatcggacgg gggtagtctc aagctggccg   2940
gcctgctctg gtgcctggcc tcgcgccgcc gtgtatcgcc ccgccctggg cggcaaggct   3000
ggcccggtcg gcaccagttg cgtgagcgga aagatggccg cttcccggcc ctgctgcagg   3060
gagctcaaaa tggaggacgc ggcgctcggg agagcgggcg ggtgagtcac ccacacaaag   3120
gaaaagggcc tttccgtcct cagccgtcgc ttcatgtgac tccacggagt accgggcgcc   3180
gtccaggcac ctcgattagt tctcgagctt ttggagtacg tcgtctttag gttgggggga   3240
ggggttttat gcgatggagt ttccccacac tgagtgggtg gagactgaag ttaggccagc   3300
ttggcacttg atgtaattct ccttggaatt tgcccttttt gagtttggat cttggttcat   3360
tctcaagcct cagacagtgg ttcaaagttt ttttcttcca tttcaggtgt cgtgagagga   3420
```

-continued

```
attctgcagt cgagcggagc gcgcgtaata cgactcacta tagggcgcca tgggtaccgg   3480
gcccccccctc gatcgaacaa caacaacaat aacacatggt tccgcgtggc tctcatatgg   3540
cggcccggcg cggggctctc atagtgctgg agggcgtgga cggcgccggg aagagcacgc   3600
agagccgcaa gctggtggaa gcgctgtgcg ccgcgggcca ccgcgccgaa ctgctccggt   3660
tcccggaaag atcaactgaa atcggcaaac ttctgagttc ctacttgcaa aagaaaagtg   3720
acgtggagga tcactcggtg cacctgcttt tttctgcaaa tcgctgggaa caagtgccgt   3780
taattaagga aaagttgagc cagggcgtga ccctcgtcgt ggacagatac gcattttctg   3840
gtgtggcctt caccggtgcc aaggagaatt tttccctaga ctggtgtaaa cagccagacg   3900
tgggccttcc caaacccgac ctggtcctgt tcctgcagtt aactccggaa gttggcttaa   3960
aacgcgcacg tgctcgcggc gagcttgacc gctatgagaa cggggctttc caggagcggg   4020
cgctccggtg tttccaccag ctcatgaaag acacgacttt gaactggaag atggtggatg   4080
cttccaaaag catcgaagct gtccatgagg acatccgcgt gctctctgag gacgccatcg   4140
ccactgccac agagaagccg ctgggggagc tatggaagtg aggatcagtc gacggtatcg   4200
attcccccctc tccctccccc ccccctaacg ttactggccg aagccgcttg gaataaggcc   4260
ggtgtgcgtt tgtctatatg ttattttcca ccatattgcc gtcttttggc aatgtgaggg   4320
cccggaaacc tggccctgtc ttcttgacga gcattcctag gggtctttcc cctctcgcca   4380
aaggaatgca aggtctgttg aatgtcgtga aggaagcagt tcctctggaa gcttcttgaa   4440
gacaaacaac gtctgtagcg accctttgca ggcagcggaa ccccccacct ggcgacaggt   4500
gcctctgcgg ccaaaagcca cgtgtataag atacacctgc aaaggcggca caaccccagt   4560
gccacgttgt gagttggata gttgtggaaa gagtcaaatg gctctcctca agcgtattca   4620
acaaggggct gaaggatgcc cagaaggtac cccattgtat gggatctgat ctggggcctc   4680
ggtgcacatg ctttacgtgt gtttagtcga ggttaaaaaa cgtctaggcc ccccgaacca   4740
cggggacgtg gttttccttt gaaaaacacg atgatatcga attcctgcag cccgggggat   4800
ccgccccctc tgaccaccat gccacctcct cgcctcctct tcttcctcct cttcctcacc   4860
cccatggaag tcaggcccga ggaacctcta gtggtgaagg tggaagaggg agataacgct   4920
gtgctgcagt gcctcaaggg gacctcagat ggccccactc agcagctgac ctggtctcgg   4980
gagtccccgc ttaaaccctt cttaaaactc agcctggggc tgccaggcct gggaatccac   5040
atgaggcccc tggcatcctg gcttttcatc ttcaacgtct ctcaacagat ggggggcttc   5100
tacctgtgcc agccggggcc cccctctgag aaggcctggc agcctggctg gacagtcaat   5160
gtggagggca gcggggagct gttccggtgg aatgtttcgg acctaggtgg cctgggctgt   5220
ggcctgaaga acaggtcctc agagggcccc agctcccctt ccgggaagct catgagcccc   5280
aagctgtatg tgtgggccaa agaccgccct gagatctggg agggagagcc tccgtgtgtc   5340
ccaccgaggg acagcctgaa ccagagcctc agccaggacc tcaccatggc ccctggctcc   5400
acactctggc tgtcctgtgg ggtacccccct gactctgtgt ccaggggccc cctctcctgg   5460
acccatgtgc accccaaggg gcctaagtca ttgctgagcc tagagctgaa ggacgatcgc   5520
ccggccagag atatgtgggt aatggagacg ggtctgttgt tgccccgggc cacagctcaa   5580
gacgctggaa agtattattg tcaccgtggc aacctgacca tgtcattcca cctggagatc   5640
actgctcggc cagtactatg gcactggctg ctgaggactg gtggctggaa ggtctcagct   5700
gtgactttgg cttatctgat cttctgcctg tgttcccttg tgggcattct tcatctttaa   5760
ggcgcgcccc gggatccaag cttcaattgt ggtcactcga caatcaacct ctggattaca   5820
```

aaatttgtga aagattgact ggtattctta actatgttgc tccttttacg ctatgtggat 5880
acgctgcttt aatgcctttg tatcatgcta ttgcttcccg tatggctttc attttctcct 5940
ccttgtataa atcctggttg ctgtctcttt atgaggagtt gtggcccgtt gtcaggcaac 6000
gtggcgtggt gtgcactgtg tttgctgacg caacccccac tggttggggc attgccacca 6060
cctgtcagct cctttccggg actttcgctt tccccctccc tattgccacg gcggaactca 6120
tcgccgcctg ccttgcccgc tgctggacag gggctcggct gttgggcact gacaattccg 6180
tggtgttgtc ggggaagctg acgtcctttc catggctgct cgcctgtgtt gccacctgga 6240
ttctgcgcgg gacgtccttc tgctacgtcc cttcggccct caatccagcg gaccttcctt 6300
cccgcggcct gctgccggct ctgcggcctc ttccgcgtct tcgccttcgc cctcagacga 6360
gtcggatctc cctttgggcc gcctccccgc ctgtctcgag acctagaaaa acatggagca 6420
atcacaagta gcaatacagc agctaccaat gctgattgtg cctggctaga agcacaagag 6480
gaggaggagg tgggttttcc agtcacacct caggtacctt taagaccaat gacttacaag 6540
gcagatctta gccacttttt aaaagaaaag gggggactgg aagggctaat tcactcccaa 6600
cgaagacaag atctgctttt tgcttgtact gggtctctct ggttagacca gatctgagcc 6660
tgggagctct ctggctaact agggaaccca ctgcttaagc ctcaataaag cttgccttga 6720
gtgcttcaag tagtgtgtgc ccgtctgttg tgtgactctg gtaactagag atccctcaga 6780 ccctttagt cagtgtggaa aatctctagc a 6811

<210> SEQ ID NO 14
<211> LENGTH: 6805
<212> TYPE: DNA
<213> ORGANISM: Artificial Sequence
<220> FEATURE:
<223> OTHER INFORMATION: Vector

<400> SEQUENCE: 14
tggaagggct aattcactcc caacgaagac aagatatcct tgatctgtgg atctaccaca 60
cacaaggcta cttccctgat tggcagaact acacaccagg accagggatc agatatccac 120
tgacctttgg atggtgctac aagctagtac cagttgagcc agataaggta gaagaggcca 180
acaaaggaga gaacaccagc ttgttacacc ctgtgagcct gcatggaatg gatgacccgg 240
agagagaagt gttagagtgg aggtttgaca gccgcctagc atttcatcac gtggcccgag 300
agctgcatcc ggagtacttc aagaactgct gatatcgagc ttgctacaag ggactttccg 360
ctggggactt tccagggagg cgtggcctgg gcgggactgg ggagtggcga gccctcagat 420
gctgcatata agcagctgct ttttgcctgt actgggtctc tctggttaga ccagatctga 480
gcctgggagc tctctggcta actagggaac ccactgctta agcctcaata aagcttgcct 540
tgagtgcttc aagtagtgtg tgcccgtctg ttgtgtgact ctggtaacta gagatccctc 600
agaccctttt agtcagtgtg gaaaatctct agcagtggcg cccgaacagg gacttgaaag 660
cgaaagggaa accagaggag ctctctcgac gcaggactcg gcttgctgaa gcgcgcacgg 720
caagaggcga ggggcggcga ctggtgagta cgccaaaaat tttgactagc ggaggctaga 780
aggagagaga tgggtgcgag agcgtcagta ttaagcgggg gagaattaga tcgcgatggg 840
aaaaaattcg gttaaggcca gggggaaaga aaaaatataa attaaaacat atagtatggg 900
caagcaggga gctagaacga ttcgcagtta atcctggcct gttagaaaca tcagaaggct 960
gtagacaaat actgggacag ctacaaccat cccttcagac aggatcagaa gaacttagat 1020

-continued

```
cattatataa tacagtagca accctctatt gtgtgcatca aaggatagag ataaaagaca   1080
ccaaggaagc tttagacaag atagaggaag agcaaaacaa aagtaagacc accgcacagc   1140
aagcggccgc tgatcttcag acctggagga ggagatatga gggacaattg gagaagtgaa   1200
ttatataaat ataaagtagt aaaaattgaa ccattaggag tagcacccac caaggcaaag   1260
agaagagtgg tgcagagaga aaaaagagca gtgggaatag gagctttgtt ccttgggttc   1320
ttgggagcag caggaagcac tatgggcgca gcgtcaatga cgctgacggt acaggccaga   1380
caattattgt ctggtatagt gcagcagcag aacaatttgc tgagggctat tgaggcgcaa   1440
cagcatctgt tgcaactcac agtctggggc atcaagcagc tccaggcaag aatcctggct   1500
gtggaaagat acctaaagga tcaacagctc ctggggattt ggggttgctc tggaaaactc   1560
atttgcacca ctgctgtgcc ttggaatgct agttggagta ataaatctct ggaacagatt   1620
tggaatcaca cgacctggat ggagtgggac agagaaatta acaattacac aagcttaata   1680
cactccttaa ttgaagaatc gcaaaaccag caagaaaaga atgaacaaga attattggaa   1740
ttagataaat gggcaagttt gtggaattgg tttaacataa caaattggct gtggtatata   1800
aaattattca taatgatagt aggaggcttg gtaggtttaa gaatagtttt tgctgtactt   1860
tctatagtga atagagttag gcagggatat tcaccattat cgtttcagac ccacctccca   1920
accccgaggg gacccgacag gcccgaagga atagaagaag aaggtggaga gagagacaga   1980
gacagatcca ttcgattagt gaacggatct cgacggtatc gcttttaaaa gaaaaggggg   2040
gattgggggg tacagtgcag gggaaagaat agtagacata atagcaacag acatacaaac   2100
taaagaatta caaaaacaaa ttacaaaaat tcaaaatttt atcgataagc tttgcaaaga   2160
tggataaagt tttaaacaga gaggaatctt tgcagctaat ggaccttcta ggtcttgaaa   2220
ggagtgggaa ttggctccgg tgcccgtcag tgggcagagc gcacatcgcc cacagtcccc   2280
gagaagttgg ggggaggggt cggcaattga accggtgcct agagaaggtg gcgcggggta   2340
aactgggaaa gtgatgtcgt gtactggctc cgcctttttc ccgagggtgg gggagaaccg   2400
tatataagtg cagtagtcgc cgtgaacgtt ctttttcgca acgggtttgc cgccagaaca   2460
caggtaagtg ccgtgtgtgg ttcccgcggg cctggcctct ttacgggtta tggcccttgc   2520
gtgccttgaa ttacttccac gcccctggct gcagtacgtg attcttgatc ccgagcttcg   2580
ggttggaagt gggtgggaga gttcgaggcc ttgcgcttaa ggagcccctt cgcctcgtgc   2640
ttgagttgag gcctggcctg ggcgctgggg ccgccgcgtg cgaatctggt ggcaccttcg   2700
cgcctgtctc gctgctttcg ataagtctct agccatttaa aatttttgat gacctgctgc   2760
gacgcttttt ttctggcaag atagtcttgt aaatgcgggc caagatctgc acactggtat   2820
ttcggttttt ggggccgcgg gcggcgacgg ggcccgtgcg tcccagcgca catgttcggc   2880
gaggcggggc ctgcgagcgc ggccaccgag aatcggacgg gggtagtctc aagctggccg   2940
gcctgctctg gtgcctggcc tcgcgccgcc gtgtatcgcc ccgccctggg cggcaaggct   3000
ggcccggtcg gcaccagttg cgtgagcgga aagatggccg cttcccggcc ctgctgcagg   3060
gagctcaaaa tggaggacgc ggcgctcggg agagcgggcg ggtgagtcac ccacacaaag   3120
gaaaagggcc tttccgtcct cagccgtcgc ttcatgtgac tccacggagt accgggcgcc   3180
gtccaggcac ctcgattagt tctcgagctt ttggagtacg tcgtctttag gttgggggga   3240
ggggttttat gcgatggagt ttccccacac tgagtgggtg gagactgaag ttaggccagc   3300
ttggcacttg atgtaattct ccttggaatt tgcccttttt gagtttggat cttggttcat   3360
tctcaagcct cagacagtgg ttcaaagttt ttttcttcca tttcaggtgt cgtgagagga   3420
```

-continued

```
attctgcagt cgagcggagc gcgcgtaata cgactcacta tagggcgcca tgggtaccgg   3480
gcccccccctc gatcgaacaa caacaacaat aacacatggt tccgcgtggc tctcatatgg   3540
cggcccggcg cggggctctc atagtgctgg agggcgtgga ccgcgccggg aagagcacgc   3600
agagccgcaa gctggtggaa gcgctgtgcg ccgcgggcca ccgcgccgaa ctgctccggt   3660
tcccggaaag atcaactgaa atcggcaaac ttctgagttc ctacttgcaa aagaaaagtg   3720
acgtggagga tcactcggtg cacctgcttt tttctgcaaa tcgctgggaa caagtgccgt   3780
taattaagga aaagttgagc cagggcgtga ccctcgtcgt ggacagatac gcattttctg   3840
gtgtggccta cacaggtgcc aaggagaatt tttccctaga ctggtgtaaa cagccagacg   3900
tgggccttcc caaacccgac ctggtcctgt tcctccagtt acagctggcg gatgctgcca   3960
agcggggagc gtttggccat gagcgctatg agaacggggc tttccaggag cgggcgctcc   4020
ggtgtttcca ccagctcatg aaagacacga ctttgaactg gaagatggtg gatgcttcca   4080
aaagcatcga agctgtccat gaggacatcc gcgtgctctc tgaggacgcc atcgccactg   4140
ccacagagaa gccgctgggg gagctatgga agtgaggatc agtcgacggt atcgattccc   4200
cctctccctc cccccccct aacgttactg gccgaagccg cttggaataa ggccggtgtg   4260
cgtttgtcta tatgttattt tccaccatat tgccgtcttt tggcaatgtg agggcccgga   4320
aacctggccc tgtcttcttg acgagcattc ctaggggtct ttcccctctc gccaaaggaa   4380
tgcaaggtct gttgaatgtc gtgaaggaag cagttcctct ggaagcttct tgaagacaaa   4440
caacgtctgt agcgaccctt tgcaggcagc ggaacccccc acctggcgac aggtgcctct   4500
gcggccaaaa gccacgtgta taagatacac ctgcaaaggc ggcacaaccc cagtgccacg   4560
ttgtgagttg gatagttgtg gaaagagtca aatggctctc ctcaagcgta ttcaacaagg   4620
ggctgaagga tgcccagaag gtaccccatt gtatgggatc tgatctgggg cctcggtgca   4680
catgctttac gtgtgtttag tcgaggttaa aaaacgtcta ggccccccga accacgggga   4740
cgtggttttc ctttgaaaaa cacgatgata tcgaattcct gcagcccggg ggatccgccc   4800
cctctgacca ccatgccacc tcctcgcctc ctcttcttcc tcctcttcct cacccccatg   4860
gaagtcaggc ccgaggaacc tctagtggtg aaggtggaag agggagataa cgctgtgctg   4920
cagtgcctca aggggacctc agatggcccc actcagcagc tgacctggtc tcgggagtcc   4980
ccgcttaaac ccttcttaaa actcagcctg ggctgccag gcctgggaat ccacatgagg    5040
cccctggcat cctggctttt catcttcaac gtctctcaac agatgggggg cttctacctg   5100
tgccagccgg ggcccccctc tgagaaggcc tggcagcctg gctggacagt caatgtggag   5160
ggcagcgggg agctgttccg gtggaatgtt tcggacctag gtggcctggg ctgtggcctg   5220
aagaacaggt cctcagaggg ccccagctcc ccttccggga agctcatgag ccccaagctg   5280
tatgtgtggg ccaaagaccg ccctgagatc tgggagggag agcctccgtg tgtcccaccg   5340
agggacagcc tgaaccagag cctcagccag gacctcacca tggcccctgg ctccacactc   5400
tggctgtcct gtggggtacc ccctgactct gtgtccaggg gcccccctc ctggacccat    5460
gtgcacccca aggggcctaa gtcattgctg agcctagagc tgaaggacga tcgcccggcc   5520
agagatatgt gggtaatgga gacgggtctg ttgttgcccc gggccacagc tcaagacgct   5580
ggaaagtatt attgtcaccg tggcaacctg accatgtcat tccacctgga gatcactgct   5640
cggccagtac tatggcactg gctgctgagg actggtggct ggaaggtctc agctgtgact   5700
ttggcttatc tgatcttctg cctgtgttcc cttgtgggca ttcttcatct ttaaggcgcg   5760
```

-continued

```
ccccgggatc caagcttcaa ttgtggtcac tcgacaatca acctctggat tacaaaattt   5820

gtgaaagatt gactggtatt cttaactatg ttgctccttt tacgctatgt ggatacgctg   5880

ctttaatgcc tttgtatcat gctattgctt cccgtatggc tttcattttc tcctccttgt   5940

ataaatcctg gttgctgtct ctttatgagg agttgtggcc cgttgtcagg caacgtggcg   6000

tggtgtgcac tgtgtttgct gacgcaaccc ccactggttg gggcattgcc accacctgtc   6060

agctcctttc cgggactttc gctttccccc tccctattgc cacggcggaa ctcatcgccg   6120

cctgccttgc ccgctgctgg acaggggctc ggctgttggg cactgacaat tccgtggtgt   6180

tgtcggggaa gctgacgtcc tttccatggc tgctcgcctg tgttgccacc tggattctgc   6240

gcgggacgtc cttctgctac gtcccttcgg ccctcaatcc agcggacctt ccttcccgcg   6300

gcctgctgcc ggctctgcgg cctcttccgc gtcttcgcct tcgccctcag acgagtcgga   6360

tctccctttg ggccgcctcc ccgcctgtct cgagacctag aaaaacatgg agcaatcaca   6420

agtagcaata cagcagctac caatgctgat tgtgcctggc tagaagcaca agaggaggag   6480

gaggtgggtt ttccagtcac acctcaggta cctttaagac caatgactta caaggcagat   6540

cttagccact tttaaaaga aaagggggga ctggaagggc taattcactc ccaacgaaga   6600

caagatctgc tttttgcttg tactgggtct ctctggttag accagatctg agcctgggag   6660

ctctctggct aactagggaa cccactgctt aagcctcaat aaagcttgcc ttgagtgctt   6720

caagtagtgt gtgcccgtct gttgtgtgac tctggtaact agagatccct cagacccttt   6780

tagtcagtgt ggaaaatctc tagca                                          6805
```

<210> SEQ ID NO 15
<211> LENGTH: 639
<212> TYPE: DNA
<213> ORGANISM: Homo sapiens

<400> SEQUENCE: 15

```
atggcggccc ggcgcggggc tctcatagtg ctggagggcg tggaccgcgc cgggaagagc     60

acgcagagcc gcaagctggt ggaagcgctg tgcgccgcgg gccaccgcgc cgaactgctc    120

cggttcccgg aaagatcaac tgaaatcggc aaacttctga gttcctactt gcaaaagaaa    180

agtgacgtgg aggatcactc ggtgcacctg ctttttctg caaatcgctg ggaacaagtg    240

ccgttaatta aggaaaagtt gagccagggc gtgaccctcg tcgtggacag atacgcattt    300

tctggtgtgg ccttcacagg tgccaaggag aatttttccc tagactggtg taaacagcca    360

gacgtgggcc ttcccaaacc cgacctggtc ctgttcctcc agttacagct ggcggatgct    420

gccaagcggg gagcgtttgg ccatgagcgc tatgagaacg gggctttcca ggagcgggcg    480

ctccggtgtt tccaccagct catgaaagac acgactttga actggaagat ggtggatgct    540

tccaaaagca tcgaagctgt ccatgaggac atccgcgtgc tctctgagga cgccatcgcc    600

actgccacag agaagccgct gggggagcta tggaagtga                           639
```

<210> SEQ ID NO 16
<211> LENGTH: 212
<212> TYPE: PRT
<213> ORGANISM: Homo sapiens

<400> SEQUENCE: 16

```
Met Ala Ala Arg Arg Gly Ala Leu Ile Val Leu Glu Gly Val Asp Arg
1               5                   10                  15

Ala Gly Lys Ser Thr Gln Ser Arg Lys Leu Val Glu Ala Leu Cys Ala
            20                  25                  30
```

```
Ala Gly His Arg Ala Glu Leu Leu Arg Phe Pro Glu Arg Ser Thr Glu
        35                  40                  45

Ile Gly Lys Leu Leu Ser Ser Tyr Leu Gln Lys Lys Ser Asp Val Glu
    50                  55                  60

Asp His Ser Val His Leu Leu Phe Ser Ala Asn Arg Trp Glu Gln Val
65                  70                  75                  80

Pro Leu Ile Lys Glu Lys Leu Ser Gln Gly Val Thr Leu Val Val Asp
                85                  90                  95

Arg Tyr Ala Phe Ser Gly Val Ala Phe Thr Gly Ala Lys Glu Asn Phe
            100                 105                 110

Ser Leu Asp Trp Cys Lys Gln Pro Asp Val Gly Leu Pro Lys Pro Asp
        115                 120                 125

Leu Val Leu Phe Leu Gln Leu Gln Leu Ala Asp Ala Ala Lys Arg Gly
    130                 135                 140

Ala Phe Gly His Glu Arg Tyr Glu Asn Gly Ala Phe Gln Glu Arg Ala
145                 150                 155                 160

Leu Arg Cys Phe His Gln Leu Met Lys Asp Thr Thr Leu Asn Trp Lys
                165                 170                 175

Met Val Asp Ala Ser Lys Ser Ile Glu Ala Val His Glu Asp Ile Arg
            180                 185                 190

Val Leu Ser Glu Asp Ala Ile Ala Thr Ala Thr Glu Lys Pro Leu Gly
        195                 200                 205

Glu Leu Trp Lys
    210


<210> SEQ ID NO 17
<211> LENGTH: 15
<212> TYPE: PRT
<213> ORGANISM: E. coli

<400> SEQUENCE: 17

Thr Pro Glu Val Gly Leu Lys Arg Ala Arg Ala Arg Gly Glu Leu
1               5                   10                  15


<210> SEQ ID NO 18
<211> LENGTH: 118
<212> TYPE: DNA
<213> ORGANISM: HIV

<400> SEQUENCE: 18

ttttaaaaga aaagggggga ttggggggta cagtgcaggg gaaagaatag tagacataat      60

agcaacagac atacaaacta aagaattaca aaaacaaatt acaaaaattc aaaatttt       118


<210> SEQ ID NO 19
<211> LENGTH: 592
<212> TYPE: DNA
<213> ORGANISM: Woodchuck Hepatitus Virus

<400> SEQUENCE: 19

aatcaacctc tggattacaa aatttgtgaa agattgactg gtattcttaa ctatgttgct      60

ccttttacgc tatgtggata cgctgcttta atgcctttgt atcatgctat tgcttcccgt     120

atggctttca ttttctcctc cttgtataaa tcctggttgc tgtctcttta tgaggagttg     180

tggcccgttg tcaggcaacg tggcgtggtg tgcactgtgt ttgctgacgc aacccccact     240

ggttggggca ttgccaccac ctgtcagctc ctttccggga ctttcgcttt ccccctccct     300

attgccacgg cggaactcat cgccgcctgc cttgcccgct gctggacagg ggctcggctg     360
```

ttgggcactg acaattccgt ggtgttgtcg gggaagctga cgtcctttcc atggctgctc 420
gcctgtgttg ccacctggat tctgcgcggg acgtccttct gctacgtccc ttcggccctc 480
aatccagcgg accttccttc ccgcggcctg ctgccggctc tgcggcctct tccgcgtctt 540
cgccttcgcc ctcagacgag tcggatctcc ctttgggccg cctccccgcc tg 592

<210> SEQ ID NO 20
<211> LENGTH: 13
<212> TYPE: PRT
<213> ORGANISM: Homo sapiens

<400> SEQUENCE: 20

Gln Leu Ala Asp Ala Ala Lys Arg Gly Ala Phe Gly His
1 5 10

<210> SEQ ID NO 21
<211> LENGTH: 639
<212> TYPE: DNA
<213> ORGANISM: Homo sapiens

<400> SEQUENCE: 21
atggcggccc ggcgcggggc tctcatagtg ctggagggcg tggaccgcgc cgggaagagc 60
acgcagagcc gcaagctggt ggaagcgctg tgcgccgcgg gccaccgcgc cgaactgctc 120
cggttcccgg aaagatcaac tgaaatcggc aaacttctga gttcctactt gcaaaagaaa 180
agtgacgtgg aggatcactc ggtgcacctg ctttttctg caaatcgctg ggaacaagtg 240
ccgttaatta aggaaaagtt gagccagggc gtgaccctcg tcgtggacag atacgcattt 300
tctggtgtgg cctacacagg tgccaaggag aatttttccc tagactggtg taaacagcca 360
gacgtgggcc ttcccaaacc cgacctggtc ctgttcctcc agttacagct ggcggatgct 420
gccaagcggg gagcgtttgg ccatgagcgc tatgagaacg gggctttcca ggagcgggcg 480
ctccggtgtt tccaccagct catgaaagac acgactttga actggaagat ggtggatgct 540
tccaaaagca tcgaagctgt ccatgaggac atccgcgtgc tctctgagga cgccatcgcc 600
actgccacag agaagccgct gggggagcta tggaagtga 639

<210> SEQ ID NO 22
<211> LENGTH: 645
<212> TYPE: DNA
<213> ORGANISM: Homo sapiens

<400> SEQUENCE: 22
atggcggccc ggcgcggggc tctcatagtg ctggagggcg tggacggcgc cgggaagagc 60
acgcagagcc gcaagctggt ggaagcgctg tgcgccgcgg gccaccgcgc cgaactgctc 120
cggttcccgg aaagatcaac tgaaatcggc aaacttctga gttcctactt gcaaaagaaa 180
agtgacgtgg aggatcactc ggtgcacctg ctttttctg caaatcgctg ggaacaagtg 240
ccgttaatta aggaaaagtt gagccagggc gtgaccctcg tcgtggacag atacgcattt 300
tctggtgtgg ccttcaccgg tgccaaggag aatttttccc tagactggtg taaacagcca 360
gacgtgggcc ttcccaaacc cgacctggtc ctgttcctgc agttaactcc ggaagttggc 420
ttaaaacgcg cacgtgctcg cggcgagctt gaccgctatg agaacggggc tttccaggag 480
cgggcgctcc ggtgtttcca ccagctcatg aaagacacga ctttgaactg gaagatggtg 540
gatgcttcca aaagcatcga agctgtccat gaggacatcc gcgtgctctc tgaggacgcc 600
atcgccactg ccacagagaa gccgctgggg gagctatgga agtga 645

-continued

<210> SEQ ID NO 23
<211> LENGTH: 28
<212> TYPE: DNA
<213> ORGANISM: Homo sapiens

<400> SEQUENCE: 23
atgccacctc ctcgcctcct cttcttcc 28

<210> SEQ ID NO 24
<211> LENGTH: 22
<212> TYPE: DNA
<213> ORGANISM: Homo sapiens

<400> SEQUENCE: 24
tcacctggtg ctccaggtgc cc 22

<210> SEQ ID NO 25
<211> LENGTH: 23
<212> TYPE: DNA
<213> ORGANISM: Homo sapiens

<400> SEQUENCE: 25
ccgccaccgc ggtggagctc cag 23

<210> SEQ ID NO 26
<211> LENGTH: 26
<212> TYPE: DNA
<213> ORGANISM: Homo sapiens

<400> SEQUENCE: 26
ttaaagatga agaatgccca caaggg 26

<210> SEQ ID NO 27
<211> LENGTH: 1966
<212> TYPE: DNA
<213> ORGANISM: Homo sapiens

<400> SEQUENCE: 27
aggcccctgc ctgccccagc atcccctgcg cgaagctggg tgccccggag agtctgacca 60
ccatgccacc tcctcgcctc ctcttcttcc tcctcttcct cacccccatg gaagtcaggc 120
ccgaggaacc tctagtggtg aaggtggaag agggagataa cgctgtgctg cagtgcctca 180
aggggacctc agatggcccc actcagcagc tgacctggtc tcgggagtcc ccgcttaaac 240
ccttcttaaa actcagcctg gggctgccag gcctgggaat ccacatgagg cccctggcca 300
tctggctttt catcttcaac gtctctcaac agatgggggg cttctacctg tgccagccgg 360
ggcccccctc tgagaaggcc tggcagcctg gctggacagt caatgtggag ggcagcgggg 420
agctgttccg gtggaatgtt tcggacctag gtggcctggg ctgtggcctg aagaacaggt 480
cctcagaggg ccccagctcc ccttccggga agctcatgag ccccaagctg tatgtgtggg 540
ccaaagaccg ccctgagatc tgggagggag agcctccgtg tctcccaccg agggacagcc 600
tgaaccagag cctcagccag gacctcacca tggcccctgg ctccacactc tggctgtcct 660
gtggggtacc ccctgactct gtgtccaggg gcccctctc ctggacccat gtgcacccca 720
aggggcctaa gtcattgctg agcctagagc tgaaggacga tcgcccggcc agagatatgt 780
gggtaatgga gacgggtctg ttgttgcccc gggccacagc tcaagacgct ggaaagtatt 840
attgtcaccg tggcaacctg accatgtcat tccacctgga gatcactgct cggccagtac 900

-continued

```
tatggcactg gctgctgagg actggtggct ggaaggtctc agctgtgact ttggcttatc    960

tgatcttctg cctgtgttcc cttgtgggca ttcttcatct tcaaagagcc ctggtcctga   1020

ggaggaaaag aaagcgaatg actgacccca ccaggagatt cttcaaagtg acgcctcccc   1080

caggaagcgg gccccagaac cagtacggga acgtgctgtc tctccccaca cccacctcag   1140

gcctcggacg cgcccagcgt tgggccgcag gcctgggggg cactgccccg tcttatggaa   1200

acccgagcag cgacgtccag gcggatggag ccttggggtc ccggagcccg ccgggagtgg   1260

gcccagaaga agaggaaggg gagggctatg aggaacctga cagtgaggag gactccgagt   1320

tctatgagaa cgactccaac cttgggcagg accagctctc ccaggatggc agcggctacg   1380

agaaccctga ggatgagccc ctgggtcctg aggatgaaga ctccttctcc aacgctgagt   1440

cttatgagaa cgaggatgaa gagctgaccc agccggtcgc caggacaatg gacttcctga   1500

gccctcatgg gtcagcctgg gaccccagcc gggaagcaac ctccctgggg tcccagtcct   1560

atgaggatat gagaggaatc ctgtatgcag ccccccagct ccgctccatt cggggccagc   1620

ctggacccaa tcatgaggaa gatgcagact cttatgagaa catggataat cccgatgggc   1680

cagacccagc ctggggagga gggggccgca tgggcacctg gagcaccagg tgatcctcag   1740

gtggccagcc tggatctcct caagtcccca agattcacac ctgactctga aatctgaaga   1800

cctcgagcag atgatgccaa cctctggagc aatgttgctt aggatgtgtg catgtgtgta   1860

agtgtgtgtg tgtgtgtgtg tgtgtataca tgccagtgac acttccagtc ccctttgtat   1920

tccttaaata aactcaatga gctcttccaa aaaaaaaaaa aaaaaa                  1966


<210> SEQ ID NO 28
<211> LENGTH: 556
<212> TYPE: PRT
<213> ORGANISM: Homo sapiens

<400> SEQUENCE: 28

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190
```

```
Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Phe Lys Val
                325                 330                 335

Thr Pro Pro Pro Gly Ser Gly Pro Gln Asn Gln Tyr Gly Asn Val Leu
            340                 345                 350

Ser Leu Pro Thr Pro Thr Ser Gly Leu Gly Arg Ala Gln Arg Trp Ala
        355                 360                 365

Ala Gly Leu Gly Gly Thr Ala Pro Ser Tyr Gly Asn Pro Ser Ser Asp
    370                 375                 380

Val Gln Ala Asp Gly Ala Leu Gly Ser Arg Ser Pro Pro Gly Val Gly
385                 390                 395                 400

Pro Glu Glu Glu Glu Gly Glu Gly Tyr Glu Glu Pro Asp Ser Glu Glu
                405                 410                 415

Asp Ser Glu Phe Tyr Glu Asn Asp Ser Asn Leu Gly Gln Asp Gln Leu
            420                 425                 430

Ser Gln Asp Gly Ser Gly Tyr Glu Asn Pro Glu Asp Glu Pro Leu Gly
        435                 440                 445

Pro Glu Asp Glu Asp Ser Phe Ser Asn Ala Glu Ser Tyr Glu Asn Glu
    450                 455                 460

Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Gly
                485                 490                 495

Ser Gln Ser Tyr Glu Asp Met Arg Gly Ile Leu Tyr Ala Ala Pro Gln
            500                 505                 510

Leu Arg Ser Ile Arg Gly Gln Pro Gly Pro Asn His Glu Glu Asp Ala
        515                 520                 525

Asp Ser Tyr Glu Asn Met Asp Asn Pro Asp Gly Pro Asp Pro Ala Trp
    530                 535                 540

Gly Gly Gly Gly Arg Met Gly Thr Trp Ser Thr Arg
545                 550                 555


<210> SEQ ID NO 29
<211> LENGTH: 313
<212> TYPE: PRT
<213> ORGANISM: Homo sapiens

<400> SEQUENCE: 29

Met Pro Pro Pro Arg Leu Leu Phe Phe Leu Leu Phe Leu Thr Pro Met
```

```
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu
305                 310


<210> SEQ ID NO 30
<211> LENGTH: 939
<212> TYPE: DNA
<213> ORGANISM: Homo sapiens
<220> FEATURE:
<221> NAME/KEY: exon
<222> LOCATION: (1)..(939)

<400> SEQUENCE: 30

atg cca cct cct cgc ctc ctc ttc ttc ctc ctc ttc ctc acc ccc atg       48
Met Pro Pro Pro Arg Leu Leu Phe Phe Leu Leu Phe Leu Thr Pro Met
1               5                   10                  15

gaa gtc agg ccc gag gaa cct cta gtg gtg aag gtg gaa gag gga gat       96
Glu Val Arg Pro Glu Glu Pro Leu Val Val Lys Val Glu Glu Gly Asp
            20                  25                  30

aac gct gtg ctg cag tgc ctc aag ggg acc tca gat ggc ccc act cag      144
```

-continued

Asn Ala Val Leu Gln Cys Leu Lys Gly Thr Ser Asp Gly Pro Thr Gln
35 40 45 cag ctg acc tgg tct cgg gag tcc ccg ctt aaa ccc ttc tta aaa ctc 192
Gln Leu Thr Trp Ser Arg Glu Ser Pro Leu Lys Pro Phe Leu Lys Leu
50 55 60 agc ctg ggg ctg cca ggc ctg gga atc cac atg agg ccc ctg gcc atc 240
Ser Leu Gly Leu Pro Gly Leu Gly Ile His Met Arg Pro Leu Ala Ile
65 70 75 80 tgg ctt ttc atc ttc aac gtc tct caa cag atg ggg ggc ttc tac ctg 288
Trp Leu Phe Ile Phe Asn Val Ser Gln Gln Met Gly Gly Phe Tyr Leu
85 90 95 tgc cag ccg ggg ccc ccc tct gag aag gcc tgg cag cct ggc tgg aca 336
Cys Gln Pro Gly Pro Pro Ser Glu Lys Ala Trp Gln Pro Gly Trp Thr
100 105 110 gtc aat gtg gag ggc agc ggg gag ctg ttc cgg tgg aat gtt tcg gac 384
Val Asn Val Glu Gly Ser Gly Glu Leu Phe Arg Trp Asn Val Ser Asp
115 120 125 cta ggt ggc ctg ggc tgt ggc ctg aag aac agg tcc tca gag ggc ccc 432
Leu Gly Gly Leu Gly Cys Gly Leu Lys Asn Arg Ser Ser Glu Gly Pro
130 135 140 agc tcc cct tcc ggg aag ctc atg agc ccc aag ctg tat gtg tgg gcc 480
Ser Ser Pro Ser Gly Lys Leu Met Ser Pro Lys Leu Tyr Val Trp Ala
145 150 155 160 aaa gac cgc cct gag atc tgg gag gga gag cct ccg tgt ctc cca ccg 528
Lys Asp Arg Pro Glu Ile Trp Glu Gly Glu Pro Pro Cys Leu Pro Pro
165 170 175 agg gac agc ctg aac cag agc ctc agc cag gac ctc acc atg gcc cct 576
Arg Asp Ser Leu Asn Gln Ser Leu Ser Gln Asp Leu Thr Met Ala Pro
180 185 190 ggc tcc aca ctc tgg ctg tcc tgt ggg gta ccc cct gac tct gtg tcc 624
Gly Ser Thr Leu Trp Leu Ser Cys Gly Val Pro Pro Asp Ser Val Ser
195 200 205 agg ggc ccc ctc tcc tgg acc cat gtg cac ccc aag ggg cct aag tca 672
Arg Gly Pro Leu Ser Trp Thr His Val His Pro Lys Gly Pro Lys Ser
210 215 220 ttg ctg agc cta gag ctg aag gac gat cgc ccg gcc aga gat atg tgg 720
Leu Leu Ser Leu Glu Leu Lys Asp Asp Arg Pro Ala Arg Asp Met Trp
225 230 235 240 gta atg gag acg ggt ctg ttg ttg ccc cgg gcc aca gct caa gac gct 768
Val Met Glu Thr Gly Leu Leu Leu Pro Arg Ala Thr Ala Gln Asp Ala
245 250 255 gga aag tat tat tgt cac cgt ggc aac ctg acc atg tca ttc cac ctg 816
Gly Lys Tyr Tyr Cys His Arg Gly Asn Leu Thr Met Ser Phe His Leu
260 265 270 gag atc act gct cgg cca gta cta tgg cac tgg ctg ctg agg act ggt 864
Glu Ile Thr Ala Arg Pro Val Leu Trp His Trp Leu Leu Arg Thr Gly
275 280 285 ggc tgg aag gtc tca gct gtg act ttg gct tat ctg atc ttc tgc ctg 912
Gly Trp Lys Val Ser Ala Val Thr Leu Ala Tyr Leu Ile Phe Cys Leu
290 295 300 tgt tcc ctt gtg ggc att ctt cat ctt 939
Cys Ser Leu Val Gly Ile Leu His Leu
305 310

<210> SEQ ID NO 31
<211> LENGTH: 313
<212> TYPE: PRT
<213> ORGANISM: Homo sapiens

<400> SEQUENCE: 31

```
Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ser
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Val Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu
305                 310


<210> SEQ ID NO 32
<211> LENGTH: 6
<212> TYPE: PRT
<213> ORGANISM: Artificial Sequence
<220> FEATURE:
<223> OTHER INFORMATION: Linker

<400> SEQUENCE: 32

Ala Gly Gly Ala Ala Gly
1               5


<210> SEQ ID NO 33
<211> LENGTH: 18
<212> TYPE: DNA
<213> ORGANISM: Artificial Sequence
<220> FEATURE:
```

<223> OTHER INFORMATION: Linker

<400> SEQUENCE: 33
gccggcgggg ctgcaggg 18

<210> SEQ ID NO 34
<211> LENGTH: 639
<212> TYPE: DNA
<213> ORGANISM: Artificial Sequence
<220> FEATURE:
<223> OTHER INFORMATION: Tmpk polynucleotide

<400> SEQUENCE: 34
atggcggccc ggcgcggggc tctcatagtg ctggagggcg tggaccgcgc cgggaagagc 60
acgcagagcc gcaagctggt ggaagcgctg tgcgccgcgg gccaccgcgc cgaactgctc 120
cggttcccgg aaagatcaac tgaaatcggc aaacttctga gttcctactt gcaaaagaaa 180
agtgacgtgg aggatcactc ggtgcacctg ctttttctg caaatcgctg ggaacaagtg 240
ccgttaatta aggaaaagtt gagccagggc gtgaccctcg tcgtggacag atacgcattt 300
tctggtgtgg cctacacagg tgccaaggag aatttttccc tagactggtg taaacagcca 360
gacgtgggcc ttcccaaacc cgacctggtc ctgttcctcc agttacagct ggcggatgct 420
gccaagcggg gagcgtttgg ccatgagcgc tatgagaacg gggctttcca ggagcgggcg 480
ctccggtgtt tccaccagct catgaaagac acgactttga actggaagat ggtggatgct 540
tccaaaagca tcgaagctgt ccatgaggac atccgcgtgc tctctgagga cgccatcgcc 600
actgccacag agaagccgct gggggagcta tggaagtga 639

<210> SEQ ID NO 35
<211> LENGTH: 939
<212> TYPE: DNA
<213> ORGANISM: Artificial Sequence
<220> FEATURE:
<223> OTHER INFORMATION: Truncated CD19

<400> SEQUENCE: 35
atgccacctc ctcgcctcct cttcttcctc ctcttcctca cccccatgga agtcaggccc 60
gaggaacctc tagtggtgaa ggtggaagag ggagataacg ctgtgctgca gtgcctcaag 120
gggacctcag atggccccac tcagcagctg acctggtctc gggagtcccc gcttaaaccc 180
ttcttaaaac tcagcctggg gctgccaggc ctgggaatcc acatgaggcc cctggcatcc 240
tggcttttca tcttcaacgt ctctcaacag atggggggct tctacctgtg ccagccgggg 300 ccccctctg agaaggcctg gcagcctggc tggacagtca atgtggaggg cagcggggag 360
ctgttccggt ggaatgtttc ggacctaggt ggcctgggct gtggcctgaa gaacaggtcc 420
tcagagggcc ccagctcccc ttccgggaag ctcatgagcc ccaagctgta tgtgtgggcc 480
aaagaccgcc ctgagatctg ggagggagag cctccgtgtg tcccaccgag ggacagcctg 540
aaccagagcc tcagccagga cctcaccatg gcccctggct ccacactctg gctgtcctgt 600
ggggtacccc ctgactctgt gtccaggggc cccctctcct ggacccatgt gcaccccaag 660
gggcctaagt cattgctgag cctagagctg aaggacgatc gcccggccag agatatgtgg 720
gtaatggaga cgggtctgtt gttgccccgg gccacagctc aagacgctgg aaagtattat 780
tgtcaccgtg gcaacctgac catgtcattc cacctggaga tcactgctcg gccagtacta 840
tggcactggc tgctgaggac tggtggctgg aaggtctcag ctgtgacttt ggcttatctg 900
atcttctgcc tgtgttccct tgtgggcatt cttcatctt 939

<210> SEQ ID NO 36
<211> LENGTH: 212
<212> TYPE: PRT
<213> ORGANISM: Artificial Sequence
<220> FEATURE:
<223> OTHER INFORMATION: TmpkF105YR200A

<400> SEQUENCE: 36

```
Met Ala Ala Arg Arg Gly Ala Leu Ile Val Leu Glu Gly Val Asp Arg
1               5                   10                  15

Ala Gly Lys Ser Thr Gln Ser Arg Lys Leu Val Glu Ala Leu Cys Ala
            20                  25                  30

Ala Gly His Arg Ala Glu Leu Leu Arg Phe Pro Glu Arg Ser Thr Glu
        35                  40                  45

Ile Gly Lys Leu Leu Ser Ser Tyr Leu Gln Lys Lys Ser Asp Val Glu
    50                  55                  60

Asp His Ser Val His Leu Leu Phe Ser Ala Asn Arg Trp Glu Gln Val
65                  70                  75                  80

Pro Leu Ile Lys Glu Lys Leu Ser Gln Gly Val Thr Leu Val Val Asp
                85                  90                  95

Arg Tyr Ala Phe Ser Gly Val Ala Tyr Thr Gly Ala Lys Glu Asn Phe
            100                 105                 110

Ser Leu Asp Trp Cys Lys Gln Pro Asp Val Gly Leu Pro Lys Pro Asp
        115                 120                 125

Leu Val Leu Phe Leu Gln Leu Gln Leu Ala Asp Ala Ala Lys Arg Gly
    130                 135                 140

Ala Phe Gly His Glu Arg Tyr Glu Asn Gly Ala Phe Gln Glu Arg Ala
145                 150                 155                 160

Leu Arg Cys Phe His Gln Leu Met Lys Asp Thr Thr Leu Asn Trp Lys
                165                 170                 175

Met Val Asp Ala Ser Lys Ser Ile Glu Ala Val His Glu Asp Ile Arg
            180                 185                 190

Val Leu Ser Glu Asp Ala Ile Ala Thr Ala Thr Glu Lys Pro Leu Gly
        195                 200                 205

Glu Leu Trp Lys
    210
```

<210> SEQ ID NO 37
<211> LENGTH: 313
<212> TYPE: PRT
<213> ORGANISM: Artificial Sequence
<220> FEATURE:
<223> OTHER INFORMATION: Truncated CD19

<400> SEQUENCE: 37

```
Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ser
65                  70                  75                  80

Trp Leu Phe Ile Phe Asn Val Ser Gln Gln Met Gly Gly Phe Tyr Leu
```

```
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Val Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu
305                 310


<210> SEQ ID NO 38
<211> LENGTH: 531
<212> TYPE: PRT
<213> ORGANISM: Artificial Sequence
<220> FEATURE:
<223> OTHER INFORMATION: Truncated CD19-Linker-TmpkF105YR200A

<400> SEQUENCE: 38

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ser
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
```

-continued

```
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Val Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Ala Gly Gly Ala Ala Gly Met
305                 310                 315                 320

Ala Ala Arg Arg Gly Ala Leu Ile Val Leu Glu Gly Val Asp Arg Ala
                325                 330                 335

Gly Lys Ser Thr Gln Ser Arg Lys Leu Val Glu Ala Leu Cys Ala Ala
            340                 345                 350

Gly His Arg Ala Glu Leu Leu Arg Phe Pro Glu Arg Ser Thr Glu Ile
        355                 360                 365

Gly Lys Leu Leu Ser Ser Tyr Leu Gln Lys Lys Ser Asp Val Glu Asp
    370                 375                 380

His Ser Val His Leu Leu Phe Ser Ala Asn Arg Trp Glu Gln Val Pro
385                 390                 395                 400

Leu Ile Lys Glu Lys Leu Ser Gln Gly Val Thr Leu Val Val Asp Arg
                405                 410                 415

Tyr Ala Phe Ser Gly Val Ala Tyr Thr Gly Ala Lys Glu Asn Phe Ser
            420                 425                 430

Leu Asp Trp Cys Lys Gln Pro Asp Val Gly Leu Pro Lys Pro Asp Leu
        435                 440                 445

Val Leu Phe Leu Gln Leu Gln Leu Ala Asp Ala Ala Lys Arg Gly Ala
    450                 455                 460

Phe Gly His Glu Arg Tyr Glu Asn Gly Ala Phe Gln Glu Arg Ala Leu
465                 470                 475                 480

Arg Cys Phe His Gln Leu Met Lys Asp Thr Thr Leu Asn Trp Lys Met
                485                 490                 495

Val Asp Ala Ser Lys Ser Ile Glu Ala Val His Glu Asp Ile Arg Val
            500                 505                 510

Leu Ser Glu Asp Ala Ile Ala Thr Ala Thr Glu Lys Pro Leu Gly Glu
        515                 520                 525

Leu Trp Lys
    530
```

<210> SEQ ID NO 39

<211> LENGTH: 1596
<212> TYPE: DNA
<213> ORGANISM: Artificial Sequence
<220> FEATURE:
<223> OTHER INFORMATION: Truncated CD19-Linker-TmpkF105YR200A

<400> SEQUENCE: 39

```
atgccacctc ctcgcctcct cttcttcctc ctcttcctca cccccatgga agtcaggccc     60

gaggaacctc tagtggtgaa ggtggaagag ggagataacg ctgtgctgca gtgcctcaag    120

gggacctcag atggccccac tcagcagctg acctggtctc gggagtcccc gcttaaaccc    180

ttcttaaaac tcagcctggg gctgccaggc ctgggaatcc acatgaggcc cctggcatcc    240

tggcttttca tcttcaacgt ctctcaacag atgggggggct tctacctgtg ccagccgggg    300

ccccctctg agaaggcctg gcagcctggc tggacagtca atgtggaggg cagcggggag    360

ctgttccggt ggaatgtttc ggacctaggt ggcctgggct gtggcctgaa gaacaggtcc    420

tcagagggcc ccagctcccc ttccgggaag ctcatgagcc ccaagctgta tgtgtgggcc    480

aaagaccgcc ctgagatctg ggagggagag cctccgtgtg tcccaccgag ggacagcctg    540

aaccagagcc tcagccagga cctcaccatg gcccctggct ccacactctg gctgtcctgt    600

ggggtacccc ctgactctgt gtccaggggc cccctctcct ggacccatgt gcaccccaag    660

gggcctaagt cattgctgag cctagagctg aaggacgatc gcccggccag agatatgtgg    720

gtaatggaga cgggtctgtt gttgccccgg gccacagctc aagacgctgg aaagtattat    780

tgtcaccgtg gcaacctgac catgtcattc cacctggaga tcactgctcg gccagtacta    840

tggcactggc tgctgaggac tggtggctgg aaggtctcag ctgtgacttt ggcttatctg    900

atcttctgcc tgtgttccct tgtgggcatt cttcatcttg ccggcggggc tgcagggatg    960

gcggcccggc gcggggctct catagtgctg gagggcgtgg accgcgccgg gaagagcacg   1020

cagagccgca agctggtgga agcgctgtgc gccgcgggcc accgcgccga actgctccgg   1080

ttcccggaaa gatcaactga aatcggcaaa cttctgagtt cctacttgca aaagaaaagt   1140

gacgtggagg atcactcggt gcacctgctt ttttctgcaa atcgctggga acaagtgccg   1200

ttaattaagg aaaagttgag ccagggcgtg accctcgtcg tggacagata cgcattttct   1260

ggtgtggcct acacaggtgc caaggagaat ttttccctag actggtgtaa acagccagac   1320

gtgggccttc ccaaacccga cctggtcctg ttcctccagt tacagctggc ggatgctgcc   1380

aagcggggag cgtttggcca tgagcgctat gagaacgggg ctttccagga gcgggcgctc   1440

cggtgtttcc accagctcat gaaagacacg actttgaact ggaagatggt ggatgcttcc   1500

aaaagcatcg aagctgtcca tgaggacatc cgcgtgctct ctgaggacgc catcgccact   1560

gccacagaga agccgctggg ggagctatgg aagtga                              1596
```

<210> SEQ ID NO 40
<211> LENGTH: 1596
<212> TYPE: DNA
<213> ORGANISM: Artificial Sequence
<220> FEATURE:
<223> OTHER INFORMATION: CD19deltaTmpkF105YR200A Fusion Polynucleotide
<220> FEATURE:
<221> NAME/KEY: misc_feature
<222> LOCATION: (1)..(939)
<223> OTHER INFORMATION: CD19delta
<220> FEATURE:
<221> NAME/KEY: misc_feature
<222> LOCATION: (940)..(957)
<223> OTHER INFORMATION: linker
<220> FEATURE:
<221> NAME/KEY: misc_feature
<222> LOCATION: (958)..(1596)
<223> OTHER INFORMATION: TmpkF105YR200A

<400> SEQUENCE: 40

```
atgccacctc ctcgcctcct cttcttcctc ctcttcctca cccccatgga agtcaggccc     60

gaggaacctc tagtggtgaa ggtggaagag ggagataacg ctgtgctgca gtgcctcaag    120

gggacctcag atggccccac tcagcagctg acctggtctc gggagtcccc gcttaaaccc    180

ttcttaaaac tcagcctggg gctgccaggc ctgggaatcc acatgaggcc cctggcatcc    240

tggcttttca tcttcaacgt ctctcaacag atgggggggct tctacctgtg ccagccgggg    300

ccccctctg agaaggcctg gcagcctggc tggacagtca atgtggaggg cagcggggag    360

ctgttccggt ggaatgtttc ggacctaggt ggcctgggct gtggcctgaa gaacaggtcc    420

tcagagggcc ccagctcccc ttccgggaag ctcatgagcc ccaagctgta tgtgtgggcc    480

aaagaccgcc ctgagatctg ggagggagag cctccgtgtg tcccaccgag ggacagcctg    540

aaccagagcc tcagccagga cctcaccatg gcccctggct ccacactctg gctgtcctgt    600

ggggtacccc ctgactctgt gtccaggggc cccctctcct ggacccatgt gcaccccaag    660

gggcctaagt cattgctgag cctagagctg aaggacgatc gcccggccag agatatgtgg    720

gtaatggaga cgggtctgtt gttgccccgg gccacagctc aagacgctgg aaagtattat    780

tgtcaccgtg gcaacctgac catgtcattc cacctggaga tcactgctcg gccagtacta    840

tggcactggc tgctgaggac tggtggctgg aaggtctcag ctgtgacttt ggcttatctg    900

atcttctgcc tgtgttccct tgtgggcatt cttcatcttg ccggcggggc tgcagggatg    960

gcggcccggc gcggggctct catagtgctg gagggcgtgg accgcgccgg gaagagcacg   1020

cagagccgca agctggtgga agcgctgtgc gccgcgggcc accgcgccga actgctccgg   1080

ttcccggaaa gatcaactga aatcggcaaa cttctgagtt cctacttgca aaagaaaagt   1140

gacgtggagg atcactcggt gcacctgctt ttttctgcaa atcgctggga acaagtgccg   1200

ttaattaagg aaaagttgag ccagggcgtg accctcgtcg tggacagata cgcattttct   1260

ggtgtggcct acacaggtgc caaggagaat ttttccctag actggtgtaa acagccagac   1320

gtgggccttc ccaaacccga cctggtcctg ttcctccagt tacagctggc ggatgctgcc   1380

aagcggggag cgtttggcca tgagcgctat gagaacgggg ctttccagga gcgggcgctc   1440

cggtgtttcc accagctcat gaaagacacg actttgaact ggaagatggt ggatgcttcc   1500

aaaagcatcg aagctgtcca tgaggacatc cgcgtgctct ctgaggacgc catcgccact   1560

gccacagaga agccgctggg ggagctatgg aagtga                             1596
```

<210> SEQ ID NO 41
<211> LENGTH: 531
<212> TYPE: PRT
<213> ORGANISM: Artificial Sequence
<220> FEATURE:
<223> OTHER INFORMATION: CD19deltaTmpkF105YR200A Fusion Polypeptide
<220> FEATURE:
<221> NAME/KEY: MISC_FEATURE
<222> LOCATION: (1)..(313)
<223> OTHER INFORMATION: CD19delta
<220> FEATURE:
<221> NAME/KEY: MISC_FEATURE
<222> LOCATION: (314)..(319)
<223> OTHER INFORMATION: Linker
<220> FEATURE:
<221> NAME/KEY: MISC_FEATURE
<222> LOCATION: (320)..(531)
<223> OTHER INFORMATION: TmpkF105YR200A

<400> SEQUENCE: 41

```
Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ser
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Val Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Ala Gly Gly Ala Ala Gly Met
305                 310                 315                 320

Ala Ala Arg Arg Gly Ala Leu Ile Val Leu Glu Gly Val Asp Arg Ala
                325                 330                 335

Gly Lys Ser Thr Gln Ser Arg Lys Leu Val Glu Ala Leu Cys Ala Ala
            340                 345                 350

Gly His Arg Ala Glu Leu Leu Arg Phe Pro Glu Arg Ser Thr Glu Ile
        355                 360                 365

Gly Lys Leu Leu Ser Ser Tyr Leu Gln Lys Lys Ser Asp Val Glu Asp
    370                 375                 380

His Ser Val His Leu Leu Phe Ser Ala Asn Arg Trp Glu Gln Val Pro
385                 390                 395                 400

Leu Ile Lys Glu Lys Leu Ser Gln Gly Val Thr Leu Val Val Asp Arg
                405                 410                 415
```

Tyr Ala Phe Ser Gly Val Ala Tyr Thr Gly Ala Lys Glu Asn Phe Ser
420 425 430

Leu Asp Trp Cys Lys Gln Pro Asp Val Gly Leu Pro Lys Pro Asp Leu
435 440 445

Val Leu Phe Leu Gln Leu Gln Leu Ala Asp Ala Ala Lys Arg Gly Ala
450 455 460

Phe Gly His Glu Arg Tyr Glu Asn Gly Ala Phe Gln Glu Arg Ala Leu
465 470 475 480

Arg Cys Phe His Gln Leu Met Lys Asp Thr Thr Leu Asn Trp Lys Met
485 490 495

Val Asp Ala Ser Lys Ser Ile Glu Ala Val His Glu Asp Ile Arg Val
500 505 510

Leu Ser Glu Asp Ala Ile Ala Thr Ala Thr Glu Lys Pro Leu Gly Glu
515 520 525

Leu Trp Lys
530

<210> SEQ ID NO 42
<211> LENGTH: 9339
<212> TYPE: DNA
<213> ORGANISM: Artificial Sequence
<220> FEATURE:
<223> OTHER INFORMATION: pCCL.SIN.cPPT.EF. CD19deltaTmpkF105YR200A.WPRE
<220> FEATURE:
<221> NAME/KEY: misc_feature
<222> LOCATION: (5779)..(6717)
<223> OTHER INFORMATION: CD19delta
<220> FEATURE:
<221> NAME/KEY: misc_feature
<222> LOCATION: (6718)..(6735)
<223> OTHER INFORMATION: Linker
<220> FEATURE:
<221> NAME/KEY: misc_feature
<222> LOCATION: (6736)..(7374)
<223> OTHER INFORMATION: Tmpk Mutant

<400> SEQUENCE: 42
caggtggcac ttttcgggga aatgtgcgcg gaacccctat ttgtttattt ttctaaatac 60
attcaaatat gtatccgctc atgagacaat aaccctgata aatgcttcaa taatattgaa 120
aaaggaagag tatgagtatt caacatttcc gtgtcgccct tattcccttt tttgcggcat 180
tttgccttcc tgtttttgct cacccagaaa cgctggtgaa agtaaaagat gctgaagatc 240
agttgggtgc acgagtgggt tacatcgaac tggatctcaa cagcggtaag atccttgaga 300
gttttcgccc cgaagaacgt tttccaatga tgagcacttt taaagttctg ctatgtggcg 360
cggtattatc ccgtattgac gccgggcaag agcaactcgg tcgccgcata cactattctc 420
agaatgactt ggttgagtac tcaccagtca cagaaaagca tcttacggat ggcatgacag 480
taagagaatt atgcagtgct gccataacca tgagtgataa cactgcggcc aacttacttc 540
tgacaacgat cggaggaccg aaggagctaa ccgctttttt gcacaacatg ggggatcatg 600
taactcgcct tgatcgttgg gaaccggagc tgaatgaagc cataccaaac gacgagcgtg 660
acaccacgat gcctgtagca atggcaacaa cgttgcgcaa actattaact ggcgaactac 720
ttactctagc ttcccggcaa caattaatag actggatgga ggcggataaa gttgcaggac 780
cacttctgcg ctcggccctt ccggctggct ggtttattgc tgataaatct ggagccggtg 840
agcgtgggtc tcgcggtatc attgcagcac tggggccaga tggtaagccc tcccgtatcg 900
tagttatcta cacgacgggg agtcaggcaa ctatggatga acgaaataga cagatcgctg 960

-continued

```
agataggtgc ctcactgatt aagcattggt aactgtcaga ccaagtttac tcatatatac   1020
tttagattga tttaaaactt catttttaat ttaaaaggat ctaggtgaag atcctttttg   1080
ataatctcat gaccaaaatc ccttaacgtg agttttcgtt ccactgagcg tcagaccccg   1140
tagaaaagat caaaggatct tcttgagatc cttttttct gcgcgtaatc tgctgcttgc   1200
aaacaaaaaa accaccgcta ccagcggtgg tttgtttgcc ggatcaagag ctaccaactc   1260
tttttccgaa ggtaactggc ttcagcagag cgcagatacc aaatactgtc cttctagtgt   1320
agccgtagtt aggccaccac ttcaagaact ctgtagcacc gcctacatac ctcgctctgc   1380
taatcctgtt accagtggct gctgccagtg gcgataagtc gtgtcttacc gggttggact   1440
caagacgata gttaccggat aaggcgcagc ggtcgggctg aacggggggt tcgtgcacac   1500
agcccagctt ggagcgaacg acctacaccg aactgagata cctacagcgt gagctatgag   1560
aaagcgccac gcttcccgaa gggagaaagg cggacaggta tccggtaagc ggcagggtcg   1620
gaacaggaga gcgcacgagg gagcttccag ggggaaacgc ctggtatctt tatagtcctg   1680
tcgggtttcg ccacctctga cttgagcgtc gatttttgtg atgctcgtca ggggggcgga   1740
gcctatggaa aaacgccagc aacgcggcct ttttacggtt cctggccttt tgctggcctt   1800
ttgctcacat gttctttcct gcgttatccc ctgattctgt ggataaccgt attaccgcct   1860
ttgagtgagc tgataccgct cgccgcagcc gaacgaccga gcgcagcgag tcagtgagcg   1920
aggaagcgga agagcgccca atacgcaaac cgcctctccc cgcgcgttgg ccgattcatt   1980
aatgcagctg gcacgacagg tttcccgact ggaaagcggg cagtgagcgc aacgcaatta   2040
atgtgagtta gctcactcat taggcacccc aggctttaca ctttatgctt ccggctcgta   2100
tgttgtgtgg aattgtgagc ggataacaat ttcacacagg aaacagctat gaccatgatt   2160
acgccaagcg cgcaattaac cctcactaaa gggaacaaaa gctggagctg caagcttggc   2220
cattgcatac gttgtatcca tatcataata tgtacattta tattggctca tgtccaacat   2280
taccgccatg ttgacattga ttattgacta gttattaata gtaatcaatt acggggtcat   2340
tagttcatag cccatatatg gagttccgcg ttacataact tacggtaaat ggcccgcctg   2400
gctgaccgcc caacgacccc cgcccattga cgtcaataat gacgtatgtt cccatagtaa   2460
cgccaatagg gactttccat tgacgtcaat gggtggagta tttacggtaa actgcccact   2520
tggcagtaca tcaagtgtat catatgccaa gtacgccccc tattgacgtc aatgacggta   2580
aatggcccgc ctggcattat gcccagtaca tgaccttatg ggactttcct acttggcagt   2640
acatctacgt attagtcatc gctattacca tggtgatgcg gttttggcag tacatcaatg   2700
ggcgtggata gcggtttgac tcacggggat ttccaagtct ccaccccatt gacgtcaatg   2760
ggagtttgtt ttggcaccaa aatcaacggg actttccaaa atgtcgtaac aactccgccc   2820
cattgacgca aatgggcggt aggcgtgtac ggtgggaggt ctatataagc agagctcgtt   2880
tagtgaaccg gggtctctct ggttagacca gatctgagcc tgggagctct ctggctaact   2940
agggaaccca ctgcttaagc ctcaataaag cttgccttga gtgcttcaag tagtgtgtgc   3000
ccgtctgttg tgtgactctg gtaactagag atccctcaga cccttttagt cagtgtggaa   3060
aatctctagc agtggcgccc gaacagggac ctgaaagcga aagggaaacc agagctctct   3120
cgacgcagga ctcggcttgc tgaagcgcgc acggcaagag gcgaggggcg gcgactggtg   3180
agtacgccaa aaattttgac tagcggaggc tagaaggaga gagatgggtg cgagagcgtc   3240
agtattaagc gggggagaat tagatcgcga tgggaaaaaa ttcggttaag gccaggggga   3300
aagaaaaaat ataaattaaa acatatagta tgggcaagca gggagctaga acgattcgca   3360
```

-continued gttaatcctg gcctgttaga aacatcagaa ggctgtagac aaatactggg acagctacaa 3420
ccatcccttc agacaggatc agaagaactt agatcattat ataatacagt agcaaccctc 3480
tattgtgtgc atcaaaggat agagataaaa gacaccaagg aagctttaga caagatagag 3540
gaagagcaaa acaaaagtaa gaccaccgca cagcaagcgg ccgctgatct tcagacctgg 3600
aggaggagat atgagggaca attggagaag tgaattatat aaatataaag tagtaaaaat 3660
tgaaccatta ggagtagcac ccaccaaggc aaagagaaga gtggtgcaga gagaaaaaag 3720
agcagtggga ataggagctt tgttccttgg gttcttggga gcagcaggaa gcactatggg 3780
cgcagcctca atgacgctga cggtacaggc cagacaatta ttgtctggta tagtgcagca 3840
gcagaacaat ttgctgaggg ctattgaggc gcaacagcat ctgttgcaac tcacagtctg 3900
gggcatcaag cagctccagg caagaatcct ggctgtggaa agatacctaa aggatcaaca 3960
gctcctgggg atttggggtt gctctggaaa actcatttgc accactgctg tgccttggaa 4020
tgctagttgg agtaataaat ctctggaaca gattggaatc acacgacctg gatggagtgg 4080
gacagagaaa ttaacaatta cacaagctta atacactcct taattgaaga atcgcaaaac 4140
cagcaagaaa agaatgaaca agaattattg gaattagata aatgggcaag tttgtggaat 4200
tggtttaaca taacaaattg gctgtggtat ataaaattat tcataatgat agtaggaggc 4260
ttggtaggtt taagaatagt ttttgctgta ctttctatag tgaatagagt taggcaggga 4320
tattcaccat tatcgtttca gacccacctc ccaaccccga ggggacccga caggcccgaa 4380
ggaatagaag aagaaggtgg agagagagac agagacagat ccattcgatt agtgaacgga 4440
tctcgacggt atcggttaac ttttaaaaga aaagggggga ttggggggta cagtgcaggg 4500
gaaagaatag tagacataat agcaacagac atacaaacta aagaattaca aaaacaaatt 4560
acaaaaattc aaaattttat cgatggctcc ggtgcccgtc agtgggcaga gcgcacatcg 4620
cccacagtcc ccgagaagtt ggggggaggg gtcggcaatt gaaccggtgc ctagagaagg 4680
tggcgcgggg taaactggga aagtgatgtc gtgtactggc tccgcctttt tcccgagggt 4740
gggggagaac cgtatataag tgcagtagtc gccgtgaacg ttcttttctg caacgggttt 4800
gccgccagaa cacaggtaag tgccgtgtgt ggttcccgcg ggcctggcct ctttacgggt 4860
tatggccctt gcgtgccttg aattacttcc acctggctgc agtacgtgat tcttgatccc 4920
gagcttcggg ttggaagtgg gtgggagagt tcgaggcctt gcgcttaagg agccccttcg 4980
cctcgtgctt gagttgaggc ctggcctggg cgctggggcc gccgcgtgcg aatctggtgg 5040
caccttcgcg cctgtctcgc tgctttcgat aagtctctag ccatttaaaa tttttgatga 5100
cctgctgcga cgcttttttt ctggcaagat agtcttgtaa atgcgggcca agatctgcac 5160
actggtattt cggtttttgg ggccgcgggc ggcgacgggg cccgtgcgtc ccagcgcaca 5220
tgttcggcga ggcggggcct gcgagcgcgg ccaccgagaa tcggacgggg gtagtctcaa 5280
gctggccggc ctgctctggt gcctggcctc gcgccgccgt gtatcgcccc gccctgggcg 5340
gcaaggctgg cccggtcggc accagttgcg tgagcggaaa gatggccgct tcccggccct 5400
gctgcaggga gctcaaaatg gaggacgcgg cgctcgggag agcgggcggg tgagtcaccc 5460
acacaaagga aaagggcctt tccgtcctca gccgtcgctt catgtgactc cacggagtac 5520
cgggcgccgt ccaggcacct cgattagttc tcgagctttt ggagtacgtc gtctttaggt 5580
tggggggagg ggttttatgc gatggagttt ccccacactg agtgggtgga gactgaagtt 5640
aggccagctt ggcacttgat gtaattctcc ttggaatttg ccctttttga gtttggatct 5700

-continued

```
tggttcattc tcaagcctca gacagtggtt caaagttttt ttcttccatt tcaggtgtcg   5760
tgaggcgcgc ccgccaccat gccacctcct cgcctcctct tcttcctcct cttcctcacc   5820
cccatggaag tcaggcccga ggaacctcta gtggtgaagg tggaagaggg agataacgct   5880
gtgctgcagt gcctcaaggg gacctcagat ggccccactc agcagctgac ctggtctcgg   5940
gagtccccgc ttaaaccctt cttaaaactc agcctggggc tgccaggcct gggaatccac   6000
atgaggcccc tggcatcctg gcttttcatc ttcaacgtct ctcaacagat gggggggcttc   6060
tacctgtgcc agccggggcc cccctctgag aaggcctggc agcctggctg gacagtcaat   6120
gtggagggca gcggggagct gttccggtgg aatgtttcgg acctaggtgg cctgggctgt   6180
ggcctgaaga acaggtcctc agagggcccc agctcccctt ccgggaagct catgagcccc   6240
aagctgtatg tgtgggccaa agaccgccct gagatctggg agggagagcc tccgtgtgtc   6300
ccaccgaggg acagcctgaa ccagagcctc agccaggacc tcaccatggc ccctggctcc   6360
acactctggc tgtcctgtgg ggtacccccct gactctgtgt ccaggggccc cctctcctgg   6420
acccatgtgc accccaaggg gcctaagtca ttgctgagcc tagagctgaa ggacgatcgc   6480
ccggccagag atatgtgggt aatggagacg ggtctgttgt tgccccgggc cacagctcaa   6540
gacgctggaa agtattattg tcaccgtggc aacctgacca tgtcattcca cctggagatc   6600
actgctcggc cagtactatg gcactggctg ctgaggactg gtggctggaa ggtctcagct   6660
gtgactttgg cttatctgat cttctgcctg tgttcccttg tgggcattct tcatcttgcc   6720
ggcggggctg cagggatggc ggcccggcgc ggggctctca tagtgctgga gggcgtggac   6780
cgcgccggga agagcacgca gagccgcaag ctggtggaag cgctgtgcgc cgcgggccac   6840
cgcgccgaac tgctccggtt cccggaaaga tcaactgaaa tcggcaaact tctgagttcc   6900
tacttgcaaa agaaaagtga cgtggaggat cactcggtgc acctgctttt ttctgcaaat   6960
cgctgggaac aagtgccgtt aattaaggaa aagttgagcc agggcgtgac cctcgtcgtg   7020
gacagatacg cattttctgg tgtggcctac acaggtgcca aggagaattt ttccctagac   7080
tggtgtaaac agccagacgt gggccttccc aaacccgacc tggtcctgtt cctccagtta   7140
cagctggcgg atgctgccaa gcggggagcg tttggccatg agcgctatga gaacggggct   7200
ttccaggagc gggcgctccg gtgtttccac cagctcatga aagacacgac tttgaactgg   7260
aagatggtgg atgcttccaa aagcatcgaa gctgtccatg aggacatccg cgtgctctct   7320
gaggacgcca tcgccactgc cacagagaag ccgctggggg agctatggaa gtgaggatcc   7380
tctagagtcg agtctagagt cgacaatcaa cctctggatt acaaaatttg tgaaagattg   7440
actggtattc ttaactatgt tgctcctttt acgctatgtg gatacgctgc tttaatgcct   7500
ttgtatcatg ctattgcttc ccgtatggct ttcattttct cctccttgta taaatcctgg   7560
ttgctgtctc tttatgagga gttgtggccc gttgtcaggc aacgtggcgt ggtgtgcact   7620
gtgtttgctg acgcaacccc cactggttgg ggcattgcca ccacctgtca gctcctttcc   7680
gggactttcg ctttcccccct ccctattgcc acggcggaac tcatcgccgc ctgccttgcc   7740
cgctgctgga caggggctcg gctgttgggc actgacaatt ccgtggtgtt gtcggggaag   7800
ctgacgtcct ttccatggct gctcgcctgt gttgccacct ggattctgcg cgggacgtcc   7860
ttctgctacg tcccttcggc cctcaatcca gcggaccttc cttcccgcgg cctgctgccg   7920
gctctgcggc ctcttccgcg tcttcgcctt cgccctcaga cgagtcggat ctccctttgg   7980
gccgcctccc cgcctggaat tcgagctcgg tacctttaag accaatgact tacaaggcag   8040
ctgtagatct tagccacttt ttaaaagaaa aggggggact ggaagggcta attcactccc   8100
```

aacgaagaca agatctgctt tttgcttgta ctgggtctct ctggttagac cagatctgag 8160
cctgggagct ctctggctaa ctagggaacc cactgcttaa gcctcaataa agcttgcctt 8220
gagtgcttca agtagtgtgt gcccgtctgt tgtgtgactc tggtaactag agatccctca 8280
gaccctttta gtcagtgtgg aaaatctcta gcagtagtag ttcatgtcat cttattattc 8340
agtatttata acttgcaaag aaatgaatat cagagagtga gaggaacttg tttattgcag 8400
cttataatgg ttacaaataa agcaatagca tcacaaattt cacaaataaa gcattttttt 8460
cactgcattc tagttgtggt ttgtccaaac tcatcaatgt atcttatcat gtctggctct 8520
agctatcccg cccctaactc cgcccagttc cgcccattct ccgccccatg gctgactaat 8580
ttttttattt tatgcagagg ccgaggccgc ctcggcctct gagctattcc agaagtagtg 8640
aggaggcttt tttggaggcc taggcttttg cgtcgagacg tacccaattc gccctatagt 8700
gagtcgtatt acgcgcgctc actggccgtc gttttacaac gtcgtgactg ggaaaaccct 8760
ggcgttaccc aacttaatcg ccttgcagca catccccctt tcgccagctg gcgtaatagc 8820
gaagaggccc gcaccgatcg cccttcccaa cagttgcgca gcctgaatgg cgaatggcgc 8880
gacgcgccct gtagcggcgc attaagcgcg gcgggtgtgg tggttacgcg cagcgtgacc 8940
gctacacttg ccagcgccct agcgcccgct cctttcgctt tcttcccttc ctttctcgcc 9000
acgttcgccg gctttccccg tcaagctcta aatcgggggc tccctttagg gttccgattt 9060
agtgctttac ggcacctcga ccccaaaaaa cttgattagg gtgatggttc acgtagtggg 9120
ccatcgccct gatagacggt ttttcgccct ttgacgttgg agtccacgtt ctttaatagt 9180
ggactcttgt tccaaactgg aacaacactc aaccctatct cggtctattc ttttgattta 9240
taagggattt tgccgatttc ggcctattgg ttaaaaaatg agctgattta acaaaaattt 9300
aacgcgaatt ttaacaaaat attaacgttt acaatttcc 9339

<210> SEQ ID NO 43
<211> LENGTH: 12718
<212> TYPE: DNA
<213> ORGANISM: Artificial Sequence
<220> FEATURE:
<223> OTHER INFORMATION: pHR'.cPPT.EF.CD19deltaTmpkF105YR200A.WPRE.SIN

<400> SEQUENCE: 43
aattacctgt ggtttcattt actctaaacc tgtgattcct ctgaattatt ttcattttaa 60
agaaattgta tttgttaaat atgtactaca aacttagtag ttggaagggc taattcactc 120
ccaaagaaga caagatatcc ttgatctgtg gatctaccac acacaaggct acttccctga 180
ttagcagaac tacacaccag ggccaggggt cagatatcca ctgacctttg gatggtgcta 240
caagctagta ccagttgagc cagataaggt agaagaggcc aataaaggag agaacaccag 300
cttgttacac cctgtgagcc tgcatgggat ggatgacccg gagagagaag tgttagagtg 360
gaggtttgac agccgcctag catttcatca cgtggcccga gagctgcatc cggagtactt 420
caagaactgc tgatatcgag cttgctacaa gggactttcc gctggggact ttccagggag 480
gcgtggcctg ggcgggactg gggagtggcg agccctcaga tcctgcatat aagcagctgc 540
tttttgcctg tactgggtct ctctggttag accagatctg agcctgggag ctctctggct 600
aactagggaa cccactgctt aagcctcaat aaagcttgcc ttgagtgctt caagtagtgt 660
gtgcccgtct gttgtgtgac tctggtaact agagatccct cagacccttt tagtcagtgt 720
ggaaaatctc tagcagtggc gcccgaacag ggacttgaaa gcgaaaggga aaccagagga 780

-continued

```
gctctctcga cgcaggactc ggcttgctga agcgcgcacg gcaagaggcg aggggcggcg     840

actggtgagt acgccaaaaa ttttgactag cggaggctag aaggagagag atgggtgcga     900

gagcgtcagt attaagcggg ggagaattag atcgcgatgg gaaaaaattc ggttaaggcc     960

agggggaaag aaaaaatata aattaaaaca tatagtatgg gcaagcaggg agctagaacg    1020

attcgcagtt aatcctggcc tgttagaaac atcagaaggc tgtagacaaa tactgggaca    1080

gctacaacca tcccttcaga caggatcaga agaacttaga tcattatata atacagtagc    1140

aaccctctat tgtgtgcatc aaaggataga gataaaagac accaaggaag ctttagacaa    1200

gatagaggaa gagcaaaaca aaagtaagac caccgcacag caagcggccg ctgatcttca    1260

gacctggagg aggagatatg agggacaatt ggagaagtga attatataaa tataaagtag    1320

taaaaattga accattagga gtagcaccca ccaaggcaaa gagaagagtg gtgcagagag    1380

aaaaaagagc agtgggaata ggagctttgt tccttgggtt cttgggagca gcaggaagca    1440

ctatgggcgc agcgtcaatg acgctgacgg tacaggccag acaattattg tctggtatag    1500

tgcagcagca gaacaatttg ctgagggcta ttgaggcgca acagcatctg ttgcaactca    1560

cagtctgggg catcaagcag ctccaggcaa gaatcctggc tgtggaaaga tacctaaagg    1620

atcaacagct cctggggatt tggggttgct ctggaaaact catttgcacc actgctgtgc    1680

cttggaatgc tagttggagt aataaatctc tggaacagat ttggaatcac acgacctgga    1740

tggagtggga cagagaaatt aacaattaca caagcttaat acactcctta attgaagaat    1800

cgcaaaacca gcaagaaaag aatgaacaag aattattgga attagataaa tgggcaagtt    1860

tgtggaattg gtttaacata acaaattggc tgtggtatat aaaattattc ataatgatag    1920

taggaggctt ggtaggttta agaatagttt ttgctgtact ttctatagtg aatagagtta    1980

ggcagggata ttcaccatta tcgtttcaga cccacctccc aaccccgagg ggacccgaca    2040

ggcccgaagg aatagaagaa gaaggtggag agagagacag agacagatcc attcgattag    2100

tgaacggatc tcgacggtat cgattttaaa agaaaagggg ggattggggg gtacagtgca    2160

ggggaaagaa tagtagacat aatagcaaca gacatacaaa ctaaagaatt acaaaaacaa    2220

attacaaaaa ttcaaaattt tatcgataag ctttgcaaag atggataaag ttttaaacag    2280

agaggaatct ttgcagctaa tggaccttct aggtcttgaa aggagtggga attggctccg    2340

gtgcccgtca gtgggcagag cgcacatcgc ccacagtccc cgagaagttg gggggagggg    2400

tcggcaattg aaccggtgcc tagagaaggt ggcgcggggt aaactgggaa agtgatgtcg    2460

tgtactggct ccgccttttt cccgagggtg ggggagaacc gtatataagt gcagtagtcg    2520

ccgtgaacgt tctttttcgc aacgggtttg ccgccagaac acaggtaagt gccgtgtgtg    2580

gttcccgcgg gcctggcctc tttacgggtt atggcccttg cgtgccttga attacttcca    2640

cctggctgca gtacgtgatt cttgatcccg agcttcgggt tggaagtggg tgggagagtt    2700

cgaggccttg cgcttaagga gccccttcgc ctcgtgcttg agttgaggcc tggcctgggc    2760

gctggggccg ccgcgtgcga atctggtggc accttcgcgc ctgtctcgct gctttcgata    2820

agtctctagc catttaaaat ttttgatgac ctgctgcgac gcttttttc tggcaagata     2880

gtcttgtaaa tgcgggccaa gatctgcaca ctggtatttc ggtttttggg gccgcgggcg    2940

gcgacggggc ccgtgcgtcc cagcgcacat gttcggcgag gcggggcctg cgagcgcggc    3000

caccgagaat cggacggggg tagtctcaag ctggccggcc tgctctggtg cctggcctcg    3060

cgccgccgtg tatcgccccg ccctgggcgg caaggctggc ccggtcggca ccagttgcgt    3120

gagcggaaag atggccgctt cccggccctg ctgcagggag ctcaaaatgg aggacgcggc    3180
```

-continued

```
gctcgggaga gcgggcgggt gagtcaccca cacaaaggaa aagggccttt ccgtcctcag   3240
ccgtcgcttc atgtgactcc acggagtacc gggcgccgtc caggcacctc gattagttct   3300
cgagcttttg gagtacgtcg tctttaggtt ggggggaggg gttttatgcg atggagtttc   3360
cccacactga gtgggtggag actgaagtta ggccagcttg gcacttgatg taattctcct   3420
tggaatttgc cctttttgag tttggatctt ggttcattct caagcctcag acagtggttc   3480
aaagtttttt tcttccattt caggtgtcgt gaggaattca tgccacctcc tcgcctcctc   3540
ttcttcctcc tcttcctcac ccccatggaa gtcaggcccg aggaacctct agtggtgaag   3600
gtggaagagg gagataacgc tgtgctgcag tgcctcaagg ggacctcaga tggccccact   3660
cagcagctga cctggtctcg ggagtccccg cttaaaccct tcttaaaact cagcctgggg   3720
ctgccaggcc tgggaatcca catgaggccc ctggcatcct ggcttttcat cttcaacgtc   3780
tctcaacaga tgggggggctt ctacctgtgc cagccggggc ccccctctga gaaggcctgg   3840
cagcctggct ggacagtcaa tgtggagggc agcggggagc tgttccggtg gaatgtttcg   3900
gacctaggtg gcctgggctg tggcctgaag aacaggtcct cagagggccc cagctcccct   3960
tccgggaagc tcatgagccc caagctgtat gtgtgggcca aagaccgccc tgagatctgg   4020
gagggagagc ctccgtgtgt cccaccgagg gacagcctga accagagcct cagccaggac   4080
ctcaccatgg cccctggctc cacactctgg ctgtcctgtg ggtacccccc tgactctgtg   4140
tccaggggcc ccctctcctg gacccatgtg caccccaagg ggcctaagtc attgctgagc   4200
ctagagctga aggacgatcg cccggccaga gatatgtggg taatggagac gggtctgttg   4260
ttgccccggg ccacagctca agacgctgga aagtattatt gtcaccgtgg caacctgacc   4320
atgtcattcc acctggagat cactgctcgg ccagtactat ggcactggct gctgaggact   4380
ggtggctgga aggtctcagc tgtgactttg gcttatctga tcttctgcct gtgttccctt   4440
gtgggcattc ttcatcttgc cggcggggct gcagggatgg cggcccggcg cggggctctc   4500
atagtgctgg agggcgtgga ccgcgccggg aagagcacgc agagccgcaa gctggtggaa   4560
gcgctgtgcg ccgcgggcca ccgcgccgaa ctgctccggt tcccggaaag atcaactgaa   4620
atcggcaaac ttctgagttc ctacttgcaa aagaaaagtg acgtggagga tcactcggtg   4680
cacctgcttt tttctgcaaa tcgctgggaa caagtgccgt taattaagga aaagttgagc   4740
cagggcgtga ccctcgtcgt ggacagatac gcattttctg gtgtggccta cacaggtgcc   4800
aaggagaatt tttccctaga ctggtgtaaa cagccagacg tgggccttcc caaacccgac   4860
ctggtcctgt tcctccagtt acagctggcg gatgctgcca agcggggagc gtttggccat   4920
gagcgctatg agaacggggc tttccaggag cgggcgctcc ggtgtttcca ccagctcatg   4980
aaagacacga ctttgaactg gaagatggtg gatgcttcca aaagcatcga agctgtccat   5040
gaggacatcc gcgtgctctc tgaggacgcc atcgccactg ccacagagaa gccgctgggg   5100
gagctatgga agtgaggatc caagcttcaa ttgtggtcac tcgacaatca acctctggat   5160
tacaaaattt gtgaaagatt gactggtatt cttaactatg ttgctccttt tacgctatgt   5220
ggatacgctg ctttaatgcc tttgtatcat gctattgctt cccgtatggc tttcattttc   5280
tcctccttgt ataaatcctg gttgctgtct ctttatgagg agttgtggcc cgttgtcagg   5340
caacgtggcg tggtgtgcac tgtgtttgct gacgcaaccc ccactggttg gggcattgcc   5400
accacctgtc agctcctttc cgggactttc gctttccccc tccctattgc cacggcggaa   5460
ctcatcgccg cctgccttgc ccgctgctgg acaggggctc ggctgttggg cactgacaat   5520
```

-continued

```
tccgtggtgt tgtcggggaa gctgacgtcc tttccatggc tgctcgcctg tgttgccacc   5580
tggattctgc gcgggacgtc cttctgctac gtcccttcgg ccctcaatcc agcggacctt   5640
ccttcccgcg gcctgctgcc ggctctgcgg cctcttccgc gtcttcgcct tcgccctcag   5700
acgagtcgga tctccctttg ggccgcctcc ccgcctgctc gagacctaga aaaacatgga   5760
gcaatcacaa gtagcaatac agcagctacc aatgctgatt gtgcctggct agaagcacaa   5820
gaggaggagg aggtgggttt tccagtcaca cctcaggtac ctttaagacc aatgacttac   5880
aaggcagctg tagatcttag ccactttta aaagaaaagg ggggactgga agggctaatt   5940
cactcccaac gaagacaaga tctgcttttt gcttgtactg ggtctctctg gttagaccag   6000
atctgagcct gggagctctc tggctaacta gggaacccac tgcttaagcc tcaataaagc   6060
ttgccttgag tgcttcaagt agtgtgtgcc cgtctgttgt gtgactctgg taactagaga   6120
tccctcagac ccttttagtc agtgtggaaa atctctagca gtagtagttc atgtcatctt   6180
attattcagt atttataact tgcaaagaaa tgaatatcag agagtgagag gccttgacat   6240
tataatagat ttagcaggaa ttgaactagg agtggagcac acaggcaaag ctgcagaagt   6300
acttggaaga agccaccaga gatactcacg attctgcaca tacctggcta atcccagatc   6360
ctaaggatta cattaagttt actaacattt atataatgat ttatagttta aagtataaac   6420
ttatctaatt tactattctg acagatatta attaatcctc aaatatcata agagatgatt   6480
actattatcc ccatttaaca caagaggaaa ctgagaggga aagatgttga agtaattttc   6540
ccacaattac agcatccgtt agttacgact ctatgatctt ctgacacaaa ttccatttac   6600
tcctcaccct atgactcagt cgaatatatc aaagttatgg acattatgct aagtaacaaa   6660
ttaccctttt atatagtaaa tactgagtag attgagagaa gaaattgttt gcaaacctga   6720
atagcttcaa gaagaagaga agtgaggata agaataacag ttgtcattta acaagtttta   6780
acaagtaact tggttagaaa gggattcaaa tgcataaagc aagggataaa tttttctggc   6840
aacaagacta tacaatataa ccttaaatat gacttcaaat aattgttgga acttgataaa   6900
actaattaaa tattattgaa gattatcaat attataaatg taatttactt ttaaaaaggg   6960
aacatagaaa tgtgtatcat tagagtagaa aacaatcctt attatcacaa tttgtcaaaa   7020
caagtttgtt attaacacaa gtagaatact gcattcaatt aagttgactg cagattttgt   7080
gttttgttaa aattagaaag agataacaac aatttgaatt attgaaagta acatgtaaat   7140
agttctacat acgttctttt gacatcttgt tcaatcattg atcgaagttc tttatcttgg   7200
aagaatttgt tccaaagact ctgaaataag gaaaacaatc tattatatag tctcacacct   7260
ttgttttact tttagtgatt tcaatttaat aatgtaaatg gttaaaattt attcttctct   7320
gagatcattt cacattgcag atagaaaacc tgagactggg gtaattttta ttaaaatcta   7380
atttaatctc agaaacacat ctttattcta acatcaattt ttccagtttg atattatcat   7440
ataaagtcag ccttcctcat ctgcaggttc cacaacaaaa atccaaccaa ctgtggatca   7500
aaaatattgg gaaaaaatta aaaatagcaa tacaacaata aaaaaataca aatcagaaaa   7560
acagcacagt ataacaactt tatttagcat ttacaatcta ttaggtatta taagtaatct   7620
agaattaatt ccgtgtattc tatagtgtca cctaaatcgt atgtgtatga tacataaggt   7680
tatgtattaa ttgtagccgc gttctaacga caatatgtac aagcctaatt gtgtagcatc   7740
tggcttactg aagcagaccc tatcatctct ctcgtaaact gccgtcagag tcggtttggt   7800
tggacgaacc ttctgagttt ctggtaacgc cgtcccgcac ccggaaatgg tcagcgaacc   7860
aatcagcagg gtcatcgcta gccagatcct ctacgccgga cgcatcgtgg ccggcatcac   7920
```

-continued

```
cggcgccaca ggtgcggttg ctggcgccta tatcgccgac atcaccgatg gggaagatcg   7980
ggctcgccac ttcgggctca tgagcgcttg tttcggcgtg ggtatggtgg caggccccgt   8040
ggccggggga ctgttgggcg ccatctcctt gcatgcacca ttccttgcgg cggcggtgct   8100
caacggcctc aacctactac tgggctgctt cctaatgcag gagtcgcata agggagagcg   8160
tcgaatggtg cactctcagt acaatctgct ctgatgccgc atagttaagc cagccccgac   8220
acccgccaac acccgctgac gcgccctgac gggcttgtct gctcccggca tccgcttaca   8280
gacaagctgt gaccgtctcc gggagctgca tgtgtcagag gttttcaccg tcatcaccga   8340
aacgcgcgag acgaaagggc ctcgtgatac gcctattttt ataggttaat gtcatgataa   8400
taatggtttc ttagacgtca ggtggcactt ttcggggaaa tgtgcgcgga acccctattt   8460
gtttattttt ctaaatacat tcaaatatgt atccgctcat gagacaataa ccctgataaa   8520
tgcttcaata atattgaaaa aggaagagta tgagtattca acatttccgt gtcgccctta   8580
ttcccttttt tgcggcattt tgccttcctg tttttgctca cccagaaacg ctggtgaaag   8640
taaaagatgc tgaagatcag ttgggtgcac gagtgggtta catcgaactg gatctcaaca   8700
gcggtaagat ccttgagagt tttcgccccg aagaacgttt tccaatgatg agcactttta   8760
aagttctgct atgtggcgcg gtattatccc gtattgacgc cgggcaagag caactcggtc   8820
gccgcataca ctattctcag aatgacttgg ttgagtactc accagtcaca gaaaagcatc   8880
ttacggatgg catgacagta agagaattat gcagtgctgc cataaccatg agtgataaca   8940
ctgcggccaa cttacttctg acaacgatcg gaggaccgaa ggagctaacc gcttttttgc   9000
acaacatggg ggatcatgta actcgccttg atcgttggga accggagctg aatgaagcca   9060
taccaaacga cgagcgtgac accacgatgc ctgtagcaat ggcaacaacg ttgcgcaaac   9120
tattaactgg cgaactactt actctagctt cccggcaaca attaatagac tggatggagg   9180
cggataaagt tgcaggacca cttctgcgct cggcccttcc ggctggctgg tttattgctg   9240
ataaatctgg agccggtgag cgtgggtctc gcggtatcat tgcagcactg gggccagatg   9300
gtaagccctc ccgtatcgta gttatctaca cgacggggag tcaggcaact atggatgaac   9360
gaaatagaca gatcgctgag ataggtgcct cactgattaa gcattggtaa ctgtcagacc   9420
aagtttactc atatatactt tagattgatt taaaacttca tttttaattt aaaaggatct   9480
aggtgaagat cctttttgat aatctcatga ccaaaatccc ttaacgtgag ttttcgttcc   9540
actgagcgtc agaccccgta gaaaagatca aaggatcttc ttgagatcct ttttttctgc   9600
gcgtaatctg ctgcttgcaa acaaaaaaac caccgctacc agcggtggtt tgtttgccgg   9660
atcaagagct accaactctt tttccgaagg taactggctt cagcagagcg cagataccaa   9720
atactgttct tctagtgtag ccgtagttag gccaccactt caagaactct gtagcaccgc   9780
ctacatacct cgctctgcta atcctgttac cagtggctgc tgccagtggc gataagtcgt   9840
gtcttaccgg gttggactca agacgatagt taccggataa ggcgcagcgg tcgggctgaa   9900
cggggggttc gtgcacacag cccagcttgg agcgaacgac ctacaccgaa ctgagatacc   9960
tacagcgtga gctatgagaa agcgccacgc ttcccgaagg gagaaaggcg gacaggtatc  10020
cggtaagcgg cagggtcgga acaggagagc gcacgaggga gcttccaggg ggaaacgcct  10080
ggtatcttta tagtcctgtc gggtttcgcc acctctgact tgagcgtcga tttttgtgat  10140
gctcgtcagg ggggcggagc ctatggaaaa acgccagcaa cgcggccttt ttacggttcc  10200
tggccttttg ctggcctttt gctcacatgt tctttcctgc gttatcccct gattctgtgg  10260
```

-continued

```
ataaccgtat taccgccttt gagtgagctg ataccgctcg ccgcagccga acgaccgagc  10320
gcagcgagtc agtgagcgag gaagcggaag agcgcccaat acgcaaaccg cctctccccg  10380
cgcgttggcc gattcattaa tgcagctgtg gaatgtgtgt cagttagggt gtggaaagtc  10440
cccaggctcc ccagcaggca gaagtatgca aagcatgcat ctcaattagt cagcaaccag  10500
gtgtggaaag tccccaggct ccccagcagg cagaagtatg caaagcatgc atctcaatta  10560
gtcagcaacc atagtcccgc ccctaactcc gcccatcccg cccctaactc cgcccagttc  10620
cgcccattct ccgccccatg gctgactaat tttttttatt tatgcagagg ccgaggccgc  10680
ctcggcctct gagctattcc agaagtagtg aggaggcttt tttggaggcc taggcttttg  10740
caaaaagctt ggacacaaga caggcttgcg agatatgttt gagaatacca ctttatcccg  10800
cgtcagggag aggcagtgcg taaaaagacg cggactcatg tgaaatactg gtttttagtg  10860
cgccagatct ctataatctc gcgcaaccta ttttcccctc gaacactttt taagccgtag  10920
ataaacaggc tgggacactt cacatgagcg aaaaatacat cgtcacctgg gacatgttgc  10980
agatccatgc acgtaaactc gcaagccgac tgatgccttc tgaacaatgg aaaggcatta  11040
ttgccgtaag ccgtggcggt ctgtaccggg tgcgttactg gcgcgtgaac tgggtattcg  11100
tcatgtcgat accgtttgta tttccagcta cgatcacgac aaccagcgcg agcttaaagt  11160
gctgaaacgc gcagaaggcg atggcgaagg cttcatcgtt attgatgacc tggtggatac  11220
cggtggtact gcggttgcga ttcgtgaaat gtatccaaaa gcgcactttg tcaccatctt  11280
cgcaaaaccg gctggtcgtc cgctggttga tgactatgtt gttgatatcc cgcaagatac  11340
ctggattgaa cagccgtggg atatgggcgt cgtattcgtc ccgccaatct ccggtcgcta  11400
atcttttcaa cgcctggcac tgccgggcgt tgttcttttt aacttcaggc gggttacaat  11460
agtttccagt aagtattctg gaggctgcat ccatgacaca ggcaaacctg agcgaaaccc  11520
tgttcaaacc ccgctttaaa catcctgaaa cctcgacgct agtccgccgc tttaatcacg  11580
gcgcacaacc gcctgtgcag tcggcccttg atggtaaaac catccctcac tggtatcgca  11640
tgattaaccg tctgatgtgg atctggcgcg gcattgaccc acgcgaaatc ctcgacgtcc  11700
aggcacgtat tgtgatgagc gatgccgaac gtaccgacga tgatttatac gatacggtga  11760
ttggctaccg tggcggcaac tggatttatg agtgggcccc ggatctttgt gaaggaacct  11820
tacttctgtg gtgtgacata attggacaaa ctacctacag agatttaaag ctctaaggta  11880
aatataaaat ttttaagtgt ataatgtgtt aaactactga ttctaattgt ttgtgtattt  11940
tagattccaa cctatggaac tgatgaatgg gagcagtggt ggaatgcctt taatgaggaa  12000
aacctgtttt gctcagaaga aatgccatct agtgatgatg aggctactgc tgactctcaa  12060
cattctactc ctccaaaaaa gaagagaaag gtagaagacc ccaaggactt tccttcagaa  12120
ttgctaagtt ttttgagtca tgctgtgttt agtaatagaa ctcttgcttg ctttgctatt  12180
tacaccacaa aggaaaaagc tgcactgcta tacaagaaaa ttatggaaaa atattctgta  12240
acctttataa gtaggcataa cagttataat cataacatac tgttttttct tactccacac  12300
aggcatagag tgtctgctat taataactat gctcaaaaat tgtgtacctt tagcttttta  12360
atttgtaaag gggttaataa ggaatatttg atgtatagtg ccttgactag agatcataat  12420
cagccatacc acatttgtag aggttttact tgctttaaaa aacctcccac acctcccccct  12480
gaacctgaaa cataaaatga atgcaattgt tgttgttaac ttgtttattg cagcttataa  12540
tggttacaaa taaagcaata gcatcacaaa tttcacaaat aaagcatttt tttcactgca  12600
ttctagttgt ggtttgtcca aactcatcaa tgtatcttat catgtctgga tcaactggat  12660
```

aactcaagct aaccaaaatc atcccaaact tcccacccca taccctatta ccactgcc 12718

<210> SEQ ID NO 44
<211> LENGTH: 9094
<212> TYPE: DNA
<213> ORGANISM: Artificial Sequence
<220> FEATURE:
<223> OTHER INFORMATION: pDYCD19delta tmpk

<400> SEQUENCE: 44
gggcgaattg ggcccgacgt cgcatgcttg gaagggctaa ttcactccca aagaagacaa 60
gatatccttg atctgtggat ctaccacaca caaggctact tccctgatta gcagaactac 120
acaccagggc caggggtcag atatccactg acctttggat ggtgctacaa gctagtacca 180
gttgagccag ataaggtaga agaggccaat aaaggagaga acaccagctt gttacaccct 240
gtgagcctgc atgggatgga tgacccggag agagaagtgt tagagtggag gtttgacagc 300
cgcctagcat ttcatcacgt ggcccgagag ctgcatccgg agtacttcaa gaactgctga 360
tatcgagctt gctacaaggg actttccgct ggggactttc cagggaggcg tggcctgggc 420
gggactgggg agtggcgagc cctcagatcc tgcatataag cagctgcttt ttgcctgtac 480
tgggtctctc tggttagacc agatctgagc ctgggagctc tctggctaac tagggaaccc 540
actgcttaag cctcaataaa gcttgccttg agtgcttcaa gtagtgtgtg cccgtctgtt 600
gtgtgactct ggtaactaga gatccctcag accctttag tcagtgtgga aaatctctag 660
cagtggcgcc cgaacaggga cttgaaagcg aaagggaaac cagaggagct ctctcgacgc 720
aggactcggc ttgctgaagc gcgcacggca agaggcgagg ggcggcgact ggtgagtacg 780
ccaaaaattt tgactagcgg aggctagaag gagagagatg ggtgcgagag cgtcagtatt 840
aagcggggga gaattagatc gcgatgggaa aaaattcggt taaggccagg gggaaagaaa 900
aaatataaat taaaacatat agtatgggca agcagggagc tagaacgatt cgcagttaat 960
cctggcctgt tagaaacatc agaaggctgt agacaaatac tgggacagct acaaccatcc 1020
cttcagacag gatcagaaga acttagatca ttatataata cagtagcaac cctctattgt 1080
gtgcatcaaa ggatagagat aaaagacacc aaggaagctt tagacaagat agaggaagag 1140
caaaacaaaa gtaagaccac cgcacagcaa gcggccgctg atcttcagac ctggaggagg 1200
agatatgagg gacaattgga gaagtgaatt atataaatat aaagtagtaa aaattgaacc 1260
attaggagta gcacccacca aggcaaagag aagagtggtg cagagagaaa aaagagcagt 1320
gggaatagga gctttgttcc ttgggttctt gggagcagca ggaagcacta tgggcgcagc 1380
gtcaatgacg ctgacggtac aggccagaca attattgtct ggtatagtgc agcagcagaa 1440
caatttgctg agggctattg aggcgcaaca gcatctgttg caactcacag tctggggcat 1500
caagcagctc caggcaagaa tcctggctgt ggaaagatac ctaaaggatc aacagctcct 1560
ggggatttgg ggttgctctg gaaaactcat ttgcaccact gctgtgcctt ggaatgctag 1620
ttggagtaat aaatctctgg aacagatttg gaatcacacg acctggatgg agtgggacag 1680
agaaattaac aattacacaa gcttaataca ctccttaatt gaagaatcgc aaaaccagca 1740
agaaaagaat gaacaagaat tattggaatt agataaatgg gcaagtttgt ggaattggtt 1800
taacataaca aattggctgt ggtatataaa attattcata atgatagtag gaggcttggt 1860
aggtttaaga atagtttttg ctgtactttc tatagtgaat agagttaggc agggatattc 1920
accattatcg tttcagaccc acctcccaac cccgagggga cccgacaggc ccgaaggaat 1980

-continued agaagaagaa ggtggagaga gagacagaga cagatccatt cgattagtga acggatctcg 2040
acgggatcga ttttaaaaga aaaggggga ttgggggta cagtgcaggg gaaagaatag 2100
tagacataat agcaacagac atacaaacta aagaattaca aaaacaaatt acaaaaattc 2160
aaaattttat cgataagctt tgcaaagatg gataaagttt taaacagaga ggaatctttg 2220
cagctaatgg accttctagg tcttgaaagg agtgggaatt ggctccggtg cccgtcagtg 2280
ggcagagcgc acatcgccca cagtccccga gaagttgggg ggaggggtcg gcaattgaac 2340
cggtgcctag agaaggtggc gcggggtaaa ctgggaaagt gatgtcgtgt actggctccg 2400
cctttttccc gagggtgggg gagaaccgta tataagtgca gtagtcgccg tgaacgttct 2460
ttttcgcaac gggtttgccg ccagaacaca ggtaagtgcc gtgtgtggtt cccgcgggcc 2520
tggcctcttt acgggttatg gcccttgcgt gccttgaatt acttccacct ggctgcagta 2580
cgtgattctt gatcccgagc ttcgggttgg aagtgggtgg gagagttcga ggccttgcgc 2640
ttaaggagcc ccttcgcctc gtgcttgagt tgaggcctgg cctgggcgct ggggccgccg 2700
cgtgcgaatc tggtggcacc ttcgcgcctg tctcgctgct ttcgataagt ctctagccat 2760
ttaaaatttt tgatgacctg ctgcgacgct ttttttctgg caagatagtc ttgtaaatgc 2820
gggccaagat ctgcacactg gtatttcggt ttttggggcc gcgggcggcg acggggcccg 2880
tgcgtcccag cgcacatgtt cggcgaggcg gggcctgcga gcgcggccac cgagaatcgg 2940
acgggggtag tctcaagctg gccggcctgc tctggtgcct ggcctcgcgc cgccgtgtat 3000
cgccccgccc tgggcggcaa ggctggcccg gtcggcacca gttgcgtgag cggaaagatg 3060
gccgcttccc ggccctgctg cagggagctc aaaatggagg acgcggcgct cgggagagcg 3120
ggcgggtgag tcacccacac aaaggaaaag ggcctttccg tcctcagccg tcgcttcatg 3180
tgactccacg gagtaccggg cgccgtccag gcacctcgat tagttctcga gcttttggag 3240
tacgtcgtct ttaggttggg gggaggggtt ttatgcgatg gagtttcccc acactgagtg 3300
ggtggagact gaagttaggc cagcttggca cttgatgtaa ttctccttgg aatttgccct 3360
ttttgagttt ggatcttggt tcattctcaa gcctcagaca gtggttcaaa gtttttttct 3420
tccatttcag gtgtcgtgag gaattctgca gtcgacggta ccgcgggcgc gcccgccacc 3480
atgccacctc ctcgcctcct cttcttcctc ctcttcctca cccccatgga agtcaggccc 3540
gaggaacctc tagtggtgaa ggtggaagag ggagataacg ctgtgctgca gtgcctcaag 3600
gggacctcag atggccccac tcagcagctg acctggtctc gggagtcccc gcttaaaccc 3660
ttcttaaaac tcagcctggg gctgccaggc ctgggaatcc acatgaggcc cctggcatcc 3720
tggcttttca tcttcaacgt ctctcaacag atggggggct tctacctgtg ccagccgggg 3780
ccccctctg agaaggcctg gcagcctggc tggacagtca atgtggaggg cagcggggag 3840
ctgttccggt ggaatgtttc ggacctaggt ggcctgggct gtggcctgaa gaacaggtcc 3900
tcagagggcc ccagctcccc ttccgggaag ctcatgagcc ccaagctgta tgtgtgggcc 3960
aaagaccgcc ctgagatctg ggagggagag cctccgtgtg tcccaccgag ggacagcctg 4020
aaccagagcc tcagccagga cctcaccatg gcccctggct ccacactctg gctgtcctgt 4080
ggggtacccc ctgactctgt gtccaggggc cccctctcct ggacccatgt gcaccccaag 4140
gggcctaagt cattgctgag cctagagctg aaggacgatc gcccggccag agatatgtgg 4200
gtaatggaga cgggtctgtt gttgccccgg gccacagctc aagacgctgg aaagtattat 4260
tgtcaccgtg gcaacctgac catgtcattc cacctggaga tcactgctcg gccagtacta 4320
tggcactggc tgctgaggac tggtggctgg aaggtctcag ctgtgacttt ggcttatctg 4380

-continued

```
atcttctgcc tgtgttccct tgtgggcatt cttcatcttg ccggcggggc tgcagggatg   4440
gcggcccggc gcggggctct catagtgctg gagggcgtgg accgcgccgg gaagagcacg   4500
cagagccgca agctggtgga agcgctgtgc gccgcgggcc accgcgccga actgctccgg   4560
ttcccggaaa gatcaactga aatcggcaaa cttctgagtt cctacttgca aaagaaaagt   4620
gacgtggagg atcactcggt gcacctgctt ttttctgcaa atcgctggga acaagtgccg   4680
ttaattaagg aaaagttgag ccagggcgtg accctcgtcg tggacagata cgcattttct   4740
ggtgtggcct acacaggtgc caaggagaat ttttccctag actggtgtaa acagccagac   4800
gtgggccttc ccaaacccga cctggtcctg ttcctccagt tacagctggc ggatgctgcc   4860
aagcggggag cgtttggcca tgagcgctat gagaacgggg ctttccagga gcgggcgctc   4920
cggtgtttcc accagctcat gaaagacacg actttgaact ggaagatggt ggatgcttcc   4980
aaaagcatcg aagctgtcca tgaggacatc cgcgtgctct ctgaggacgc catcgccact   5040
gccacagaga agccgctggg ggagctatgg aagtgaggat ccaagcttca attgtggtca   5100
ctcgacaatc aacctctgga ttacaaaatt tgtgaaagat tgactggtat tcttaactat   5160
gttgctcctt ttacgctatg tggatacgct gctttaatgc ctttgtatca tgctattgct   5220
tcccgtatgg ctttcatttt ctcctccttg tataaatcct ggttgctgtc tctttatgag   5280
gagttgtggc ccgttgtcag gcaacgtggc gtggtgtgca ctgtgtttgc tgacgcaacc   5340
cccactggtt ggggcattgc caccacctgt cagctccttt ccgggacttt cgctttcccc   5400
ctccctattg ccacggcgga actcatcgcc gcctgccttg cccgctgctg gacaggggct   5460
cggctgttgg gcactgacaa ttccgtggtg ttgtcgggga agctgacgtc ctttccatgg   5520
ctgctcgcct gtgttgccac ctggattctg cgcgggacgt ccttctgcta cgtcccttcg   5580
gccctcaatc cagcggacct tccttcccgc ggcctgctgc cggctctgcg gcctcttccg   5640
cgtcttcgcc ttcgccctca gacgagtcgg atctcccttt gggccgcctc cccgcctgct   5700
cgagacctag aaaaacatgg agcaatcaca agtagcaata cagcagctac caatgctgat   5760
tgtgcctggc tagaagcaca agaggaggag gaggtgggtt ttccagtcac acctcaggta   5820
cctttaagac caatgactta caaggcagct gtagatctta gccacttttt aaaagaaaag   5880
gggggactgg aagggctaat tcactcccaa cgaagacaag atctgctttt tgcttgtact   5940
gggtctctct ggttagacca gatctgagcc tgggagctct ctggctaact agggaaccca   6000
ctgcttaagc ctcaataaag cttgccttga gtgcttcaag tagtgtgtgc ccgtctgttg   6060
tgtgactctg gtaactagag atccctcaga cccttttagt cagtgtggaa aatctctagc   6120
agtagtagtt catgtcatct tattattcag tatttataac ttgcaaagaa atgaatatca   6180
gagagtgaga ggacgcgttg gatgcatagc ttgagtattc tatagtgtca cctaaatagc   6240
ttggcgtaat catggtcata gctgtttcct gtgtgaaatt gttatccgct cacaattcca   6300
cacaacatac gagccggaag cataaagtgt aaagcctggg gtgcctaatg agtgagctaa   6360
ctcacattaa ttgcgttgcg ctcactgccc gctttccagt cgggaaacct gtcgtgccag   6420
ctgcattaat gaatcggcca acgcgcgggg agaggcggtt tgcgtattgg gcgctcttcc   6480
gcttcctcgc tcactgactc gctgcgctcg gtcgttcggc tgcggcgagc ggtatcagct   6540
cactcaaagg cggtaatacg gttatccaca gaatcagggg ataacgcagg aaagaacatg   6600
tgagcaaaag gccagcaaaa ggccaggaac cgtaaaaagg ccgcgttgct ggcgtttttc   6660
cataggctcc gcccccctga cgagcatcac aaaaatcgac gctcaagtca gaggtggcga   6720
```

-continued

```
aacccgacag gactataaag ataccaggcg tttccccctg gaagctccct cgtgcgctct   6780
cctgttccga ccctgccgct taccggatac ctgtccgcct ttctcccttc gggaagcgtg   6840
gcgctttctc atagctcacg ctgtaggtat ctcagttcgg tgtaggtcgt tcgctccaag   6900
ctgggctgtg tgcacgaacc ccccgttcag cccgaccgct gcgccttatc cggtaactat   6960
cgtcttgagt ccaacccggt aagacacgac ttatcgccac tggcagcagc cactggtaac   7020
aggattagca gagcgaggta tgtaggcggt gctacagagt tcttgaagtg gtggcctaac   7080
tacggctaca ctagaagaac agtatttggt atctgcgctc tgctgaagcc agttaccttc   7140
ggaaaaagag ttggtagctc ttgatccggc aaacaaacca ccgctggtag cggtggtttt   7200
tttgtttgca agcagcagat tacgcgcaga aaaaaaggat ctcaagaaga tcctttgatc   7260
ttttctacgg ggtctgacgc tcagtggaac gaaaactcac gttaagggat tttggtcatg   7320
agattatcaa aaaggatctt cacctagatc cttttaaatt aaaaatgaag ttttaaatca   7380
atctaaagta tatatgagta aacttggtct gacagttacc aatgcttaat cagtgaggca   7440
cctatctcag cgatctgtct atttcgttca tccatagttg cctgactccc cgtcgtgtag   7500
ataactacga tacgggaggg cttaccatct ggccccagtg ctgcaatgat accgcgagac   7560
ccacgctcac cggctccaga tttatcagca ataaaccagc cagccggaag ggccgagcgc   7620
agaagtggtc ctgcaacttt atccgcctcc atccagtcta ttaattgttg ccgggaagct   7680
agagtaagta gttcgccagt taatagtttg cgcaacgttg ttgccattgc tacaggcatc   7740
gtggtgtcac gctcgtcgtt tggtatggct tcattcagct ccggttccca acgatcaagg   7800
cgagttacat gatcccccat gttgtgcaaa aaagcggtta gctccttcgg tcctccgatc   7860
gttgtcagaa gtaagttggc cgcagtgtta tcactcatgg ttatggcagc actgcataat   7920
tctcttactg tcatgccatc cgtaagatgc ttttctgtga ctggtgagta ctcaaccaag   7980
tcattctgag aatagtgtat gcggcgaccg agttgctctt gcccggcgtc aatacgggat   8040
aataccgcgc cacatagcag aactttaaaa gtgctcatca ttggaaaacg ttcttcgggg   8100
cgaaaactct caaggatctt accgctgttg agatccagtt cgatgtaacc cactcgtgca   8160
cccaactgat cttcagcatc ttttactttc accagcgttt ctgggtgagc aaaaacagga   8220
aggcaaaatg ccgcaaaaaa gggaataagg gcgacacgga aatgttgaat actcatactc   8280
ttcctttttc aatattattg aagcatttat cagggttatt gtctcatgag cggatacata   8340
tttgaatgta tttagaaaaa taaacaaata ggggttccgc gcacatttcc ccgaaaagtg   8400
ccacctgatg cggtgtgaaa taccgcacag atgcgtaagg agaaaatacc gcatcaggaa   8460
attgtaagcg ttaatatttt gttaaaattc gcgttaaatt tttgttaaat cagctcattt   8520
tttaaccaat aggccgaaat cggcaaaatc ccttataaat caaaagaata gaccgagata   8580
gggttgagtg ttgttccagt ttggaacaag agtccactat taaagaacgt ggactccaac   8640
gtcaaagggc gaaaaaccgt ctatcagggc gatggcccac tacgtgaacc atcaccctaa   8700
tcaagttttt tggggtcgag gtgccgtaaa gcactaaatc ggaaccctaa agggagcccc   8760
cgatttagag cttgacgggg aaagccggcg aacgtggcga gaaaggaagg gaagaaagcg   8820
aaaggagcgg gcgctagggc gctggcaagt gtagcggtca cgctgcgcgt aaccaccaca   8880
cccgccgcgc ttaatgcgcc gctacagggc gcgtccattc gccattcagg ctgcgcaact   8940
gttgggaagg gcgatcggtg cgggcctctt cgctattacg ccagctggcg aaagggggat   9000
gtgctgcaag gcgattaagt tgggtaacgc cagggttttc ccagtcacga cgttgtaaaa   9060
cgacggccag tgaattgtaa tacgactcac tata                               9094
```

<210> SEQ ID NO 45
<211> LENGTH: 10976
<212> TYPE: DNA
<213> ORGANISM: Artificial Sequence
<220> FEATURE:
<223> OTHER INFORMATION: pDY-CD19deltaTmpk-IRES-COaGalA Sequence

<400> SEQUENCE: 45
gggcgaattg ggcccgacgt cgcatgcttg gaagggctaa ttcactccca aagaagacaa 60
gatatccttg atctgtggat ctaccacaca caaggctact tccctgatta gcagaactac 120
acaccagggc caggggtcag atatccactg acctttggat ggtgctacaa gctagtacca 180
gttgagccag ataaggtaga agaggccaat aaaggagaga acaccagctt gttacaccct 240
gtgagcctgc atgggatgga tgacccggag agagaagtgt tagagtggag gtttgacagc 300
cgcctagcat ttcatcacgt ggcccgagag ctgcatccgg agtacttcaa gaactgctga 360
tatcgagctt gctacaaggg actttccgct ggggactttc cagggaggcg tggcctgggc 420
gggactgggg agtggcgagc cctcagatcc tgcatataag cagctgcttt ttgcctgtac 480
tgggtctctc tggttagacc agatctgagc ctgggagctc tctggctaac tagggaaccc 540
actgcttaag cctcaataaa gcttgccttg agtgcttcaa gtagtgtgtg cccgtctgtt 600
gtgtgactct ggtaactaga gatccctcag acccttttag tcagtgtgga aaatctctag 660
cagtggcgcc cgaacaggga cttgaaagcg aaagggaaac cagaggagct ctctcgacgc 720
aggactcggc ttgctgaagc gcgcacggca agaggcgagg ggcggcgact ggtgagtacg 780
ccaaaaattt tgactagcgg aggctagaag gagagagatg ggtgcgagag cgtcagtatt 840
aagcggggga gaattagatc gcgatgggaa aaaattcggt taaggccagg gggaaagaaa 900
aaatataaat taaaacatat agtatgggca agcagggagc tagaacgatt cgcagttaat 960
cctggcctgt tagaaacatc agaaggctgt agacaaatac tgggacagct acaaccatcc 1020
cttcagacag gatcagaaga acttagatca ttatataata cagtagcaac cctctattgt 1080
gtgcatcaaa ggatagagat aaaagacacc aaggaagctt tagacaagat agaggaagag 1140
caaaacaaaa gtaagaccac cgcacagcaa gcggccgctg atcttcagac ctggaggagg 1200
agatatgagg gacaattgga gaagtgaatt atataaatat aaagtagtaa aaattgaacc 1260
attaggagta gcacccacca aggcaaagag aagagtggtg cagagagaaa aaagagcagt 1320
gggaatagga gctttgttcc ttgggttctt gggagcagca ggaagcacta tgggcgcagc 1380
gtcaatgacg ctgacggtac aggccagaca attattgtct ggtatagtgc agcagcagaa 1440
caatttgctg agggctattg aggcgcaaca gcatctgttg caactcacag tctggggcat 1500
caagcagctc caggcaagaa tcctggctgt ggaaagatac ctaaaggatc aacagctcct 1560
ggggatttgg ggttgctctg gaaaactcat ttgcaccact gctgtgcctt ggaatgctag 1620
ttggagtaat aaatctctgg aacagatttg gaatcacacg acctggatgg agtgggacag 1680
agaaattaac aattacacaa gcttaataca ctccttaatt gaagaatcgc aaaaccagca 1740
agaaaagaat gaacaagaat tattggaatt agataaatgg gcaagtttgt ggaattggtt 1800
taacataaca aattggctgt ggtatataaa attattcata atgatagtag gaggcttggt 1860
aggtttaaga atagtttttg ctgtactttc tatagtgaat agagttaggc agggatattc 1920
accattatcg tttcagaccc acctcccaac cccgagggga cccgacaggc ccgaaggaat 1980
agaagaagaa ggtggagaga gagacagaga cagatccatt cgattagtga acggatctcg 2040

-continued

```
acgggatcga ttttaaaaga aaaggggga ttgggggta cagtgcaggg gaaagaatag   2100
tagacataat agcaacagac atacaaacta aagaattaca aaaacaaatt acaaaaattc   2160
aaaattttat cgataagctt tgcaaagatg gataaagttt taaacagaga ggaatctttg   2220
cagctaatgg accttctagg tcttgaaagg agtgggaatt ggctccggtg cccgtcagtg   2280
ggcagagcgc acatcgccca cagtccccga gaagttgggg ggaggggtcg gcaattgaac   2340
cggtgcctag agaaggtggc gcggggtaaa ctgggaaagt gatgtcgtgt actggctccg   2400
cctttttccc gagggtgggg gagaaccgta tataagtgca gtagtcgccg tgaacgttct   2460
ttttcgcaac gggtttgccg ccagaacaca ggtaagtgcc gtgtgtggtt cccgcgggcc   2520
tggcctcttt acgggttatg gcccttgcgt gccttgaatt acttccacct ggctgcagta   2580
cgtgattctt gatcccgagc ttcgggttgg aagtgggtgg gagagttcga ggccttgcgc   2640
ttaaggagcc ccttcgcctc gtgcttgagt tgaggcctgg cctgggcgct ggggccgccg   2700
cgtgcgaatc tggtggcacc ttcgcgcctg tctcgctgct ttcgataagt ctctagccat   2760
ttaaaatttt tgatgacctg ctgcgacgct ttttttctgg caagatagtc ttgtaaatgc   2820
gggccaagat ctgcacactg gtatttcggt ttttggggcc gcgggcggcg acggggcccg   2880
tgcgtcccag cgcacatgtt cggcgaggcg gggcctgcga gcgcggccac cgagaatcgg   2940
acgggggtag tctcaagctg gccggcctgc tctggtgcct ggcctcgcgc cgccgtgtat   3000
cgccccgccc tgggcggcaa ggctggcccg gtcggcacca gttgcgtgag cggaaagatg   3060
gccgcttccc ggccctgctg cagggagctc aaaatggagg acgcggcgct cgggagagcg   3120
ggcgggtgag tcacccacac aaaggaaaag ggcctttccg tcctcagccg tcgcttcatg   3180
tgactccacg gagtaccggg cgccgtccag gcacctcgat tagttctcga gcttttggag   3240
tacgtcgtct ttaggttggg gggaggggtt ttatgcgatg gagtttcccc acactgagtg   3300
ggtggagact gaagttaggc cagcttggca cttgatgtaa ttctccttgg aatttgccct   3360
ttttgagttt ggatcttggt tcattctcaa gcctcagaca gtggttcaaa gtttttttct   3420
tccatttcag gtgtcgtgag gaattctgca gtcgacggta ccgcgggcgc gcccgccacc   3480
atgccacctc ctcgcctcct cttcttcctc ctcttcctca cccccatgga agtcaggccc   3540
gaggaacctc tagtggtgaa ggtggaagag ggagataacg ctgtgctgca gtgcctcaag   3600
gggacctcag atggccccac tcagcagctg acctggtctc gggagtcccc gcttaaaccc   3660
ttcttaaaac tcagcctggg gctgccaggc ctgggaatcc acatgaggcc cctggcatcc   3720
tggcttttca tcttcaacgt ctctcaacag atggggggct tctacctgtg ccagccgggg   3780
ccccctctg agaaggcctg gcagcctggc tggacagtca atgtggaggg cagcggggag   3840
ctgttccggt ggaatgtttc ggacctaggt ggcctgggct gtggcctgaa gaacaggtcc   3900
tcagagggcc ccagctcccc ttccgggaag ctcatgagcc ccaagctgta tgtgtgggcc   3960
aaagaccgcc ctgagatctg ggagggagag cctccgtgtg tcccaccgag ggacagcctg   4020
aaccagagcc tcagccagga cctcaccatg gcccctggct ccacactctg gctgtcctgt   4080
ggggtacccc ctgactctgt gtccaggggc cccctctcct ggacccatgt gcaccccaag   4140
gggcctaagt cattgctgag cctagagctg aaggacgatc gcccggccag agatatgtgg   4200
gtaatggaga cgggtctgtt gttgccccgg gccacagctc aagacgctgg aaagtattat   4260
tgtcaccgtg gcaacctgac catgtcattc cacctggaga tcactgctcg gccagtacta   4320
tggcactggc tgctgaggac tggtggctgg aaggtctcag ctgtgacttt ggcttatctg   4380
atcttctgcc tgtgttccct tgtgggcatt cttcatcttg ccggcggggc tgcagggatg   4440
```

gcggcccggc gcggggctct catagtgctg gagggcgtgg accgcgccgg gaagagcacg 4500
cagagccgca agctggtgga agcgctgtgc gccgcgggcc accgcgccga actgctccgg 4560
ttcccggaaa gatcaactga aatcggcaaa cttctgagtt cctacttgca aaagaaaagt 4620
gacgtggagg atcactcggt gcacctgctt ttttctgcaa atcgctggga acaagtgccg 4680
ttaattaagg aaaagttgag ccagggcgtg accctcgtcg tggacagata cgcatttttct 4740 ggtgtggcct acacaggtgc caaggagaat ttttccctag actggtgtaa acagccagac 4800
gtgggccttc ccaaacccga cctggtcctg ttcctccagt tacagctggc ggatgctgcc 4860
aagcggggag cgtttggcca tgagcgctat gagaacgggg ctttccagga gcgggcgctc 4920
cggtgtttcc accagctcat gaaagacacg actttgaact ggaagatggt ggatgcttcc 4980
aaaagcatcg aagctgtcca tgaggacatc cgcgtgctct ctgaggacgc catcgccact 5040
gccacagaga agccgctggg ggagctatgg aagtgaggat ctcgattccc cctctccctc 5100 cccccccct aacgttactg gccgaagccg cttggaataa ggccggtgtg cgtttgtcta 5160
tatgttattt tccaccatat tgccgtcttt tggcaatgtg agggcccgga aacctggccc 5220
tgtcttcttg acgagcattc ctaggggtct ttcccctctc gccaaaggaa tgcaaggtct 5280
gttgaatgtc gtgaaggaag cagttcctct ggaagcttct tgaagacaaa caacgtctgt 5340
agcgaccctt tgcaggcagc ggaacccccc acctggcgac aggtgcctct gcggccaaaa 5400
gccacgtgta taagatacac ctgcaaaggc ggcacaaccc cagtgccacg ttgtgagttg 5460
gatagttgtg gaaagagtca aatggctctc ctcaagcgta ttcaacaagg ggctgaagga 5520
tgcccagaag gtaccccatt gtatgggatc tgatctgggg cctcggtgca catgctttac 5580
atgtgtttag tcgaggttaa aaaaacgtct aggccccccg aaccacgggg acgtggtttt 5640
cctttgaaaa acacgattct agaccaccat gcaacttcga aacccagagc tccacctcgg 5700
atgtgccctt gctctgaggt tcctggcgct ggtgtcttgg gatatacccg gagcacgcgc 5760
tctggacaac gggctggccc ggactccaac catgggttgg ctccattggg aaaggtttat 5820
gtgcaacttg gactgccagg aagaacccga ctcctgtatt tccgagaaac tcttcatgga 5880
gatggccgag ctgatggtta gcgaaggctg gaaggatgcc ggttatgaat acttgtgtat 5940
cgacgattgt tggatggctc cccagcggga cagtgaagga cgactccagg cagatccgca 6000
acggttccct catggcatac ggcagctcgc caattacgtg cacagcaagg gtttgaagct 6060
ggggatatat gctgacgtgg gcaacaaaac ctgtgctggt ttccccggca gcttcggcta 6120
ctatgatata gatgcacaaa ccttcgctga ttggggcgtg gacctgctta aatttgacgg 6180
ctgttactgc gacagcttgg aaaacctcgc cgatggatat aaacacatga gccttgcact 6240
caatcggact ggccggagca ttgtctactc ttgcgagtgg ccattgtaca tgtggccttt 6300
ccagaagcct aactatacgg agattagaca gtattgtaat cactggagaa actttgcaga 6360
tatcgacgac tcatggaagt ccatcaaatc tattctggac tggacttcat tcaatcagga 6420
gcgcatcgtc gatgttgccg gtccaggtgg atggaacgac cctgacatgc tcgtaattgg 6480
gaatttcgga ctgtcctgga atcagcaggt cacacagatg gctttgtggg ctatcatggc 6540
agccccactc tttatgtcta acgatttgcg gcatatttca ccacaggcca aagccctgct 6600
gcaagataag gacgtcatag cgattaacca ggacccactg ggaaagcagg gctaccagct 6660
gagacagggc gacaattttg aggtctggga aagacctctt agcgggctgg cgtgggccgt 6720
agccatgatt aatcgccagg aaattggcgg ccctcgctct tacactatcg cggtcgccag 6780

-continued

```
tctgggcaag ggagtcgctt gtaaccccgc ctgcttcata actcagttgc tgcccgtgaa   6840
acggaagctg ggcttctatg aatggactag cagactccgc agtcatatta atccgactgg   6900
tacggtgctg ctgcaactgg agaataccat gcagatgtca cttaaggatc ttctgtgagg   6960
atccaagctt caattgtggt cactcgacaa tcaacctctg gattacaaaa tttgtgaaag   7020
attgactggt attcttaact atgttgctcc ttttacgcta tgtggatacg ctgctttaat   7080
gcctttgtat catgctattg cttcccgtat ggctttcatt ttctcctcct tgtataaatc   7140
ctggttgctg tctctttatg aggagttgtg gcccgttgtc aggcaacgtg gcgtggtgtg   7200
cactgtgttt gctgacgcaa cccccactgg ttggggcatt gccaccacct gtcagctcct   7260
ttccgggact ttcgctttcc ccctccctat tgccacggcg gaactcatcg ccgcctgcct   7320
tgcccgctgc tggacagggg ctcggctgtt gggcactgac aattccgtgg tgttgtcggg   7380
gaagctgacg tcctttccat ggctgctcgc ctgtgttgcc acctggattc tgcgcgggac   7440
gtccttctgc tacgtccctt cggccctcaa tccagcggac cttccttccc gcggcctgct   7500
gccggctctg cggcctcttc cgcgtcttcg ccttcgccct cagacgagtc ggatctccct   7560
ttgggccgcc tccccgcctg ctcgagacct agaaaaacat ggagcaatca caagtagcaa   7620
tacagcagct accaatgctg attgtgcctg gctagaagca caagaggagg aggaggtggg   7680
ttttccagtc acacctcagg tacctttaag accaatgact tacaaggcag ctgtagatct   7740
tagccacttt ttaaaagaaa aggggggact ggaagggcta attcactccc aacgaagaca   7800
agatctgctt tttgcttgta ctgggtctct ctggttagac cagatctgag cctgggagct   7860
ctctggctaa ctagggaacc cactgcttaa gcctcaataa agcttgcctt gagtgcttca   7920
agtagtgtgt gcccgtctgt tgtgtgactc tggtaactag agatccctca gaccctttta   7980
gtcagtgtgg aaaatctcta gcagtagtag ttcatgtcat cttattattc agtatttata   8040
acttgcaaag aaatgaatat cagagagtga gaggacgcgt tggatgcata gcttgagtat   8100
tctatagtgt cacctaaata gcttggcgta atcatggtca tagctgtttc ctgtgtgaaa   8160
ttgttatccg ctcacaattc cacacaacat acgagccgga agcataaagt gtaaagcctg   8220
gggtgcctaa tgagtgagct aactcacatt aattgcgttg cgctcactgc ccgctttcca   8280
gtcgggaaac ctgtcgtgcc agctgcatta atgaatcggc caacgcgcgg ggagaggcgg   8340
tttgcgtatt gggcgctctt ccgcttcctc gctcactgac tcgctgcgct cggtcgttcg   8400
gctgcggcga gcggtatcag ctcactcaaa ggcggtaata cggttatcca cagaatcagg   8460
ggataacgca ggaaagaaca tgtgagcaaa aggccagcaa aaggccagga accgtaaaaa   8520
ggccgcgttg ctggcgtttt tccataggct ccgcccccct gacgagcatc acaaaaatcg   8580
acgctcaagt cagaggtggc gaaacccgac aggactataa agataccagg cgtttccccc   8640
tggaagctcc ctcgtgcgct ctcctgttcc gaccctgccg cttaccggat acctgtccgc   8700
ctttctccct tcgggaagcg tggcgctttc tcatagctca cgctgtaggt atctcagttc   8760
ggtgtaggtc gttcgctcca agctgggctg tgtgcacgaa ccccccgttc agcccgaccg   8820
ctgcgcctta tccggtaact atcgtcttga gtccaacccg gtaagacacg acttatcgcc   8880
actggcagca gccactggta acaggattag cagagcgagg tatgtaggcg gtgctacaga   8940
gttcttgaag tggtggccta actacggcta cactagaaga acagtatttg gtatctgcgc   9000
tctgctgaag ccagttacct tcggaaaaag agttggtagc tcttgatccg gcaaacaaac   9060
caccgctggt agcggtggtt tttttgtttg caagcagcag attacgcgca gaaaaaaagg   9120
atctcaagaa gatcctttga tcttttctac ggggtctgac gctcagtgga acgaaaactc   9180
```

```
acgttaaggg attttggtca tgagattatc aaaaaggatc ttcacctaga tccttttaaa   9240

ttaaaaatga agttttaaat caatctaaag tatatatgag taaacttggt ctgacagtta   9300

ccaatgctta atcagtgagg cacctatctc agcgatctgt ctatttcgtt catccatagt   9360

tgcctgactc cccgtcgtgt agataactac gatacgggag ggcttaccat ctggccccag   9420

tgctgcaatg ataccgcgag acccacgctc accggctcca gatttatcag caataaacca   9480

gccagccgga agggccgagc gcagaagtgg tcctgcaact ttatccgcct ccatccagtc   9540

tattaattgt tgccgggaag ctagagtaag tagttcgcca gttaatagtt tgcgcaacgt   9600

tgttgccatt gctacaggca tcgtggtgtc acgctcgtcg tttggtatgg cttcattcag   9660

ctccggttcc caacgatcaa ggcgagttac atgatccccc atgttgtgca aaaaagcggt   9720

tagctccttc ggtcctccga tcgttgtcag aagtaagttg gccgcagtgt tatcactcat   9780

ggttatggca gcactgcata attctcttac tgtcatgcca tccgtaagat gcttttctgt   9840

gactggtgag tactcaacca agtcattctg agaatagtgt atgcggcgac cgagttgctc   9900

ttgcccggcg tcaatacggg ataataccgc gccacatagc agaactttaa aagtgctcat   9960

cattggaaaa cgttcttcgg ggcgaaaact ctcaaggatc ttaccgctgt tgagatccag  10020

ttcgatgtaa cccactcgtg cacccaactg atcttcagca tcttttactt tcaccagcgt  10080

ttctgggtga gcaaaaacag gaaggcaaaa tgccgcaaaa aagggaataa gggcgacacg  10140

gaaatgttga atactcatac tcttcctttt tcaatattat tgaagcattt atcagggtta  10200

ttgtctcatg agcggataca tatttgaatg tatttagaaa aataaacaaa taggggttcc  10260

gcgcacattt ccccgaaaag tgccacctga tgcggtgtga aataccgcac agatgcgtaa  10320

ggagaaaata ccgcatcagg aaattgtaag cgttaatatt ttgttaaaat tcgcgttaaa  10380

tttttgttaa atcagctcat tttttaacca ataggccgaa atcggcaaaa tcccttataa  10440

atcaaaagaa tagaccgaga tagggttgag tgttgttcca gtttggaaca agagtccact  10500

attaaagaac gtggactcca acgtcaaagg gcgaaaaacc gtctatcagg gcgatggccc  10560

actacgtgaa ccatcaccct aatcaagttt tttggggtcg aggtgccgta aagcactaaa  10620

tcggaaccct aaagggagcc cccgatttag agcttgacgg ggaaagccgg cgaacgtggc  10680

gagaaaggaa gggaagaaag cgaaaggagc gggcgctagg gcgctggcaa gtgtagcggt  10740

cacgctgcgc gtaaccacca cacccgccgc gcttaatgcg ccgctacagg gcgcgtccat  10800

tcgccattca ggctgcgcaa ctgttgggaa gggcgatcgg tgcgggcctc ttcgctatta  10860

cgccagctgg cgaaaggggg atgtgctgca aggcgattaa gttgggtaac gccagggttt  10920

tcccagtcac gacgttgtaa aacgacggcc agtgaattgt aatacgactc actata      10976
```

<210> SEQ ID NO 46
<211> LENGTH: 1307
<212> TYPE: DNA
<213> ORGANISM: Artificial Sequence
<220> FEATURE:
<223> OTHER INFORMATION: Human Codon Optimized alpha-galA
<220> FEATURE:
<221> NAME/KEY: CDS
<222> LOCATION: (12)..(1298)

<400> SEQUENCE: 46

```
tctagaccac c atg caa ctt cga aac cca gag ctc cac ctc gga tgt gcc      50
             Met Gln Leu Arg Asn Pro Glu Leu His Leu Gly Cys Ala
             1               5                   10

ctt gct ctg agg ttc ctg gcg ctg gtg tct tgg gat ata ccc gga gca       98
```

-continued

```
Leu Ala Leu Arg Phe Leu Ala Leu Val Ser Trp Asp Ile Pro Gly Ala
    15                  20                  25

cgc gct ctg gac aac ggg ctg gcc cgg act cca acc atg ggt tgg ctc      146
Arg Ala Leu Asp Asn Gly Leu Ala Arg Thr Pro Thr Met Gly Trp Leu
30                  35                  40                  45

cat tgg gaa agg ttt atg tgc aac ttg gac tgc cag gaa gaa ccc gac      194
His Trp Glu Arg Phe Met Cys Asn Leu Asp Cys Gln Glu Glu Pro Asp
                50                  55                  60

tcc tgt att tcc gag aaa ctc ttc atg gag atg gcc gag ctg atg gtt      242
Ser Cys Ile Ser Glu Lys Leu Phe Met Glu Met Ala Glu Leu Met Val
            65                  70                  75

agc gaa ggc tgg aag gat gcc ggt tat gaa tac ttg tgt atc gac gat      290
Ser Glu Gly Trp Lys Asp Ala Gly Tyr Glu Tyr Leu Cys Ile Asp Asp
        80                  85                  90

tgt tgg atg gct ccc cag cgg gac agt gaa gga cga ctc cag gca gat      338
Cys Trp Met Ala Pro Gln Arg Asp Ser Glu Gly Arg Leu Gln Ala Asp
    95                  100                 105

ccg caa cgg ttc cct cat ggc ata cgg cag ctc gcc aat tac gtg cac      386
Pro Gln Arg Phe Pro His Gly Ile Arg Gln Leu Ala Asn Tyr Val His
110                 115                 120                 125

agc aag ggt ttg aag ctg ggg ata tat gct gac gtg ggc aac aaa acc      434
Ser Lys Gly Leu Lys Leu Gly Ile Tyr Ala Asp Val Gly Asn Lys Thr
                130                 135                 140

tgt gct ggt ttc ccc ggc agc ttc ggc tac tat gat ata gat gca caa      482
Cys Ala Gly Phe Pro Gly Ser Phe Gly Tyr Tyr Asp Ile Asp Ala Gln
            145                 150                 155

acc ttc gct gat tgg ggc gtg gac ctg ctt aaa ttt gac ggc tgt tac      530
Thr Phe Ala Asp Trp Gly Val Asp Leu Leu Lys Phe Asp Gly Cys Tyr
        160                 165                 170

tgc gac agc ttg gaa aac ctc gcc gat gga tat aaa cac atg agc ctt      578
Cys Asp Ser Leu Glu Asn Leu Ala Asp Gly Tyr Lys His Met Ser Leu
    175                 180                 185

gca ctc aat cgg act ggc cgg agc att gtc tac tct tgc gag tgg cca      626
Ala Leu Asn Arg Thr Gly Arg Ser Ile Val Tyr Ser Cys Glu Trp Pro
190                 195                 200                 205

ttg tac atg tgg cct ttc cag aag cct aac tat acg gag att aga cag      674
Leu Tyr Met Trp Pro Phe Gln Lys Pro Asn Tyr Thr Glu Ile Arg Gln
                210                 215                 220

tat tgt aat cac tgg aga aac ttt gca gat atc gac gac tca tgg aag      722
Tyr Cys Asn His Trp Arg Asn Phe Ala Asp Ile Asp Asp Ser Trp Lys
            225                 230                 235

tcc atc aaa tct att ctg gac tgg act tca ttc aat cag gag cgc atc      770
Ser Ile Lys Ser Ile Leu Asp Trp Thr Ser Phe Asn Gln Glu Arg Ile
        240                 245                 250

gtc gat gtt gcc ggt cca ggt gga tgg aac gac cct gac atg ctc gta      818
Val Asp Val Ala Gly Pro Gly Gly Trp Asn Asp Pro Asp Met Leu Val
    255                 260                 265

att ggg aat ttc gga ctg tcc tgg aat cag cag gtc aca cag atg gct      866
Ile Gly Asn Phe Gly Leu Ser Trp Asn Gln Gln Val Thr Gln Met Ala
270                 275                 280                 285

ttg tgg gct atc atg gca gcc cca ctc ttt atg tct aac gat ttg cgg      914
Leu Trp Ala Ile Met Ala Ala Pro Leu Phe Met Ser Asn Asp Leu Arg
                290                 295                 300

cat att tca cca cag gcc aaa gcc ctg ctg caa gat aag gac gtc ata      962
His Ile Ser Pro Gln Ala Lys Ala Leu Leu Gln Asp Lys Asp Val Ile
            305                 310                 315

gcg att aac cag gac cca ctg gga aag cag ggc tac cag ctg aga cag     1010
Ala Ile Asn Gln Asp Pro Leu Gly Lys Gln Gly Tyr Gln Leu Arg Gln
        320                 325                 330
```

```
ggc gac aat ttt gag gtc tgg gaa aga cct ctt agc ggg ctg gcg tgg     1058
Gly Asp Asn Phe Glu Val Trp Glu Arg Pro Leu Ser Gly Leu Ala Trp
    335                 340                 345

gcc gta gcc atg att aat cgc cag gaa att ggc ggc cct cgc tct tac     1106
Ala Val Ala Met Ile Asn Arg Gln Glu Ile Gly Gly Pro Arg Ser Tyr
350                 355                 360                 365

act atc gcg gtc gcc agt ctg ggc aag gga gtc gct tgt aac ccc gcc     1154
Thr Ile Ala Val Ala Ser Leu Gly Lys Gly Val Ala Cys Asn Pro Ala
                370                 375                 380

tgc ttc ata act cag ttg ctg ccc gtg aaa cgg aag ctg ggc ttc tat     1202
Cys Phe Ile Thr Gln Leu Leu Pro Val Lys Arg Lys Leu Gly Phe Tyr
            385                 390                 395

gaa tgg act agc aga ctc cgc agt cat att aat ccg act ggt acg gtg     1250
Glu Trp Thr Ser Arg Leu Arg Ser His Ile Asn Pro Thr Gly Thr Val
        400                 405                 410

ctg ctg caa ctg gag aat acc atg cag atg tca ctt aag gat ctt ctg     1298
Leu Leu Gln Leu Glu Asn Thr Met Gln Met Ser Leu Lys Asp Leu Leu
    415                 420                 425

tgaggatcc                                                           1307


<210> SEQ ID NO 47
<211> LENGTH: 429
<212> TYPE: PRT
<213> ORGANISM: Artificial Sequence
<220> FEATURE:
<223> OTHER INFORMATION: Synthetic Construct

<400> SEQUENCE: 47

Met Gln Leu Arg Asn Pro Glu Leu His Leu Gly Cys Ala Leu Ala Leu
1               5                   10                  15

Arg Phe Leu Ala Leu Val Ser Trp Asp Ile Pro Gly Ala Arg Ala Leu
            20                  25                  30

Asp Asn Gly Leu Ala Arg Thr Pro Thr Met Gly Trp Leu His Trp Glu
        35                  40                  45

Arg Phe Met Cys Asn Leu Asp Cys Gln Glu Glu Pro Asp Ser Cys Ile
    50                  55                  60

Ser Glu Lys Leu Phe Met Glu Met Ala Glu Leu Met Val Ser Glu Gly
65                  70                  75                  80

Trp Lys Asp Ala Gly Tyr Glu Tyr Leu Cys Ile Asp Asp Cys Trp Met
                85                  90                  95

Ala Pro Gln Arg Asp Ser Glu Gly Arg Leu Gln Ala Asp Pro Gln Arg
            100                 105                 110

Phe Pro His Gly Ile Arg Gln Leu Ala Asn Tyr Val His Ser Lys Gly
        115                 120                 125

Leu Lys Leu Gly Ile Tyr Ala Asp Val Gly Asn Lys Thr Cys Ala Gly
    130                 135                 140

Phe Pro Gly Ser Phe Gly Tyr Tyr Asp Ile Asp Ala Gln Thr Phe Ala
145                 150                 155                 160

Asp Trp Gly Val Asp Leu Leu Lys Phe Asp Gly Cys Tyr Cys Asp Ser
                165                 170                 175

Leu Glu Asn Leu Ala Asp Gly Tyr Lys His Met Ser Leu Ala Leu Asn
            180                 185                 190

Arg Thr Gly Arg Ser Ile Val Tyr Ser Cys Glu Trp Pro Leu Tyr Met
        195                 200                 205

Trp Pro Phe Gln Lys Pro Asn Tyr Thr Glu Ile Arg Gln Tyr Cys Asn
    210                 215                 220

His Trp Arg Asn Phe Ala Asp Ile Asp Asp Ser Trp Lys Ser Ile Lys
```

```
225                 230                 235                 240

Ser Ile Leu Asp Trp Thr Ser Phe Asn Gln Glu Arg Ile Val Asp Val
                245                 250                 255

Ala Gly Pro Gly Gly Trp Asn Asp Pro Asp Met Leu Val Ile Gly Asn
            260                 265                 270

Phe Gly Leu Ser Trp Asn Gln Gln Val Thr Gln Met Ala Leu Trp Ala
        275                 280                 285

Ile Met Ala Ala Pro Leu Phe Met Ser Asn Asp Leu Arg His Ile Ser
    290                 295                 300

Pro Gln Ala Lys Ala Leu Leu Gln Asp Lys Asp Val Ile Ala Ile Asn
305                 310                 315                 320

Gln Asp Pro Leu Gly Lys Gln Gly Tyr Gln Leu Arg Gln Gly Asp Asn
                325                 330                 335

Phe Glu Val Trp Glu Arg Pro Leu Ser Gly Leu Ala Trp Ala Val Ala
            340                 345                 350

Met Ile Asn Arg Gln Glu Ile Gly Gly Pro Arg Ser Tyr Thr Ile Ala
        355                 360                 365

Val Ala Ser Leu Gly Lys Gly Val Ala Cys Asn Pro Ala Cys Phe Ile
    370                 375                 380

Thr Gln Leu Leu Pro Val Lys Arg Lys Leu Gly Phe Tyr Glu Trp Thr
385                 390                 395                 400

Ser Arg Leu Arg Ser His Ile Asn Pro Thr Gly Thr Val Leu Leu Gln
                405                 410                 415

Leu Glu Asn Thr Met Gln Met Ser Leu Lys Asp Leu Leu
            420                 425


<210> SEQ ID NO 48
<211> LENGTH: 28
<212> TYPE: DNA
<213> ORGANISM: Artificial Sequence
<220> FEATURE:
<223> OTHER INFORMATION: Primer

<400> SEQUENCE: 48

gctagaattc atgccacctc ctcgcctc                                    28


<210> SEQ ID NO 49
<211> LENGTH: 32
<212> TYPE: DNA
<213> ORGANISM: Artificial Sequence
<220> FEATURE:
<223> OTHER INFORMATION: Primer

<400> SEQUENCE: 49

gctagccggc aagatgaaga atgcccacaa gg                               32


<210> SEQ ID NO 50
<211> LENGTH: 28
<212> TYPE: DNA
<213> ORGANISM: Artificial Sequence
<220> FEATURE:
<223> OTHER INFORMATION: Primer

<400> SEQUENCE: 50

aaactgcagg gatggcggcc cggcgcgg                                    28


<210> SEQ ID NO 51
<211> LENGTH: 37
<212> TYPE: DNA
<213> ORGANISM: Artificial Sequence
```

-continued

```
<220> FEATURE:
<223> OTHER INFORMATION: Primer

<400> SEQUENCE: 51

gctctagaat cgtgtttttc aaaggaaaac cacgtcc                            37


<210> SEQ ID NO 52
<211> LENGTH: 77
<212> TYPE: DNA
<213> ORGANISM: Artificial Sequence
<220> FEATURE:
<223> OTHER INFORMATION: Cloning Insert

<400> SEQUENCE: 52

gcttacgaat tctgacgcta gccggcgggg ctgcagcatt acatctagat accgtgagga   60

tccgtcgcat gccatcg                                                  77


<210> SEQ ID NO 53
<211> LENGTH: 37
<212> TYPE: DNA
<213> ORGANISM: Artificial Sequence
<220> FEATURE:
<223> OTHER INFORMATION: Primer

<400> SEQUENCE: 53

aggcgcgccc gccaccatgc cacctcctcg cctcctc                            37


<210> SEQ ID NO 54
<211> LENGTH: 35
<212> TYPE: DNA
<213> ORGANISM: Artificial Sequence
<220> FEATURE:
<223> OTHER INFORMATION: Primer

<400> SEQUENCE: 54

gcattacggg atcctcactt ccatagctcc cccag                              35
```